(12) United States Patent
Yuen

(10) Patent No.: US 8,965,730 B2
(45) Date of Patent: Feb. 24, 2015

(54) FITNESS MONITORING DEVICE WITH ALTIMETER AND AIRPLANE MODE

(71) Applicant: Fitbit, Inc., San Francisco, CA (US)

(72) Inventor: Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/297,397

(22) Filed: Jun. 5, 2014

(65) Prior Publication Data
US 2014/0297218 A1 Oct. 2, 2014

Related U.S. Application Data

(63) Continuation of application No. 14/292,523, filed on May 30, 2014, which is a continuation-in-part of application No. 13/924,784, filed on Jun. 24, 2013.

(60) Provisional application No. 61/662,961, filed on Jun. 22, 2012, provisional application No. 61/752,826, filed on Jan. 15, 2013, provisional application No. 61/946,439, filed on Feb. 28, 2014, provisional application No. 61/955,045, filed on Mar. 18, 2014, provisional application No. 61/973,614, filed on Apr. 1, 2014, provisional application No. 61/830,600, filed on Jun. 3, 2013, provisional application No. 62/001,624, filed on May 21, 2014.

(51) Int. Cl.
*G06F 19/00* (2011.01)
*G01B 21/16* (2006.01)

(52) U.S. Cl.
CPC .................................... *G01B 21/16* (2013.01)
USPC ........................................................ 702/141

(58) Field of Classification Search
CPC ......... G06F 3/011; G06F 3/016; H04N 5/225; G01C 21/3629; G06K 9/00523
USPC .................. 702/141, 150–155, 182–185, 188
See application file for complete search history.

(56) References Cited

U.S. PATENT DOCUMENTS 6,583,369 B2   6/2003  Montagnino et al.
8,660,355 B2 *  2/2014  Rodriguez et al. ............ 382/181
(Continued)

FOREIGN PATENT DOCUMENTS

EP       1 721 237       8/2012

OTHER PUBLICATIONS

"Activator is One of the Best Cydia iPhone Hacks { Control your iPhone with Gestures," iPhone-Tips-And-Advice.Com, [retrieved on Jul. 9, 2013 at http://www.iphone-tips-and-advice.com/activatior.html], 10 pp.

(Continued)

*Primary Examiner* — Edward Raymond
(74) *Attorney, Agent, or Firm* — Weaver Austin Villeneuve & Sampson, LLP

(57) ABSTRACT

Biometric monitoring devices, including various technologies that may be implemented in such devices, are discussed herein. Additionally, techniques for utilizing altimeters in biometric monitoring devices are provided. Such techniques may, in some implementations, involve recalibrating a biometric monitoring device altimeter based on location data; using altimeter data as an aid to gesture recognition; and/or using altimeter data to manage an airplane mode of a biometric monitoring device.

28 Claims, 53 Drawing Sheets

(56) References Cited

U.S. PATENT DOCUMENTS

| | | | |
|---|---|---|---|
| 8,737,986 B2* | 5/2014 | Rhoads et al. | 455/426.1 |
| 2010/0331145 A1 | 12/2010 | Lakovic et al. | |
| 2011/0032105 A1 | 2/2011 | Hoffman et al. | |
| 2012/0274508 A1 | 11/2012 | Brown et al. | |
| 2013/0106684 A1 | 5/2013 | Weast et al. | |

OTHER PUBLICATIONS

Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.

DesMarais, Christina (posted on Sep. 3, 2013) "Which New Activity Tracker is Best for You?" *Health and Home, Health & Fitness, Guides & Reviews*, [Retrieved on Sep. 23, 2013 at http://www.techlicious.com/guide/which-new-activity-tracker-is-right-for-you] 4 pp.

Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.

U.S. Appl. No. 14/292,523, filed May 30, 2014, Yuen et al.

U.S. Appl. No. 14/297,384, filed Jun. 5, 2014, Yuen.

Fitbit User's Manual, Last Updated Oct. 22, 2009, 15 pages.

Forerunner® 201 personal trainer owner's manual, (Feb. 2006) Garmin Ltd., 48 pp.

Forerunner® 301 personal trainer owner's manual, (Feb. 2006) Garmin Ltd., 66 pp.

Forerunner® 50 with ANT+Sport™ wireless technology, Owner's Manual, (Nov. 2007) Garmin Ltd., 44 pp.

Forerunner® 205/305 Owner's Manual, GPS-enabled trainer for runners, (2006-2008), Garmin Ltd., 80 pp.

Forerunner® 405CX Owner's Manual, "GPS-Enabled Sports Watch With Wireless Sync," (Mar. 2009), Garmin Ltd., 56 pp.

Forerunner® 110 Owner's Manual, (2010) "GPS-Enabled Sport Watch," Garmin Ltd., 16 pp.

Forerunner® 210 Owner's Manual, (2010) "GPS-Enabled Sport Watch," Garmin Ltd., 28 pp.

Forerunner® 410 Owner's Manual, (Jul. 2012) "GPS-Enabled Sport Watch With Wireless Sync," Garmin Ltd., 52 pp.

Forerunner® 10 Owner's Manual (Aug. 2012), Garmin Ltd., 10 pp.

Forerunner® 310XT Owner's Manual, Multisport GPS Training Device, (2009-2013), Garmin Ltd., 56 pp.

Forerunner® 405 Owner's Manual, (Mar. 2011) "GPS-Enabled Sport Watch With Wireless Sync," Garmin Ltd., 56 pp.

Forerunner® 910XT Owner's Manual, (Jan. 2013) Garmin Ltd., 56 pp.

Garmin Swim™ Owner's Manual (Jun. 2012), 12 pp.

Larklife, User Manual, (2012) *Lark Technologies*, 7 pp.

Lark/Larkpro, User Manual, (2012) "What's in the box," *Lark Technologies*, 7 pp.

Nike+ FuelBand Gps Manual, User's Guide (Product Release Date Unknown, downloaded Jul. 22, 2013), 26 pages.

Nike+ SportBand User's Guide, (Product Release Date Unknown, downloaded Jul. 22, 2013), 36 pages.

Nike+SportWatch GPS Manual, User's Guide, Powered by TOMTOM, (Product Release Date Unknown, downloaded Jul. 22, 2013), 42 pages.

"Parts of Your Band," (Product Release Date Unknown, downloaded Jul. 22, 2013) Jawbone UP Band, 1 page.

Polar WearLink® + Coded Transmitter 31 Coded Transmitter W.I.N.D. User Manual, Polar® Listen to Your Body, *Manufactured by Polar Electro Oy*, 11 pages.

Rainmaker, (Jun. 25, 2012, updated Feb 16, 2013) "Garmin Swim watch In-Depth Review," [retrieved on Sep. 9, 2013 at http://www.dcrainmaker.com/2012/06/garmin-swim-in-depth-review.html, 38 pp.

* cited by examiner

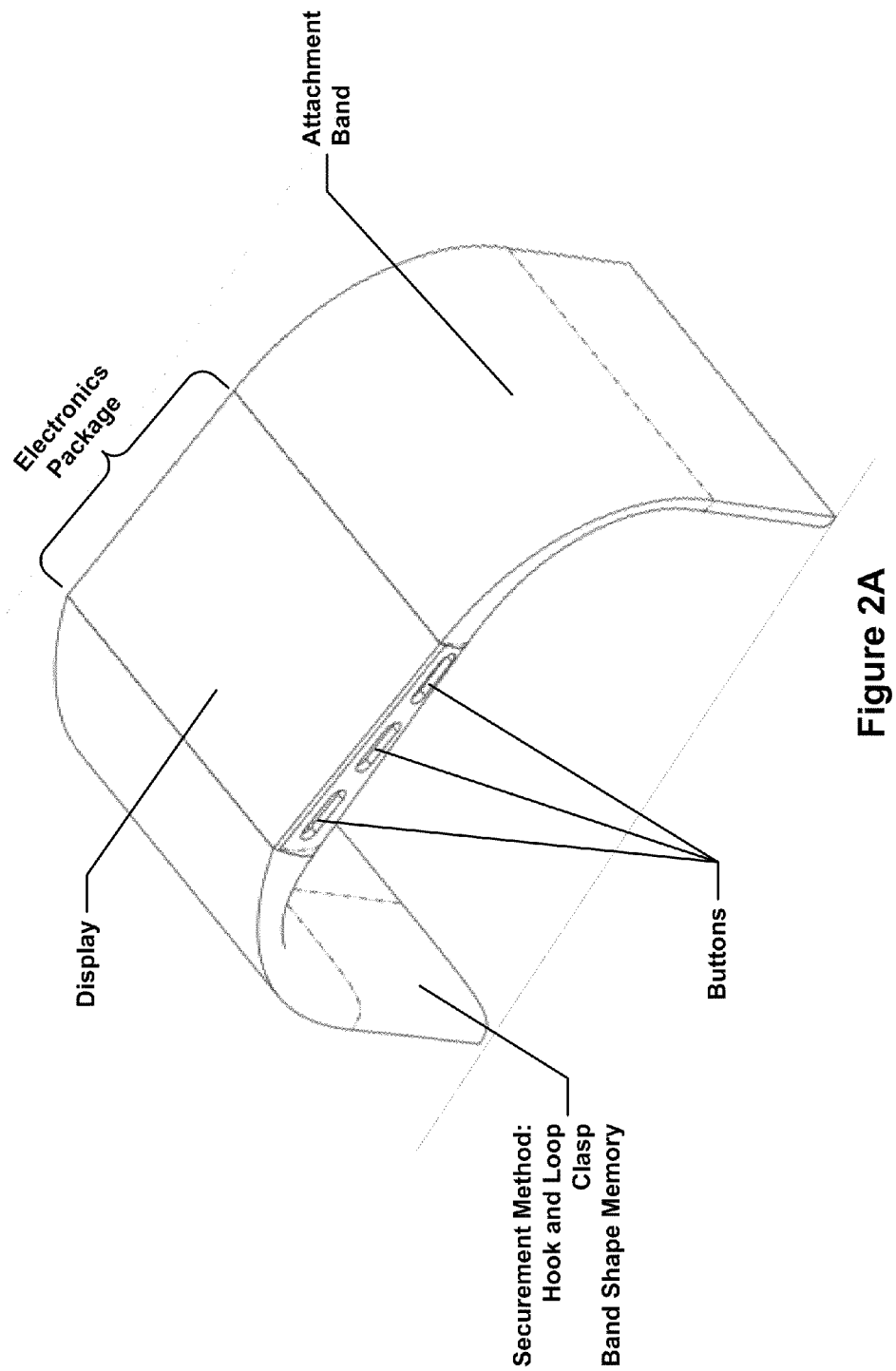

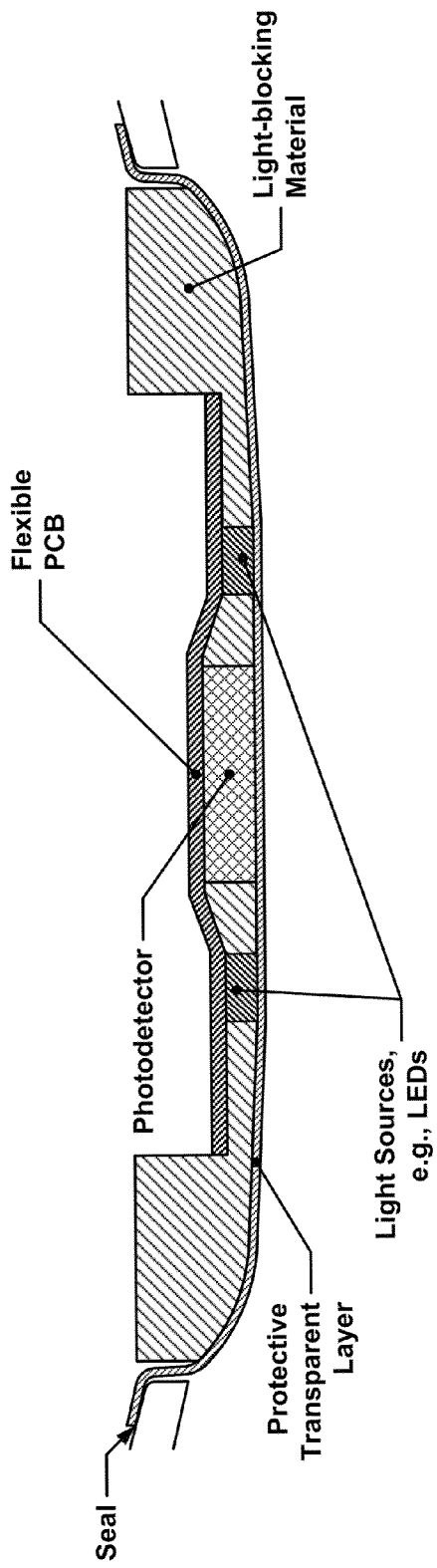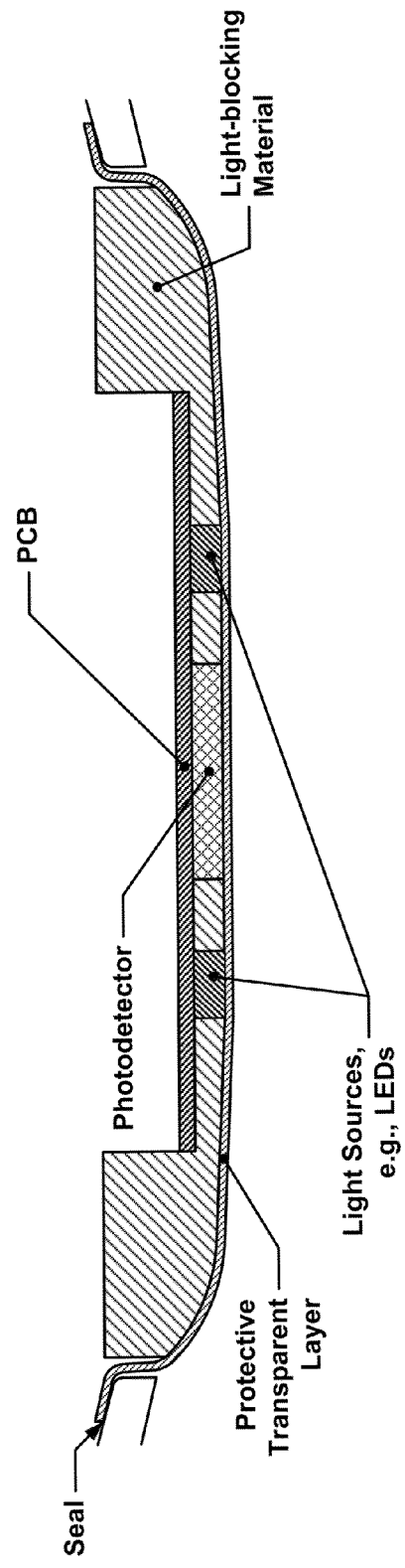
Figure 3A
Figure 3B

Band-Mounted Optical Sensors and Light Emitters

Display

Wristband

Side-Mounted Optical Heart Rate Detection Sensors and/or Emitters

FITNESS MONITORING DEVICE WITH ALTIMETER AND AIRPLANE MODE

CROSS REFERENCE TO RELATED APPLICATIONS

This application is a continuation of U.S. patent application Ser. No. 14/292,523, titled "FITNESS MONITORING DEVICE WITH ALTIMETER" and filed on May 30, 2014, which is itself a continuation-in-part of U.S. patent application Ser. No. 13/924,784, titled "PORTABLE BIOMETRIC MONITORING DEVICES AND METHODS OF OPERATING SAME" and filed on Jun. 24, 2013, which claims benefit of priority under 35 U.S.C. §119(e) to U.S. Provisional Patent Application Nos. 61/662,961, titled "WIRELESS PERSONAL BIOMETRICS MONITOR" and filed on Jun. 22, 2012, titled "PORTABLE MONITORING DEVICES AND METHODS OF OPERATING SAME" and filed on Jan. 15, 2013; U.S. patent application Ser. No. 14/292,523 also claims benefit of priority under 35 U.S.C. §119(e) to U.S. Provisional Patent Application Nos. 61/830,600, titled "PORTABLE MONITORING DEVICES AND METHODS OF OPERATING SAME" and filed on Jun. 3, 2013, 61/946,439, titled "HEART RATE DATA COLLECTION" and filed on Feb. 28, 2014, 61/955,045, titled "GPS POWER CONSERVATION USING ENVIRONMENTAL DATA" and filed on Mar. 18, 2014, 61/973,614, titled "GPS ACCURACY REFINEMENT USING EXTERNAL SENSORS" and filed on Apr. 1, 2014, and 62/001,624, titled "FITNESS MONITORING DEVICE WITH ALTIMETER, and filed on May 21, 2014, all of which are hereby incorporated by reference herein in their entireties.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be offered in extremely small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

Discussed herein are various embodiments of biometric monitoring devices and technologies that may be used therein (and in other devices, in some instances, not necessarily providing biometric tracking functionality).

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, a wearable biometric tracking device may be provided. The wearable biometric tracking device may include a pressure sensor configured to detect ambient atmospheric air pressure around the wearable biometric tracking device and to output data representative of altitude, wherein the data representative of altitude is based, at least in part, on air pressure measured by the pressure sensor data representative of altitude, a motion sensor, the motion sensor configured to detect motion of the wearable biometric tracking device and to output corresponding motion data, and control logic, wherein the pressure sensor, the motion sensor, and the control logic are communicatively connected. The control logic is may be configured to (a) receive the data representative of altitude, (b) receive the motion data, (c) determine when the data representative of altitude and the motion data, in combination, correlate with a first arm movement profile of a plurality of arm movement profiles, and (d) store data associated with the first arm movement profile responsive to the determination in (c).

In some such implementations of the wearable biometric tracking device, the wearable biometric tracking device may be configured to be worn in a location selected from the group consisting of: a person's arm, a person's forearm, a person's hand, and a person's finger.

In some other or additional implementations of the wearable biometric tracking device, the pressure sensor may be a barometric altimeter.

In some other or additional implementations of the wearable biometric tracking device, the motion sensor may include one or more sensors selected from the group consisting of: accelerometers, gyroscopes, magnetometers, piezoelectric sensors, electromagnetic trackers, and camera-based imaging sensors.

In some other or additional implementations of the wearable biometric tracking device, the plurality of arm movement profiles may include one or more arm movement profiles approximating arm motions representative of one or more activities, each selected from the group consisting of: running, walking, elliptical exercises, resistance-training exercises, pull-ups, push-ups, sit-ups, jumping rope, and aerobic dancing.

In some other or additional implementations of the wearable biometric tracking device, the control logic is further configured to determine a first arm motion profile associated with the first arm movement profile, and determine a degree of deviation between the first arm motion profile and a first reference motion profile associated with the first arm movement profile. In some such implementations, the first arm movement profile and the first reference motion profile may both be associated with a gesture or gestures associated with a common action selected from the group consisting of swinging a baseball bat, swinging a softball bat, swinging a tennis racket, swinging a badminton racket, swinging a squash racket, swinging a racketball racket, swinging a golfing wood, swinging a golfing iron, swinging a golfing wedge, swinging a golfing putter, swinging a golfing chipper, swinging a golfing hybrid, performing a resistance-training exercise, performing a martial arts motion, performing a gymnastics motion, performing a yoga exercise, taking a shot in a cue sport such as billiards, taking a shot in a cue sport such as snooker, taking a shot in a cue sport such as pool, taking a swimming stroke, bowling a bowling ball, firing a rifle, firing a pistol, thrusting a blade, swinging a blade, and parrying with a blade. In some other or additional implementations, the wearable biometric tracking device may further include an interface device communicatively connected with the control logic, the control logic further configured to determine when the degree of deviation exceeds a first threshold amount of deviation, and cause, responsive to the determination that the degree of deviation exceeds the first threshold amount, the interface device to provide an indication that the degree of deviation exceeded the first threshold amount. The interface device may include one or more items selected from the group consisting of a display, one or more lights, a vibramotor, and an audio device. The indication may include one or more items selected from the group consisting of a numerical score, a vibration, a sound, a graphic, an icon, an animation, a message indicating fatigue, a message cautioning the wearer to slow down, and a message cautioning the wearer to take a rest.

In some other or additional implementations of the wearable biometric tracking device, the first arm movement profile may be associated with a resistance-training bicep-curl-type activity and the motion data and the data representative of altitude may correlate with the first arm movement profile when the motion data and the data representative of altitude include one instance or two or more substantially consecutive instances in which the motion data indicates that a forearm upon which the wearable biometric tracking device is worn transitioned from a downward-sloping orientation to an upward-sloping orientation during a first time period, the motion data indicates that the forearm upon which the wearable biometric tracking device is worn transitioned from the upward-sloping orientation to a downward-sloping orientation during a second time period following the first time period, and the data representative of altitude indicates that the wearable biometric tracking device experienced an increase in altitude of between 1 ft and 2 ft during the first time period. In some such implementations, the motion data and the data representative of altitude may be correlated with the first arm movement profile for one instance. In some other or additional implementations the number of instances may be selected from the group consisting of i) 1 to 5 instances, ii) 5 to 8 instances, iii) 8 to 10 instances, iv) 10 to 12 instances, v) 12 to 15 instances, and vi) 15 to 20 instances. In some such implementations, the range of the number of instances (i) through (vi) may be selected based on data indicating whether a wearer of the wearable biometric tracking device is pursuing resistance-training for purposes selected from the group consisting of I) emphasizing strength, II) emphasizing strength and muscle bulk substantially equally, III) emphasizing muscle bulk with some emphasis on strength, IV) emphasizing muscle bulk with some emphasis on endurance, V) emphasizing endurance with some emphasis on muscle, and VI) emphasizing mostly endurance, respectively.

In some other or additional implementations of the wearable biometric tracking device, the first arm movement profile may be associated with a resistance-training deadlift-type activity and the motion data and the data representative of altitude correlate with the first arm movement profile when the motion data and the data representative of altitude include one instance or two or more substantially consecutive instances in which the data representative of altitude indicates that the wearable biometric tracking device experienced an increase in altitude of between 1.5 ft and 2 ft during a first time period, the data representative of altitude indicates that the wearable biometric tracking device experienced a decrease in altitude of between 1.5 ft and 2 ft during a second time period, and the motion data indicates that a forearm upon which the wearable biometric tracking device is worn maintained a substantially vertical and downward orientation during substantially all of the first time period and the second time period.

In some other or additional implementations of the wearable biometric tracking device, the first arm movement profile may be associated with a resistance-training, squats, or bench-press-type activity and the motion data and the data representative of altitude correlate with the first arm movement profile when the motion data and the data representative of altitude include one instance or two or more substantially consecutive instances in which the data representative of altitude indicates that the wearable biometric tracking device experienced an increase in altitude of between 0.5 ft. and 2 ft. during a first time period, the data representative of altitude indicates that the wearable biometric tracking device experienced a decrease in altitude of between 0.5 ft. and 2 ft. during a second time period, and the motion data indicates that a forearm upon which the wearable biometric tracking device is worn maintained a substantially vertical and upward orientation during substantially all of the first time period and the second time period.

In some other or additional implementations of the wearable biometric tracking device, the first arm movement profile may be associated with a resistance-training front- or lateral-raise-type activity and the motion data and the data representative of altitude may correlate with the first arm movement profile when the motion data and the data representative of altitude include one instance or two or more substantially consecutive instances in which the data representative of altitude indicates that the wearable biometric tracking device experienced an increase in altitude of between 1 ft. and 2 ft. during a first time period, the data representative of altitude indicates that the wearable biometric tracking device experienced a decrease in altitude of between 1 ft. and 2 ft. during a second time period, the motion data indicates that a forearm upon which the wearable biometric tracking device is worn transitions from a substantially vertical and downward orientation at the start of the first time period to a substantially horizontal orientation at the end of the first time period, and the motion data indicates that the forearm upon which the wearable biometric tracking device is worn transitions from a substantially horizontal orientation at the start of the second time period to a substantially vertical and downward orientation at the end of the second time period.

In some other or additional implementations of the wearable biometric tracking device, first arm movement profile may be associated with a resistance-training good-morning-sir-type activity and the motion data and the data representative of altitude may correlate with the first arm movement profile when the motion data and the data representative of altitude include one instance or two or more substantially consecutive instances in which the data representative of altitude indicates that the wearable biometric tracking device experienced an increase in altitude of between 1.5 ft. and 2 ft. during a first time period, the data representative of altitude indicates that the wearable biometric tracking device experienced a decrease in altitude of between 1.5 ft. and 2 ft. during a second time period, the motion data indicates that a forearm upon which the wearable biometric tracking device is worn transitions from a substantially horizontal orientation at the start of the first time period to a substantially vertical and upward orientation at the end of the first time period, and the motion data indicates that the forearm upon which the wearable biometric tracking device is worn transitions from a substantially vertical and upward orientation at the start of the second time period to a substantially horizontal orientation at the end of the second time period.

In some other or additional implementations of the wearable biometric tracking device, the first arm movement profile may be associated with an elliptical machine activity and the motion data and the data representative of altitude may correlate with the first arm movement profile when the data representative of altitude exhibits cyclic behavior during a first time period with small altitude changes during each cycle commensurate with altitude changes experienced by handles of an elliptical machine during normal use, the motion data exhibits cyclic behavior that is substantially of the same frequency as the cyclic behavior of the data representative of altitude during the first time period, and the motion data includes acceleration data and the acceleration data indicates acceleration magnitudes during the first time period that are less than acceleration magnitudes used by the control logic in other circumstances to determine if a step counter should be incremented due to acceleration data that indicates that a person wearing the wearable biometric tracking device is engaged in normal walking or running activity in which the person's feet leave the ground.

In some other or additional implementations of the wearable biometric tracking device, a display may be communicatively connected with the control logic and the control logic may be further configured such that: I) the first arm movement profile may be associated with a watch-viewing activity, II) the motion data and the data representative of altitude may correlate with the first arm movement profile when the data representative of altitude indicates that the wearable biometric tracking device experienced an increase in altitude of approximately 1 ft. during a first time period, and the motion data indicates that a forearm upon which the wearable biometric tracking device is worn transitions from a substantially vertical and downwards orientation to a substantially horizontal orientation during the first time period, and III) the control logic may be further configured to cause the display to present clock-related data responsive to a determination that the motion data and the data representative of altitude correlate with the watch-viewing activity first movement profile. In some such implementations, the motion data and the data representative of altitude may correlate with the first arm movement profile when the motion data additionally indicates that the forearm upon which the wearable biometric tracking device is worn remains in the substantially horizontal orientation for a second time period immediately following the first time period, the second time period having a non-zero duration.

In some other or additional implementations of the wearable biometric tracking device, the plurality of arm movement profiles may include an arm movement profile approximating the user resting and the control logic may be further configured to track a duration where the first arm movement profile is substantially similar to the user resting arm movement profile, and determine that the duration where the first arm movement profile is substantially similar to the user resting arm movement profile is greater than a rest duration threshold.

In some implementations, a wearable biometric tracking device may be provided. The wearable biometric tracking device may include a pressure sensor configured to detect altitude of the wearable biometric tracking device and to output corresponding data representative of altitude, and a motion sensor, the motion sensor configured to detect motion of the wearable biometric tracking device and to output corresponding motion data, and control logic. The biometric monitoring device, the pressure sensor, and the control logic are communicatively connected. The control logic may be configured to determine when the data representative of altitude indicates that the wearable biometric tracking device has not experienced an altitude rate-of-change exceeding a first altitude rate-of-change threshold during a first time period, and place the wearable biometric tracking device into a lower power-consumption state during a second time period following the first time period responsive to, at least, determining that the data representative of altitude indicates that the wearable biometric tracking device has not experienced an altitude rate-of-change exceeding the first altitude rate-of-change threshold during the first time period.

In some such implementations of the wearable biometric tracking device, the control logic may be further configured to determine when the motion data indicates that the wearable biometric tracking device experienced an impact event immediately prior to the first time period, and may place the wearable biometric tracking device into a lower power-consumption state by placing the wearable biometric tracking device into the lower power-consumption state responsive to determining that the motion data indicates that the wearable biometric tracking device experienced an impact event immediately prior to the first time period in addition to determining in that the data representative of altitude indicates that the wearable biometric tracking device has not experienced an altitude rate-of-change exceeding the first altitude rate-of-change threshold during the first time period.

In some other or additional implementations of the wearable biometric tracking device, the control logic may be further configured to determine when the data representative of altitude indicates that the wearable biometric tracking device experienced an altitude rate-of-change exceeding a second altitude rate-of-change threshold during the second time period, and cause the wearable biometric tracking device to exit the lower power-consumption state responsive to determining in that the data representative of altitude indicates that the wearable biometric tracking device experienced an altitude rate-of-change exceeding the second altitude rate-of-change threshold during the second time period. In some such implementations, the control logic may be further configured to cause, responsive to determining that the data representative of altitude indicates that the wearable biometric tracking device experienced an altitude rate-of-change exceeding the second altitude rate-of-change threshold during the second time period, a display of the wearable biometric tracking device to transition to an on state from an off or standby state and to display a message.

In some implementations, a wearable biometric tracking device may be provided. The wearable biometric tracking device may include one or more biometric sensors, an altitude sensor, the altitude sensor configured to detect altitude of the wearable biometric tracking device and to output altitude sensor data, and control logic. The one or more biometric sensors, the altitude sensor, and the control logic are communicatively coupled and the control logic is configured to receive the altitude sensor data, analyze the altitude sensor data to determine if the altitude sensor data is indicative of flight in an airplane, and place, responsive at least in part to a determination in (b) that the altitude sensor data is indicative of flight in an airplane, the wearable biometric tracking device into a mode associated with air travel.

In some such implementations of the wearable biometric tracking device, the altitude sensor data may be indicative of flight in an airplane when the altitude sensor data indicates a rate of altitude change that exceeds a rate of altitude change threshold. In some such implementations the rate of altitude change threshold may be above 500 feet per minute.

In some other or additional implementations of the wearable biometric tracking device the altitude sensor data may be indicative of flight in an airplane when the altitude sensor data indicates a total altitude increase over an altitude increase time period for the wearable biometric tracking device, and the total altitude increase over the altitude increase time period exceeds a total altitude increase threshold. In some such implementations, the total altitude increase threshold may be at least 1500 feet in altitude and the altitude increase time period may be 180 seconds or less.

In some other or additional implementations of the wearable biometric tracking device, the altitude sensor data may be indicative of flight in an airplane when the altitude sensor data indicates a rate of altitude change that exceeds an altitude rate of change threshold throughout an altitude change time period, and the rate of altitude change threshold is at least 500 feet per minute. In some such implementations, the altitude change time period may be a time period of at least 60 seconds. In some implementations, a biometric monitoring device with an altimeter may be configured to detect rates of altitude change or altitude changes that are indicative of airplane ascent or descent, and may, prior to automatically engaging or disengaging an airplane mode of the biometric monitoring device, instead prompt the wearer of the device to confirm whether or not the wearer is in an airplane that is ascending or that has just landed prior to engaging or disengaging the airplane mode. If the user confirms the behavior of the airplane, the biometric monitoring device may proceed to engage or disengage the airplane mode, as appropriate.

In some other or additional implementations of the wearable biometric tracking device, the mode associated with air travel may be a mode in which the wearable biometric tracking device is placed in a low power state.

In some other or additional implementations of the wearable biometric tracking device, the wearable biometric tracking device may further include wireless communication circuitry, the communication circuitry communicatively coupled to the control logic and configured to wirelessly communicate with associated devices, wherein the mode associated with air travel may be a mode in which the communication circuitry is placed in a standby or off state.

In some other or additional implementations of the wearable biometric tracking device, the control logic may be further configured to further analyze the altitude sensor data to determine if the altitude sensor data is indicative of landing of the airplane, and cause, responsive at least in part to a determination in that the altitude sensor data is indicative of landing of the airplane, the wearable biometric tracking device to exit the mode associated with air travel. In some such implementations, the altitude sensor data may be indicative of the landing of the airplane when the altitude sensor data indicates a total altitude decrease for the wearable biometric tracking device that exceeds a total altitude decrease threshold over an altitude decrease time period, and the altitude sensor data indicates a rate of altitude change of less than 50 feet per minute for a period of 300 seconds after the altitude sensor data indicates a total altitude decrease for the wearable biometric tracking device that exceeds a total altitude decrease threshold over an altitude decrease time period. In some other or additional implementations, the altitude decrease time period may be 180 seconds or less. In some other or additional implementations, the control logic may be further configured to receive biometric data from the one or more biometric sensors, analyze the biometric data to determine if the biometric data indicates that a wearer of the wearable biometric tracking device has taken at least a predetermined number of steps, and determine that the altitude sensor data is indicative of the landing of the airplane when the control logic further detects that a wearer of the wearable biometric tracking device has taken at least a predetermined number of steps after the altitude sensor data indicates a total altitude decrease for the wearable biometric tracking device that exceeds a total altitude decrease threshold over an altitude decrease time period. In some other or additional implementations, the total altitude decrease threshold may be an altitude decrease of at least 1500 feet.

In some other or additional implementations of the wearable biometric tracking device, the control logic may be further configured to monitor biometric data from the one or more biometric sensors and to determine when the biometric data indicates that a wearer of the biometric monitoring device has not moved more than a threshold movement amount relative to an aircraft reference frame within a first time period after analyzing the altitude sensor data to determine if the altitude sensor data is indicative of flight in an airplane. In some such implementations, the wearable biometric tracking device may further include a user interface. The control logic may be further configured to cause a notification to be provided to the wearer via the user interface responsive, at least in part, to the determination that the wearer of the biometric monitoring device has not moved more than the threshold movement amount relative to the aircraft reference frame within the first time period. In some such implementations, the wearable biometric tracking device further includes a light sensor configured to measure an amount of ambient light around the biometric tracking device and to output detected light data. The control logic may be further configured to analyze the detected light data to determine if the detected light data is indicative of light levels normally associated with a sleeping environment in an airplane, and cause the notification to be provided to the wearer via the user interface responsive to the determination that the wearer of the biometric monitoring device has not moved more than the threshold movement amount relative to the aircraft reference frame within the first time period and responsive to a determination that the detected light data is not indicative of the light levels normally associated with the sleeping environment in an airplane. In some other or additional implementations, the control logic may be further configured to place the wearable biometric tracking device into a sleep-tracking mode responsive to a stimulus selected from the group consisting of: (i) a deliberate request provided by the wearer of the wearable biometric tracking device and (ii) analysis of the biometric data indicating that the wearer of the wearable biometric tracking device is likely asleep, and cause the notification to be provided to the wearer via the user interface when the wearable biometric tracking device is not in the sleep-tracking mode and responsive to the determination that the wearer of the biometric monitoring device has not moved more than the threshold movement amount relative to the aircraft reference frame within the first time period. In some other or additional implementations, the user interface may include a digital display and the notification may be a message displayed on the digital display. In some other or additional implementations, the user interface may include an audio device and the notification may be an audio notification. In some other or additional implementations, the user interface may include a haptic feedback mechanism and the notification may be a tactile notification.

In some other or additional implementations of the wearable biometric tracking device, the wearable biometric tracking device may further include an audio sensor configured to output audio data such that the control logic may be further configured to receive the audio data, and analyze the audio data to determine whether the audio data indicates background noise consistent with engine noise of an aircraft, wherein the control logic is further configured to place the wearable biometric monitoring device into the mode associated with air travel responsive, at least in part, to the determination in that the altitude sensor data is indicative of flight of the airplane and to the determination that the audio data indicates background noise consistent with the engine noise of the aircraft.

In some other or additional implementations of the wearable biometric tracking device, the wearable biometric tracking device may further include an acceleration sensor configured to detect acceleration and output acceleration data. The control logic may be further configured to receive the acceleration data, and analyze the acceleration data to determine whether the acceleration data indicates vibration consistent with vibration from an aircraft engine, wherein the control logic is further configured to place the wearable biometric monitoring device into the mode associated with air travel responsive, at least in part, to the determination in that the altitude data is indicative of flight of the airplane and to the determination that the acceleration data indicates vibration consistent with the vibration of the aircraft engine.

In some other or additional implementations of the wearable biometric tracking device, the wearable biometric tracking device may further include a communications interface configured to receive communications data, wherein the control logic may be further configured to receive the communications data, and analyze the communications data to determine whether the communications data indicates communications consistent with communications from an airplane communications device, wherein the control logic may be further configured to place the wearable biometric monitoring device into the mode associated with air travel responsive, at least in part, to the determination in that the altitude sensor data is indicative of flight of the airplane and also to the determination that the communications data indicates communications consistent with the communications from the airplane communications device.

In some other or additional implementations of the wearable biometric tracking device, the control logic may be further configured to provide a stair-climbing mode that tracks a number of flights of stairs climbed by a wearer of the wearable biometric tracking device, and turn off the stair-climbing mode responsive to placing the wearable biometric tracking device into a mode associated with air travel.

In some other or additional implementations of the wearable biometric tracking device, the wearable biometric tracking device may further include a wireless communications interface, the control logic may be further configured to receive a first input signal via the wireless communications interface, and cause, responsive to the receipt of the first input signal, the wearable biometric tracking device to enter into the mode associated with air travel. In some such implementations, the control logic may be further configured to cause the wearable biometric tracking device to exit the mode associated with air travel upon receipt of a second input signal indicative of activity. The second input signal may be selected from the group consisting of an associated external device powering on, tapping the wearable biometric tracking device, selection of a menu option through a user interface of the wearable biometric tracking device, and pressing of a button of the wearable biometric monitoring device.

In some implementations, a system may be provided. The system may include a wearable biometric tracking device and a mobile communications device separate from the wearable biometric tracking device. The wearable biometric tracking device may include one or more biometric sensors, a biometric tracking device communications interface, and biometric tracking device control logic such that the one or more biometric sensors, the biometric tracking device communications interface, and the biometric tracking device control logic are communicatively coupled and the biometric tracking device control logic is configured to receive a signal associated with an airplane mode, and responsive to receiving the signal associated with the airplane mode, place the wearable biometric tracking device into a mode associated with air travel. The mobile communications device may include a mobile communications device communications interface, and mobile communications device control logic such that the mobile communications device communications interface and the mobile communications device control logic are communicatively coupled and the mobile communications device control logic is configured to transmit the signal associated with the airplane mode via the mobile communications device communications interface.

In some implementations, a wearable biometric tracking device may be provided. The wearable biometric tracking device may include one or more biometric sensors, a pressure sensor, the pressure sensor configured to detect ambient atmospheric air pressure around the wearable biometric tracking device and to output data representative of altitude, wherein the data representative of altitude is based, at least in part, on air pressure measured by the pressure sensor, a location-determining device configured to determine location based on data received from one or more devices remote from the wearable biometric tracking device and to output corresponding location data, and control logic. The one or more biometric sensors, the pressure sensor, the location-determining device, and the control logic may be communicatively connected and the control logic may be configured to receive the location data from the location-determining device, analyze the location data to determine a first location of the wearable biometric tracking device, determine a first topographic altitude from historical topographic data, wherein the first topographic altitude is an altitude correlated with the first location, receive the data representative of altitude from the pressure sensor, analyze the data representative of altitude to determine if the pressure sensor should be recalibrated based on a first difference between the first topographic altitude and an altitude (i) calculated from the data representative of altitude and (ii) associated with the first location, and recalibrate the pressure sensor based on the first difference when the control logic determines in that the pressure sensor should be recalibrated.

In some such implementations of the wearable biometric tracking device, the pressure sensor may be a barometric altimeter or a barometric pressure sensor.

In some other or additional implementations of the wearable biometric tracking device, the location-determining device may include one or more systems selected from the group consisting of satellite-based global positioning systems, Wi-Fi-based positioning systems, cell-tower-location-based systems, near-field-communications tag look-up systems, radio-frequency identification tag look-up systems, camera-image-based look-up systems, and systems that are configured to interrogate a nearby, external paired device for location information.

In some other or additional implementations of the wearable biometric tracking device, the control logic may be further configured to, responsive to a determination that the pressure sensor should be recalibrated, recalibrate the pressure sensor so as to produce corrected data representative of altitude based on the first difference. In some such implementations, the control logic may be further configured to at least repeat, one or more times, receiving the location data from the location-determining device, analyzing the location data to determine a first location of the wearable biometric tracking device, determining a first topographic altitude from historical topographic data, wherein the first topographic altitude is an altitude correlated with the first location, receive the data representative of altitude from the pressure sensor, and analyzing the data representative of altitude to determine if the pressure sensor should be recalibrated based on a first difference between the first topographic altitude and an altitude (i) calculated from the data representative of altitude and (ii) associated with the first location. In some such implementations, each repetition may be separated from the immediately preceding performance by a set time interval. In some such implementations, the set time interval may be between 1 second to 24 hours.

In some other or additional implementations of the wearable biometric tracking device, the historical topographic data may be stored within the wearable biometric tracking device.

In some other or additional implementations of the wearable biometric tracking device, the wearable biometric tracking device may further include wireless communication circuitry communicatively coupled with the control logic. The historical topographic data may be obtained from a secondary source remote from the biometric tracking device via the wireless communication circuitry.

In some other or additional implementations of the wearable biometric tracking device, the control logic may be further configured to analyze the first location to determine an update time period and repeat, according to the update time period at least receiving the location data from the location-determining device, analyzing the location data to determine a first location of the wearable biometric tracking device, determining a first topographic altitude from historical topographic data, wherein the first topographic altitude is an altitude correlated with the first location, receive the data representative of altitude from the pressure sensor, and analyzing the data representative of altitude to determine if the pressure sensor should be recalibrated based on a first difference between the first topographic altitude and an altitude (i) calculated from the data representative of altitude and (ii) associated with the first location. In some such implementations, analyze the first location to determine an update time period may include determining that the historical topographic data indicates a second location with a second topographic altitude, determining that the first location and the second location are separated by an first distance, determining that the second location is the closest location to the first location where the absolute difference between the first topographic altitude and the second topographic altitude is greater than a first topographic altitude difference threshold, and determining the update time period based, at least in part, on the first distance. In some other or additional implementations, analyzing the first location to determine an update time period may include determining that the first location is within a first threshold distance of a location of a building according to the historical topographic data. In some such implementations, the control logic may be further configured to cease recalibrating the pressure sensor while the first location is within the first threshold distance of the location of the building.

In some other or additional implementations of the biometric tracking device, the memory may further store program instructions for controlling the one or more processors to detect when the wearable biometric tracking device has traveled to a second location at least a first distance away from the first location and repeat, responsive to the first distance exceeding a translation distance threshold, at least receiving the location data from the location-determining device, analyzing the location data to determine a first location of the wearable biometric tracking device, determining a first topographic altitude from historical topographic data, wherein the first topographic altitude is an altitude correlated with the first location, receive the data representative of altitude from the pressure sensor, and analyzing the data representative of altitude to determine if the pressure sensor should be recalibrated based on a first difference between the first topographic altitude and an altitude (i) calculated from the data representative of altitude and (ii) associated with the first location. In some such implementations, the translation distance threshold may be a distance between 50 feet and 200 feet. In some other or additional implementations, the translation distance threshold may be a distance between 500 feet and 1000 feet.

In some other or additional implementations of the biometric tracking device, the memory may further store program instructions for controlling the one or more processors to detect when the wearable biometric tracking device has traveled at least a first distance, and repeat, responsive to the first distance exceeding a translation distance threshold, at least receiving the location data from the location-determining device, analyzing the location data to determine a first location of the wearable biometric tracking device, determining a first topographic altitude from historical topographic data, wherein the first topographic altitude is an altitude correlated with the first location, receive the data representative of altitude from the pressure sensor, and analyzing the data representative of altitude to determine if the pressure sensor should be recalibrated based on a first difference between the first topographic altitude and an altitude (i) calculated from the data representative of altitude and (ii) associated with the first location.

In some other or additional implementations of the biometric tracking device, the control logic may be further configured to analyze the data representative of altitude over a period time to determine when there is a change in altitude beyond a first threshold altitude change amount for the wearable biometric tracking device over the period of time and while the location data indicates that the wearable biometric tracking device has not traveled more than a first threshold distance away from the first location, and perform, responsive to determining that there is a change in altitude beyond a first threshold altitude change amount while the location data indicates that the wearable biometric tracking device has not traveled more than a first threshold distance, at least receiving the location data from the location-determining device, analyzing the location data to determine a first location of the wearable biometric tracking device, determining a first topographic altitude from historical topographic data, wherein the first topographic altitude is an altitude correlated with the first location, receive the data representative of altitude from the pressure sensor, and analyzing the data representative of altitude to determine if the pressure sensor should be recalibrated based on a first difference between the first topographic altitude and an altitude (i) calculated from the data representative of altitude and (ii) associated with the first location.

In some other or additional implementations of the biometric tracking device, the biometric tracking device may further include an image acquisition interface. The control logic may be further configured to obtain a first image associated with the data representative of altitude, cause the first image to be analyzed to determine a first image-based altitude, analyze the data representative of altitude to determine if the pressure sensor should be recalibrated based on a second difference between the first image-based altitude and the altitude (i) calculated from the data representative of altitude and (ii) associated with the first location, and recalibrate the pressure sensor based on the second difference when the control logic determines in (i) that the pressure sensor should be recalibrated. In some such implementations, the control logic may be further configured to cause the first image to be analyzed by causing the first image to be compared against a plurality of reference images, each reference image associated with an image-based altitude, and receiving a determination that a first reference image with the first image-based altitude meets one or more matching criteria with respect to the first image. In some other or additional implementations, the control logic may be further configured to cause the first image to be analyzed by performing optical-character-recognition on the first image, extracting first text-based information from the first image, and determining the first image-based altitude from the first text-based information. In some such implementations, the control logic may be further configured to determine the first image-based altitude from the first text-based information by extracting the first image-based altitude from the first text-based information. In some other or additional implementations, the control logic may be further configured to determine the first image-based altitude from the first text-based information by causing the first text-based information to be compared against a plurality of textual records in a database, each textual record associated with a text-based altitude, receiving a determination that a first textual record meets one or more matching criteria with respect to the first text-based information, and using the text-based altitude for the first textual record as the first image-based altitude.

BRIEF DESCRIPTION OF DRAWINGS

The various implementations disclosed herein are illustrated by way of example, and not by way of limitation, in the figures of the accompanying drawings, in which like reference numerals may refer to similar elements.

FIG. 2A illustrates an example portable monitoring device which may be secured to the user through the use of a band.

FIG. 3A provides a cross sectional view of a sensor protrusion of an example portable monitoring device.

FIG. 3B depicts a cross sectional view of a sensor protrusion of an example portable monitoring device; this protrusion is similar to that presented in FIG. 3A with the exception that the light sources and photodetector are placed on a flat and/or rigid PCB.

DETAILED DESCRIPTION

Figure 1:
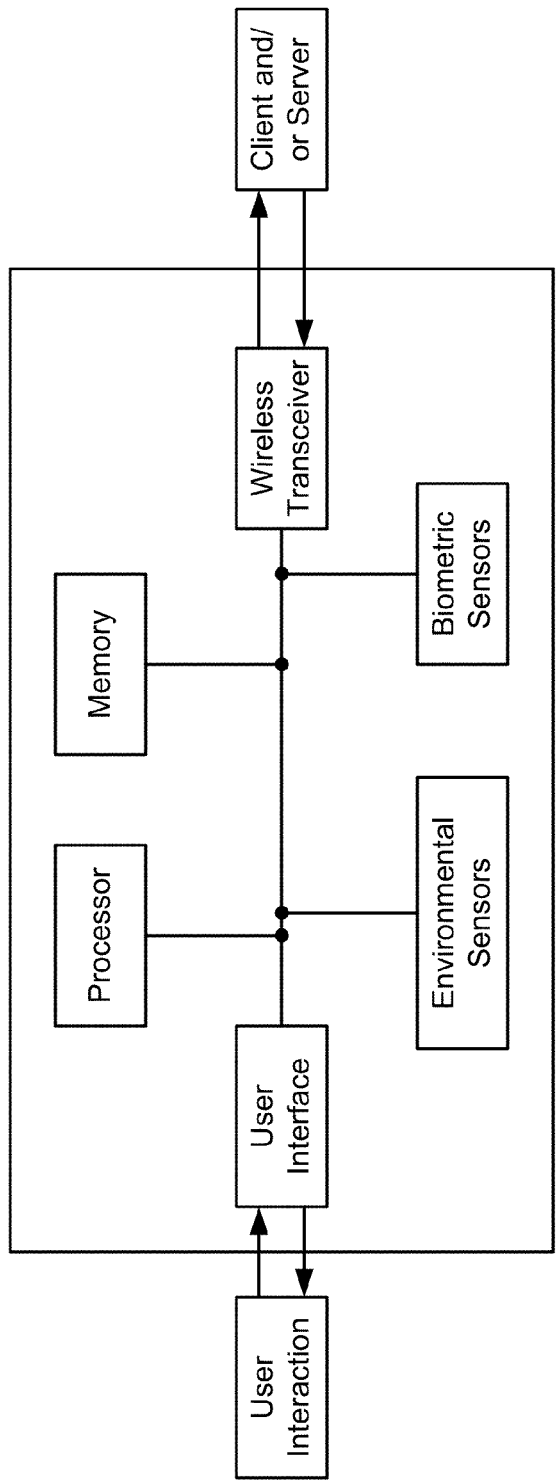
FIG. 1 illustrates an example portable monitoring device which enables user interaction via a user interface.

This disclosure is directed at biometric monitoring devices (which may also be referred to herein and in any references incorporated by reference as "biometric tracking devices," "personal health monitoring devices," "portable monitoring devices," "portable biometric monitoring devices," "biometric monitoring devices," or the like), which may be generally described as wearable devices, typically of a small size, that are designed to be worn relatively continuously by a person. When worn, such biometric monitoring devices gather data regarding activities performed by the wearer or the wearer's physiological state. Such data may include data representative of the ambient environment around the wearer or the wearer's interaction with the environment, e.g., motion data regarding the wearer's movements, ambient light, ambient noise, air quality, etc., as well as physiological data obtained by measuring various physiological characteristics of the wearer, e.g., heart rate, perspiration levels, etc.

Biometric monitoring devices, as mentioned above, are typically small in size so as to be unobtrusive for the wearer. Fitbit offers several varieties of biometric monitoring devices that are all quite small and very light, e.g., the Fitbit Flex is a wristband with an insertable biometric monitoring device that is about 0.5" wide by 1.3" long by 0.25" thick. Biometric monitoring devices are typically designed to be able to be worn without discomfort for long periods of time and to not interfere with normal daily activity.

In some cases, a biometric monitoring device may leverage other devices external to the biometric monitoring device, e.g., an external heart rate monitor in the form of an EKG sensor on a chest strap may be used to obtain heart rate data or a GPS receiver in a smartphone may be used to obtain position data. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

In general, the concepts discussed herein may be implemented in stand-alone biometric monitoring devices as well as, when appropriate, biometric monitoring devices that leverage external devices.

It is to be understood that while the concepts and discussion included herein are presented in the context of biometric monitoring devices, these concepts may also be applied in other contexts as well if the appropriate hardware is available. For example, many modern smartphones include motion sensors, such as accelerometers, that are normally included in biometric monitoring devices, and the concepts discussed herein may, if appropriate hardware is available in a device, be implemented in that device. In effect, this may be viewed as turning the smartphone into some form of biometric monitoring device (although one that is larger than a typical biometric monitoring device and that may not be worn in the same manner). Such implementations are also to be understood to be within the scope of this disclosure.

The functionality discussed herein may be provided using a number of different approaches. For example, in some implementations a processor may be controlled by computer-executable instructions stored in memory so as to provide functionality such as is described herein. In other implementations, such functionality may be provided in the form of an electrical circuit. In yet other implementations, such functionality may be provided by a processor or processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Standalone biometric monitoring devices may be provided in a number of form factors and may be designed to be worn in a variety of ways. In some implementations, a biometric monitoring device may be designed to be insertable into a wearable case or into multiple, different wearable cases, e.g., a wristband case, a belt-clip case, a pendant case, a case configured to be attached to a piece of exercise equipment such as a bicycle, etc. Such implementations are described in more detail in, for example, U.S. patent application Ser. No. 14/029,764, filed Sep. 17, 2013, which is hereby incorporated by reference for such purpose. In other implementations, a biometric monitoring device may be designed to be worn in only one manner, e.g., a biometric monitoring device that is integrated into a wristband in a non-removable manner may be intended to be worn only on a person's wrist (or perhaps ankle).

Figure 2B:
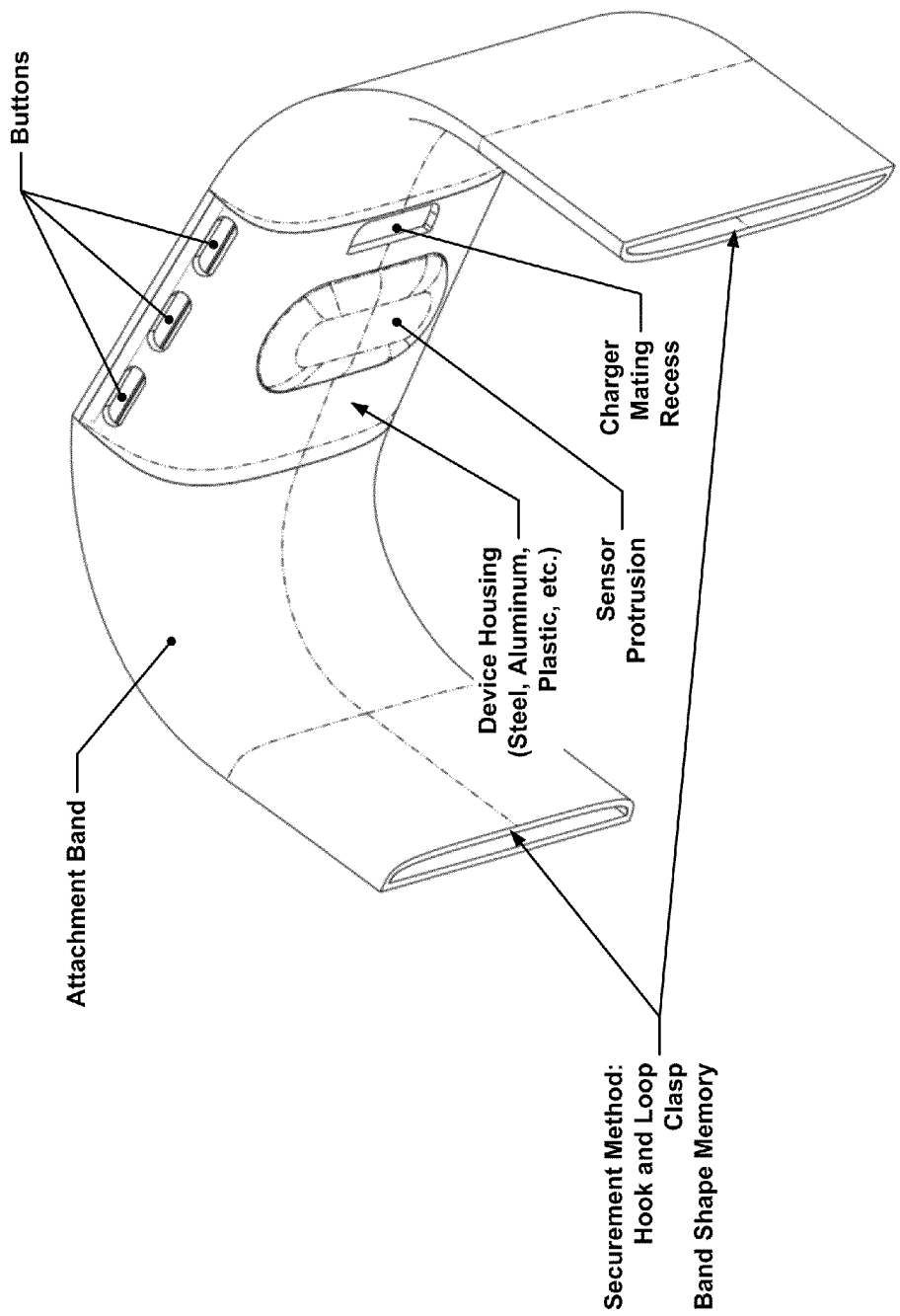
FIG. 2B provides a view of the example portable monitoring device of FIG. 2A which shows the skin-facing portion of the device.
Figure 2C:
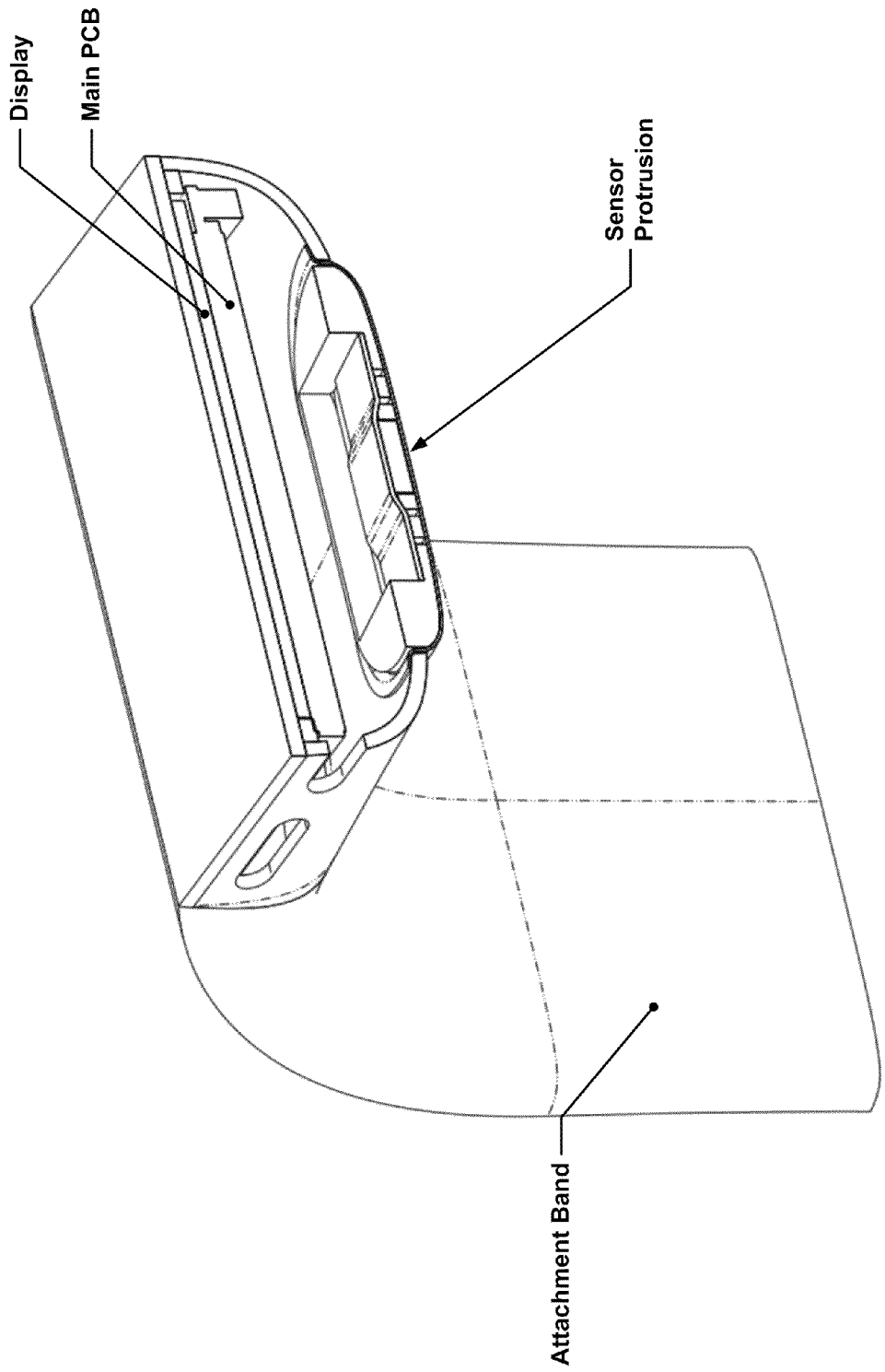
FIG. 2C provides a cross-sectional view of the portable monitoring device of FIG. 2A.

Portable biometric monitoring devices according to embodiments and implementations described herein may have shapes and sizes adapted for coupling to (e.g., secured to, worn, borne by, etc.) the body or clothing of a user. An example of a portable biometric monitoring devices is shown in FIG. 1; the example portable monitoring device may have a user interface, processor, biometric sensor(s), memory, environmental sensor(s) and/or a wireless transceiver which may communicate with a client and/or server. An example of a wrist-worn portable biometric monitoring device is shown in FIGS. 2A through 2C. This device may have a display, button(s), electronics package, and/or an attachment band. The attachment band may be secured to the user through the use of hooks and loops (e.g., Velcro), a clasp, and/or a band having memory of its shape, e.g., through the use of a spring metal band. In FIG. 2B, a sensor protrusion and recess for mating a charger and/or data transmission cable can be seen. In FIG. 2C, a cross-section through the electronics package is shown. Of note are the sensor protrusion, main PCB board, and display.

Portable biometric monitoring devices may collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the biometric monitoring device may calculate and store the user's step count using one or more biometric sensors. The biometric monitoring device may then transmit data representative of the user's step count to an account on a web service (e.g., www.fitbit.com), computer, mobile phone, or health station where the data may be stored, processed, and visualized by the user. Indeed, the biometric monitoring device may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS, GLONASS, or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics. The biometric monitoring device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the biometric monitoring device or the system collating the data streams from the biometric monitoring device may calculate metrics derived from such data. For example, the device or system may calculate the user's stress and/or relaxation levels through a combination of heart rate variability, skin conduction, noise pollution, and sleep quality. In another example, the device or system may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. patent application Ser. No. 13/156,304, titled "Portable Biometric Monitoring Devices and Methods of Operating Same" filed Jun. 8, 2011 and U.S. Patent Application 61/680,230, titled "Fitbit Tracker" filed Aug. 6, 2012, which are both hereby incorporated herein by reference in their entireties.

Physiological Sensors

Biometric monitoring devices as discussed herein may use one, some or all of the following sensors to acquire physiological data, including, but not limited to, the physiological data outlined in the table below. All combinations and permutations of physiological sensors and/or physiological data are intended to fall within the scope of this disclosure. Biometric monitoring devices may include but are not limited to types of one, some, or all of the sensors specified below for the acquisition of corresponding physiological data; indeed, other type(s) of sensors may also or alternatively be employed to acquire the corresponding physiological data, and such other types of sensors are also intended to fall within the scope of the present disclosure. Additionally, the biometric monitoring device may derive the physiological data from the corresponding sensor output data, but is not limited to the number or types of physiological data that it could derive from said sensor.

| Physiological Sensors | Physiological data acquired |
|---|---|
| Optical Reflectometer | Heart Rate, Heart Rate Variability |
| Example Sensors: | SpO₂ (Saturation of Peripheral Oxygen) |
| Light emitter and receiver | Respiration |
| Multi or single LED and photo diode arrangement | Stress |
| | Blood pressure |
| Wavelength tuned for specific physiological signals | Arterial Stiffness |
| | Blood glucose levels |
| Synchronous detection/amplitude modulation | Blood volume |
| | Heart rate recovery |
| | Cardiac health |
| Motion Detector | Activity level detection |
| Example Sensors: | Sitting/standing detection |
| Inertial sensors, Gyroscopic sensors, and/or Accelerometers GPS | Fall detection |
| Skin Temperature | Stress |
| EMG (eletromyographic sensor) | Muscle tension |
| EKG or ECG (electrocardiographic sensor) | Heart Rate |
| | Heart Rate Variability |
| Example Sensors: | Heart Rate Recovery |
| Single-lead ECG or EKG | Stress |
| Dual-lead ECG or EKG | Cardiac health |
| Magnetometer | Activity level based on rotation |
| Laser Doppler | |
| Power Meter | |
| Ultrasonic Sensor | Blood flow |
| Audio Sensor | Heart Rate |
| | Heart Rate Variability |
| | Heart Rate Recovery |
| | Laugh detection |
| | Respiration |
| | Respiration type, e.g., snoring, breathing, breathing problems (such as sleep apnea) |
| | User's voice |
| Strain gauge | Heart Rate |
| Example: | Heart Rate Variability |
| In a wrist band | Stress |
| Wet/Immersion Sensor | Stress |
| Example Sensor: | Swimming detection |
| Galvanic skin response | Shower detection |

In one example embodiment, the biometric monitoring device may include an optical sensor to detect, sense, sample and/or generate data that may be used to determine information representative of, for example, stress (or level thereof), blood pressure, and/or heart rate of a user. (See, for example, FIGS. 2A through 3C and 11A through KKG). In such embodiments, the biometric monitoring device may include an optical sensor having one or more light sources (LED, laser, etc.) to emit or output light into the user's body, as well as light detectors (photodiodes, phototransistors, etc.) to sample, measure and/or detect a response or reflection of such light from the user's body and provide data used to determine data that is representative of stress (or level thereof), blood pressure, and/or heart rate of a user (e.g., such as by using photoplethysmography).

In one example embodiment, a user's heart rate measurement may be triggered by criteria determined by one or more sensors (or processing circuitry connected to them). For instance, when data from a motion sensor(s) indicates a period of stillness or of little motion, the biometric monitoring device may trigger, acquire, and/or obtain a heart rate measurement or data. (See, for example, FIGS. 9, 12A, and 12B).

Figure 12A:
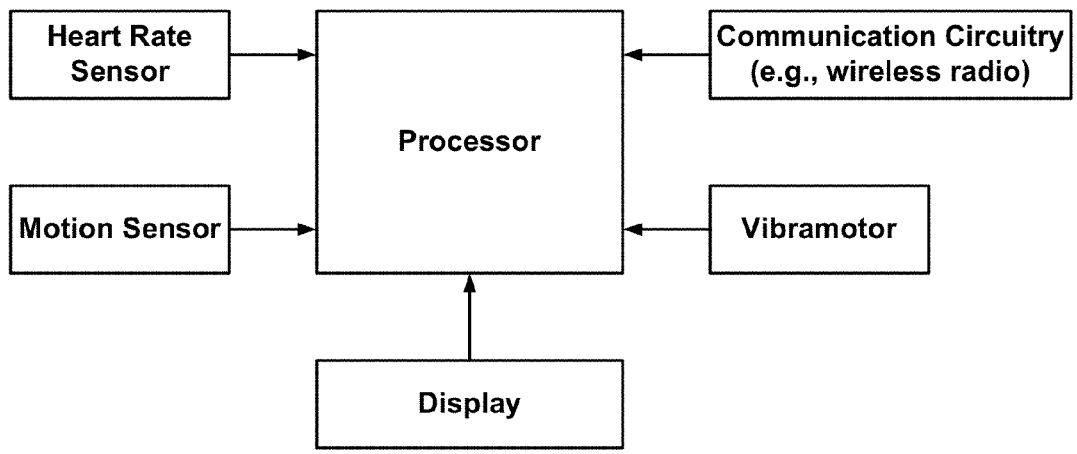
FIG. 12A illustrates an example of a portable biometric monitoring device having a heart rate or PPG sensor, motion sensor, display, vibromotor, and communication circuitry which is connected to a processor.

FIG. 12A illustrates an example of a portable biometric monitoring device having a heart rate or PPG sensor, motion sensor, display, vibromotor, and communication circuitry which is connected to a processor.

Figure 12B:
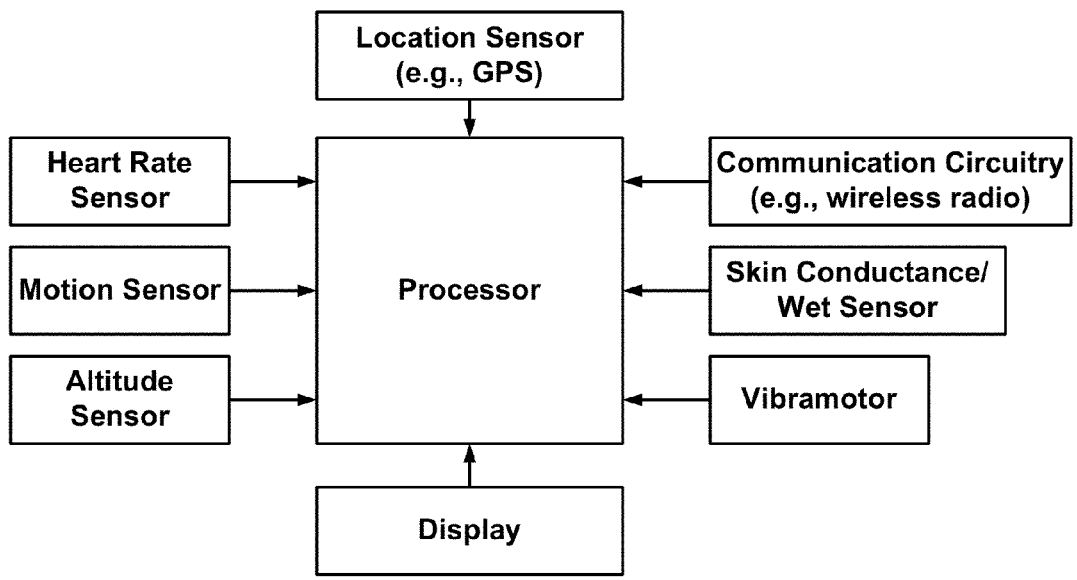
FIG. 12B illustrates an example of a portable biometric monitoring device having a heart rate or PPG sensor, motion sensor, display, vibromotor, location sensor, altitude sensor, skin conductance/wet sensor and communication circuitry which is connected to a processor.

FIG. 12B illustrates an example of a portable biometric monitoring device having a heart rate or PPG sensor, motion sensor, display, vibromotor, location sensor, altitude sensor, skin conductance/wet sensor and communication circuitry which is connected to a processor.

In one embodiment, when the motion sensor(s) indicate user activity or motion (for example, motion that is not suitable or optimum to trigger, acquire, and/or obtain desired heart rate measurement or data (for example, data used to determine a user's resting heart rate)), the biometric monitoring device and/or the sensor(s) employed to acquire and/or obtain a desired heart rate measurement or data may be placed in, or remain in, a low power state. Since heart rate measurements taken during motion may be less reliable and may be corrupted by motion artifacts, it may be desirable to decrease the frequency with which heart rate data samples are collected (thus decreasing power usage) when the biometric monitoring device is in motion.

In another embodiment, a biometric monitoring device may employ data (for example, from one or more motion sensors) indicative of user activity or motion to adjust or modify characteristics of triggering, acquiring, and/or obtaining desired heart rate measurements or data (for example, to improve robustness to motion artifact). For instance, if the biometric monitoring device receives data indicative of user activity or motion, the biometric monitoring device may adjust or modify the sampling rate and/or resolution mode of sensors used to acquire heart rate data (for example, where the amount of user motion exceeds a certain threshold, the biometric monitoring device may increase the sampling rate and/or increase the sampling resolution mode of sensors employed to acquire heart rate measurement or data.) Moreover, the biometric monitoring device may adjust or modify the sampling rate and/or resolution mode of the motion sensor(s) during such periods of user activity or motion (for example, periods where the amount of user motion exceeds a certain threshold). In this way, when the biometric monitoring device determines or detects such user activity or motion, the biometric monitoring device may place the motion sensor(s) into a higher sampling rate and/or higher sampling resolution mode to, for example, enable more accurate adaptive filtering of the heart rate signal. (See, for example, FIG. 9).

Figure 9:
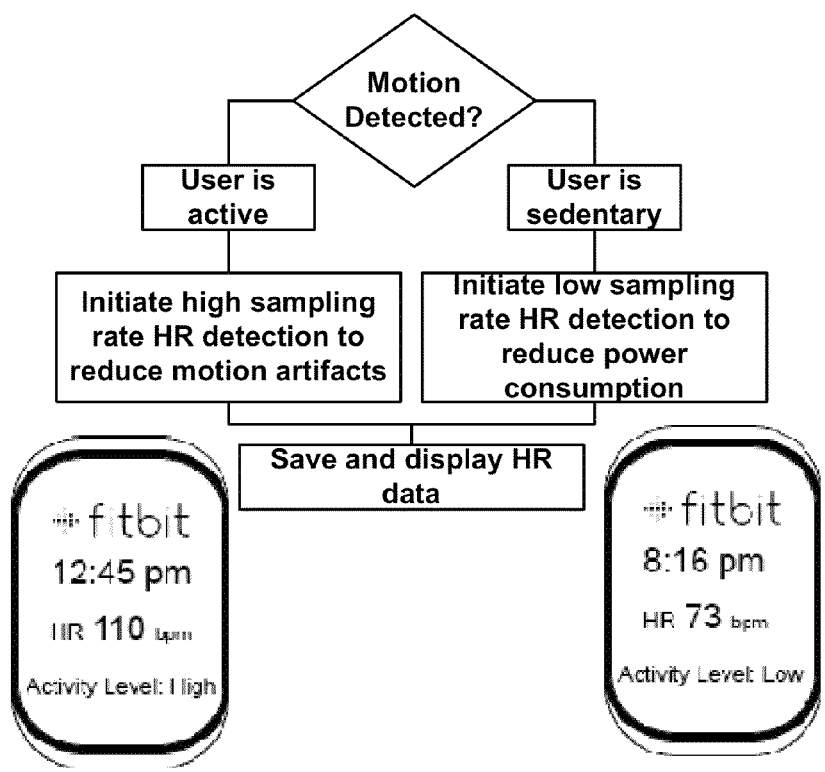
FIG. 9 illustrates an example of a portable biometric monitoring device that changes how it detects a user's heart rate based on how much movement the biometric monitoring device is experiencing.

FIG. 9 illustrates an example of a portable biometric monitoring device that changes how it detects a user's heart rate based on how much movement the biometric monitoring device is experiencing. In the case where there is motion detected (e.g., through the use of an accelerometer), the user may be considered by the biometric monitoring device to be "active" and high-sampling-rate heart rate detection may occur to reduce motion artifacts in the heart rate measurement. This data may be saved and/or displayed. In the case that the user is determined by the biometric monitoring device to not be moving (or to be relatively sedentary), low-sampling-rate heart rate detection (which does not consume as much power) may be adequate to measure a heart rate and may thus be used.

Notably, where a biometric monitoring device employs optical techniques to acquire heart rate measurements or data, e.g., by using photoplethysmography, a motion signal may be employed to determine or establish a particular approach or technique to data acquisition or measurement by the heart rate sensor (e.g., synchronous detection rather than a non-amplitude-modulated approach) and/or analysis thereof. (See, for example, FIG. 11E). In this way, the data which is indicative of the amount of user motion or activity may cause the biometric monitoring device to establish or adjust the type or technique of data acquisition or measurement used by an optical heart rate sensor or sensors.

For example, in one embodiment, a biometric monitoring device (or heart-rate measurement technique as disclosed herein may adjust and/or reduce the sampling rate of optical heart rate sampling when motion detector circuitry detects or determines that the biometric monitoring device wearer's motion is below a threshold (for example, if the biometric monitoring device determines the user is sedentary or asleep). (See, for example, FIG. 9). In this way, the biometric monitoring device may control its power consumption. For example, the biometric monitoring device may reduce power consumption by reducing the sensor sampling rate—for instance, the biometric monitoring device may sample the heart rate (via the heart rate sensor) once every 10 minutes, or 10 seconds out of every 1 minute. Notably, the biometric monitoring device may, in addition thereto or in lieu thereof, control power consumption via controlling data processing circuitry analysis and/or data analysis techniques in accordance with motion detection. As such, the motion of the user may impact the heart rate data acquisition parameters and/or data analysis or processing thereof.

Motion Artifact Suppression in Heart Rate Sensors

As discussed above, the raw heart rate signal measured by a PPG sensor may be improved by using one or more algorithms to remove motion artifacts. Movement of the user (for determining motion artifacts) may be measured using sensors including, but not limited to, accelerometers, gyroscopes, proximity detectors, magnetometers, etc. The goal of such algorithms is to remove components os the PPG signal attributable to movement (movement artifacts) using the movement signal captured from the other sensors as a guide. In one embodiment the movement artifacts in the PPG signal may be removed using an adaptive filter based on a hybrid Kalman filter and a least mean square filter or a recursive least squares filter. The heart rate may then be extracted from the cleaned/filtered signal using a peak counting algorithm or a power spectral density estimation algorithm. Alternatively, a Kalman filter or particle filter may be used to remove such movement artifacts.

Another approach that may be used to calculate the heart rate frequency is to create a model of the heart rate signal as $Y=Y_{dc}+\Sigma a_k * \cos k\theta + b_k * \sin k\theta$, where k is the order of harmonic components, and $\theta$ is a model parameter for heart rate. This model may then be fit to the signal using either an extended Kalman filter or a particle filter. This model exploits the fact that the signal is not sinusoidal so contains power both at the fundamental harmonic as well as multiple additional harmonics.

Alternately, the signal may be modeled as $Y=Y_{dc}+\Sigma a_k * \sin(k*w_{motion}t+\theta)+\Sigma b_k * \sin(k*w_{HR}t+\emptyset)$, where $w_{motion}$ is estimated directly from the accelerometer signal (or another motion sensor signal).

Ambient Light and Skin Color

Ambient light and skin color may make it difficult to extract a user's heart rate from a PPG signal. The effect of ambient light may be reduced by subtracting a value of the received detected light signal when the PPG light source is off from the value of the received detected light signal when the PPG light source is on (assuming that both signals are obtained in close temporal proximity to each other).

The effect of skin color may be reduced by changing the intensity of the PPG light source, the wavelength of the light emitted from the light source, and/or by using the ratio or difference of received signal corresponding to two different wavelengths. Skin color may be determined by using user input (e.g. the user entering their skin color), an image of the person's face, etc., and may then subsequently be used to calibrate the algorithm, light source brightness, light source wavelength, and the receiver gain. The effect of skin color (and tightness with which the user is wearing the device) on the raw PPG signal may also be measured by sending in a signal of known amplitude to the light source(s) and then measuring the received signal from the photodetector(s). Such a signal may be sent for a prolonged period of time (so as to capture data through multiple expected heart beats) and then averaged to produce a steady-state data set that is not heart-rate dependent. This amplitude may then be compared to a set of values stored in a table to determine algorithm calibration, transmitter amplitude and the receiver gain.

Heart Rate Estimate Improvement Using Heuristics

After getting an initial estimate of the heart rate (e.g. by peak counting of a power spectral density estimation), it may be useful to apply bounds on the allowable rates for heart rate. These bounds may be optimized on a per-user basis since each user will have a unique heart rate profile. For example, the sedentary rate of each user may be estimated when they are stationary and this may be used as a lower bound when the user is walking. Similarly, half the frequency of walking as calculated from the pedometer may serve as a good lower bound for the expected heart rate.

The heart rate algorithm may be tailored for each user and may learn the heart rate profile of the user and adapt to the user's behaviors and/or characteristics so as to perform better with time. For example, the algorithm may set bounds on the heart rate expected during a particular physical activity or rate of walking based on historical data from that user. This may help provide better results when the heart rate data is corrupted by noise and/or motion artifacts.

HR Quality Metric

In another example embodiment, a signal quality metric of the heart rate/PPG signal may be used to provide a quantification of the accuracy/precision of the signal being generated. Depending on the values of this metric, the algorithm that determines what the user's heart rate (or other PPG-derived metric such as respiration) is may take certain actions, including asking the user to tighten the watch band, ignoring certain portions of collected heart-rate data (e.g. sections of data that have a low quality metric), and weighting certain portions of the heart-rate data (e.g., data with a higher quality metric may be weighted more heavily when the heart rate is being calculated).

In one embodiment, the signal quality metric may be derived as follows: make a scatter plot where the x-axis is time, and the y-axis is the frequency of a peak in the PPG signal at that given instant in time. An issue to be overcome using this strategy is that there may be multiple and/or zero peaks at a given instant in time. A best fit line captures the linear relationship in this scatter plot. A high quality signal should have a set of peaks that fit well to a line (in a short time span), whereas a bad signal will have a set of peaks that are not well described by a line. Therefore, the quality of the fit to the line provides a good metric for the quality of the PPG signal itself.

Sedentary, Sleep, and Active Classified Metrics

In yet another example embodiment, the biometric monitoring device may employ sensors to calculate heart rate variability when the device determines the user to be sedentary or asleep. Here, the biometric monitoring device may operate the sensors in a higher-rate sampling mode (relative to non-sedentary periods or periods of user activity that exceed a predetermined threshold) to calculate heart rate variability. The biometric monitoring device (or an external device) may employ heart rate variability as an indicator of cardiac health or stress.

Indeed, in some embodiments, the biometric monitoring device may measure and/or determine the user's stress level and/or cardiac health when the user is sedentary and/or asleep (for example, as detected and/or determined by the biometric monitoring device). Some embodiments of a biometric monitoring device of the present disclosure may determine the user's stress level, health state (e.g., risk, onset, or progression of fever or cold), and/or cardiac health using sensor data that is indicative of the heart rate variability, galvanic skin response, skin temperature, body temperature, and/or heart rate. In this way, processing circuitry of the biometric monitoring device may determine and/or track the user's "baseline" stress levels over time and/or cardiac "health" over time. In another embodiment, the device may measure a physiologic parameter of the user during one or more periods where the user is motionless (or the user's motion is below a predetermined threshold), such as when the user is sitting, lying down, asleep, or in a sleep stage (e.g., deep sleep). Such data may also be employed by the biometric monitoring device as a "baseline" for stress-related parameters, health-related parameters (e.g., risk or onset of fever or cold), cardiac health, heart rate variability, galvanic skin response, skin temperature, body temperature and/or heart rate.

Sleep Monitoring

In some embodiments, the biometric monitoring device may automatically detect or determine when the user is attempting to go to sleep, is entering sleep, is asleep, and/or is awoken from a period of sleep. In such embodiments, the biometric monitoring device may employ physiological sensors to acquire data and the data processing circuitry of the biometric monitoring device may correlate a combination of heart rate, heart rate variability, respiration rate, galvanic skin response, motion, skin temperature, and/or body temperature data collected from sensors of the biometric monitoring device to detect or determine if the user is attempting to go to sleep, is entering sleep, is asleep, and/or is awoken from a period of sleep. In response, the biometric monitoring device may, for example, acquire physiological data (of the types, and in the manners, as described herein) and/or determine physiological conditions of the user (of the types, and in the manners, as described herein). For example, a decrease or cessation of user motion combined with a reduction in user heart rate and/or a change in heart rate variability may indicate that the user has fallen asleep. Subsequent changes in heart rate variability and galvanic skin response may then be used by the biometric monitoring device to determine transitions of the user's sleep state between two or more stages of sleep (for example, into lighter and/or deeper stages of sleep). Motion by the user and/or an elevated heart rate and/or a change in heart rate variability may be used by the biometric monitoring device to determine that the user has awoken.

Real-time, windowed, or batch processing to maybe used to determine the transitions between wake, sleep, and sleep stages. For instance, a decrease in heart rate may be measured in a time window where the heart rate is elevated at the start of the window and reduced in the middle (and/or end) of the window. The awake and sleep stages may be classified by a hidden Markov model using changes in motion signal (e.g., decreasing motion intensity), heart rate, heart rate variability, skin temperature, galvanic skin response, and/or ambient light levels. The transition points may be determined through a changepoint algorithm (e.g., Bayesian changepoint analysis). The transition between awake and sleep may be determined by observing periods where the user's heart rate decreases over a predetermined time duration by at least a certain threshold but within a predetermined margin of the user's resting heart rate (that is observed as, for example, the minimum heart rate of the user while sleeping). Similarly, the transition between sleep and awake may be determined by observing an increase in the user's heart rate above a predetermined threshold of the user's resting heart rate.

In some embodiments, the biometric monitoring device may be one component of a system for monitoring sleep, where the system includes a secondary device configured to communicate with the biometric monitoring device and adapted to be placed near the sleeper (e.g., an alarm clock). The secondary device may, in some implementations, have a shape and mechanical and/or magnetic interface to accept the biometric monitoring device for safe keeping, communication, and/or charging. However, the secondary device may also be generic to the biometric monitoring device, e.g., a smartphone that is not specifically designed to physically interface with the biometric monitoring device. The communication between the biometric monitoring device and the secondary device may be provided through wired communication interfaces or through wireless communication interfaces and protocols such as Bluetooth (including, for example, Bluetooth 4.0 and Bluetooth Low Energy protocols), RFID, NFC, or WLAN. The secondary device may include sensors to assist in sleep monitoring or environmental monitoring such as, for example, sensors that measure ambient light, noise and/or sound (e.g., to detect snoring), temperature, humidity, and air quality (pollen, dust, $CO_2$, etc.). In one embodiment, the secondary device may communicate with an external service such as www.fitbit.com or a server (e.g., a personal computer). Communication with the secondary device may be achieved through wired (e.g., Ethernet, USB) or wireless (e.g., WLAN, Bluetooth, RFID, NFC, cellular) circuitry and protocols to transfer data to and/or from the secondary device. The secondary device may also act as a relay to transfer data to and/or from the biometric monitoring device to and/or from an external service such as www.fitbit.com or other service (e.g., data such as news, social network updates, email, calendar notifications) or server (e.g., personal computer, mobile phone, tablet). Calculation of the user's sleep data may be performed on one or both devices or an external service (e.g., a cloud server) using data from one or both devices.

The secondary device may be equipped with a display to display data obtained by the secondary device or data transferred to it by the biometric monitoring device, the external service, or a combination of data from the biometric monitoring device, the secondary device, and/or the external service. For example, the secondary device may display data indicative of the user's heart rate, total steps for the day, activity and/or sleep goal achievement, the day's weather (measured by the secondary device or reported for a location by an external service), etc. In another example, the secondary device may display data related to the ranking of the user relative to other users, such as total weekly step count. In yet another embodiment, the biometric monitoring device may be equipped with a display to display data obtained by the biometric monitoring device, the secondary device, the external service, or a combination of the three sources. In embodiments where the first device is equipped with a wakeup alarm (e.g., vibramotor, speaker), the secondary device may act as a backup alarm (e.g., using an audio speaker). The secondary device may also have an interface (e.g., display and buttons or touch screen) to create, delete, modify, or enable alarms on the first and/or the secondary device.

Sensor-Based Standby Mode

In another embodiment, the biometric monitoring device may automatically detect or determine whether it is or is not attached to, disposed on, and/or being worn by a user. In response to detecting or determining that the biometric monitoring device is not attached to, disposed on, and/or being worn by a user, the biometric monitoring device (or selected portions thereof) may implement or be placed in a low power mode of operation—for example, the optical heart rate sensor and/or circuitry may be placed in a lower power or sleep mode. For example, in one embodiment, the biometric monitoring device may include one or more light detectors (photodiodes, phototransistors, etc.). If, at a given light intensity setting (for example, with respect to the light emitted by a light source that is part of the biometric monitoring device), one or more light detectors provides a low return signal, the biometric monitoring device may interpret the data as indicative of the device not being worn. Upon such a determination, the device may reduce its power consumption—for example, by "disabling" or adjusting the operating conditions of the stress and/or heart rate detection sensors and/or circuitry in addition to other device circuitry or displays (for example, by reducing the duty cycle of or disabling the light source(s) and/or detector(s), turning off the device display, and/or disabling or attenuating associated circuitry or portions thereof). In addition, the biometric monitoring device may periodically determine (e.g., once per second) if the operating conditions of the stress and/or heart rate detection sensors and/or associated circuitry should be restored to a normal operating condition (for example, light source(s), detector(s) and/or associated circuitry should return to a normal operating mode for heart rate detection). In another embodiment, the biometric monitoring device may restore the operating conditions of the stress and/or heart rate detection sensors and/or associated circuitry upon detection of a triggerable event—for example, upon detecting motion of the device (for example, based on data from one or more motion sensor(s)) and/or detecting a user input via the user interface (for example, a tap, bump or swipe interaction with the biometric monitoring device). In some related embodiments, the biometric monitoring device may, for power saving purposes, reduce its default rate of heart rate measurement collection to, for instance, one measurement per minute while the user is not highly active and the user may have the option of putting the device into a mode of operation to generate measurements on demand or at a faster rate (e.g., once per second), for instance, by pushing a button.

Optical Sensor(s)

In one embodiment, the optical sensors (sources and/or detectors) may be disposed on an interior or skin-side of the biometric monitoring device (i.e., a side of the biometric monitoring device that contacts, touches, and/or faces the skin of the user (hereinafter "skin-side"). (See, for example, FIGS. 2A through 3C). In another embodiment, the optical sensors may be disposed on one or more sides of the device, including the skin-side and one or more sides of the device that face or are exposed to the ambient environment (environmental side). (See, for example, FIGS. 6A through 7).

Figure 6A:
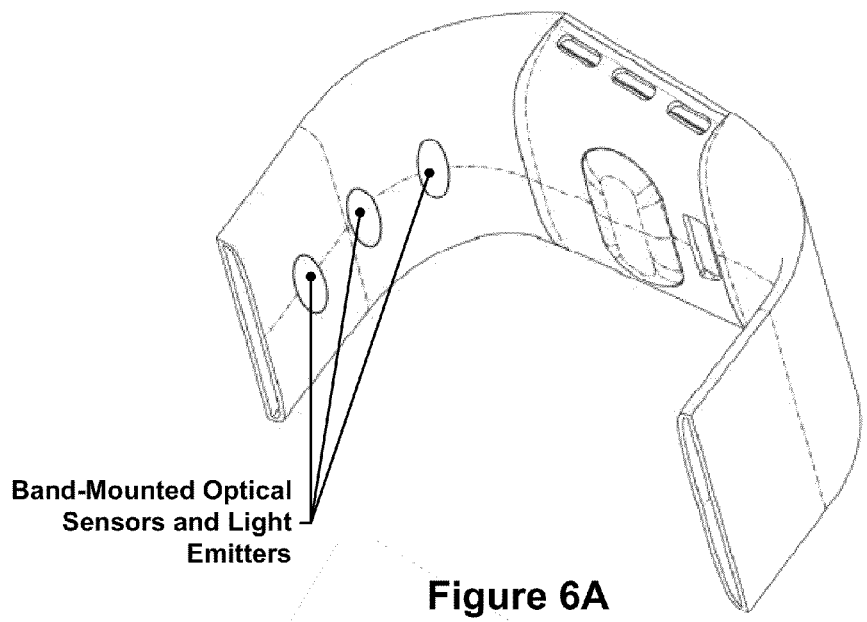
FIG. 6A illustrates an example of a portable monitoring device having a band; optical sensors and light emitters may be placed on the band.

FIG. 6A illustrates an example of a portable monitoring device having a band; optical sensors and light emitters may be placed on the band.

Figure 6B:
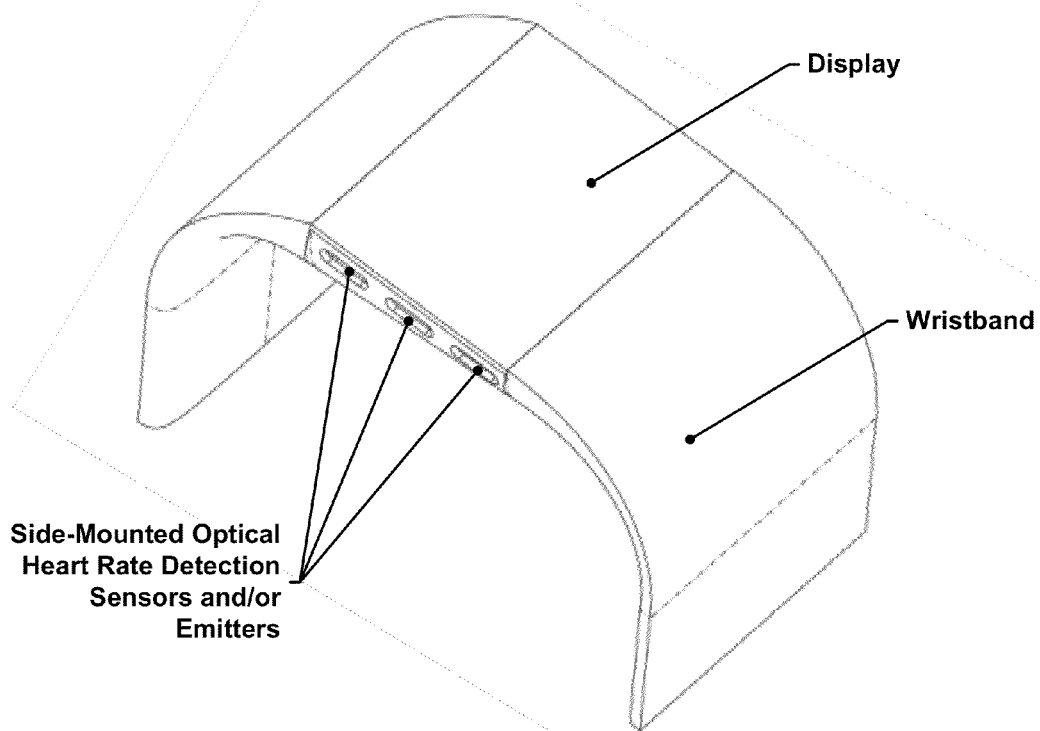
FIG. 6B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

FIG. 6B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

Figure 7:
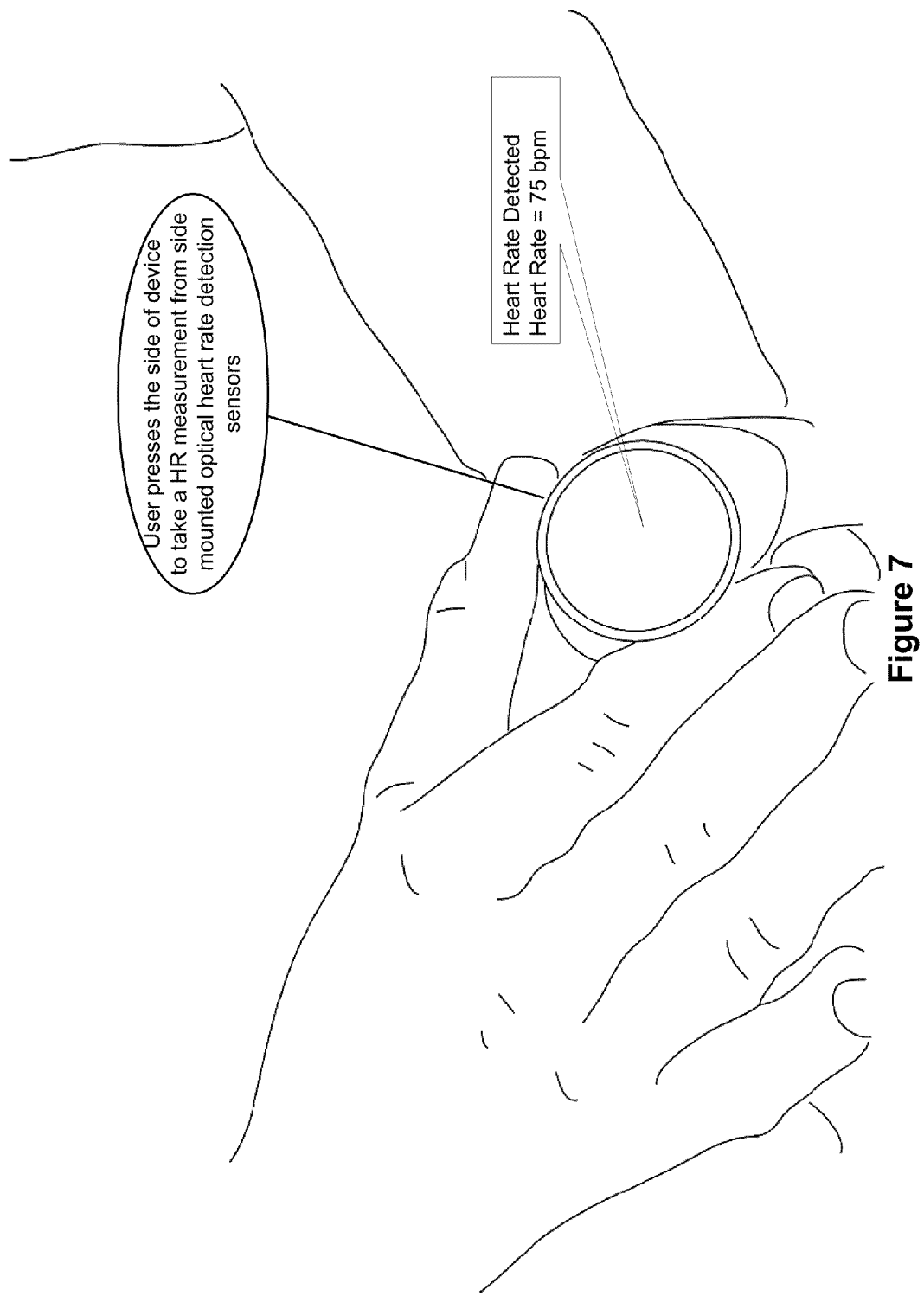
FIG. 7 depicts a user pressing the side of a portable biometric monitoring device to take a heart rate measurement from a side-mounted optical heart rate detection sensor. The display of the biometric monitoring device may show whether or not the heart rate has been detected and/or display the user's heart rate.

FIG. 7 depicts a user pressing the side of a portable biometric monitoring device to take a heart rate measurement from a side-mounted optical heart rate detection sensor. The display of the biometric monitoring device may show whether or not the heart rate has been detected and/or display the user's heart rate.

Notably, the data from such optical sensors may be representative of physiological data and/or environmental data. Indeed, in one embodiment, the optical sensors provide, acquire and/or detect information from multiple sides of the biometric monitoring device whether or not the sensors are disposed on one or more of the multiple sides. For example, the optical sensors may obtain data related to the ambient light conditions of the environment.

Where optical sensors are disposed or arranged on the skin-side of the biometric monitoring device, in operation, a light source in the biometric monitoring device may emit light upon the skin of the user and, in response, a light detector in the biometric monitoring device may sample, acquire, and/or detect corresponding reflected and/or emitted light from the skin (and from inside the body). The one or more light sources and light detectors may be arranged in an array or pattern that enhances or optimizes the signal-to-noise ratio and/or serves to reduce or minimize power consumption by the light sources and light detectors. These optical sensors may sample, acquire and/or detect physiological data which may then be processed or analyzed (for example, by resident processing circuitry) to obtain data that is representative of, for example, a user's heart rate, respiration, heart rate variability, oxygen saturation ($SpO_2$), blood volume, blood glucose, skin moisture, and/or skin pigmentation level.

The light source(s) may emit light having one or more wavelengths that are specific or directed to a type of physiological data to be collected. Similarly, the optical detectors may sample, measure and/or detect one or more wavelengths that are also specific or directed to a type of physiological data to be collected and/or a physiological parameter (of the user) to be assessed or determined. For instance, in one embodiment, a light source emitting light having a wavelength in the green spectrum (for example, an LED that emits light having wavelengths corresponding to the green spectrum) and a photodiode positioned to sample, measure, and/or detect a response or reflection corresponding with such light may provide data that may be used to determine or detect heart rate. In contrast, a light source emitting light having a wavelength in the red spectrum (for example, an LED that emits light having wavelengths corresponding to the red spectrum) and a light source emitting light having a wavelength in the infrared spectrum (for example, an LED that emits light having wavelengths corresponding to the IR spectrum) and photodiode positioned to sample, measure and/or detect a response or reflection of such light may provide data used to determine or detect $SpO_2$.

Indeed, in some embodiments, the color or wavelength of the light emitted by the light source, e.g., an LED (or set of LEDs), may be modified, adjusted, and/or controlled in accordance with a predetermined type of physiological data being acquired or conditions of operation. Here, the wavelength of the light emitted by the light source may be adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity. (See, for example, FIG. 11D).

The biometric monitoring device, in some embodiments, may include a window (for example, a window that is, to casual inspection, opaque) in the housing to facilitate optical transmission between the optical sensors and the user. Here, the window may permit light (for example, of a selected wavelength) to be emitted by, for example, one or more LEDs, onto the skin of the user and a response or reflection of that light to pass back through the window to be sampled, measured, and/or detected by, for example, one or more photodiodes. In one embodiment, the circuitry related to emitting and receiving light may be disposed in the interior of the device housing and underneath or behind a plastic or glass layer (for example, painted with infrared ink) or an infrared lens or filter that permits infrared light to pass but not light in the human visual spectrum. In this way, the light transmissivity of the window may be invisible to the human eye.

The biometric monitoring device may employ light pipes or other light-transmissive structures to facilitate transmission of light from the light sources to the user's body and skin. (See, for example, FIGS. 4A through 5). In this regard, in some embodiments, light may be directed from the light source to the skin of the user through such light pipes or other light-transmissive structures. Scattered light from the user's body may be directed back to the optical circuitry in the biometric monitoring device through the same or similar structures. Indeed, the light-transmissive structures may employ a material and/or optical design to facilitate low light loss (for example, the light-transmissive structures may include a lens to facilitate light collection, and portions of the light-transmissive structures may be coated with or adjacent to reflective materials to promote internal reflection of light within the light-transmissive structures) thereby improving the signal-to-noise-ratio of the photo detector and/or facilitating reduced power consumption of the light source(s) and/or light detectors. In some embodiments, the light pipes or other light-transmissive structures may include a material that selectively transmits light having one or more specific or predetermined wavelengths with higher efficiency than others, thereby acting as a bandpass filter. Such a bandpass filter may be tuned to improve the signal of a specific physiological data type. For example, in one embodiment, an In-Mold-Labeling or "IML" light-transmissive structure may be implemented wherein the light-transmissive structure uses a material with predetermined or desired optical characteristics to create a specific bandpass characteristic, for example, so as to pass infrared light with greater efficiency than light of other wavelengths (for example, light having a wavelength in human visible spectrum). In another embodiment, a biometric monitoring device may employ a light-transmissive structure having an optically opaque portion (including certain optical properties) and an optically-transparent portion (including optical properties different from the optically-opaque portion). Such a light-transmissive structure may be provided via a double-shot or two-step molding process wherein optically opaque material and optically transparent material are separately injected into a mold. A biometric monitoring device implementing such a light-transmissive structure may include different light transmissivity properties for different wavelengths depending on the direction of light travel through the light-transmissive structure. For example, in one embodiment, the optically-opaque material may be reflective to a specific wavelength range so as to more efficiently transport light from the user's body back to the light detector (which may be of a different wavelength(s) relative to the wavelength(s) of the emitted light).

In another embodiment, reflective structures may be placed in the field of view of the light emitter(s) and/or light detector(s). For example, the sides of holes that channel light from light emitter(s) to a user's skin and/or from the user's skin to light detector(s) (or through which light-transmissive structures that perform such channeling travel) may be covered in a reflective material (e.g., chromed) to facilitate light transmission. The reflective material may increase the efficiency with which the light is transported to the skin from the light source(s) and then from the skin back into the detector(s). The reflectively-coated hole may be filled in with an optical epoxy or other transparent material to prevent liquid from entering the device body while still allowing light to be transmitted with low transmission loss.

In another embodiment that implements light-transmissive structures (for example, structures created or formed through IML), such light-transmissive structures may include a mask consisting of an opaque material that limits the aperture of one, some, or all of the light source(s) and/or detector(s). In this way, the light-transmissive structures may selectively "define" a preferential volume of the user's body that light is emitted into and/or detected from. Notably, other mask configurations may be employed or implemented in connection with the concepts described and/or illustrated herein; all such masking configurations to, for example, improve the photoplethysmography signal and which are implemented in connection with the concepts described and/or illustrated herein are intended to fall within the scope of the present disclosure.

In another embodiment, the light emitter(s) and/or detector(s) may be configured to transmit light through a hole or series of holes in the device exterior. This hole or series of holes may be filled in with light-transmissive epoxy (e.g. optical epoxy). The epoxy may form a light pipe that allows light to be transmitted from the light emitter(s) to the skin and from the skin back into the light detector(s). This technique also has the advantage that the epoxy may form a watertight seal, preventing water, sweat or other liquid from entering the device body though the hole(s) on the device exterior that allow the light emitter(s) and detector(s) to transmit to, and receive light from, the biometric monitoring device body exterior. An epoxy with a high thermal conductivity may be used to help prevent the light source(s) (e.g., LED's) from overheating.

In any of the light-transmissive structures described herein, the exposed surfaces of the optics (light-transmissive structures) or device body may include a hard coat paint, hard coat dip, or optical coatings (such as anti-reflection, scratch resistance, anti-fog, and/or wavelength band block (such as ultraviolet light blocking) coatings). Such characteristics or materials may improve the operation, accuracy and/or longevity of the biometric monitoring device.

Figure 4A:
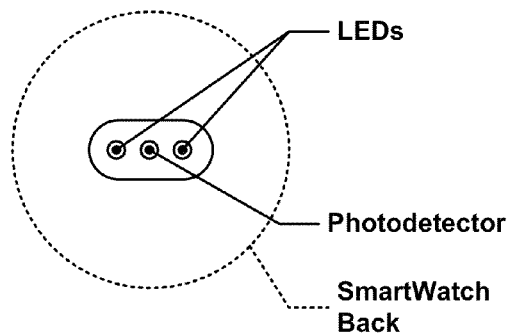
FIG. 4A illustrates an example of one potential PPG light source and photodetector geometry.

FIG. 4A illustrates an example of one potential PPG light source and photodetector geometry. In this embodiment, two light sources are placed on either side of a photodetector. These three devices are located in a protrusion on the back of a wristband-type biometric monitoring device (the side which faces the skin of the user).

Figure 4B:
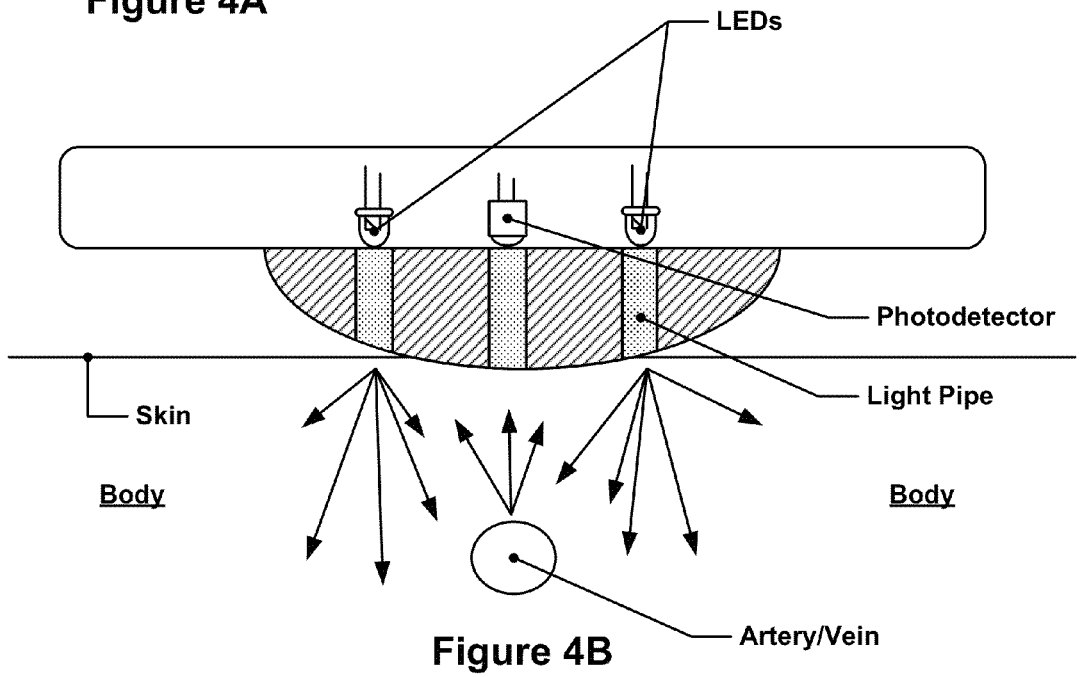
FIGS. 4B and 4C illustrate examples of a PPG sensor having a photodetector and two LED light sources.
Figure 4C:
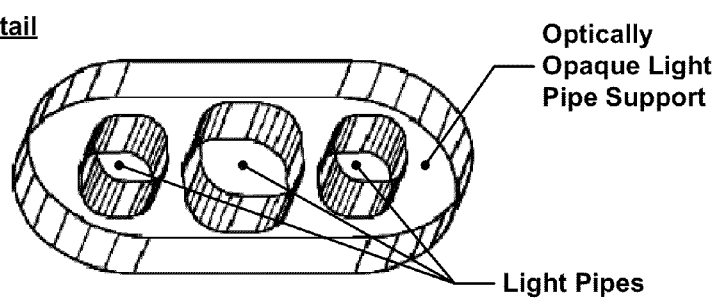

FIGS. 4B and 4C illustrate examples of a PPG sensor having a photodetector and two LED light sources. These components are placed in a biometric monitoring device that has a protrusion on the back side. Light pipes optically connect the LEDs and photodetector with the surface of the user's skin. Beneath the skin, the light from the light sources scatters off of blood in the body, some of which may be scattered or reflected back into the photodetector.

Figure 5:
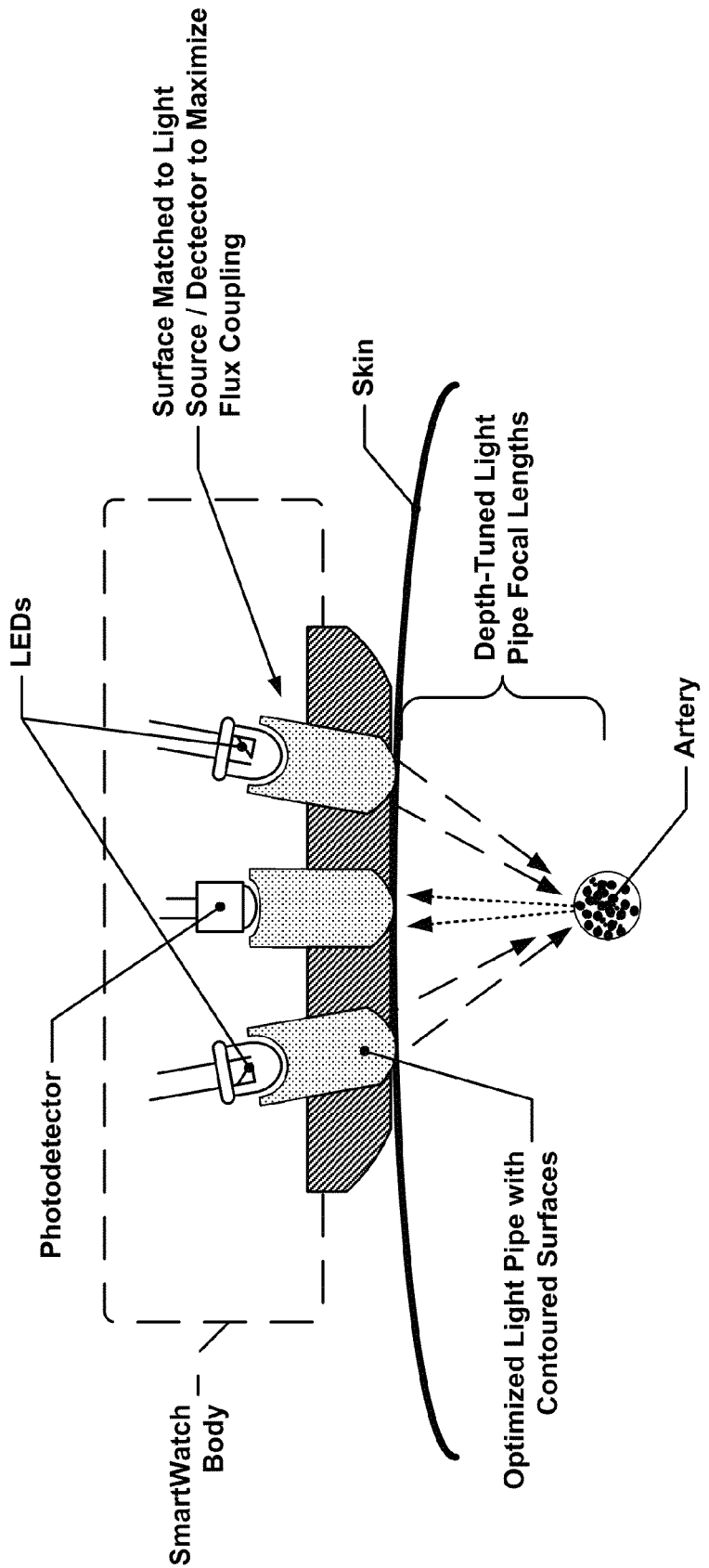
FIG. 5 Illustrates an example of an optimized PPG detector that has a protrusion with curved sides so as not to discomfort the user.

FIG. 5 Illustrates an example of a biometric monitoring device with an optimized PPG detector that has a protrusion with curved sides so as not to discomfort the user. Additionally, the surface of light pipes that optically couple the photodetector and the LEDs to the wearer's skin are contoured to maximize light flux coupling between the LEDs and photodetectors and the light pipes. The ends of the light pipes that face the user's skin are also contoured. This contour may focus or defocus light to optimize the PPG signal. For example, the contour may focus emitted light to a certain depth and location that coincides with an area where blood flow is likely to occur. The vertex of these foci may overlap or be very close together so that the photodetector receives the maximum possible amount of scattered light.

In some embodiments, the biometric monitoring device may include a concave or convex shape, e.g., a lens, on the skin-side of the device, to focus light towards a specific volume at a specific depth in the skin and increase the efficiency of light collected from that point into the photodetector. (See, for example, FIGS. 4A through 5). Where such a biometric monitoring device also employs light pipes to selectively and controllably route light, it may be advantageous to shape the end of the light pipe with a degree of cylindricity, e.g., the end of the light pipe may be a be a cylindrical surface (or portion thereof) defined by a cylinder axis that is nominally parallel to the skin-side (for example, rather than use an axially-symmetric lens). For example, in a wristband-style biometric monitoring device, such a cylindrical lens may be oriented such that the cylinder axis is nominally parallel to the wearer's forearm, which may have the effect of limiting the amount of light that enters such a lens from directions parallel to the person's forearm and increasing the amount of light that enters such a lens from directions perpendicular to the person's forearm—since ambient light is more likely to reach the sensor detection area from directions that are not occluded by the straps of the biometric monitoring device, i.e., along the user's forearm axis, than from directions that are occluded by the straps, i.e., perpendicular to the user's forearm. Such a configuration may improve the signal-to-noise-ratio by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's skin/body response to such emitted light (signal or data that is representative of the response to the emitted light).

In another embodiment, light-transmissive epoxy may be molded into a concave or convex shape so as to provide beneficial optical properties to sensors as well. For example, during the application of light transmissive epoxy, the top of the light-transmissive structure that is formed by the epoxy may be shaped into a concave surface so that light couples more effectively into the light-transmissive structure.

In one embodiment, the components of the optical sensor may be positioned on the skin-side of the device and arranged or positioned to reduce or minimize the distance between (i) the light source(s) and/or the associated detector(s) and (ii) the skin of the user. See, for example, FIG. 3A, which provides a cross-sectional view of a sensor protrusion of an example portable monitoring device. In FIG. 3A, two light sources (e.g., LEDs) are placed on either side of a photodetector to enable PPG sensing. A light-blocking material is placed between the light sources and the photodetector to prevent any light from the light sources from reaching photodetector without first exiting the body of the biometric monitoring device. A flexible transparent layer may be placed on the lower surface of the sensor protrusion to form a seal. This transparent layer may serve other functions such as preventing liquid from entering the device where the light sources or photodetectors are placed. This transparent layer may be formed through in-mold labeling or "IML". The light sources and photodetector may be placed on a flexible PCB.

Such a configuration may improve the efficiency of light flux coupling between the components of the optical sensor and the user's body. For example, in one embodiment, the light source(s) and/or associated detector(s) may be disposed on a flexible or pliable substrate that may flex, allowing the skin-side of the biometric monitoring device, which may be made from a compliant material, to conform (for example, without additional processing) or be capable of being shaped (or compliant) to conform to the shape of the body part (for example, the user's wrist, arm, ankle, and/or leg) to which the biometric monitoring device is coupled to or attached during normal operation so that the light source(s) and/or associated detector(s) are/is close to the skin of the user (i.e., with little to no gap between the skin-side of the device and the adjacent surface of the skin of the user. See, for example, FIG. 6A. In one embodiment, the light source(s) and/or associated detector(s) may be disposed on a Flat Flex Cable or "FFC" or flexible PCB. In this embodiment, the flexible or pliable substrate (for example, an FFC or flexible PCB) may connect to a second substrate (for example, PCB) within the device having other components disposed thereon (for example, the data processing circuitry). Optical components of differing heights may be mounted to different "fingers" of flexible substrate and pressed or secured to the housing surface such that the optical components are flush to the housing surface. In one embodiment, the second substrate may be a relatively inflexible or non-pliable substrate, fixed within the device, having other circuitry and components (passive and/or active) disposed thereon.

FIG. 3B depicts a cross-sectional view of a sensor protrusion of an example portable monitoring device; this protrusion is similar to that presented in FIG. 3A with the exception that the light sources and photodetector are placed on a flat and/or rigid PCB.

Figure 3C:
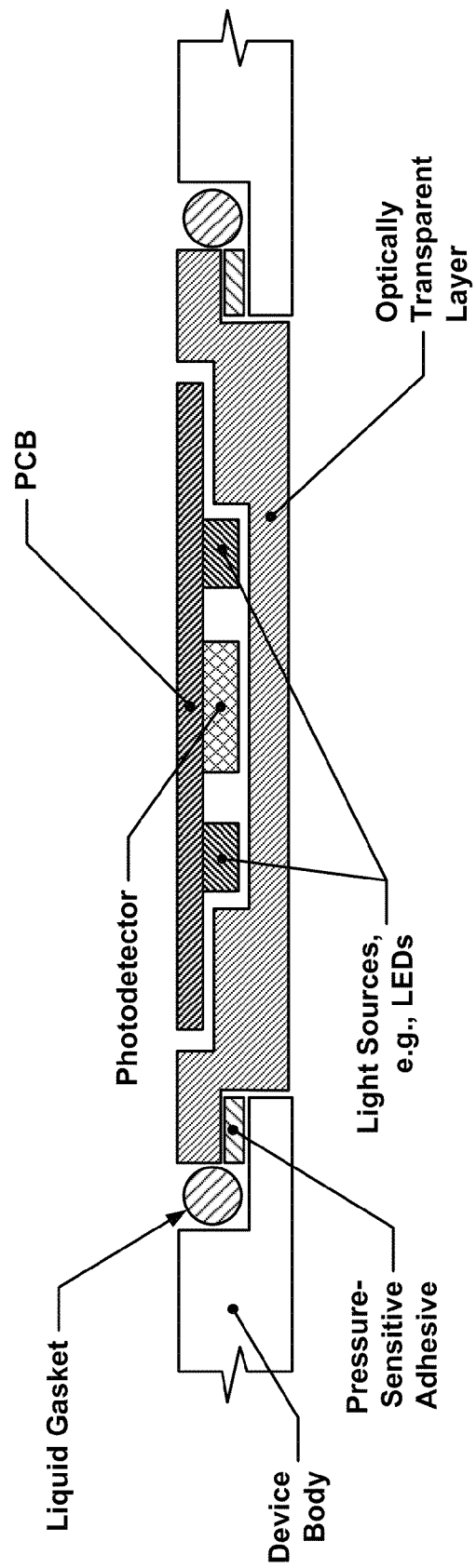
FIG. 3C provides another cross-sectional view of an example PPG sensor implementation.

FIG. 3C provides another cross-sectional view of an example PPG sensor implementation. Of note in this PPG sensor is the lack of a protrusion. Additionally, a liquid gasket and/or a pressure sensitive adhesive are used to prevent liquid from entering the biometric monitoring device body.

Some embodiments of biometric monitoring devices may be adapted to be worn or carried on the body of a user. In some embodiments including the optical heart rate monitor, the device may be a wrist-worn or arm-mounted accessory such as a watch or bracelet. (See, for example, FIGS. 2A through 7). In one embodiment, optical elements of the optical heart rate monitor may be located on the interior or skin-side of the biometric monitoring device, for example, facing the top of the wrist (i.e., the optical heart rate monitor may be adjacent to and facing the wrist) when the biometric monitoring device is worn on the wrist. (See, for example, FIGS. 2A through 3C).

In another embodiment, the optical heart rate monitor may be located on one or more external or environmental side surfaces of the biometric monitoring device. (See, for example, FIGS. 6B and 7). In such embodiments, the user may touch an optical window (behind which optical elements of the optical heart rate monitor are located) with a finger on the opposing hand to initiate a heart rate measurement (and/or other metrics related to heart rate such as heart rate variability) and/or collect data which may be used to determine the user's heart rate (and/or other metrics related to heart rate). (See, for example, FIG. 6B). In one embodiment, the biometric monitoring device may trigger or initiate the measurement(s) by detecting a (sudden) drop in incident light on the photodiode—for example, when the user's finger is placed over the optical window. In addition thereto, or in lieu thereof, a heart rate measurement (or other such metric) may be trigged by an IR-based proximity detector and/or capacitive touch/proximity detector (which may be separate from other detectors). Such IR-based proximity detector and/or capacitive touch/proximity detector may be disposed in or on and/or functionally, electrically and/or physically coupled to the optical window to detect or determine the presence of, for example, the user's finger.

In yet another embodiment, the biometric monitoring device may include a button that, when depressed, triggers or initiates heart rate measurement (and/or other metrics related to heart rate). The button may be disposed in close proximity to the optical window to facilitate the user pressing the button while the finger is disposed on the optical window. (See, for example, FIG. 7). In one embodiment, the optical window may be embedded in a push button. Thus, when the user presses the button, it may trigger a measurement of the finger that depresses the button. Indeed, the button may be given a shape and/or resistance to pressing that enhances or optimizes a pressure profile of the button against the finger to provide a high signal-to-noise-ratio during measurement or data acquisition. In other embodiments (not illustrated), the biometric monitoring device may take the form of a clip, a smooth object, a pendant, an anklet, a belt, etc. that is adapted to be worn on the body, clipped or mounted to an article of clothing, deposited in clothing (e.g., in a pocket), or deposited in an accessory (e.g., handbag).

In one specific embodiment, the biometric monitoring device may include a protrusion on the skin- or interior side of the device. (See, FIGS. 2A through 6A). When coupled to the user, the protrusion may engage the skin with more force than the surrounding device body. In this embodiment, an optical window or light transmissive structure (both of which are discussed in detail above) may form or be incorporated in a portion of the protrusion. The light emitter(s) and/or detector(s) of the optical sensor may be disposed or arranged in the protrusion near the window or light transmissive structure. (See, for example, FIGS. 2B and 6A). As such, when attached to the user's body, the window portion of the protrusion of the biometric monitoring device may engage the user's skin with more force than the surrounding device body—thereby providing a more secure physical coupling between the user's skin and the optical window. That is, the protrusion may cause sustained contact between the biometric monitoring device and the user's skin that may reduce the amount of stray light measured by the photodetector, decrease relative motion between the biometric monitoring device and the user, and/or provide improved local pressure to the user's skin; all of which may increase the quality of the cardiac signal of interest. Notably, the protrusion may contain other sensors that benefit from close proximity and/or secure contact to the user's skin. These may be included in addition to or in lieu of a heart rate sensor and include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

In addition thereto, or in lieu thereof, a portion of the skin-side of the biometric monitoring device may include a friction enhancing mechanism or material. For example, the skin-side of the biometric monitoring device may include a plurality of raised or depressed regions or portions (for example, small bumps, ridges, grooves, and/or divots). Moreover, a friction enhancing material (for example, a gel-like material such as silicone or other elastomeric material) may be disposed on the skin-side. Indeed, a device back made out of gel may also provide friction while also improving user comfort and preventing stray light from entering. As noted above, a friction-enhancing mechanism or material may be used alone or in conjunction with the biometric monitoring device having a protrusion as described herein. In this regard, the biometric monitoring device may include a plurality of raised or depressed regions portions (for example, small bumps, ridges, grooves, and/or divots) in or on the protrusion portion of the device. Indeed, such raised or depressed regions portions may be incorporated/embedded into or on a window portion of the protrusion. In addition thereto, or in lieu thereof, the protrusion portion may consist of or be coated with a friction enhancing material (for example, a gel-like material such as silicone). Notably, the use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motion of the biometric monitoring device (and thus of the sensor) relative to the user's skin during operation, especially while the user is in motion.

Some or all of the interior or skin-side housing of the biometric monitoring device may also consist of a metal material (for example, steel, stainless steel, aluminum, magnesium, or titanium). Such a configuration may provide a structural rigidity. (See, for example, FIG. 2B). In such an embodiment, the device body may be designed to be hypoallergenic through the use of a hypoallergenic "nickel-free" stainless steel. Notably, it may be advantageous to employ (at least in certain locations) a type of metal that is at least somewhat ferrous (for example, a grade of stainless steel that is ferrous). In such embodiments, the biometric monitoring device (where it includes a rechargeable energy source (for example, rechargeable battery)) may interconnect with a charger via a connector that secures itself to the biometric monitoring device using magnets that couple to the ferrous material. In addition, biometric monitoring device may also engage a dock or dock station, using such magnetic properties, to facilitate data transfer. Moreover, such a housing may provide enhanced electromagnetic shielding that would enhance the integrity and reliability of the optical heart rate sensor and the heart rate data acquisition process/operation. Furthermore, a skin temperature sensor may be physically and thermally coupled, for example, with thermal epoxy, to the metal body to sense the temperature of the user. In embodiments including a protrusion, the sensor may be positioned near or in the protrusion to provide secure contact and localized thermal coupling to the user's skin.

In a preferred embodiment, one or more components of the optical sensor (which may, in one embodiment, be located in a protrusion, and/or in another embodiment, may be disposed or placed flush to the surface of the biometric monitoring device) are attached, fixed, included, and/or secured to the biometric monitoring device via a liquid-tight seal (i.e., a method/mechanism that prevents liquid ingress into the body of the biometric monitoring device). For example, in one embodiment, a device back made out of a metal such as, but not limited to, stainless steel, aluminum, magnesium, or titanium, or from a rigid plastic may provide a structure that is stiff enough to maintain the structural integrity of the device while accommodating a watertight seal for the sensor package. (See, for example, FIGS. 2B through 3C).

In a preferred embodiment, a package or module of the optical sensor may be connected to the device with a pressure-sensitive adhesive and a liquid gasket. See, for example, FIG. 3C, which provides another cross-sectional view of a PPG sensor implementation. Of note in this PPG sensor is the lack of a protrusion. Additionally, a liquid gasket and/or a pressure sensitive adhesive are used to prevent liquid from entering the device body. Screws, rivets or the like may also be used, for example, if a stronger or more durable connection is required between the optical sensor package/module and the device body. Notably, the present embodiments may also use watertight glues, hydrophobic membranes such as Gore-Tex, o-rings, sealant, grease, or epoxy to secure or attach the optical sensor package/module to the biometric monitoring device body.

As discussed above, the biometric monitoring device may include a material disposed on the skin- or interior side that includes high reflectivity characteristics—for example, polished stainless steel, reflective paint, and polished plastic. In this way, light scattered off the skin-side of the device may be reflected back into the skin in order to, for example, improve the signal-to-noise-ratio of an optical heart rate sensor. Indeed, this effectively increases the input light signal as compared with a device body back that is non-reflective (or less reflective). Notably, in one embodiment, the color of the skin or interior side of the biometric monitoring device may be selected to provide certain optical characteristics (for example, reflect certain or predetermined wavelengths of light), in order to improve the signal with respect to certain physiological data types. For example, where the skin- or interior side of the biometric monitoring is green, the measurements of the heart rate may be enhanced due to the preferential emission of a wavelength of the light corresponding to the green spectrum. Where the skin- or interior side of the biometric monitoring is red, the measurements of the $SpO_2$ may be enhanced due to the emission preferential of a wavelength of the light corresponding to the red spectrum. In one embodiment, the color of the skin- or interior side of the biometric monitoring may be modified, adjusted and/or controlled in accordance with a predetermined type of physiological data being acquired.

Figure 11A:
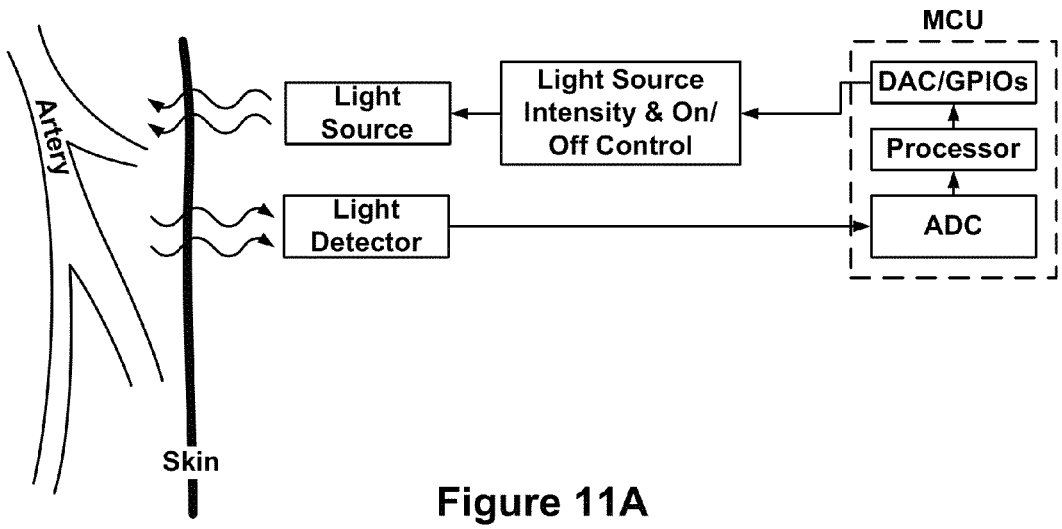
FIG. 11A illustrates an example block diagram of a PPG sensor which has a light source, light detector, ADC, processor, DAC/GPIOs, and light source intensity and on/off control.

FIG. 11A depicts an example schematic block diagram of an optical heart rate sensor where light is emitted from a light source toward the user's skin and the reflection of such light from the skin/internal body of the user is sensed by a light detector, the signal from which is subsequently digitized by an analog to digital converter (ADC). The intensity of the light source may be modified (e.g., through a light source intensity control module) to maintain a desirable reflected signal intensity. For example, the light source intensity may be reduced to avoid saturation of the output signal from the light detector. As another example, the light source intensity may be increased to maintain the output signal from the light detector within a desired range of output values. Notably, active control of the system may be achieved through linear or nonlinear control methods such as proportional-integral-derivative (PID) control, fixed step control, predictive control, neural networks, hysteresis, and the like, and may also employ information derived from other sensors in the device such as motion, galvanic skin response, etc. FIG. 11A is provided for illustration and does not limit the implementation of such a system to, for instance, an ADC integrated within a MCU, or the use of a MCU for that matter. Other possible implementations include the use of one or more internal or external ADCs, FPGAs, ASICs, etc.

Figure 11B:
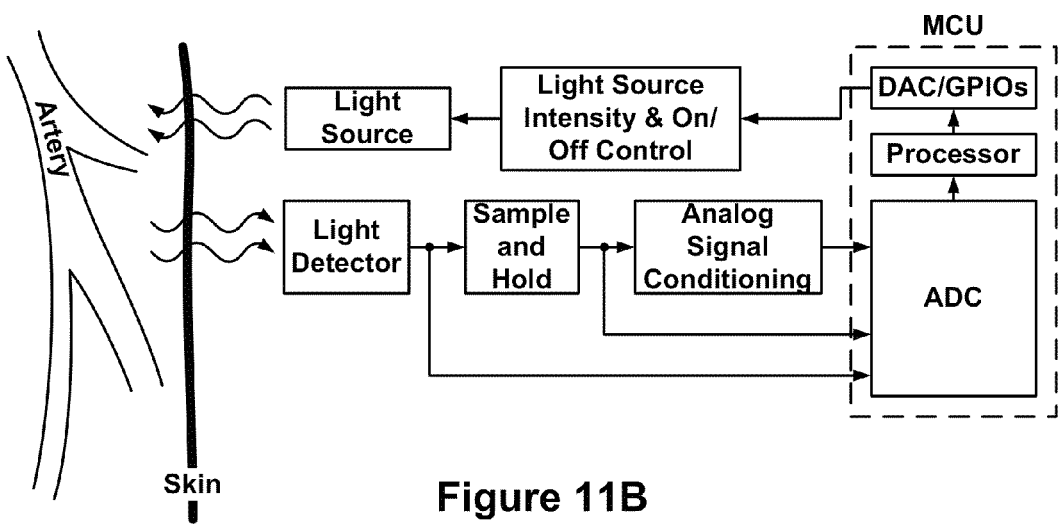
FIG. 11B illustrates an example block diagram of a PPG sensor that is similar to that of FIG. 11A which additionally uses a sample-and-hold circuit as well as analog signal conditioning.

In another embodiment, system with an optical heart rate sensor may incorporate the use of a sample-and-hold circuit (or equivalent) to maintain the output of the light detector while the light source is turned off or attenuated to save power. In embodiments where relative changes in the light detector output are of primary importance (e.g., heart rate measurement), the sample-and-hold circuit may not have to maintain an accurate copy of the output of the light detector. In such cases, the sample-and-hold may be reduced to, for example, a diode (e.g., Schottky diode) and capacitor. The output of the sample-and-hold circuit may be presented to an analog signal conditioning circuit (e.g., a Sallen-Key band-pass filter, level shifter, and/or gain circuit) to condition and amplify the signal within frequency bands of interest (e.g., 0.1 Hz to 10 Hz for cardiac or respiratory function), which may then be digitized by the ADC. See, for example, FIG. 11B.

Figure 11C:
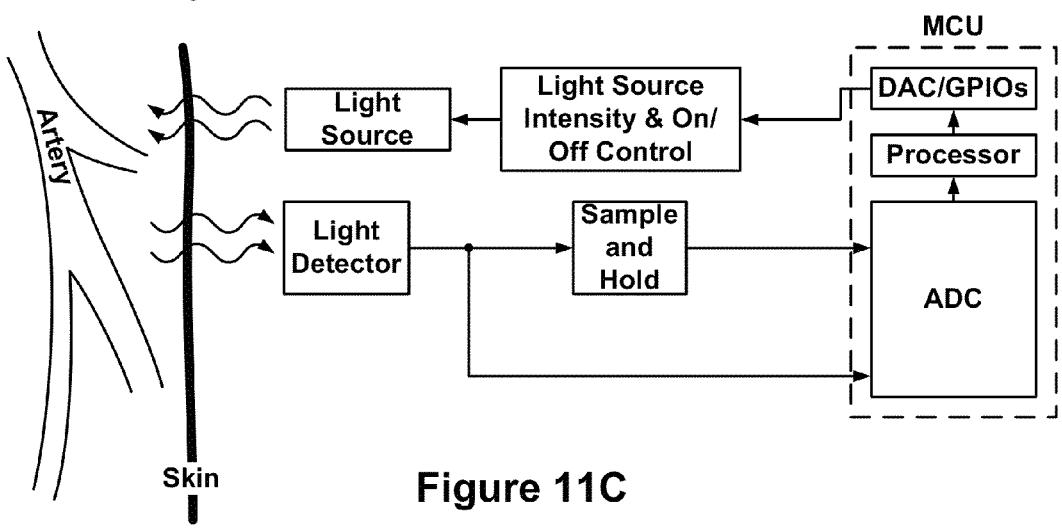
FIG. 11C illustrates an example block diagram of a PPG sensor that is similar to that of FIG. 11A which additionally uses a sample-and-hold circuit.
Figure 11D:
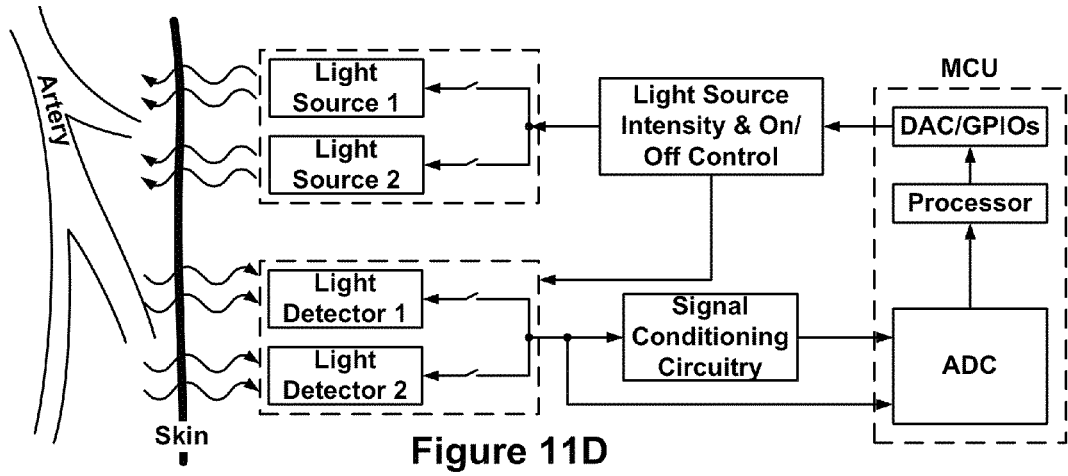
FIG. 11D illustrates an example block diagram of a a PPG sensor having multiple switchable light sources and detectors, light source intensity/on and off control, and signal conditioning circuitry.
Figure 11E:
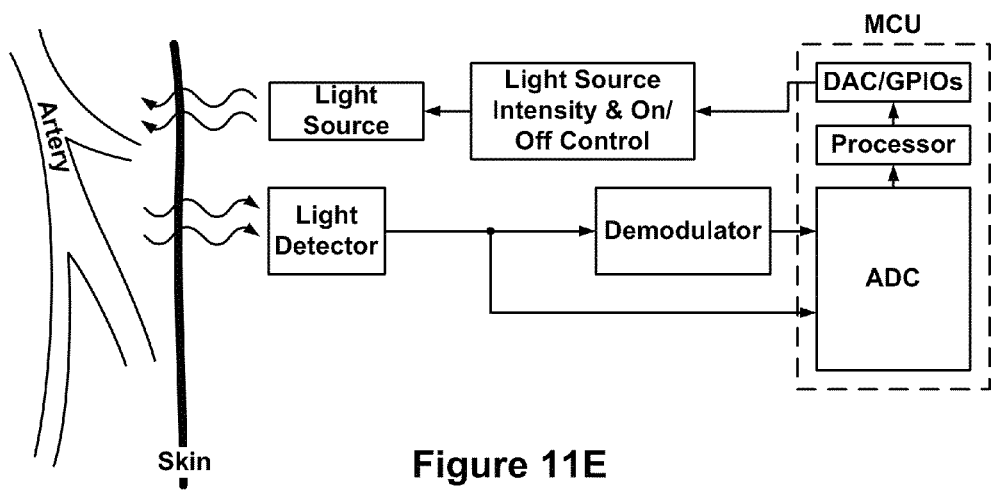
FIG. 11E illustrates an example block diagram of a PPG sensor which uses synchronous detection. To perform this type of PPG detection, it has a demodulator.

In operation, circuit topologies such as those already described herein (e.g. a sample-and-hold circuit) remove the DC and low frequency components of the signal and help resolve the AC component related to heart rate and/or respiration. The embodiment may also include the analog signal conditioning circuitry for variable gain settings that can be controlled to provide a suitable signal (e.g., not saturated). The performance characteristics (e.g., slew rate and/or gain bandwidth product) and power consumption of the light source, light detector, and/or sample-and-hold may be significantly higher than the analog signal conditioning circuit to enable fast duty cycling of the light source. In some embodiments, the power provided to the light source and light detector may be controlled separately from the power provided to the analog signal conditioning circuit to provide additional power savings. Alternatively or additionally, the circuitry can use functionality such as an enable, disable and/or shutdown to achieve power savings. In another embodiment, the output of the light detector and/or sample-and-hold circuit may be sampled by an ADC in addition to or in lieu of the analog signal conditioning circuit to control the light intensity of the light source or to measure the physiologic parameters of interest when, for example, the analog signal conditioning circuit is not yet stable after a change to the light intensity setting. Notably, because the physiologic signal of interest is typically small relative to the inherent resolution of the ADC, in some embodiments, the reference voltages and/or gain of the ADC may be adjusted to enhance signal quality and/or the ADC may be oversampled. In yet another embodiment, the device may digitize the output of only the sample-and-hold circuit by, for example, oversampling, adjusting the reference voltages and/or gain of the ADC, or using a high resolution ADC. See, for example, FIG. 11C.

PPG DC Offset Removal Techniques

Figure 11F:
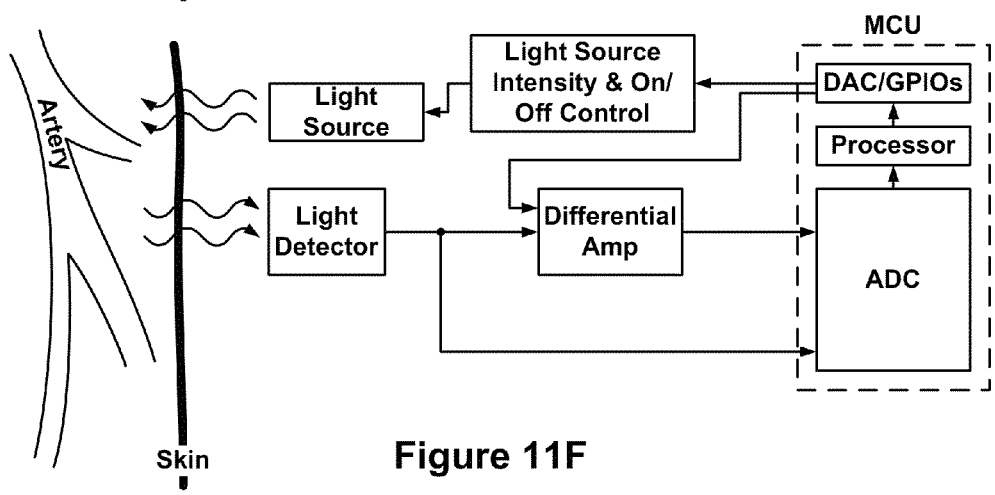
FIG. 11F illustrates an example block diagram of a PPG sensor which, in addition to the features of the sensor illustrated in FIG. 11A, has a differential amplifier.

In another embodiment, the sensor device may incorporate a differential amplifier to amplify the relative changes in the output of the light detector. See, for example, FIG. 11F. In some embodiments, a digital average or digital low-pass filtered signal may be subtracted from the output of the light detector. This modified signal may then be amplified before it is digitized by the ADC. In another embodiment, an analog average or analog low-pass filtered signal may be subtracted from the output of the light detector through, for example, the use of a sample-and-hold circuit and analog signal conditioning circuitry. The power provided to the light source, light detector, and differential amplifier may be controlled separately from the power provided to the analog signal conditioning circuit to improve power savings.

In another embodiment, a signal (voltage or current, depending on the specific sensor implementation) may be subtracted from the raw PPG signal to remove any bias in the raw PPG signal and therefore increase the gain or amplification of the PPG signal that contains heart rate (or other circulatory parameters such as heart rate variability) information. This signal may be set to a default value in the factory, to a value based on the user's specific skin reflectivity, absorption, and/or color, and/or may change depending on feedback from an ambient light sensor, or depending on analytics of the PPG signal itself. For example, if the PPG signal is determined to have a large DC offset, a constant voltage may be subtracted from the PPG signal to remove the DC offset and enable a larger gain, therefore improving the PPG signal quality. The DC offset in this example may result from ambient light (for example from the sun or from indoor lighting) reaching the photodetector from or reflected light from the PPG light source.

In another embodiment, a differential amplifier may be used to measure the difference between current and previous samples rather than the magnitude of each signal. Since the magnitude of each sample is typically much greater than the difference between each sample, a larger gain can be applied to each measurement, therefore improving the PPG signal quality. The signal may then be integrated to obtain the original time domain signal.

In another embodiment, the light detector module may incorporate a transimpedance amplifier stage with variable gain. Such a configuration may avoid or minimize saturation from bright ambient light and/or bright emitted light from the light source. For example, the gain of the transimpedance amplifier may be automatically reduced with a variable resistor and/or multiplexed set of resistors in the negative feedback path of the transimpedance amplifier. In some embodiments, the device may incorporate little to no optical shielding from ambient light by amplitude-modulating the intensity of the light source and then demodulating the output of the light detector (e.g., synchronous detection). See, for instance, FIG. 11E. In other aspects, if the ambient light is of sufficient brightness to obtain a heart rate signal, the light source may be reduced in brightness and/or turned off completely.

Figure 11G:
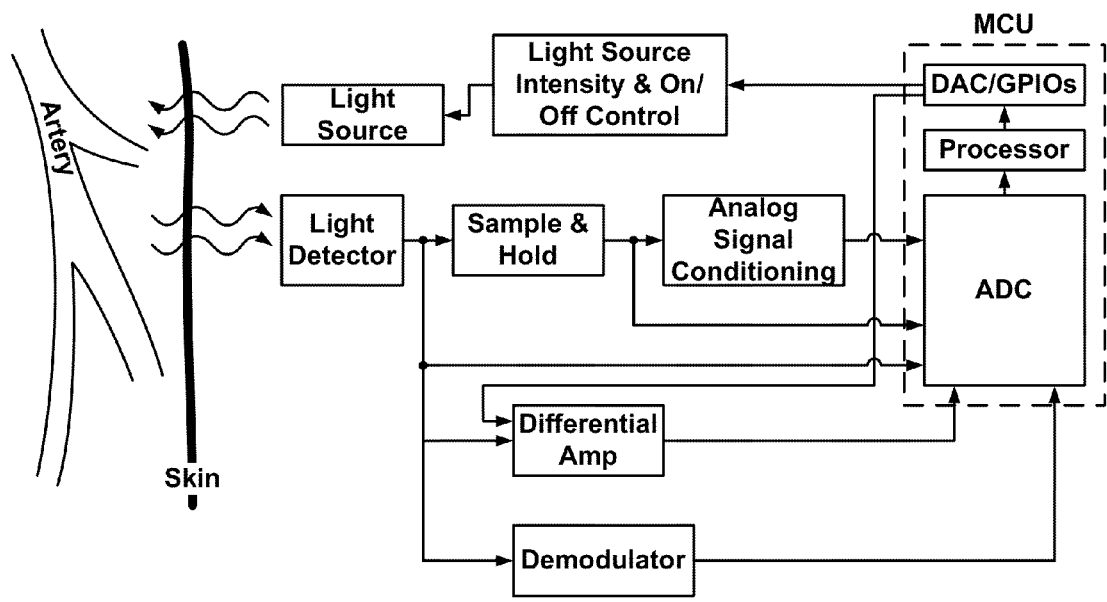
FIG. 11G illustrates an example block diagram of a PPG sensor which has the features of the PPG sensors shown in FIGS. 11A-KKF.

In yet another embodiment, the aforementioned processing techniques may be used in combination to optically measure physiological parameters of the user. See, for example, FIG. 11G. This topology may allow the system to operate in a low power measurement state and circuit topology when applicable and adapt to a higher power measurement state and circuit topology as necessary. For instance, the system may measure the physiologic parameter (e.g., heart rate) of interest using analog signal-conditioning circuitry while the user is immobile or sedentary to reduce power consumption, but switch to oversampled sampling of the light detector output directly while the user is active.

In embodiments where the biometric monitoring device includes a heart rate monitor, processing of the signal to obtain heart rate measurements may include filtering and/or signal conditioning such as band-pass filtering (e.g., Butterworth filter). To counteract large transients that may occur in the signal and/or to improve convergence of said filtering, nonlinear approaches may be employed such as neural networks or slew rate limiting. Data from the sensors on the device such as motion, galvanic skin response, skin temperature, etc., may be used to adjust the signal conditioning methods employed. Under certain operating conditions, the heart rate of the user may be measured by counting the number of signal peaks within a time window or by utilizing the fundamental frequency or second harmonic of the signal (e.g., through a fast Fourier transform (FFT)). In other cases, such as heart rate data acquired while the user is in motion, FFTs may be performed on the signal and spectral peaks extracted, which may then be subsequently processed by a multiple-target tracker which starts, continues, merges, and deletes tracks of the spectra. In some embodiments, a similar set of operations may be performed on the motion signal and the output may be used to do activity discrimination (e.g., sedentary, walking, running, sleeping, lying down, sitting, biking, typing, elliptical, weight training) which is used to assist the multiple-target tracker. For instance, it may be determined that the user was stationary and has begun to move. This information may be used to preferentially bias the track continuation toward increasing frequencies. Similarly, the activity discriminator may determine that the user has stopped running or is running slower and this information may be used to preferentially bias the track continuation toward decreasing frequencies. Tracking may be achieved with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc. A track selector module may use the output tracks from the multiple-spectra tracker and estimate the user's heart rate. The estimate may be taken as the maximum likelihood track, a weight sum of the tracks against their probabilities of being the heart rate, etc. The activity discriminator may furthermore influence the selection and/or fusion to get the heart rate estimate. For instance, if the user is sleeping, sitting, lying down, or sedentary, a prior probability may be skewed toward heart rates in the 40-80 bpm range; whereas if the user is running, jogging, or doing other vigorous exercise, a prior probability may be skewed toward elevated heart rates in the 90-180 bpm range. The influence of the activity discriminator may be based on the speed of the user. The estimate may be shifted toward (or wholly obtained by) the fundamental frequency of the signal when the user is not moving. The track that corresponds to the user's heart rate may be selected based on criteria that are indicative of changes in activity; for instance, if the user begins to walk from being stationary, the track that illustrates a shift toward higher frequency may be preferentially chosen.

The acquisition of a good heart rate signal may be indicated to the user through a display on the biometric monitoring device or another device in wired or wireless communication with the biometric monitoring device (e.g., a Bluetooth Low Energy-equipped mobile phone). In some embodiments, the biometric monitoring device may include a signal-strength indicator that is represented by the pulsing of an LED viewable by the user. The pulsing may be timed or correlated to be coincident with the user's heartbeat. The intensity, pulsing rate and/or color of the LED may be modified or adjusted to suggest signal strength. For example, a brighter LED intensity may represent a stronger signal or in an RGB LED configuration, a green colored LED may represent a stronger signal.

In some embodiments, the strength of the heart rate signal may be determined by the energy (e.g., squared sum) of the signal in a frequency band of, for instance, 0.5 Hz to 4 Hz. In other embodiments, the biometric monitoring device may have a strain gauge, pressure sensor, force sensor, or other contact-indicating sensor that may be incorporated or constructed into the housing and/or in the band (in those embodiments where the biometric monitoring device is attached to or mounted with a band like a watch, bracelet, and/or armband—which may then be secured to the user). A signal quality metric (e.g. heart rate signal quality) may be calculated based on data from these contact sensors either alone or in combination with data from the heart rate signal.

In another embodiment, the biometric monitoring device may monitor heart rate optically through an array of photodetectors such as a grid of photodiodes or a CCD camera. Motion of the optical device with respect to the skin may be tracked through feature-tracking of the skin and/or adaptive motion correction using an accelerometer and gyroscope. The detector array may be in contact with the skin or offset at a small distance away from the skin. The detector array and its associated optics may be actively controlled (e.g., with a motor) to maintain a stabilized image of the target and acquire a heart rate signal. This optomechanical stabilization may be achieved using information from motion sensors (e.g., a gyroscope) or image features. In one embodiment, the biometric monitoring device may implement relative motion cancellation using a coherent or incoherent light source to illuminate the skin and a photodetector array with each photodetector associated with comparators for comparing the intensity between neighboring detectors—obtaining a so-called speckle pattern which may be tracked using a variety of image tracking techniques such as optical flow, template matching, edge tracking, etc. In this embodiment, the light source used for motion tracking may be different than the light source used in the optical heart rate monitor.

In another embodiment, the biometric monitoring device may consist of a plurality of photodetectors and photoemitters distributed along a surface of the device that touches the user's skin (i.e., the skin-side of the biometric monitoring device). (See, for example, FIGS. 2A through 6A). In the example of a bracelet, for instance, there may be a plurality of photodetectors and photoemitters placed at various sites along the circumference of the interior of the band. (See, for example, FIG. 6A). A heart rate signal-quality metric associated with each site may be calculated to determine the best or set of best sites for estimating the user's heart rate. Subsequently, some of the sites may be disabled or turned off to, for example, reduce power consumption. The device may periodically check the heart rate signal quality at some or all of the sites to enhance, monitor and/or optimize signal and/or power efficiency.

In another embodiment, a biometric monitoring device may include a heart rate monitoring system including a plurality of sensors such as optical, acoustic, pressure, electrical (e.g., ECG or EKG), and motion and fuse the information from two or more of these sensors to provide an estimate of heart rate and/or mitigate noise induced from motion.

In addition to heart rate monitoring (or other biometric monitoring), or in lieu thereof, the biometric monitoring device, in some embodiments, may include optical sensors to track or detect time and duration of ultraviolet light exposure, total outdoor light exposure, the type of light source and duration and intensity of that light source (fluorescent light exposure, incandescent bulb light exposure, halogen, etc.), exposure to television (based on light type and flicker rate), whether the user is indoors or outdoors, time of day and location based on light conditions. In one embodiment, the ultraviolet detection sensor may consist of a reverse biased LED emitter driven as a light detector. The photocurrent produced by this detector may be characterized by, for instance, measuring the time it takes for the LED's capacitance (or alternately a parallel capacitor) to discharge.

All of the optical sensors discussed herein may be used in conjunction with other sensors to improve detection of the data described above or be used to augment detection of other types of physiological or environmental data.

Where the biometric monitoring device includes an audio or passive acoustic sensor, the device may contain one or more passive acoustic sensors that detect sound and pressure and that can include, but are not limited to, microphones, piezo films, etc. The acoustic sensors may be disposed on one or more sides of the device, including the side that touches or faces the skin (skin-side) and the sides that face the environment (environmental sides).

Skin-side acoustic or audio sensors may detect any type of sound transmitted through the body and such sensors may be arranged in an array or pattern that optimizes both the signal-to-noise-ratio and power consumption of such sensors. These sensors may detect respiration (e.g., by listening to the lung), respiratory sounds (e.g., breathing, snoring) and problems (e.g., sleep apnea, etc.), heart rate (listening to the heart beat), user's voice (via sound transmitted from the vocal cords throughout the body).

The biometric monitoring devices of the present disclosure may also include galvanic skin-response (GSR) circuitry to measure the response of the user's skin to emotional and physical stimuli or physiological changes (e.g., the transition of sleep stage). In some embodiments, the biometric monitoring device may be a wrist- or arm-mounted device incorporating a band made of conductive rubber or fabric so that the galvanic skin response electrodes may be hidden in the band. Because the galvanic skin response circuitry may be subjected to changing temperatures and environmental conditions, it may also include circuitry to enable automatic calibration, such as two or more switchable reference resistors in parallel or in series with the human skin/electrode path that allows real-time measurement of known resistors to characterize the response of the galvanic skin response circuit. The reference resistors may be switched into and out of the measurement path such that they are measured independently and/or simultaneously with the resistance of the human skin.

Circuits for Performing PPG

PPG circuitry may be optimized to obtain the best quality signal regardless of a variety of environmental conditions including, but not limited to, motion, ambient light, and skin color. The following circuits and techniques may be used to perform such optimization (see FIGS. 16A through 16J);

- a sample-and-hold circuit and differential/instrumentation amplifier which may be used in PPG sensing. The output signal is an amplified difference between current and previous sample, referenced to a given voltage.
- controlled current source to offset "bias" current prior to transimpedance amplifier. This allows greater gain to be applied at transimpedance amplifier stage.
- a sample-and-hold circuit for current feedback applied to photodiode (prior to transimpedance amplifier). This can be used for ambient light removal, or "bias" current removal, or as a pseudo differential amplifier (may require dual rails).
- a differential/instrumentation amplifier with ambient light cancellation.
- a photodiode offset current generated dynamically by a DAC.
- a photodiode offset current generated dynamically by controlled voltage source.
- ambient light removal using a "switched capacitor" method.
- photodiode offset current generated by a constant current source (also can be done with a constant voltage source and a resistor).
- ambient light removal and differencing between consecutive samples.
- ambient light removal and differencing between consecutive samples.

Figure 16A:
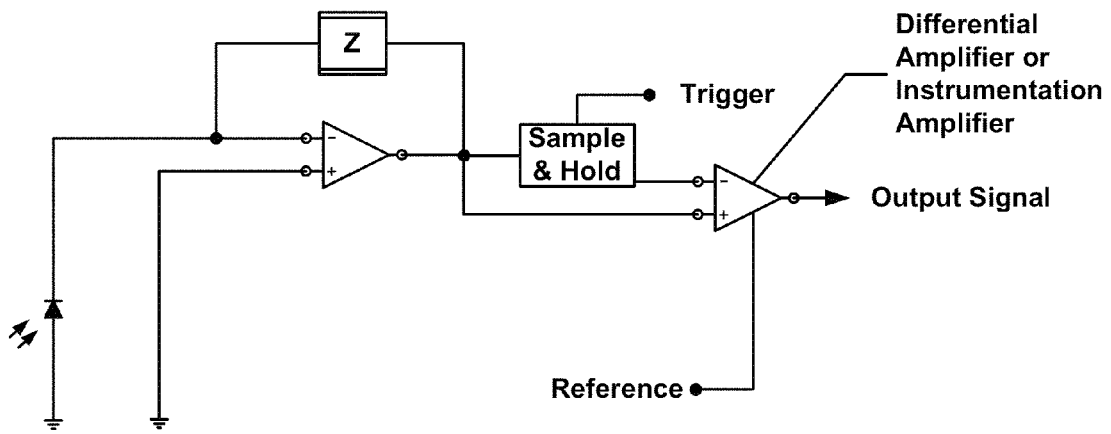
FIG. 16A illustrates an example schematic of a sample-and-hold circuit and differential/instrumentation amplifier which may be used in PPG sensing.

FIG. 16A illustrates an example schematic of a sample-and-hold circuit and differential/instrumentation amplifier which may be used in PPG sensing. The output signal in such a circuit may be an amplified difference between a current sample and a previous sample, referenced to a given voltage.

Figure 16B:
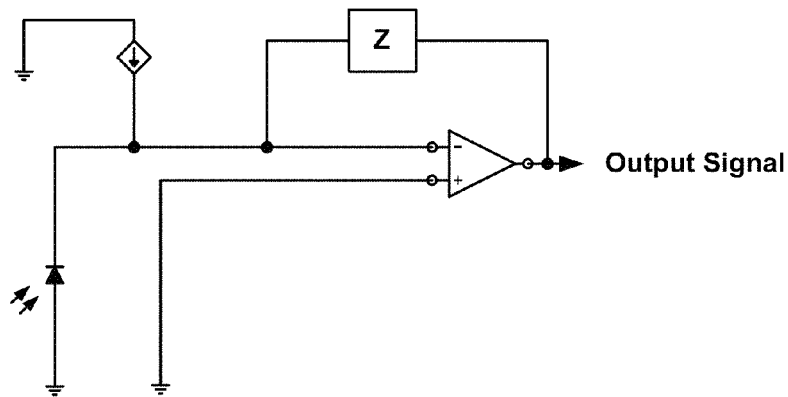
FIG. 16B illustrates an example schematic of a circuit for a PPG sensor using a controlled current source to offset "bias" current prior to a transimpedance amplifier

FIG. 16B illustrates an example schematic of a circuit for a PPG sensor using a controlled current source to offset "bias" current prior to a transimpedance amplifier. This allows greater gain to be applied at the transimpedance amplifier stage.

Figure 16C:
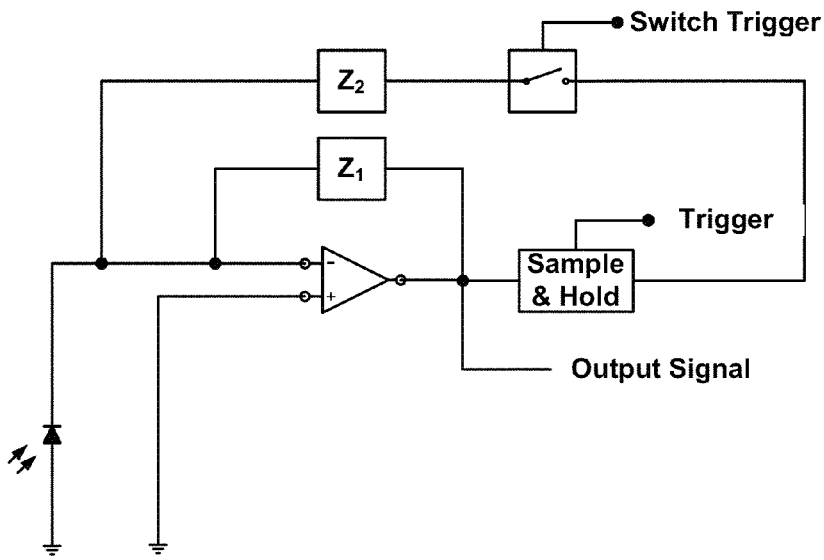
FIG. 16C illustrates an example schematic of a circuit for a PPG sensor using a sample-and-hold circuit for current feedback applied to photodiode (prior to a transimpedance amplifier).

FIG. 16C illustrates an example schematic of a circuit for a PPG sensor using a sample-and-hold circuit for current feedback applied to photodiode (prior to a transimpedance amplifier). This circuit may be used for ambient light removal, or "bias" current removal, or as a pseudo-differential amplifier.

Figure 16D:
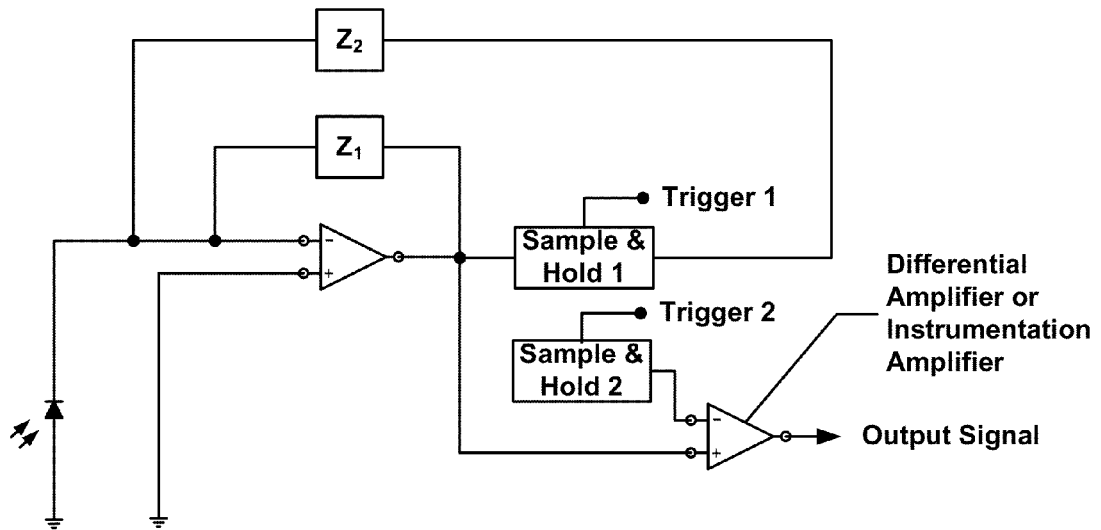
FIG. 16D illustrates an example schematic of a circuit for a PPG sensor using a differential/instrumentation amplifier with ambient light cancellation functionality.

FIG. 16D illustrates an example schematic of a circuit for a PPG sensor using a differential/instrumentation amplifier with ambient light cancellation functionality.

Figure 16E:
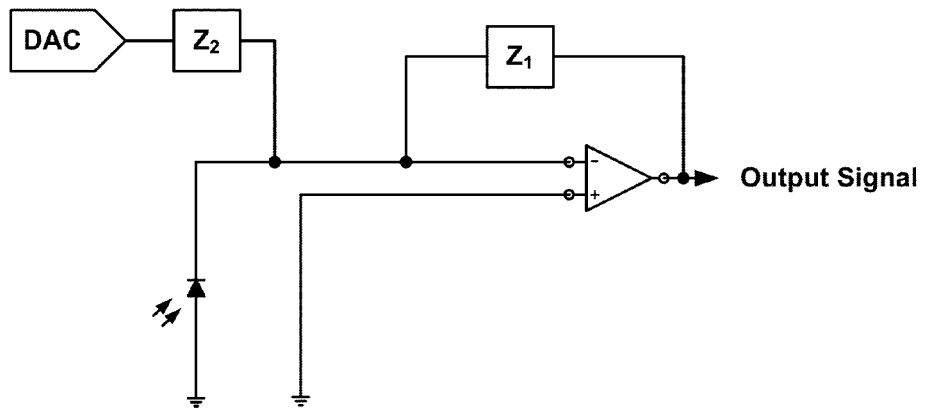
FIG. 16E illustrates an example schematic of a circuit for a PPG sensor using a photodiode offset current generated dynamically by a DAC.

FIG. 16E illustrates an example schematic of a circuit for a PPG sensor using a photodiode offset current generated dynamically by a DAC.

Figure 16F:
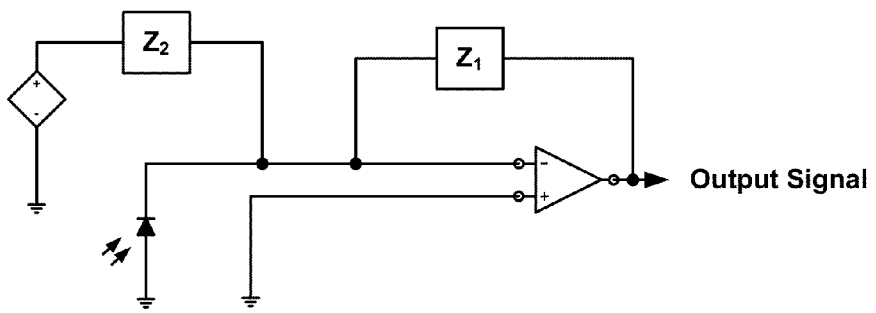
FIG. 16F illustrates an example schematic of a circuit for a PPG sensor using a photodiode offset current generated dynamically by a controlled voltage source.

FIG. 16F illustrates an example schematic of a circuit for a PPG sensor using a photodiode offset current generated dynamically by a controlled voltage source.

Figure 16G:
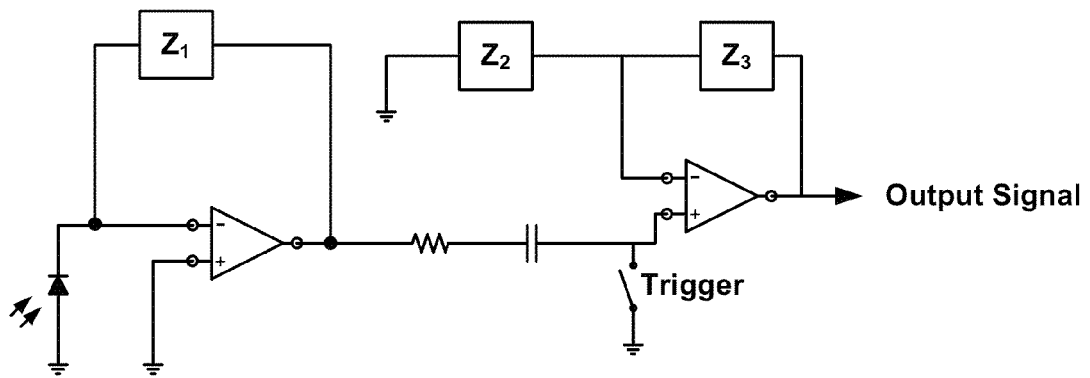
FIG. 16G illustrates an example schematic of a circuit for a PPG sensor including ambient light removal functionality using a "switched capacitor" method.

FIG. 16G illustrates an example schematic of a circuit for a PPG sensor including ambient light removal functionality using a "switched capacitor" method.

Figure 16H:
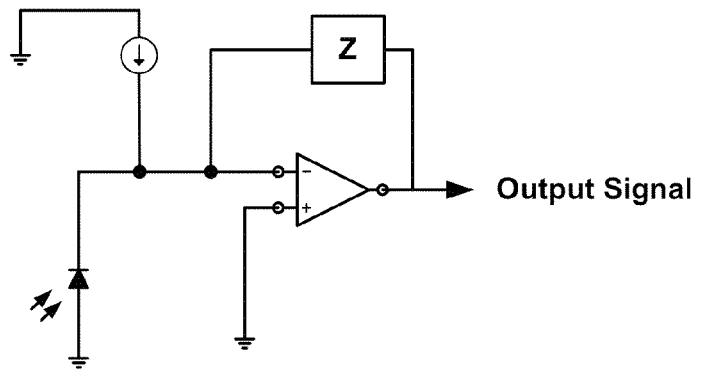
FIG. 16H illustrates an example schematic of a circuit for a PPG sensor that uses a photodiode offset current generated by a constant current source (this may also be done using a constant voltage source and a resistor).

FIG. 16H illustrates an example schematic of a circuit for a PPG sensor that uses a photodiode offset current generated by a constant current source (this may also be done using a constant voltage source and a resistor).

Figure 16I:
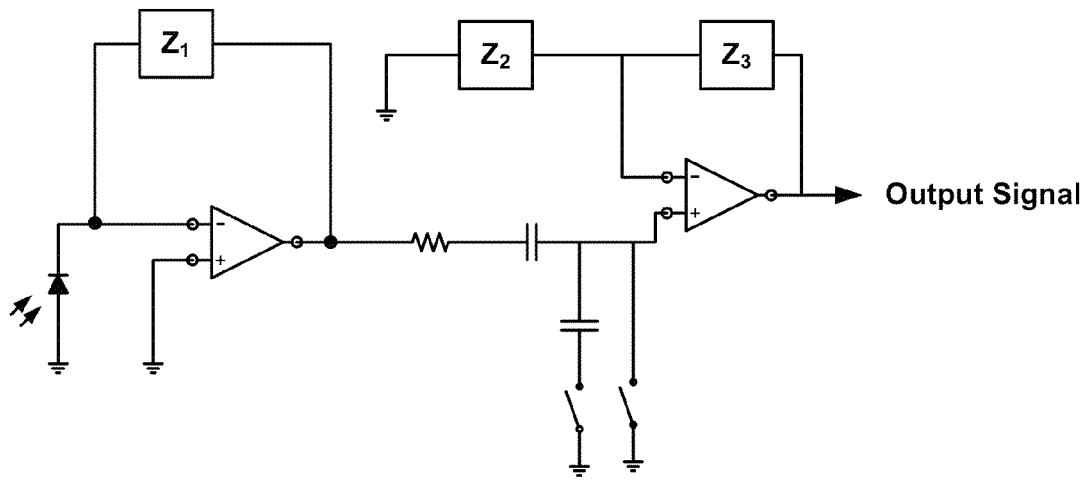
FIG. 16I illustrates an example schematic of a circuit for a PPG sensor that includes ambient light removal functionality and differencing between consecutive samples.

FIG. 16I illustrates an example schematic of a circuit for a PPG sensor that includes ambient light removal functionality and differencing between consecutive samples.

Figure 16J:
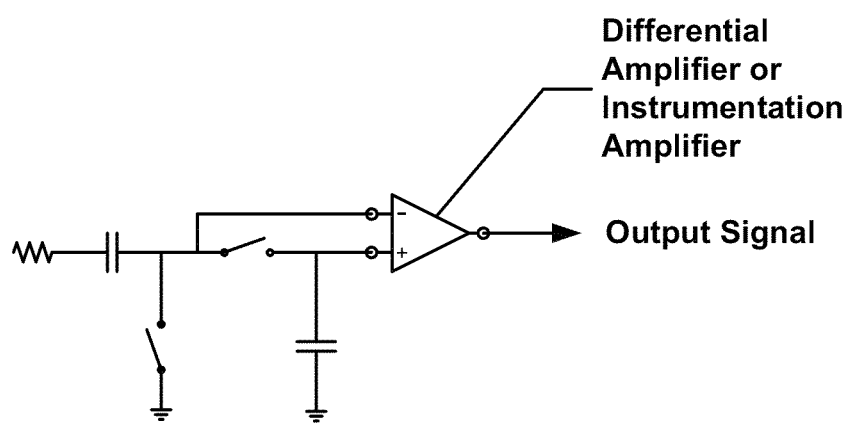
FIG. 16J illustrates an example schematic of a circuit for ambient light removal and differencing between consecutive samples.

FIG. 16J illustrates an example schematic of a circuit for ambient light removal and differencing between consecutive samples.

Various circuits and concepts related to heart rate measurement using a PPG sensor are discussed in more detail in U.S. Provisional Patent Application No. 61/946,439, filed Feb. 28, 2014, which was previously incorporated herein by reference in the "Cross-Reference to Related Applications" section and which is again hereby incorporated by reference with respect to content directed at heart rate measurements with a PPG sensor and at circuits, methods, and systems for performing such measurements, e.g., to compensate for sensor saturation, ambient light, and skin tone.

Biometric Feedback

Some embodiments of biometric monitoring devices may provide feedback to the user based on one or more biometric signals. In one embodiment, a PPG signal may be presented to the user as a real-time or near-real-time waveform on a display of the biometric monitoring device (or on a display of a secondary device in communication with the biometric monitoring device). This waveform may provide similar feedback to the waveform displayed on an ECG or EKG machine. In addition to providing the user with an indication of the PPG signal which may be used to estimate various heart metrics (e.g., heart rate), the waveform may also provide feedback that may enable the user to optimize the position and pressure with which they are wearing the biometric monitoring device. For example, the user may see that the waveform has a low amplitude. In response to this, the user may try moving the position of the biometric monitoring device to a different location which gives a higher amplitude signal. In some implementations, the biometric monitoring device may, based on such indications, provide instructions to the user to move or adjust the fit of the biometric monitoring device so as to improve the signal quality.

In another embodiment, feedback about the quality of the PPG signal may be provided to the user through a method other than displaying the waveform. The biometric monitoring device may emit an auditory alarm (e.g. a beep) if the signal quality (e.g. signal to noise ratio) exceeds a certain threshold. The biometric monitoring device may provide a visual cue (through the use of a display for example) to the user to either change the position of the sensor and/or increase the pressure with which the device is being worn (for example by tightening a wrist strap in the case that the device is worn on the wrist).

Biometric feedback may be provided for sensors other than PPG sensors. For example, if the device uses ECG, EMG, or is connected to a device which performs either of these, it may provide feedback to the user regarding the waveform from those sensors. If the signal-to-noise-ratio of these sensors is low, or the signal quality is otherwise compromised, the user may be instructed on how they can improve the signal. For example, if the heart rate cannot be detected from the ECG sensor, the device may provide a visual message to the user instructing them to wet or moisten the ECG electrodes to improve the signal.

Environmental Sensors

Some embodiments of biometric monitoring devices of the present disclosure may use one, some or all of the following environmental sensors to, for example, acquire the environmental data, including environmental data outlined in the table below. Such biometric monitoring devices are not limited to the number or types of sensors specified below but may employ other sensors that acquire environmental data outlined in the table below. All combinations and permutations of environmental sensors and/or environmental data are intended to fall within the scope of the present disclosure. Additionally, the device may derive environmental data from the corresponding sensor output data, but is not limited to the types of environmental data that it could derive from said sensor.

Notably, embodiments of biometric monitoring devices of the present disclosure may use one or more, or all of the environmental sensors described herein and one or more, or all of the physiological sensors described herein. Indeed, biometric monitoring device of the present disclosure may acquire any or all of the environmental data and physiological data described herein using any sensor now known or later developed—all of which are intended to fall within the scope of the present disclosure.

| Environmental Sensors | Environmental data acquired |
| --- | --- |
| Motion Detector<br>Potential Embodiments:<br>Inertial, Gyroscopic or Accelerometer-based Sensors<br>GPS | Location |
| Pressure/Altimeter sensor | Elevation |
| Ambient Temp | Temperature |
| Light Sensor | Indoor vs outdoor<br>Watching TV (spectrum/flicker rate detection)<br>Optical data transfer-initiation, QR codes, etc.<br>Ultraviolet light exposure |
| Audio | Indoor vs. Outdoor |
| Compass<br>Potential Embodiments:<br>3 Axis Compass | Location and/or orientation |

Figure 12C:
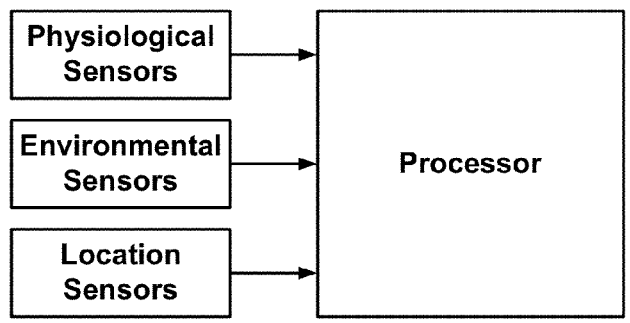
FIG. 12C illustrates an example of a portable biometric monitoring device having physiological sensors, environmental sensors, and location sensors connected to a processor.
Figure 13A:
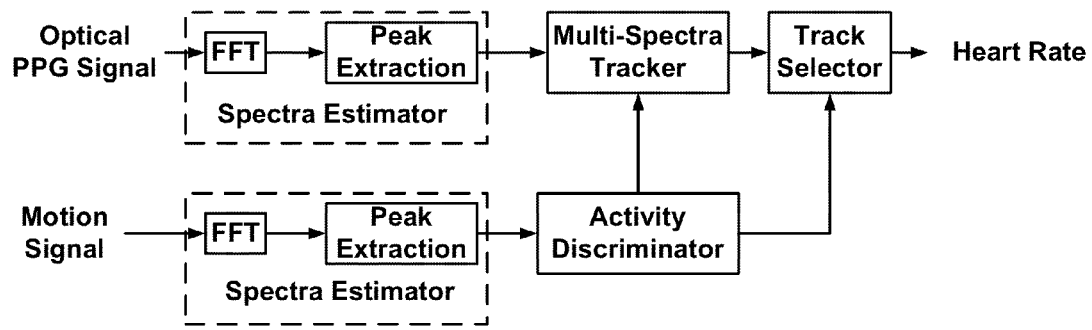
FIG. 13A illustrates an example of the use of a motion signal and an optical PPG signal to measure a heart rate.
Figure 13B:
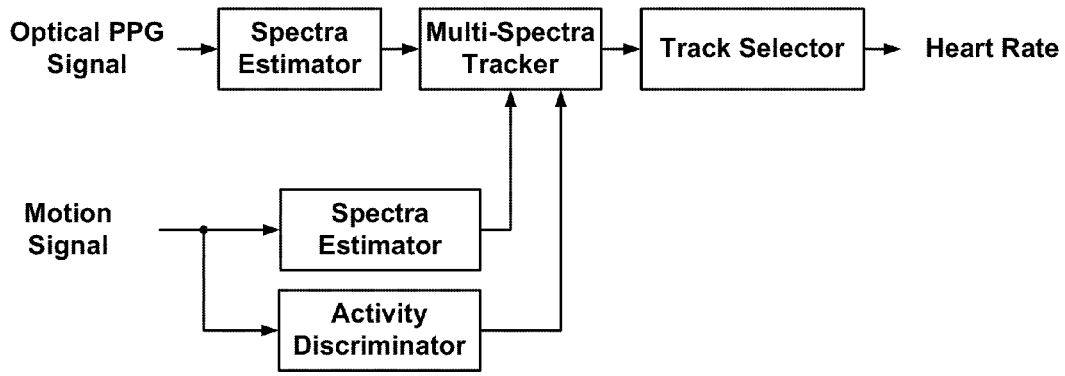
FIG. 13B illustrates another example of the use of a motion signal and an optical PPG signal to measure heart rate.
Figure 14A:
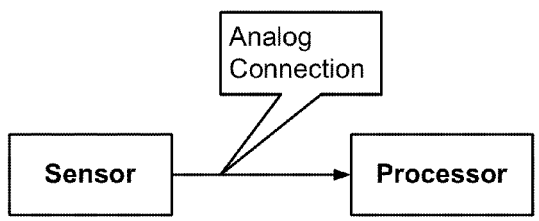
FIG. 14A illustrates an example of a sensor which has an analog connection to a sensor processor.
Figure 14B:
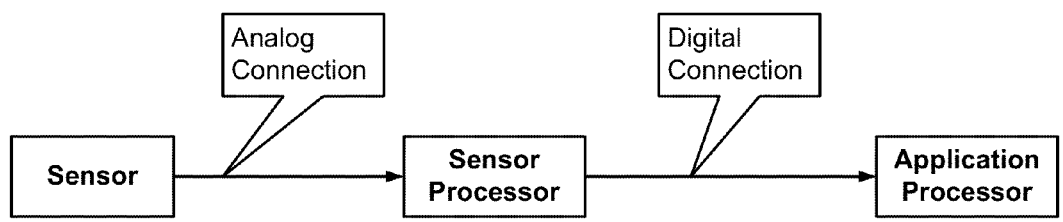
FIG. 14B illustrates an example of a sensor which has an analog connection to a sensor processor which, in turn, has a digital connection to an application processor.
Figure 14C:
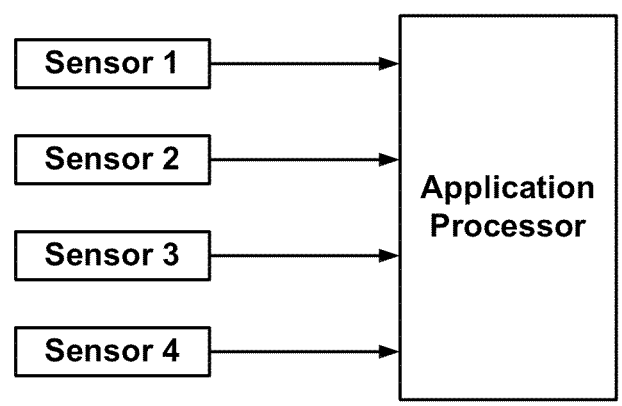
FIG. 14C illustrates an example of a sensor device which has one or multiple sensors connected to an application processor.
Figure 14D:
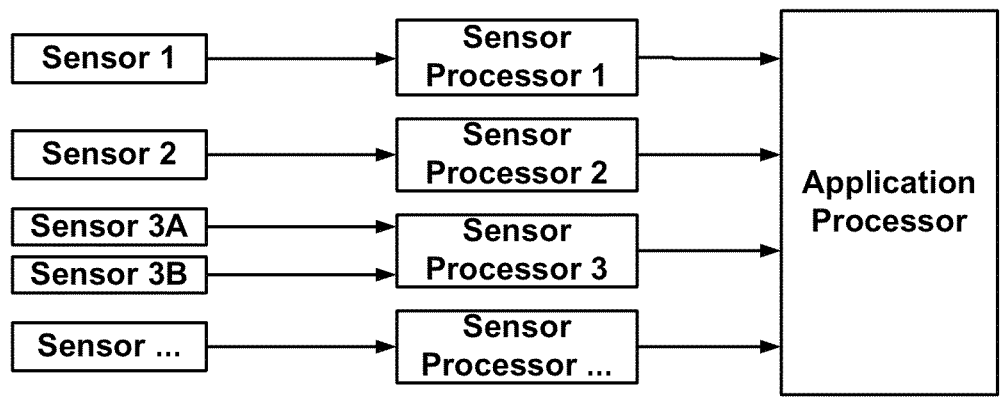
FIG. 14D illustrates an example of a sensor device which has one or multiple sensors connected to sensor processors which, in turn, are connected to an application processor.

In one embodiment, the biometric monitoring device may include an altimeter sensor, for example, disposed or located in the interior of the device housing. (See, for example, FIGS. 12B and 12C; FIG. 12C illustrates an example of a portable biometric monitoring device having physiological sensors, environmental sensors, and location sensors connected to a processor). In such a case, the device housing may have a vent that allows the interior of the device to measure, detect, sample and/or experience any changes in exterior pressure. In one embodiment, the vent may prevent water from entering the device while facilitating measuring, detecting and/or sampling changes in pressure via the altimeter sensor. For example, an exterior surface of the biometric monitoring device may include a vent type configuration or architecture (for example, a Gore™ vent) that allows ambient air to move in and out of the housing of the device (which allows the altimeter sensor to measure, detect and/or sample changes in pressure), but reduces, prevents, and/or minimizes water and other liquids from flowing into the housing of the device.

The altimeter sensor, in one embodiment, may be filled with gel that allows the sensor to experience pressure changes outside of the gel. The gel may act as a relatively impervious, incompressible, yet flexible, membrane that transmits external pressure variations to the altimeter while physically separating the altimeter (and other internal components) from the outside environment. The use of a gel-filled altimeter may give the device a higher level of environmental protection with or without the use of an environmentally sealed vent. The device may have a higher survivability rate with a gel-filled altimeter in locations including, but not limited to, locations that have high humidity, clothes washers, dish washers, clothes dryers, a steam room or sauna, a shower, a pool, a bath, and any location where the device may be exposed to moisture, exposed to liquid, or submerged in liquid.

Sensors Integration/Signal Processing

Some embodiments of the biometric monitoring devices of the present disclosure may use data from two or more sensors to calculate the corresponding physiological or environmental data as seen in the table below (for example, data from two or more sensors may be used in combination to determine metrics such as those listed below). The biometric monitoring device may include, but is not limited to, the number, types, or combinations of sensors specified below. Additionally, such biometric monitoring devices may derive the included data from the corresponding sensor combinations, but are not limited to the number or types of data that may be calculated from the corresponding sensor combinations.

| Sensor Integrations | Data derived from signal processing of multiple sensors |
| --- | --- |
| Skin Temp and Ambient Temp | Heat Flux |
| Heart Rate and Motion | Elevation gain |
| Motion detector and other user's motion detector (linked by wireless communication path) | Users in the proximity |
| Motion, any heart rate sensor, galvanic skin response | Sit/ Standing detection |
| Any heart rate, heart rate variability sensor, respiration, motion | Sleep Phase detection<br>Sleep Apnea detection |
| Any heart rate sensor and/or wetness sensor, and/or motion detector | Resting Heart rate<br>Active Heart Rate<br>Heart rate while asleep<br>Heart rate while sedentary |
| Any heart rate detector | Early detection of heart problems:<br>Cardiac Arrhythmia<br>Cardiac Arrest |
| Multiple heart rate detectors | Pulse transit time |
| Audio and/or strain gauge | Typing detection |
| GPS and photoplethysmography (PPG) | Location-stress correlation:<br>determination of stressful regions<br>determination of low stress regions<br>Activity-specific heart rate<br>resting heart rate<br>active heart rate<br>Automatic activity classification and activity heart rate determination |
| Heart rate, galvanic skin response, accelerometer and respiration | User fatigue, for example while exercising |

In some embodiments, the biometric monitoring device may also include a near-field communication (NFC) receiver/transmitter to detect proximity to another device, such as a mobile phone. When the biometric monitoring device is brought into close or detectable proximity to the second device, it may trigger the start of new functionality on the second device (e.g., the launching of an "app" on the mobile phone and radio syncing of physiological data from the device to the second device). (See, for example, FIG. 10). Indeed, the biometric monitoring device of the present disclosure may implement any of the circuitry and techniques described and/or illustrated in U.S. Provisional Patent Application 61/606,559, filed Mar. 5, 2012, "Near Field Communication System, and Method of Operating Same", inventor: James Park (the contents of which are incorporated herein by reference for such purpose).

Figure 10:
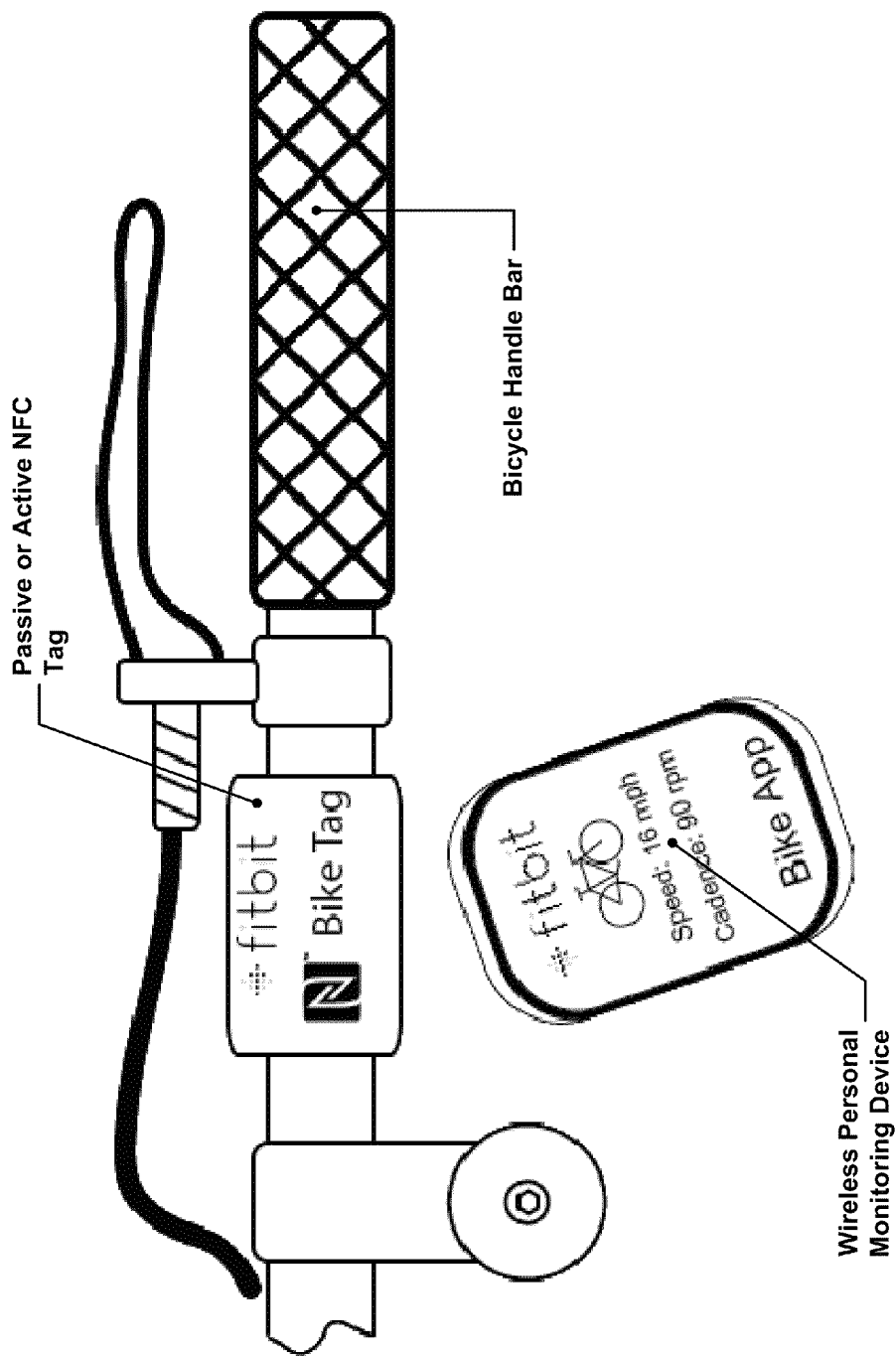
FIG. 10 illustrates an example of a portable biometric monitoring device that has a bicycle application on it that may display bicycle speed and/or pedaling cadence, among other metrics.

FIG. 10 illustrates an example of a portable biometric monitoring device that has a bicycle application on it that may display bicycle speed and/or pedaling cadence, among other metrics. The app may be activated whenever the biometric monitoring device comes into proximity of a passive or active NFC tag. This NFC tag may be attached to the user's handlebars.

In another embodiment, the biometric monitoring device may include a location sensor (for example, GPS circuitry) and heart rate sensor (for example, photoplethysmography circuitry) to generate GPS- or location-related data and heart rate-related data, respectively. (See, for example, FIGS. 12B and 12C). The biometric monitoring device may then fuse, process and/or combine data from these two sensors/circuitries to, for example, determine, correlate, and/or "map" geographical regions according to physiological data (for example, heart rate, stress, activity level, quantity of sleep and/or caloric intake). In this way, the biometric monitoring device may identify geographical regions that increase or decrease a measurable user metric including, but not limited to, heart rate, stress, activity, level, quantity of sleep and/or caloric intake.

In addition thereto, or in lieu thereof, some embodiments of biometric monitoring devices may employ GPS-related data and photoplethysmography-related data (notably, each of which may be considered data streams) to determine or correlate the user's heart rate according to activity levels—for example, as determined by the user's acceleration, speed, location and/or distance traveled (as measured by the GPS and/or determined from GPS-related data). (See, for example, FIGS. 12B and 12C). Here, in one embodiment, heart rate as a function of speed may be "plotted" for the user, or the data may be broken down into different levels including, but not limited to, sleeping, resting, sedentary, moderately active, active, and highly active.

Indeed, some embodiments of biometric monitoring devices may also correlate GPS-related data to a database of predetermined geographic locations that have activities associated with them for a set of predetermined conditions. For example, activity determination and corresponding physiological classification (for example, heart rate classification) may include correlating a user's GPS coordinates that correspond to location(s) of exercise equipment, health club and/or gym and physiological data. Under these circumstances, a user's heart rate during, for example a gym workout, may be automatically measured and displayed. Notably, many physiological classifications may be based on GPS-related data including location, acceleration, altitude, distance and/or velocity. Such a database including geographic data and physiological data may be compiled, developed and/or stored on the biometric monitoring device and/or external computing device. Indeed, in one embodiment, the user may create their own location database or add to or modify the location database to better classify their activities.

In another embodiment, the user may simultaneously wear multiple biometric monitoring devices (having any of the features described herein). The biometric monitoring devices of this embodiment may communicate with each other or a remote device using wired or wireless circuitry to calculate, for example, biometric or physiologic qualities or quantities that, for example, may be difficult or inaccurate to calculate otherwise, such as pulse transit time. The use of multiple sensors may also improve the accuracy and/or precision of biometric measurements over the accuracy and/or precision of a single sensor. For example, having a biometric tracking device on the waist, wrist, and ankle may improve the detection of the user taking a step over that of a single device in only one of those locations. Signal processing may be performed on the biometric tracking devices in a distributed or centralized method to provide measurements improved over that of a single device. This signal processing may also be performed remotely and communicated back to the biometric tracking devices after processing.

In another embodiment, heart rate or other biometric data may be correlated to a user's food log (a log of foods ingested by a user, their nutritional content, and portions thereof). Food log entries may be entered into the food log automatically or may be entered by the user themselves through interaction with the biometric monitoring device (or a secondary or remote device, e.g., a smartphone, in communication with the biometric monitoring device or some other device, e.g., a server, in communication with the biometric monitoring device). Information may be presented to the user regarding the biometric reaction of their body to one or more food inputs. For example, if a user has coffee, their heart rate may rise as a result of the caffeine. In another example, if a user has a larger portion of food late at night, it may take longer for them to fall asleep than usual. Any combination of food input and corresponding result in biometrics may be incorporated into such a feedback system.

The fusion of food intake data and biometric data may also enable some embodiments of biometric monitoring device to make an estimation of a user's glucose level. This may be particularly useful for users who have diabetes. With an algorithm which relates the glucose level to the user's activity (e.g. walking, running, calorie burn) and nutritional intake, a biometric monitoring device may be able to advise the user when they are likely to have an abnormal blood sugar level.

Processing Task Delegation

Embodiments of biometric monitoring devices may include one or more processors. Figures. For example, an independent application processor may be used to store and execute applications that utilize sensor data acquired and processed by one or more sensor processors (processor(s) that process data from physiological, environmental, and/or activity sensors). In the case where there are multiple sensors, there may also be multiple sensor processors. An application processor may have sensors directly connected to it as well. Sensor and application processors may exist as separate discrete chips or exist within the same packaged chip (multi-core). A device may have a single application processor, or an application processor and sensor processor, or a plurality of application processors and sensor processors.

In one embodiment, the sensor processor may be placed on a daughterboard that consists of all of the analog components. This board may have some of the electronics typically found on the main PCB such as, but not limited to, transimpedance amplifiers, filtering circuits, level shifters, sample-and-hold circuits, and a microcontroller unit. Such a configuration may allow the daughterboard to be connected to the main PCB through the use of a digital connection rather than an analog connection (in addition to any necessary power or ground connections). A digital connection may have a variety of advantages over an analog daughterboard to main PCB connection, including, but not limited to, a reduction in noise and a reduction in the number of necessary cables. The daughterboard may be connected to the main board through the use of a flex cable or set of wires.

Multiple applications may be stored on an application processor. An application may consist of executable code and data for the application, but is not limited to these. Data may consist of graphics or other information required to execute the application or it may be information output generated by the application. The executable code and data for the application may both reside on the application processor (or memory incorporated therein) or the data for the application may be stored and retrieved from an external memory. External memory may include but is not limited to NAND flash, NOR flash, flash on another processor, other solid-state storage, mechanical or optical disks, RAM, etc.

The executable code for an application may also be stored in an external memory. When a request to execute an application is received by the application processor, the application processor may retrieve the executable code and/or data from the external storage and execute it. The executable code may be temporarily or permanently stored on the memory or storage of the application processor. This allows the application to be executed more quickly on the next execution request, since the step of retrieval is eliminated. When the application is requested to be executed, the application processor may retrieve all of the executable code of the application or portions of the executable code. In the latter case, only the portion of executable code required at that moment is retrieved. This allows applications that are larger than the application processor's memory or storage to be executed.

The application processor may also have memory protection features to prevent applications from overwriting, corrupting, interrupting, blocking, or otherwise interfering with other applications, the sensor system, the application processor, or other components of the system.

Applications may be loaded onto the application processor and/or any external storage via a variety of wired, wireless, optical, or capacitive mechanisms including, but not limited to, USB, Wi-Fi, Bluetooth, Bluetooth Low Energy, NFC, RFID, Zigbee.

Applications may also be cryptographically signed with an electronic signature. The application processor may restrict the execution of applications to those that have the correct signature.

Integration of Systems in a Biometric Monitoring Device

In some implementations of biometric monitoring devices, some sensors or electronic systems in the biometric monitoring device may be integrated with one another or may share components or resources. For example, a photodetector for an optically-based heart rate sensor (such as may be used in the heart-rate sensors discussed in U.S. Provisional Patent Application No. 61/946,439, filed Feb. 28, 2014, and previously incorporated by reference herein, may also serve as a photodetector for determining ambient light level, such as may be used to correct for the effects of ambient light on the heart rate sensor reading. For example, if the light source for such a heart rate detector is turned off, the light that is measured by the photodetector may be indicative of the amount of ambient light that is present.

In some implementations of a biometric monitoring device, the biometric monitoring device may be configured or communicated with using onboard optical sensors such as the components in an optical heart rate monitor. For example, the photodetectors of an optical heart-rate sensor (or, if present, an ambient light sensor) may also serve as a receiver for an optically-based transmission channel, e.g., infrared communications.

In some implementations of a biometric monitoring device, a hybrid antenna may be included that combines a radio frequency antenna, e.g., a Bluetooth antenna or GPS antenna, with an inductive loop, such as may be used in a near-field communications (NFC) tag or in an inductive charging system. In such implementations, the functionality for two different systems may be provided in one integrated system, saving packing volume. In such a hybrid antenna, an inductive loop may be placed in close proximity to the radiator of an inverted-F antenna. The inductive loop may inductively couple with the radiator, allowing the inductive loop to serve as a planar element of the antenna for radio-frequency purposes, thus forming, for example, a planar inverted-F antenna. At the same time, the inductive loop may also serve its normal function, e.g., such as providing current to an NFC chip through inductive coupling with an electromagnetic field generated by an NFC reader. Examples of such hybrid antenna systems are discussed in more detail in U.S. Provisional Patent Application No. 61/948,470, filed Mar. 5, 2014, which was previously incorporated herein by reference in the "Cross-Reference to Related Applications" section and which is again hereby incorporated by reference with respect to content directed at hybrid antenna structures. Of course, such hybrid antennas may also be used in other electronic devices other than biometric monitoring devices, and such non-biometric-monitoring-device use of hybrid antennas is contemplated as being within the scope of this disclosure.

Methods of Wearing the Device

Some embodiments of biometric monitoring devices may include a housing having a size and shape that facilitates fixing the biometric monitoring device to the user's body during normal operation wherein the device, when coupled to the user, does not measurably or appreciably impact the user's activity. The biometric monitoring device may be worn in different ways depending on the specific sensor package that is integrated into the biometric monitoring device and the data that the user would like to acquire.

A user may wear some embodiments of the biometric monitoring devices of the present disclosure on their wrist or ankle (or arm or leg) with the use of a band that is flexible and thereby readily fitted to the user. The band may have an adjustable circumference, therefore allowing it to be fitted to the user. The band may be constructed from a material that shrinks when exposed to heat, therefore allowing the user to create a custom fit. The band may be detachable from the "electronics" portion of the biometric monitoring device and, if necessary, replaceable.

In some embodiments, the biometric monitoring device may consist of two major components—a body (containing the "electronics") and a band (that facilitates attaching the device to the user). The body may include a housing (made, for example, of a plastic or plastic-like material) and extension tabs projecting from the body (made, for example, from a metal or metal-like material). (See, for example, FIGS. 2C through 3C). The band (made, for example, of a thermoplastic urethane) may be attachable to the body, e.g., mechanically or adhesively. The band may extend out a fraction of the circumference of the user's wrist. The distal ends of the urethane band may be connected with a Velcro or a hook-and-loop elastic fabric band that loops around a D-Ring on one side and then attaches back to itself. In this embodiment, the closure mechanism may allow the user infinite band length adjustment (unlike an indexed hole and mechanical clasp closure). The Velcro or elastic fabric may be attached to the band in a manner that allows it to be replaced (for example, if it is worn or otherwise undesirable to wear before the useful end of life of the device). In one embodiment, the Velcro or fabric may be attached with screws or rivets and/or glue, adhesives, and/or a clasp to the band.

Embodiments of the biometric monitoring devices of the present disclosure may also be integrated into and worn in a necklace, chest band, bra, adhesive patch, glasses, earring, or toe band. Such biometric monitoring devices may be built in such a way that the sensor package/portion of the biometric monitoring device is removable and may be worn in any number of ways including, but not limited to, those listed above.

In another embodiment, embodiments of biometric monitoring devices of the present disclosure may be worn clipped to an article of clothing or deposited in clothing (e.g., pocket) or an accessory (e.g., handbag, backpack, wallet). Because such biometric monitoring devices may not be near the user's skin, in embodiments that include heart rate measurements, the measurements may be obtained in a discrete, "on demand" context by the user manually placing the device into a specific mode (e.g., by depressing a button, covering a capacitive touch sensor with a fingertip, etc., possibly with the heart rate sensor embedded in the button/sensor) or automatically once the user places the device against the skin (e.g., applying the finger to an optical heart rate sensor).

User Interface with the Device

Some embodiments of a biometric monitoring device may include functionality for allowing one or more methods of interacting with the device either locally or remotely.

In some embodiments, the biometric monitoring device may convey data visually through a digital display. The physical embodiment of this display may use any one or a plurality of display technologies including, but not limited to one or more of LED, LCD, AMOLED, E-Ink, Sharp display technology, graphical displays, and other display technologies such as TN, HTN, STN, FSTN, TFT, IPS, and OLET. This display may show data acquired or stored locally on the device or may display data acquired remotely from other devices or Internet services. The biometric monitoring device may use a sensor (for example, an Ambient Light Sensor, "ALS") to control or adjust the amount of screen backlighting, if backlighting is used. For example, in dark lighting situations, the display may be dimmed to conserve battery life, whereas in bright lighting situations, the display brightness may be increased so that it is more easily read by the user.

In another embodiment, the biometric monitoring device may use single or multicolor LEDs to indicate a state of the device. States that the biometric monitoring device may indicate using LEDs may include, but are not limited to, biometric states such as heart rate or application states such as an incoming message or that a goal has been reached. These states may be indicated through the LED's color, the LED being on or off (or in an intermediate intensity), pulsing (and/or rate thereof) of the LEDs, and/or a pattern of light intensities from completely off to highest brightness. In one embodiment, an LED may modulate its intensity and/or color with the phase and frequency of the user's heart rate.

In some embodiments, the use of an E-Ink display may allow the display to remain on without the battery drain of a non-reflective display. This "always-on" functionality may provide a pleasant user experience in the case of, for example, a watch application where the user may simply glance at the biometric monitoring device to see the time. The E-Ink display always displays content without comprising the battery life of the device, allowing the user to see the time as they would on a traditional watch.

Some implementations of a biometric monitoring device may use a light such as an LED to display the heart rate of the user by modulating the amplitude of the light emitted at the frequency of the user's heart rate. The device may depict heart rate zones (e.g., aerobic, anaerobic, etc.) through the color of an LED (e.g., green, red) or a sequence of LEDs that light up in accordance with changes in heart rate (e.g., a progress bar). The biometric monitoring device may be integrated or incorporated into another device or structure, for example, glasses or goggles, or communicate with glasses or goggles to display this information to the user.

Some embodiments of a biometric monitoring device may also convey information to a user through the physical motion of the device. One such embodiment of a method to physically move the device is the use of a vibration-inducing motor. The device may use this method alone, or in combination with a plurality of other motion-inducing technologies.

In some implementations, a biometric monitoring device may convey information to a user through audio feedback. For example, a speaker in the biometric monitoring device may convey information through the use of audio tones, voice, songs, or other sounds.

These three information communication methods—visual, motion, and auditory—may, in various embodiments of biometric monitoring devices, be used alone or in any combination with each other or another method of communication to communicate any one or plurality of the following information:

That a user needs to wake up at certain time

That a user should wake up as they are in a certain sleep phase

That a user should go to sleep as it is a certain time

That a user should wake up as they are in a certain sleep phase and in a preselected time window bounded by the earliest and latest time that the user wants to wake up.

That an email was received

That the user has been inactive for a certain period of time. Notably, this may integrate with other applications like, for instance, a meeting calendar or sleep tracking application to block out, reduce, or adjust the behavior of the inactivity alert.

That the user has been active for a certain period of time

That the user has an appointment or calendar event

That the user has reached a certain activity metric

That the user has gone a certain distance

That the user has reached a certain mile pace

That the user has reached a certain speed

That the user has accumulated a certain elevation gain

That the user has taken a certain number of steps

That the user has had a heart rate measurement recently

That the user's heart rate has reached a certain level

That the user has a normal, active, or resting heart rate of a specific value or in a specific range That the user's heart rate has enter or exited a certain goal range or training zone That the user has a new heart rate "zone" goal to reach, as in the case of heart rate zone training for running, bicycling, swimming, etc. activities That the user has swum a lap or completed a certain number of laps in a pool An external device has information that needs to be communicated to the user such as an incoming phone call or any one of the above alerts That the user has reached a certain fatigue goal or limit. In one embodiment, fatigue may be determined through a combination of heart rate, galvanic skin response, motion sensor, and/or respiration data These examples are provided for illustration and are not intended to limit the scope of information that may be communicated by such embodiments of biometric monitoring devices (for example, to the user). Note that the data used to determine whether or not an alert condition is met may be acquired from a first device and/or one or more secondary devices. The biometric monitoring device itself may determine whether the criteria or conditions for an alert have been met. Alternatively, a computing device in communication with the biometric monitoring device (e.g., a server and/or a mobile phone) may determine when the alert should occur. In view of this disclosure, other information that the biometric monitoring device may communicate to the user may be envisioned by one of ordinary skill in the art. For example, the biometric monitoring device may communicate with the user when a goal has been met. The criteria for meeting this goal may be based on physiological, contextual, and environmental sensors on a first device, and/or other sensor data from one or more secondary devices. The goal may be set by the user or may be set by the biometric monitoring device itself and/or another computing device in communication with the biometric monitoring device (e.g. a server). In an example embodiment, the biometric monitoring device may vibrate when a biometric goal is met.

Some embodiments of biometric monitoring devices of the present disclosure may be equipped with wireless and/or wired communication circuitry to display data on a secondary device in real time. For example, such biometric monitoring devices may be able to communicate with a mobile phone via Bluetooth Low Energy in order to give real-time feedback of heart rate, heart rate variability, and/or stress to the user. Such biometric monitoring devices may coach or grant "points" for the user to breathe in specific ways that alleviate stress (e.g. by taking slow, deep breaths). Stress may be quantified or evaluated through heart rate, heart rate variability, skin temperature, changes in motion-activity data and/or galvanic skin response.

Some embodiments of biometric monitoring devices may receive input from the user through one or more local or remote input methods. One such embodiment of local user input may use a sensor or set of sensors to translate a user's movement into a command to the device. Such motions could include but may not be limited to tapping, rolling the wrist, flexing one or more muscles, and swinging one's arm. Another user input method may be through the use of a button such as, but not limited to, capacitive touch buttons, capacitive screen buttons, and mechanical buttons. In one embodiment, the user interface buttons may be made of metal. In embodiments where the screen uses capacitive touch detection, it may always be sampling and ready to respond to any gesture or input without an intervening event such as pushing a physical button. Such biometric monitoring devices may also take input through the use of audio commands. All of these input methods may be integrated into biometric monitoring devices locally or integrated into a remote device that can communicate with such biometric monitoring devices, either through a wired or wireless connection. In addition, the user may also be able to manipulate the biometric monitoring device through a remote device. In one embodiment, this remote device may have Internet connectivity.

Alarms

In some embodiments, the biometric monitoring device of the present disclosure may act as a wrist-mounted vibrating alarm to silently wake the user from sleep. Such biometric monitoring devices may track the user's sleep quality, waking periods, sleep latency, sleep efficiency, sleep stages (e.g., deep sleep vs REM), and/or other sleep-related metrics through one or a combination of heart rate, heart rate variability, galvanic skin response, motion sensing (e.g., accelerometer, gyroscope, magnetometer), and skin temperature. The user may specify a desired alarm time or window of time (e.g., set alarm to go off between 7 am and 8 am). Such embodiments may use one or more of the sleep metrics to determine an optimal time within the alarm window to wake the user. In one embodiment, when the vibrating alarm is active, the user may cause it to hibernate or turn off by slapping or tapping the device (which is detected, for example, via motion sensor(s), a pressure/force sensor, and/or capacitive touch sensor in the device). In one embodiment, the device may attempt to arouse the user at an optimum point in the sleep cycle by starting a small vibration at a specific user sleep stage or time prior to the alarm setting. It may progressively increase the intensity or noticeability of the vibration as the user progresses toward wakefulness or toward the alarm setting. (See, for example, FIG. 8).

Figure 8:
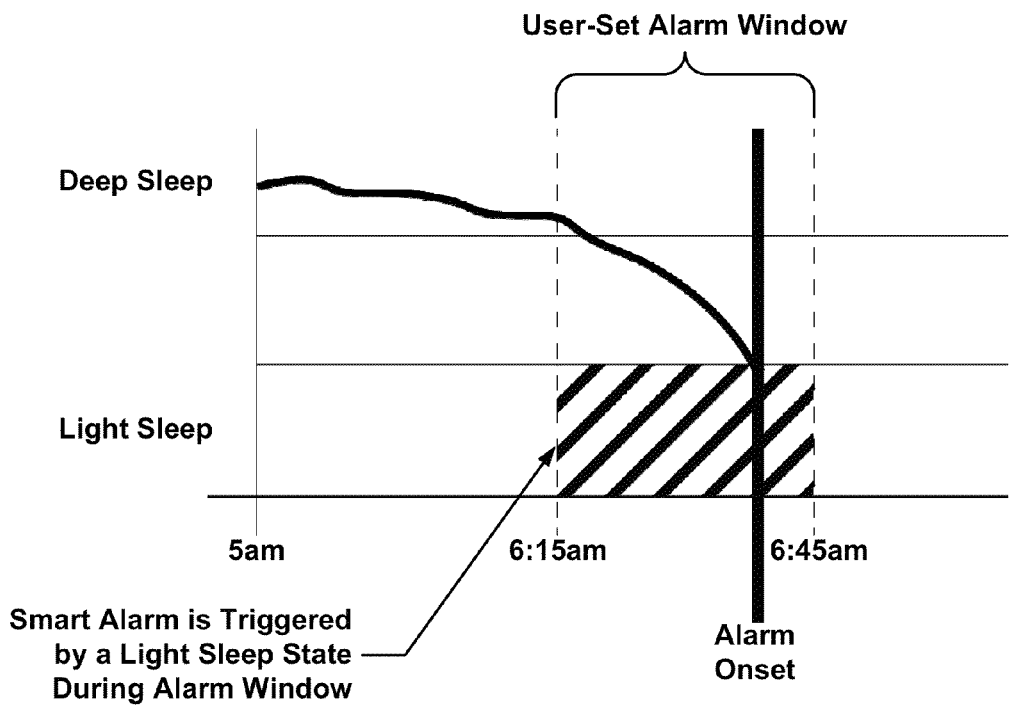
FIG. 8 illustrates functionality of an example biometric monitoring device smart alarm feature.

FIG. 8 illustrates functionality of an example portable biometric monitoring device smart alarm feature. The biometric monitoring device may be able to detect or may be in communication with a device that can detect the sleep stage or state of a user (e.g., light or deep sleep). The user may set a window of time which they would like to be awoken (e.g., 6:15 am to 6:45 am). The smart alarm may be triggered by the user going into a light sleep state during the alarm window.

The biometric monitoring device may be configured to allow the user to select or create an alarm vibration pattern of their choice. The user may have the ability to "snooze" or postpone an alarm event. In one embodiment, the user may be able to set the amount of delay for the "snooze" feature—the delay being the amount of time before the alarm will go off again. They may also be able to set how many times the snooze feature may be activated per alarm cycle. For example, a user may choose a snooze delay of 5 minutes and a maximum sequential snooze number to be 3. Therefore, they can press snooze up to 3 times to delay the alarm by 5 minutes each time they press snooze to delay the alarm. In such embodiments, the snooze function will not turn off the alarm if the user attempts to press snooze a fourth time.

Some biometric monitoring devices may have information about the user's calendar and/or schedule. The user's calendar information may be entered directly into the biometric monitoring device or it may be downloaded from a different device (e.g. a smartphone). This information may be used to automatically set alarms or alarm characteristics. For example, if a user has a meeting at 9 am in the morning, the biometric monitoring device may automatically wake the user up at 7:30 am to allow the user enough time to prepare for and/or get to the meeting. The biometric monitoring device may determine the amount of time required for the user to prepare for the meeting based on the user's current location, the location of the meeting, and the amount of time it would take to get the location of the meeting from the user's current location. Alternatively, historical data about how long the user takes to get to the meeting location and/or prepare to leave for the meeting (e.g. how long it takes to wake up, take a shower, have breakfast, etc. in the morning) may be used to determine at what time to wake the user. A similar functionality may be used for calendar events other than meetings such as eating times, sleeping times, napping times, and exercise times.

In some embodiments, the biometric monitoring device may use information on when the user went to sleep to determine when an alarm should go off to wake the user. This information may supplement calendar information described herein. The user may have a goal of approximately how many hours of sleep they would like to get each night or week. The biometric monitoring device may set the morning alarm at the appropriate time for the user to meet these sleep goals. In addition to amount of time that the user would like to sleep each night, other sleep goals that the user may set may include, but are not limited to, the amount of deep sleep, REM sleep, and light sleep that the user experiences while sleeping, all of which may be used by the biometric monitoring device to determine when to set an alarm in the morning. Additionally, the user may be alerted at night when they should go to bed to meet their sleep goals. Additionally, the user may be alerted during the day when they should take a nap to meet their sleep goals. The time at which to alert a user that they should take a nap may be determined by factors that optimize the user's sleep quality during the nap, subsequent naps, or night-time sleep. For example, the user is likely to have a hard time falling asleep at night if they took a nap in the early evening. The user may also be advised to eat certain foods or drinks or avoid certain foods or drinks to optimize their sleep quality. For example, a user may be discouraged from drinking alcohol close to their bed time as it is likely to decrease their sleep quality. The user may also be advised to perform certain activities or avoid certain activities to optimize their sleep quality. For example, a user may be encouraged to exercise in the early afternoon to improve their sleep quality. A user may be discouraged from exercising or watching TV close to their bedtime to improve their sleep quality.

User Interface with a Secondary Device

In some embodiments, the biometric monitoring device may transmit and receive data and/or commands to and/or from a secondary electronic device. The secondary electronic device may be in direct or indirect communication with the biometric monitoring device. Direct communication refers herein to the transmission of data between a first device and a secondary device without any intermediary devices. For example, two devices may communicate to one another over a wireless connection (e.g. Bluetooth) or a wired connection (e.g. USB). Indirect communication refers to the transmission of data between a first device and a secondary device with the aid of one or multiple intermediary third devices which relay the data. Third devices may include, but are not limited to, a wireless repeater (e.g. WiFi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In some embodiments, the secondary device that acts as a user interface to the biometric monitoring device may consist of a smartphone. An app on the smart phone may facilitate and/or enable the smartphone to act as a user interface to the biometric monitoring device. The biometric monitoring device may send biometric and other data to the smartphone in real-time or with some delay. The smartphone may send a command or commands to the biometric monitoring device, for example, to instruct it to send biometric and other data to the smartphone in real-time or with some delay. For example, if the user enters a mode in the app for tracking a run, the smartphone may send a command to the biometric device to instruct it to send data in real-time. Therefore, the user can track their run on their app as they go along without any delay.

Such a smartphone may have one or multiple apps to enable the user to view data from their biometric device or devices. The app may, by default, open to a "dashboard" page when the user launches or opens the app. On this page, summaries of data totals such as the total number of steps, floors climbed miles traveled, calories burned, calories consumed and water consumed may be shown. Other pertinent information such as the last time the app received data from the biometric monitoring device, metrics regarding the previous night's sleep (e.g. when the user went to sleep, woke up, and how long they slept for), and how many calories the user can eat in the day to maintain their caloric goals (e.g. a calorie deficit goal to enable weight loss) may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping to the left or right may enable the user to navigate through current and previous metrics.

The smartphone app may also have another page which provides a summary of the user's activities. Activities may include, but are not limited to, walking, running, biking, cooking, sitting, working, swimming, working out, weightlifting, commuting, and yoga. Metrics pertinent to these activities may be presented on this page. For example, a bar graph may show how the number of steps the user took for different portions of the day (e.g. how many steps every 5 minutes or 1 hour). In another example, the amount of time the user spent performing a certain activity and how many calories were burned in this period of time may be displayed. Similar to the dashboard page, the app may provide navigational functionality to allow the user to see these and other metrics for past days. Other time periods such as an hour, minute, week, month or year may also be selected by the user to enable them to view trends and metrics of their activities over shorter or larger spans of time.

The smartphone app may also have an interface to log food that has been, or will be, eaten by the user. This interface may have a keyword search feature to allow the user to quickly find the food that they would like to enter into their log. As an alternative to, or in addition to, searching for foods, users may have the ability to find a food to log by navigating through a menu or series of menus. For example, a user may choose the following series of categories—breakfast/cereal/healthy/oatmeal to arrive at the food which they would like to log (e.g., apple-flavored oatmeal). At any one of these menus, the user may be able to perform a keyword search. For example, the user may search for "oatmeal" after having selected the category "breakfast" to search for the keyword "oatmeal" within the category of breakfast foods. After having selected the food that they would like to log, the user may be able to modify or enter the serving size and nutritional content. After having logged at least one food, the app may display a summary of the foods that were logged in a certain time period (e.g. a day) and the nutritional content of the foods (individual and total calorie content, vitamin content, sugar content, etc.).

The smartphone app may also have a page that displays metrics regarding the user's body such as the user's weight, body fat percentage, BMI, and waist size. It may display a graph or graphs showing the trend of one or multiple of these metrics over a certain period of time (e.g., two weeks). The user may be able to choose the value of this period of time and view previous time periods (e.g., last month).

The smartphone app may also a page which allows the user to enter how much water the user has consumed. Each time the user drinks some water, they may enter that amount in the unit of their choice (e.g., ozs., cups, etc.). The app may display the total of all of the water the user has logged within a certain time period (e.g., a day). The app may allow the user to see previously-logged water entries and daily totals for previous days as well as the current day.

The smartphone app may also have a page that displays online friends of the user. This "friends" page may enable the user to add or request new friends (e.g., by searching for their name or by their email address). This page may also display a leaderboard of the user and his or her friends. The user and his or friends may be ranked based on one or more metrics. For example, the user and his or her friends may be ranked using the total of the past seven days' step counts.

The smartphone app may also have a page that shows metrics regarding the user's sleep for the previous night and/or previous nights. This page may also enable the user to log when they slept in the past by specifying when they went to bed and when they woke. The user may also have the ability to enter a subjective metric about their sleep (e.g., bad night's rest, good night's rest, excellent night's rest, etc.). The user may be able to view these metrics for days or time periods (e.g., two weeks) in the past. For example, the sleep page may default to showing a bar graph of the amount of time the user slept each night in the last two weeks. The user may be able to also view a bar graph of the amount of time the user slept each night in the last month.

The user may also be able to access the full capabilities of the smartphone app described herein (e.g., the ability to enter food logs, view dashboard, etc.) through an alternative or additional interface. In one embodiment, this alternative interface may consist of a webpage that is hosted by a server in indirect communication with the biometric monitoring device. The webpage may be accessed through any internet connected device using a program such as a web browser.

Wireless Connectivity and Data Transmission

Some embodiments of biometric monitoring devices of the present disclosure may include a means of wireless communication to transmit and receive information from the Internet and/or other devices. The wireless communication may consist of one or more interfaces such as Bluetooth, ANT, WLAN, power-line networking, and cell phone networks. These are provided as examples and should not be understood to exclude other existing wireless communication methods or protocols, or wireless communications techniques or protocols that are yet to be invented.

The wireless connection may be bi-directional. The biometric monitoring device may transmit, communicate and/or push its data to other devices, e.g., smart phones, computers, etc., and/or the Internet, e.g., web servers and the like. The biometric monitoring device may also receive, request and/or pull data from other devices and/or the Internet.

The biometric monitoring device may act as a relay to provide communication for other devices to each other or to the Internet. For example, the biometric monitoring device may connect to the Internet via WLAN but also be equipped with an ANT radio. An ANT device may communicate with the biometric monitoring device to transmit its data to the Internet through the biometric monitoring device's WLAN (and vice versa). As another example, the biometric monitoring device may be equipped with Bluetooth. If a Bluetooth-enabled smart phone comes within range of the biometric monitoring device, the biometric monitoring device may transmit data to, or receive data from, the Internet through the smart phone's cell phone network. Data from another device may also be transmitted to the biometric monitoring device and stored (or vice versa) or transmitted at a later time.

Embodiments of biometric monitoring devices of the present disclosure may also include functionality for streaming or transmitting web content for display on the biometric monitoring device. The following are typical examples of such content:

1. Historical graphs of heart rate and/or other data measured by the device but stored remotely
2. Historical graphs of user activity and/or foods consumed and/or sleep data that are measured by other devices and/or stored remotely (e.g., such as at a website like fitbit.com)
3. Historical graphs of other user-tracked data that are stored remotely. Examples include heart rate, blood pressure, arterial stiffness, blood glucose levels, cholesterol, duration of TV watching, duration of video game play, mood, etc.
4. Coaching and/or dieting data based on one or more of the user's heart rate, current weight, weight goals, food intake, activity, sleep, and other data.
5. User progress toward heart rate, weight, activity, sleep, and/or other goals.
6. Summary statistics, graphics, badges, and/or metrics (e.g., "grades") to describe the aforementioned data
7. Comparisons between the aforementioned data for the user and similar data for his/her "friends" with similar devices and/or tracking methods
8. Social content such as Twitter feeds, instant messaging, and/or Facebook updates
9. Other online content such as newspaper articles, horoscopes, weather reports, RSS feeds, comics, crossword puzzles, classified advertisements, stock reports, and websites
10. Email messages and calendar schedules Content may be delivered to the biometric monitoring device according to different contexts. For instance, in the morning, news and weather reports may be displayed along with the user's sleep data from the previous night. In the evening, a daily summary of the day's activities may be displayed.

Various embodiments of biometric monitoring devices as disclosed herein may also include NFC, RFID, or other short-range wireless communication circuitry that may be used to initiate functionality in other devices. For instance, a biometric monitoring device may be equipped with an NFC antenna so that when a user puts it into close proximity with a mobile phone, an app is launched automatically on the mobile phone.

These examples are provided for illustration and are not intended to limit the scope of data that may be transmitted, received, or displayed by the device, nor any intermediate processing that may occur during such transfer and display. In view of this disclosure/application, many other examples of data that may be streamed to or via a biometric monitoring device may be envisioned by one reasonably skilled in the art.

Charging and Data Transmission

Some embodiments of biometric monitoring devices may use a wired connection to charge an internal rechargeable battery and/or transfer data to a host device such as a laptop or mobile phone. In one embodiment, similar to one discussed earlier in this disclosure, the biometric monitoring device may use magnets to help the user align the biometric monitoring device to a dock or cable. The magnetic field of magnets in the dock or cable and the magnets in the device itself may be strategically oriented so as to force the biometric monitoring device to self-align with the dock or cable (or, more specifically, a connector on the cable) and so as to provide a force that holds the biometric monitoring device in the dock or to the cable. The magnets may also be used as conductive contacts for charging or data transmission purposes. In another embodiment, a permanent magnet may only be used in the dock or cable side and not in the biometric monitoring device itself. This may improve the performance of the biometric monitoring device where the biometric monitoring device employs a magnetometer. If there is a magnet in the biometric monitoring device, the strong field of a nearby permanent magnet may make it significantly more difficult for the magnetometer to accurately measure the earth's magnetic field. In such embodiments, the biometric monitoring device may utilize a ferrous material in place of a magnet, and the magnets on the dock or cable side may attach to the ferrous material.

In another embodiment, the biometric monitoring device may contain one or more electromagnets in the biometric monitoring device body. The charger or dock for charging and data transmission may also contain an electromagnet and/or a permanent magnet. The biometric monitoring device could only turn on its electromagnet when it is close to the charger or dock. The biometric monitoring device may detect proximity to the dock or charger by looking for the magnetic field signature of a permanent magnet in the charger or dock using a magnetometer. Alternatively, the biometric monitoring device may detect proximity to the charger by measuring the Received Signal Strength Indication (RSSI) of a wireless signal from the charger or dock, or, in some embodiments, by recognizing an NFC or RFID tag associated with the charger or dock. The electromagnet could be reversed, creating a force that repels the device from the charging cable or dock either when the device doesn't need to be charged, synced, or when it has completed syncing or charging. In some embodiments, the charger or dock may include the electromagnet and may be configured (e.g., a processor in the charger or dock may be configured via program instructions) to turn the electromagnet on when a biometric monitoring device is connected for charging (the electromagnet may normally be left on such that a biometric monitoring device that is placed on the charger is drawn against the charger by the electromagnet, or the electromagnet may be left off until the charger determines that a biometric monitoring device has been placed on the charger, e.g., through completion of a charging circuit, recognition of an NFC tag in the biometric monitoring device, etc., and then turned on to draw the biometric monitoring device against the charger. Upon completion of charging (or of data transfer, if the charger is actually a data transfer cradle or a combined charger/data transfer cradle), the electromagnet may be turned off (either temporarily or until the biometric monitoring device is again detected as being placed on the charger) and the biometric monitoring device may stop being drawn against the charger. In such embodiments, it may be desirable to orient the interface between the biometric monitoring device and the charger such that, in the absence of a magnetic force generated by the electromagnet, the biometric monitoring device would fall off of the charger or otherwise shift into a visibly different position from the charging position (to visually indicate to a user that charging or data transfer is complete).

Sensor Use in Data Transfer

In some implementations, biometric monitoring devices may include a communications interface that may switch between two or more protocols that have different data transmission rates and different power consumption rates. Such switching may be driven by data obtained from various sensors of the biometric monitoring device. For example, if Bluetooth is used, the communications interface may switch between using Bluetooth base rate/enhanced data rate (BR/EDR) and Bluetooth low energy (BLE) protocols responsive to determinations made based on data from the sensors of the biometric monitoring device. For example, the lower-power, slower BLE protocol may be used when sensor data from accelerometers in a biometric monitoring device indicates that the wearer is asleep or otherwise sedentary. By contrast, the higher-power, faster BR/EDR protocol may be used when sensor data from the accelerometers in a biometric monitoring device indicates that the wearer is walking around. Such adaptive data transmission techniques and functionality are discussed further in U.S. Provisional Patent Application No. 61/948,468, filed Mar. 5, 2014, which was previously incorporated herein by reference in the "Cross-Reference to Related Applications" section and which is again hereby incorporated by reference with respect to content directed at adaptive data transfer rates in biometric monitoring devices.

Such communication interfaces may also serve as a form of sensor for a biometric monitoring device. For example, a wireless communications interface may allow a biometric monitoring device to determine the number and type of devices that are within range of the wireless communications interface. Such data may be used to determine if the biometric monitoring device is in a particular context, e.g., indoors, in a car, etc., and to change its behavior in various ways in response to such a determination. For example, as discussed in U.S. Provisional Patent Application No. 61/948,468 (incorporated by reference above), such contexts may be used to drive the selection of a particular wireless communications protocol to use for wireless communications.

Configurable App Functionality

In some embodiments, biometric monitoring devices of the present disclosure may include a watch-like form factor and/or a bracelet, armlet, or anklet form factor and may be programmed with "apps" that provide specific functionality and/or display specific information. Apps may be launched or closed by a variety of means including, but not limited to, pressing a button, using a capacitive touch sensor, performing a gesture that is detected by an accelerometer, moving to a specific location or area detected by a GPS or motion sensor, compressing the biometric monitoring device body (thereby creating a pressure signal inside the device that may be detected by an altimeter inside the biometric monitoring device), or placing the biometric monitoring device close to an NFC tag that is associated with an app or set of apps. Apps may also be automatically triggered to launch or close by certain environmental or physiological conditions including, but not limited to, detection of a high heart rate, detection of water using a wet sensor (to launch a swimming application, for example), a certain time of day (to launch a sleep tracking application at night, for example), a change in pressure and motion characteristic of a plane taking off or landing to launch and close an "airplane" mode app. Apps may also be launched or closed by meeting multiple conditions simultaneously. For example, if an accelerometer detects that a user is running and the user presses a button, the biometric monitoring device may launch a pedometer application, an altimeter data collection application, and/or display. In another case where the accelerometer detects swimming and the user presses the same button, it may launch a swimming lap-counting application.

In some embodiments, the biometric monitoring device may have a swim-tracking mode that may be launched by starting a swimming app. In this mode, the biometric monitoring device's motion sensors and/or magnetometer may be used to detect swim strokes, classify swim stroke types, detect swimming laps, and other related metrics such as stroke efficiency, lap time, speed, distance, and calorie burn. Directional changes indicated by the magnetometer may be used to detect a diversity of lap turn methods. In a preferred embodiment, data from a motion sensor and/or pressure sensor may be used to detect strokes.

In another embodiment, a bicycling app may be launched by moving the biometric monitoring device within proximity of an NFC or RFID tag that is located on the bicycle, on a mount on the bicycle, or in a location associated with a bicycle including, but not limited to, a bike rack or bike storage facility. (See, for example, FIG. 10). The app launched may use a different algorithm than is normally used to determine metrics including, but not limited to, calories burned, distance traveled, and elevation gained. The app may also be launched when a wireless bike sensor is detected including, but not limited to, a wheel sensor, GPS, cadence sensor, or power meter. The biometric monitoring device may then display and/or record data from the wireless bike sensor or bike sensors.

Additional apps include, but are not limited to, a programmable or customizable watch face, stop watch, music player controller (e.g., mp3 player remote control), text message and/or email display or notifier, navigational compass, bicycle computer display (when communicating with a separate or integrated GPS device, wheel sensor, or power meter), weight-lifting tracker, sit-up reps tracker, pull up reps tracker, resistance training form/workout tracker, golf swing analyzer, tennis (or other racquet sport) swing/serve analyzer, tennis game swing detector, baseball swing analyzer, ball throw analyzer (e.g., football, baseball), organized sports activity intensity tracker (e.g., football, baseball, basketball, volleyball, soccer), disk throw analyzer, food bite detector, typing analyzer, tilt sensor, sleep quality tracker, alarm clock, stress meter, stress/relaxation biofeedback game (e.g., potentially in combination with a mobile phone that provides auditory and/or visual cues to train user breathing in relaxation exercises), teeth brushing tracker, eating rate tracker (e.g., to count or track the rate and duration by which a utensil is brought to the mouth for food intake), intoxication or suitability to drive a motor vehicle indicator (e.g., through heart rate, heart rate variability, galvanic skin response, gait analysis, puzzle solving, and the like), allergy tracker (e.g., using galvanic skin response, heart rate, skin temperature, pollen sensing and the like (possibly in combination with external seasonal allergen tracking from, for instance, the internet and possibly determining the user's response to particular forms of allergen, e.g., tree pollen, and alerting the user to the presence of such allergens, e.g., from seasonal information, pollen tracking databases, or local environmental sensors in the biometric monitoring device or employed by the user), fever tracker (e.g., measuring the risk, onset, or progress of a fever, cold, or other illness, possibly in combination with seasonal data, disease databases, user location, and/or user provided feedback to assess the spread of a particular disease (e.g., flu) in relation to a user, and possibly prescribing or suggesting the abstinence of work or activity in response), electronic games, caffeine affect tracker (e.g., monitoring the physiologic response such as heart rate, heart rate variability, galvanic skin response, skin temperature, blood pressure, stress, sleep, and/or activity in either short term or long term response to the intake or abstinence of coffee, tea, energy drinks and/or other caffeinated beverages), drug affect tracker (e.g., similar to the previously mentioned caffeine tracker but in relation to other interventions, whether they be medical or lifestyle drugs such as alcohol, tobacco, etc.), endurance sport coach (e.g., recommending or prescribing the intensity, duration, or profile of a running/bicycling/swimming workout, or suggesting the abstinence or delay of a workout, in accordance with a user specified goal such as a marathon, triathlon, or custom goal utilizing data from, for instance, historical exercise activity (e.g., distance run, pace), heart rate, heart rate variability, health/sickness/stress/fever state), weight and/or body composition, blood pressure, blood glucose, food intake or caloric balance tracker (e.g., notifying the user how many calories he may consume to maintain or achieve a weight), pedometer, and nail biting detector. In some cases, the apps may rely solely on the processing power and sensors of the present disclosure. In other cases, the apps may fuse or merely display information from an external device or set of external devices including, but not limited to, a heart rate strap, GPS distance tracker, body composition scale, blood pressure monitor, blood glucose monitor, watch, smart watch, mobile communication device such as a smart phone or tablet, or server.

In one embodiment, the biometric monitoring device may control a music player on a secondary device. Aspects of the music player that may be controlled include, but are not limited to, the volume, selection of tracks and/or playlists, skipping forward or backward, fast forwarding or rewinding of tracks, the tempo of the track, and the music player equalizer. Control of the music player may be via user input or automatic based on physiological, environmental, or contextual data. For example, a user may be able to select and play a track on their smart phone by selecting the track through a user interface on the biometric monitoring device. In another example, the biometric monitoring device may automatically choose an appropriate track based on the activity level of the user (the activity level being calculated from biometric monitoring device sensor data). This may be used to help motivate a user to maintain a certain activity level. For example, if a user goes on a run and wants to keep their heart rate in a certain range, the biometric monitoring device may play an upbeat or higher tempo track if their heart rate is below the range which they are aiming for.

Automated Functions Triggered by User's Activity

Sleep Stage Triggered Functionality

Sleep stages can be monitored through various biometric signals and methods disclosed herein, such as heart rate, heart rate variability, body temperature, body motions, ambient light intensity, ambient noise level, etc. Such biometrics may be measured using optical sensors, motion sensors (accelerometers, gyroscopic sensors, etc.), microphones, and thermometers, for example, as well as other sensors discussed herein.

The biometric monitoring device may have a communication module as well, including, but not limited to, Wi-Fi (802.xx), Bluetooth (Classic, low power), or NFC. Once the sleep stages are estimated, the sleep stages may be transmitted to a cloud-based system, home server, or main control unit that is connected to communication-enabled appliances (with Wi-Fi, Bluetooth, or NFC) wirelessly. Alternatively, the biometric monitoring device may communicate directly with the communication-enabled appliances. Such communication-enabled appliances may include, for example, kitchen appliances such as microwaves, ovens, coffee grinders/makers, toasters, etc.

Once the sleep stages indicate that it is close the time for the user to wake up, the biometric monitoring device may send out a trigger to the appliances that the user has indicated should be operated automatically. For example, the coffee grinder and maker may be caused to start making coffee, and the toaster may be caused to start warming up bread. The microwave oven may be caused to start cooking oatmeal or eggs as well, and electric kettle to start boiling water. So long as the ingredients are appropriately prepared, this automated signal may trigger breakfast-cooking.

Alertness Detection

Alertness, e.g., a low alertness may correlate with a person being drowsy, may also be detected from the biometrics listed above, and may be used to trigger an appliance such as a coffee maker to start brewing coffee automatically.

Hydration

The portable biometric monitoring device in combination with an activity level tracker may submit the user's activity level to a cloud-based system, home server, main control unit, or appliances directly. This may trigger some actions of the appliances, especially related to hydration, such as starting the ice cube maker of a refrigerator, or lowering operating temperature of a water purifier.

Power Saving

Many appliances typically operate in a low-power idle state that consumes power. Using aggregated information of the user's biometric signals, communication-enabled appliances may be caused to go into a super-low power mode. For example, a water dispenser at home may shut itself down into a super-low-power mode when the user is asleep or out for work, and may start cooling/heating water once the user's activity at home is expected.

Restaurant Recommendation System Based on Location and Activity

Aggregation of real-time biometric signals and location information may be used to create an educated-guess on one or multiple users' needs for a given time, e.g., ionized drink. Combining this guessed need with historical user data on the user's activity levels, activity types, activity time, and activity durations, as well as food intake data logged by the users, an app on a smart phone and/or smart watch may recommend a restaurant that would meet the user's life-style and current need.

For example, a user who just finished a six mile circuit may launch this app. The app may know that this person maintained a high activity level for the past hour, and thus determine that the person may be dehydrated. From the historical user data, the app may also know, for example, that the user's diet is heavy on vegetables but low in sugar. With an optimization algorithm that considers the user's current location, price ranges, and other factors mentioned above, the app may recommend a restaurant that offers smoothies, for example.

Swim Tracking

In some embodiments of a biometric tracking device, the biometric tracking may include a swimming algorithm that may utilize data from one or more motion sensors, altitude sensors (e.g., such as a barometric pressure sensor), orientation sensors (e.g., magnetometer), location service sensor (e.g., GPS, wireless triangulation), and/or temperature sensors. The sensors may be embedded in a single device mounted to, for instance, the wrist. In other embodiments, extra sensor devices may be attached to the swimmer's forehead, back of the head, goggles, back, hip, shoulder, thighs, legs, and/or feet.

Three potential functional components of swimming exercise analysis are as follows:

Stroke count detection—provides stroke counts per lap, where a lap is defined to be a one-way traverse from one end of the pool to the opposite end.

Stroke type classification—describes the swimming stroke type of the user (e.g., crawl stroke, breast stroke, back stroke, butterfly stroke, side stroke, kicking without strokes, body streamline, etc.) and can be any or a combination of:
  a. Classification of each stroke that a user takes
  b. Classification of the predominant stroke type used per complete lap.
  c. Classification of stroke type used per fractional lap (e.g. half a lap of freestyle, half a lap of breast stroke)

Lap count—counts the laps traversed by the user. One method of determining a lap is by detecting when the user turns in a pool.

Turning is defined to be a 180 degree change in heading direction. As a turn is detected, start and end of a lap may be inferred. Taking a break (no motion for a certain period of time) at a point in the pool (typically at one end or the other) before starting to swim again is also considered a turn as long as the following heading direction is opposite the heading prior to the break.

In some embodiments, these functional components may be combined in a multitude of ways.

Algorithm Structure

The three functional components of the swimming exercise analysis may be performed sequentially, in parallel, or in hybrid order (a combination of some sequential blocks and some parallel blocks).

Figure 15A:
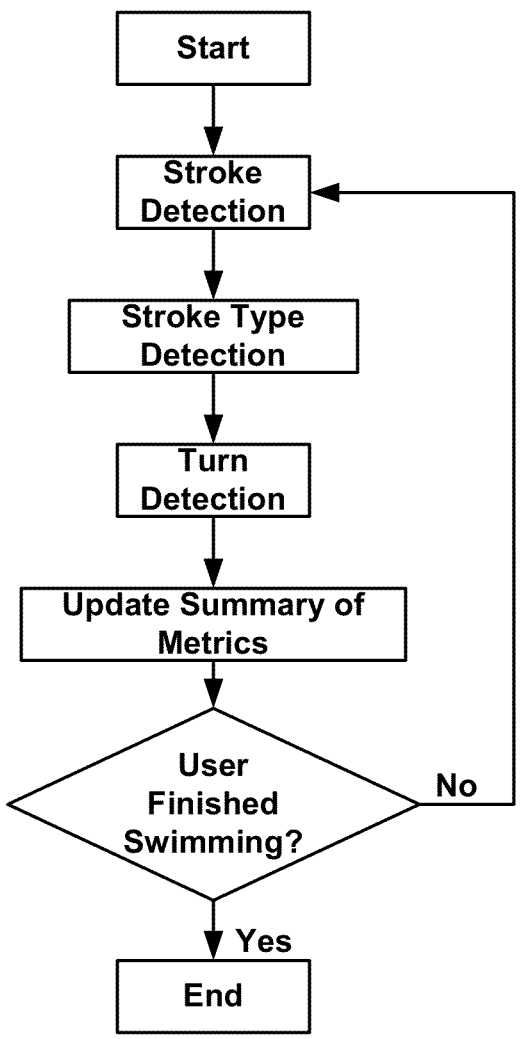
FIG. 15A illustrates an example of a swim detection algorithm using a sequential algorithm flow.

Sequential Approach (See FIG. 15A)

In one embodiment, raw and/or pre-processed sensor signals may first be analyzed by a stroke detector algorithm. The stroke detector algorithm may use temporal peaks (local maxima and/or local minima) in a motion sensor (e.g., accelerometer, gyroscope) as an indication that a stroke has been taken. Then one or more heuristic rules may also be applied to remove peaks that do not represent strokes. For example, the magnitudes of the peaks, temporal distance of two adjacent peaks, peak-to-peak amplitude, and/or morphological characteristics of the peaks (e.g., sharpness) may indicate that certain peaks do not represent strokes. When sensors provide more than one dimensional data, e.g., such as 3-axis accelerometers, or 3 axis motion sensors+altimeter (totaling 4-axis data), timings and relevant sizes of peaks in all axes may be taken into account to determine whether or not the peaks in one or more of the axes are generated by a stroke or not.

If a single peak representing a stroke or group of peaks from multiple data axes representing strokes are observed, features may be extracted from a segment of data that are obtained from the time between when the previous peak is detected and when the current peak is detected. Features include, but are not limited to, maximum and minimum values, number of ripples in the segment, powers measured in various metrics, e.g., L1 power and L2 power, standard deviation, mean, etc. The extracted features may then be put through a machine learning system where the system coefficients are computed off-line (supervised learning) or are adapted as the user uses the biometric monitoring device (unsupervised learning). The machine learning system may then return a stroke classification for each detected stroke.

The turn-detector algorithm may search for sudden changes in motion by calculating derivatives, moving average, and/or using high-pass filtering on the signals of the sensors (the sensors including, but not limited to, those listed in this disclosure). Principal Component Analysis (PCA) can also and/or alternatively be performed on the signal(s). If one principle component is different from the sub-sequential one, then it may be determined that a turn occurred. Whole or partial coefficients of a transform, such as the Fast Fourier Transform (FFT) may be used as features as well. Parametric models such as Autoregressive (AR) models may also be used. Time-varying model parameters may then be estimated using Linear Prediction Analysis (LPA), Least Mean Squares filtering (LMS), Recursive Least Squares filtering (RLS), and/or Kalman filtering. Estimated model parameters are then compared to determine if there is an abrupt change in their values.

In one embodiment, the skill level and/or swimming styles (e.g., speed) of the swimmer may be inferred from sensor data, and then used in turn detection. For example, advanced swimmers typically have more powerful strokes (i.e., large accelerometer peak magnitudes) and take fewer strokes to complete a lap. Therefore, metrics that estimate the swimmer's skill level or characteristics may be used in a turn detection algorithm. These metrics may include, but are not limited to averaged motion signals, or integrated motion signals in particular arm movements, estimated heading speed, and detected patterns of an advanced swimmer in motion signals. The swimmer's skill level or other characteristics may also be determined through user input. For example, the user may input that they are an advanced, intermediate, or beginner swimmer.

One or many (combined) features from these analyses may be used to detect if a given data sample, and/or neighboring data samples, have characteristics of a turn. To obtain the optimal combination of the features and decision boundary, one can utilize machine learning techniques such as logistic regression, decision tree, neural nets, etc.

In some embodiments, if a turn is detected, the swimming data accrued since the previous turn may be summarized, such as the number of strokes, stroke type for each stroke and for the lap, split time, etc. If no turn is detected, the stroke counter and type may be updated. Unless the user quits swimming, the algorithm may go back to stroke count detection.

Figure 15B:
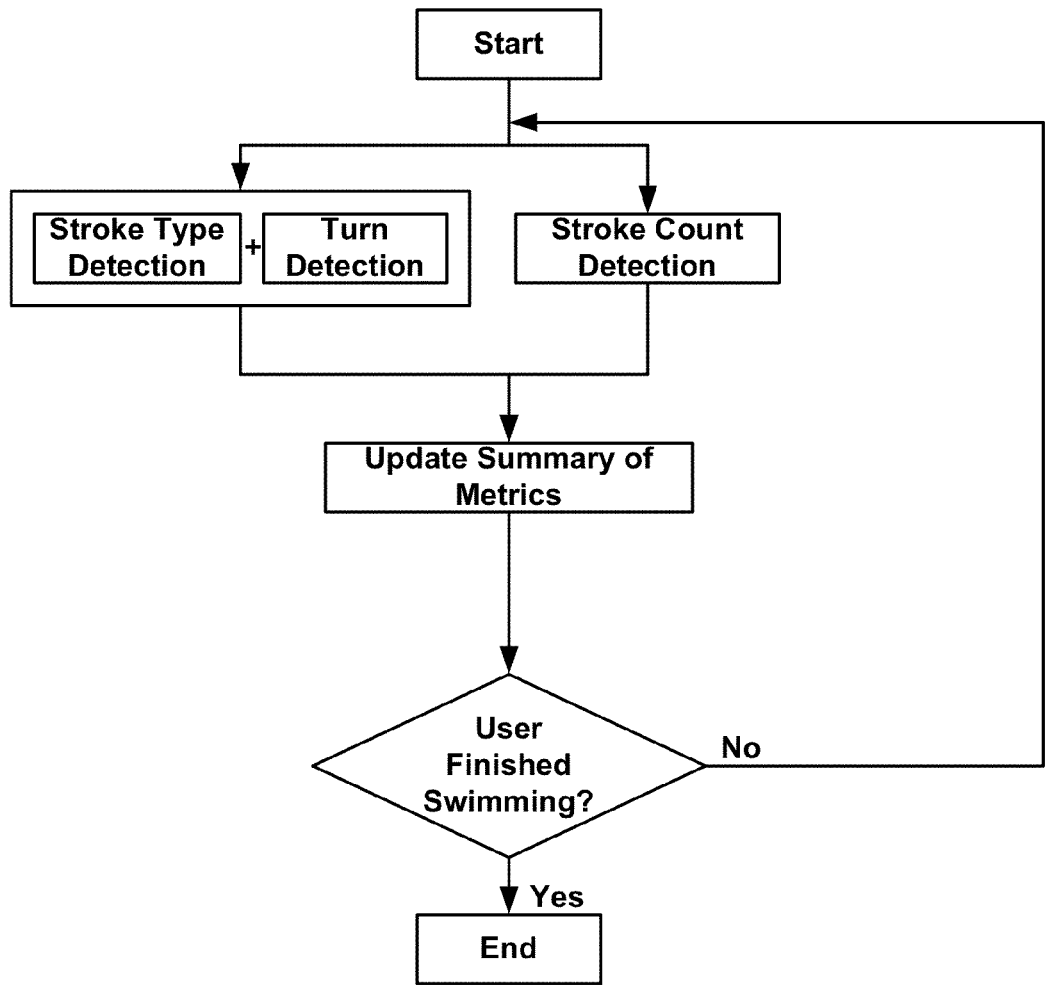
FIG. 15B illustrates an example of a swim detection algorithm which uses a parallel algorithm flow.

Parallel Approach (see FIG. 15B)

In the parallel approach, some or all of the three functional components may be executed in parallel. For example, stroke-type detection and turn detection may be performed jointly, while stroke count detection is run independently.

In such embodiments, two functional components, stroke-type and turn detection, may be implemented in a single algorithm that simultaneously detects stroke-types and turns. For example, a classifier of swimming stroke types, e.g., movement analysis that detects free style strokes, breast stroke strokes, back strokes, butterfly strokes, and of turn types (e.g. tumble turn, flip turn, two hand touch) may return a detected type of stroke or a type of detected turn. During the detection, temporal as well as spectral features may be extracted. A moving window may first be applied to multiple axes of data. Statistics of this windowed segment may then be computed, namely, maximum and minimum value, number of ripples in the segment, powers measured in various metrics (e.g., L1 power and L2 power, standard deviation, mean). Independent component analysis (ICA) and/or principal component analysis (PCA) can be applied as well to find any hidden signals that better represent turn-type and stroke-type characteristics. Temporal features may then be computed from this (potentially improved) signal representation. For temporal features, various nonparametric filtering schemes, low-pass filtering, band-pass filtering, high-pass filtering, may be applied to enhance desired signal characteristics.

Spectral analysis such as FFT, wavelet transform, Hilbert transform, etc., may be applied to this windowed segment as well. Whole or partial transform coefficients may be chosen as features. Parametric models such as AR, moving average (MA), or ARMA (autoregressive and moving average) models may be used, and the parameters of such a model may be found via autocorrelation and/or partial autocorrelation, or LPA, LMS, RLS, or Kalman filter. The entire or part of estimated coefficients may be used as features.

Different lengths of moving average windows may be run in parallel, and provide features listed above, and the whole or part of the features may be utilized as features as well.

Machine-learned coefficients (supervised learning) may then be applied to these extracted features. One or more machine learning techniques, namely multiple layers of binomial linear discriminant analysis (e.g., logistic regression), multinomial logistic regression, neural net, decision tree/forest, or support vector machine, can be trained, and then used.

As the window of interest moves, the features may be extracted and these newly-extracted features will return either a stroke type or detected turn via a machine learning system.

The stroke detector algorithm may run in parallel independent of stroke type and turn detection. Temporal peaks of raw or pre-filtered sensor signals may be detected and chosen by heuristic rules.

At the summarizing stage (the stage where metrics regarding the swim may be determined, displayed, and/or stored) of the algorithm, post-processing may be applied to the sequence of stroke type and turn detections. If a turn is confirmed with certain confidence, the swimming metric data from the previous turn may be summarized along with stroke counts detected. If no turn is confirmed, the moving average window may proceed. Until the user stops swimming, the algorithm may continue to update swimming metrics regarding the exercise of the user, including, but not limited to, a total number of turns, total number of laps, total number of strokes, average strokes per lap, number of strokes in the last lap, the change in number of strokes per lap, etc.

Figure 15C:
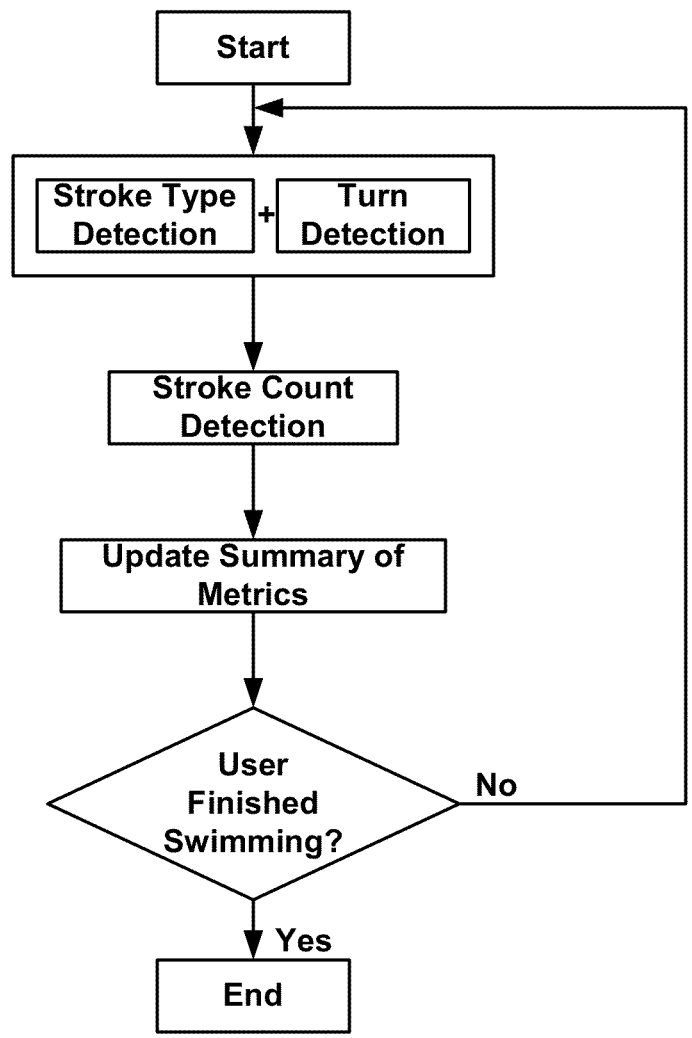
FIG. 15C illustrates an example of a swim detection algorithm which uses a hybrid of sequential and parallel algorithm flow.
Figure 15D:
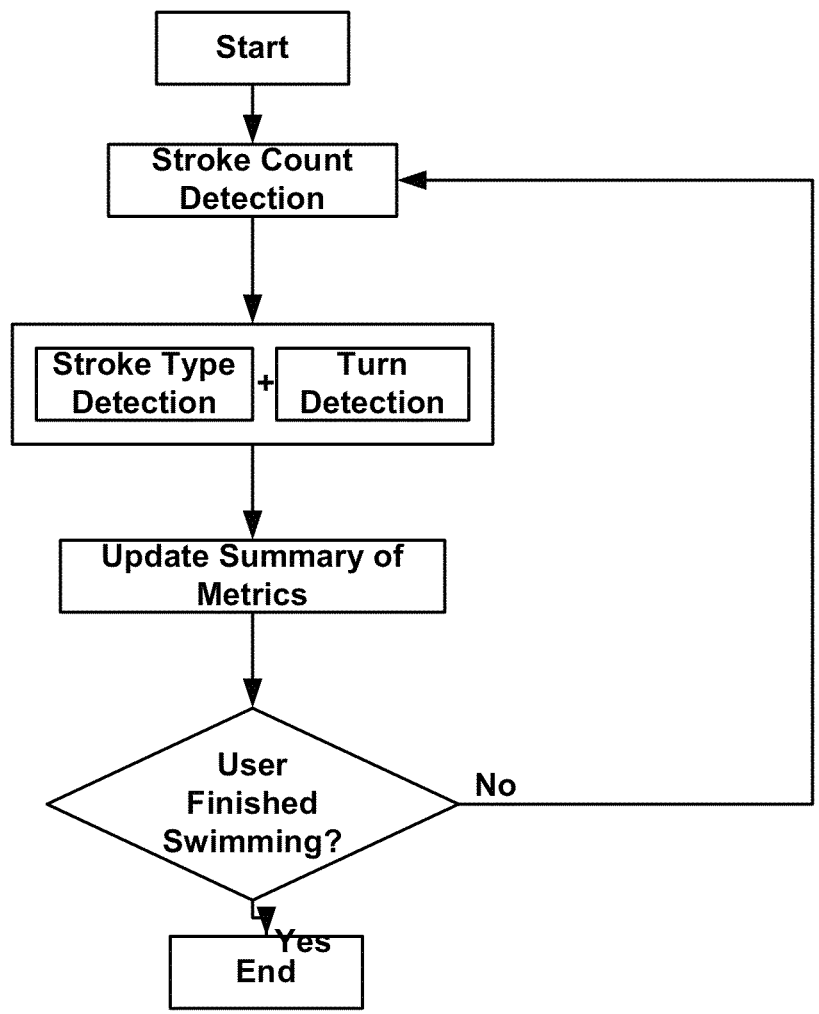
FIG. 15D illustrates an example of a swim detection algorithm which uses a hybrid of sequential and parallel algorithm flow.

Hybrid Approach (see FIGS. 15C and 15D)

In a hybrid approach, the stroke type and stroke count detection may be run in parallel, followed by turn detection.

Stroke-type detection may return a stroke type via machine learned coefficients. A first moving window may take segments of sensor signals. Then features, either entire features or a subset of the moving window features listed in herein, may be extracted. The machine learning coefficients, trained off-line, may then be applied to the features to determine which stroke-type generated the given segments of sensor signals.

Along with stroke type detection, stroke count detection may be run simultaneously.

Once the stroke type and counts are detected, turn detection may be performed with either the entire feature or a subset of the features listed.

If a turn is detected, completion of a lap may be recorded in the swimming summary metrics of the user. A post process may be applied to detected stroke types to determine the most prominent stroke type for the completed lap. Then the algorithm may move to the stroke-type and count detection stages unless the user stops swimming. If no turn is detected, the algorithm may continue updating stroke types and counts of the current lap until a turn is detected.

Blood Glucose Level and Heart Rate

Biometric monitoring devices that continuously measure biometric signals may provide meaningful information on preconditions of, progress towards, and recoveries from diseases. Such biometric monitoring devices may have sensors and run algorithms accordingly to measure and calculate biometric signals such as heart rate, heart rate variability, steps taken, calories burned, distance traveled, weight and body fat, activity intensity, activity duration and frequency, etc. In addition to the measured biometric signals, food intake logs provided by users may be used.

In one embodiment, a biometric monitoring device may observe heart rate and its changes over time, especially before and after a food intake event or events. It is known that heart rate is affected by blood sugar level, whereas it is well known that high blood sugar level is a pre-diabetic condition. Thus, mathematical models that describe the relation between time elapsed (after food intake) and blood sugar level may be found via statistical regression, where data are collected from normal, pre-diabetic, and diabetic individuals to provide respective mathematical models. With the mathematical models, one may predict whether an individual with specific heart rate patterns is healthy, pre-diabetic, or diabetic.

Knowing that many heart failures are associated with pre-diabetic or diabetic conditions, it is possible to further inform users of biometric monitoring devices with possible heart failures, e.g., coronary heart disease, cerebrovascular disease and peripheral vascular disease etc., of such risks based on their biometric data.

Users' activity intensity, type, duration, and frequency may also be taken into account, when developing the mathematical models, as an argument that controls "probability" of the disease onset, using recommended exercise guidelines such as guidelines provided by American Heart Association (http://www.heart.org/). Many guidelines on nutrition and weight management are also available in academia and to the general public to prevent cardiovascular and diabetic disease. Such guidelines may be incorporated into the mathematical models with the user data accumulated over time, such as ingredients of the food that the users consumed, and weight and body fat trends.

If users have set their family members as their friends on a social network site, which stores and displays biometric data, the likelihood of the family members getting a disease may also be analyzed and the users informed of the results.

In addition to informing users regarding a potential development of disease, recommended life-style including exercise regime and recipes with healthier ingredients and methods of preparation may be provided to the users.

Unification of Grocery Shopping, Cooking, and Food Logging

Grocery Organizing and Recipe Recognition System

Receipts from grocery shopping may contain copious information, especially regarding an individual's eating habits. A novel system that combines information from grocery store receipts with an individual's biometric data, as collected by a biometric monitoring device, for example, is presented here. The system may collect and analyze data (information) regarding an individual, and may then recommend options that may change the individual's life-style so as to improve their health. The implementation of this system may involve cloud computing, hardware platform development for sensing and interface, and mobile/website site development.

In one embodiment, when a user checks out at a grocery store, the list of groceries (as obtained from the receipt or, for example, from an email receipt or invoice) may be transmitted automatically to a remote database (e.g., a cloud server), that may also store the user's biometric data. When the user gets home and organizes items in their refrigerator and/or pantry, an app on their smart phone/watch may recommend which items in the pantry or refrigerator to throw away based on historical data on food items (e.g., if food items are expired or likely to have gone bad). Alerts indicating when food has expired or that it should be consumed in the near future to avoid spoilage may be automatically sent to the user independently of such activity. For example, these alerts may be sent out to the user whenever a certain threshold has been met (e.g., in two days the milk will expire). The alerts may also be sent to the user through means other than through a smart phone/watch. For example, the alerts may be presented to the user through a web interface, through email, through an alert on a laptop computer, on a tablet computer, desktop computer, or any other electronic device which is in direct or indirect communication with the computer which maintains and/or analyzes the database of food Using the updated list of food items, and based on the user's historical food consumption data, the app may recommend recipes to the user. In one embodiment, preference may be given to recipes that use the items what should be eaten first (e.g., before they expire, go bad, or become less fresh faster than other ingredients). To recommend the optimal recipe that is nutritionally balanced, correctly portioned, and tailored to the user's activity, the app may also analyze the user's activity data as well. For example, if the user lifted weights in the morning, high-protein meals may be recommended. In another example, if the user was not very active, the size of the recipe may be decreased to lower the number of calories that the final meal contains.

Note that these strategies may be applied to multiple users that either share the same food and/or meals. For example, a combined food database may be created for a household so that if one member of the house got eggs and another member of the house got milk from the grocery store that both eggs and milk would be represented in the food database. Similarly, the nutritional preferences (e.g., vegetarian, allergic to certain foods, etc.), activity, basal metabolic rate, and total calorie burn may be used to form a recommendation on what food/recipe to prepare and/or purchase.

Biometric signals including, but not limited to, heart rate and heart rate variability may provide indications of pre-conditions of diseases. This information may be used to recommend that the user purchase, consume, and/or prepare particular foods so as to reduce their risk of the disease(s) for which they have the pre-conditions. For example, if a user has a precondition for cardiac problems, it may be recommended that they purchase more vegetables, consume less fatty foods, and prepare food in methods which require less oil (e.g., not deep frying).

Control "Smart Appliance"

In another embodiment, various appliances may all be Wi-Fi enabled, and may communicate with servers. Since the app (which may be connected to the appliances via, for example, the cloud or the Internet) may know which food items the refrigerator contains, the app may communicate with the refrigerator to lower or raise the temperature of the refrigerator depending on the food items. For example, if many of the food items are more sensitive to cold, such as vegetables, the refrigerator may be instructed to raise the temperature. The app may also directly communicate with the refrigerator as well via Bluetooth, BTLE, or NFC.

Food Logging

The app may also provide items to log in as the user's food based on a grocery shopping list (which may, for example, be a list maintained within the app) and food recipes that the app recommended. In case of precooked meals (e.g., frozen dinner) or produce that does not require any further processing before being eaten, the user may simply input their serving size (or in the case that the user eats the whole meal, the user may not need to enter a serving size), and then the food logging will be completed. Since the grocery list or receipt provides the exact brand and maker of certain foods, more accurate nutritional information may be logged into the user's account.

When a user logs a food item that is cooked by following a recipe suggested by the app, the app may calculate nutritional information from the ingredients and cooking procedure. This may provide more accurate estimate of calorie intake than a simple categorization of the end product/meal, since many recipes exist to prepare a particular type of food, e.g., meatballs for pasta may be made with beef, turkey, pork, etc., and may include varying degrees of carbohydrates.

Sport Metric Acquisition Using a Sensor Device

In some embodiments, a sensor may be mounted on a racket, e.g., tennis racket, to help to measure the different strokes of the player. This may be applicable to most, if not all, racket sports including, but not limited to, tennis, racquetball, squash, table tennis, badminton, lacrosse, etc., as well as sports played with a bat like baseball, softball, cricket, etc. Similar techniques may also be used to measure different aspects of golf. Such a device can be mounted on the base of the racket, on the handle or on the shock absorber typically mounted on the strings. This device may have various sensors like an accelerometer, gyroscope, magnetometer, strain sensor, and/or microphone. The data from these sensors may either be stored locally or transmitted wirelessly to a host system on a smartphone or other wireless receiver.

In some embodiments of a biometric monitoring device, a wrist mounted biometric monitoring device including an accelerometer, gyroscope, magnetometer, microphone, etc. may perform similar analysis of the user's game or motions. This biometric monitoring device may take the form of a watch or other band worn on the user's wrist. Racket- or bat-mounted sensors that measure or detect the moment of impact between the bat or racket and the ball and wirelessly transmit such data to the wrist-mounted biometric monitoring device may be used to improve accuracy of such algorithms by accurately measuring the time of impact with the ball.

Both wrist and racket-/bat-mounted devices may help measure different aspects of the user's game including, but not limited to, stroke-type (forehand, backhand, serve, slice, etc.), number of forehands, number of backhands, ball spin direction, topspin, service percentage, angular velocity of racket head, backswing, shot power, shot consistency, etc. The microphone or the strain sensor may be used in addition to the accelerometer to identify the moment at which the ball impacts the racket/bat. In cricket and baseball, such a device may measure the backswing, the angular velocity of the bat at the time of impact, the number of shots on the off-side vs. leg-side (cricket). It may also measure the number of swings and misses and the number of defensive vs. offensive strokes. Such a device may also have a wireless transmitter to transmit such statistics in real time to a scoreboard or to individual devices held by spectators.

The wrist- or racket-mounted device may have a small number of buttons (e.g., two) that may be used by the player to indicate when a volley is won or when an unforced error occurs. This will allow the algorithm to calculate the fraction of winners and unforced errors that are forehands vs. backhands. The algorithm may also keep track of the number of aces vs. double-faults in tennis. If both players use such a system, the system may also automatically keep track of the score.

Bicycle Handlebar Based ECG

In some embodiments of biometric monitoring devices, a user's heart rate may be monitored using an electrode in contact with the left hand and an electrode in contact with the right hand (an ECG heart rate measurement). As riding a bicycle requires the user to make hand contact with either side of the handlebars, this particular activity is well suited to tracking user heart rate using ECG techniques. By embedding electrodes in the handlebars or handlebar grips or tape, the user's heart rate may be measured whenever the user is holding the handlebars. For bicycles that have grips (as opposed to using handlebar tape), electrodes may be incorporated into a special grip that may be used to replace the existing grips, e.g., the factory-installed grips, which are typically non-conductive. The left and right grips may be electrically connected to electronics that measure the ECG signal, using a wire, for example. In the case that the handlebars themselves are conductive, the handlebars may be used to electrically connect one of the grips to the electronics that measure the ECG signal. The electronics that measure the ECG signal may be incorporated into one or both of the grips. Alternatively, the electronics that measure the ECG signal may be located in a separate housing. In one embodiment, this separate housing may be mounted on the bicycle handlebar or stem. It may have functions and sensors that typical bicycle computers have (e.g., speed sensor, cadence sensor, GPS sensor). It may also have atypical sensors such as a wind speed sensor, GSR sensor(s), and accelerometer sensor (potentially also incorporated into the handlebars). This embodiment may use techniques described in this disclosure to calculate activity metrics including, but not limited to, calorie burn, and transmit these metrics to secondary and tertiary device(s) (e.g. smartphones and servers).

Electrodes for the ECG may be incorporated into parts of the bike or accessories other than into grip tape and handlebar grips such as into gloves, brake hoods, brake levers, or the handlebars themselves. These electrodes or additional electrodes may be used to measure GSR, body fat and hydration in addition to, or in alternative to, heart rate. In one example, the user's heart rate may be measured using conductive threads (used as ECG electrodes) sewn into grip tape installed on the handlebar. The grip tape electrodes may be connected to a central bike computer unit that contains electronics to measure GSR, hydration, and/or heart rate. The biometric monitoring device may display this information on a display. If the user's hydration or heart rate exceeds a certain threshold, the user may be alerted to drink more, drink less, increase intensity or decrease intensity. In the case that the bike computer measures only one or two of GSR, hydration or heart rate, algorithms may be used to estimate metrics which that cannot be measured directly. For example, if the biometric monitoring device can only measure heart rate and duration of exercise, a combination of heart rate and duration of exercise may be used to estimate hydration and alert the user when they should drink. Similarly, heart rate and exercise duration may be used to alert the user when they should eat or drink something other than water (e.g., a sports drink).

Indirect Metric Estimation

Bicycle computers typically measure a variety of metrics including, but not limited to, speed, cadence, power, and wind speed. In the case that the portable monitoring device does not measure these metrics or is not in communication with devices which may be able to supply these metrics, these and other metrics may be inferred using the sensors that the portable biometric monitoring device does have. In one embodiment, the portable biometric monitoring device may measure heart rate. It may use this measurement to infer/estimate the amount of power that the user is outputting. Other metrics such as the user's age, height, and weight may help inform the power measurement. Additional sensor data such as GPS-measured speed, altitude gain/descent, bicycle attitude (so as the measure the incline or decline of a slope), and accelerometer signals may be used to further inform the power estimate. In one embodiment, an approximately linear relationship between heart rate and power output may be used to calculate the user's power output.

In one embodiment, a calibration phase may occur where the user takes data from the portable biometric monitoring device and a secondary device that may be used during calibration as a baseline but not be used at a later time (e.g., a power meter). This may allow a relationship between sensor data measured by the portable monitoring device and sensor data measured by the secondary device data to be determined. This relationship may then be used when the secondary device is not present to calculate estimated values of data that is explicitly provided by the secondary device but not by the biometric monitoring device.

Activity Based Automatic Scheduling

In one embodiment, the day's travel requirements (to work, from work, between meetings) may be scheduled for the user based on the information in their calendar (or emails or text messages etc.), with the aim of meeting daily activity goal(s) or long term activity goal(s). The user's historical data may be used to help plan both meeting the goal(s) and also the transit time required. This feature may be combined with friends or colleagues. The scheduling may be done such that a user may meet a friend along the way as they walk to work, or meet a colleague on the way to a meeting (the user might need to set a rendezvous point, though). If there is real-time communication between biometric monitoring devices of the user and the user's friend, the user may be directed to walk a longer route if data from the friend's biometric monitoring device indicates that their friend is running late.

In another embodiment, walking/running/fitness routes may be suggested to the user based (in whole or in part) on their proximity to the user. The data for such recommendations could also or additionally be based on GPS info from other users. If there is real-time communication, the user may be directed to a busy route or a quiet route as preferred. Knowing heart rate and basic fitness information about other users may allow the system to suggest a route to match a user's fitness level and the desired exercise/exertion level. Again this information may be used for planning/guiding a user to longer term activity/fitness goals.

Location/Context Sensing and Applications

Through one or more methods, embodiments of the biometric monitoring devices disclosed herein may have sensors that can determine or estimate the location and or context (e.g. in a bus, at home, in a car) of the biometric monitoring device. Purpose-built location sensors such as GPS, GLONASS, or other GNSS (Global Navigation Satellite System) sensors may be used. Alternatively, location may be inferred, estimated or guessed using less precise sensors. In some embodiments in which it is difficult to know the user's location, user input may aid in the determination of their location and or context. For example, if sensor data makes it difficult to determine if a user was in a car or a bus, the biometric monitoring device or a portable communication device in communication with the biometric monitoring device or a cloud server which is in communication with the biometric monitoring device may present a query to the user asking them if they took the bus today or took a car. Similar queries may occur for locations other than vehicular contexts. For example, if sensor data indicate that the user completed a vigorous workout, but there is no location data that indicates that the user went to a gym, the user may be asked if they went to the gym today.

Vehicular Transportation Detection

In some embodiments, sensors of the biometric monitoring device and/or a portable electronic device in communication with the biometric monitoring device and/or a server which communicates with the biometric monitoring device may be used to determine what type of vehicle (if any) the user is, or was, in. Note that in the embodiments below, a sensor in one or more biometric monitoring devices and/or portable electronic devices may be used to sense the relevant signal. Also note that while specific network protocols such as WiFi or Bluetooth may be used in the following descriptions, one or more alternative protocols such as RFID, NFC, or cellular telephony may also be used.

In one embodiment, the detection of a Bluetooth device associated with a vehicle may be used to infer that the user is in a vehicle. For example, a user may have a car that has a Bluetooth multimedia system. When the user gets close enough to their car for a long enough period of time, the sensor device may recognize the Bluetooth identification of the multimedia system and assume that the user is in the car. Data from other sensors may be used to corroborate the assumption that the user is in the vehicle. Examples of data or signals from other sensors that may be used to confirm that the user is in a car include a GPS speed measurement that is higher than 30 mph and accelerometer signals that are characteristic of being in a car. Information intrinsic to the Bluetooth ID may be used to determine that it is a Wi-Fi router of a vehicle or type of vehicle. For example, the Bluetooth ID of a router in a car may be "Audi In-Car Multimedia." The keyword "Audi" or "Car" may be used to guess that the router is associated with a vehicle type of "car." Alternatively, a database of Bluetooth ID's and their associated vehicles may be used.

In one embodiment, a database of Bluetooth ID's and their associated vehicles may be created or updated by the user of a biometric monitoring device or through portable communication device data. This may be done with and/or without the aid of user input. In one embodiment if a biometric monitoring device can determine whether or not it is in a vehicle, vehicle type, or specific vehicle without the use of Bluetooth ID, and it encounters a Bluetooth ID that moves with the vehicle, it may send the Bluetooth ID and information regarding the vehicle to a central database to be catalogued as a Bluetooth ID that corresponds with a vehicle. Alternatively, if a user inputs information about the vehicle they are in or were in at a previous point in time and there is a Bluetooth ID that was encountered during or close to the time that the user indicated they were in the vehicle, the Bluetooth ID and vehicle information may be sent to a central database and associated with one another.

In another embodiment, the detection of a Wi-Fi device associated with a vehicle may be used to infer that the user is in that vehicle or type of vehicle. Some trains, buses, airplanes, cars, and other vehicles have Wi-Fi routers in them. The SSID of the router may be detected and used to infer or aid an inference that a user is in a specific vehicle or type of vehicle.

In one embodiment, a database of SSID's and their associated vehicles may be created or updated with the user of a biometric monitoring device or through portable communication device data. This may be done with and/or without the aid of user input. In one embodiment, if a biometric monitoring device can determine whether or not it is in a vehicle, vehicle type, or specific vehicle without the use of an SSID, and it encounters an SSID that moves with the vehicle, the biometric monitoring device may send the SSID and information regarding the vehicle to a central database to be catalogued as an SSID that corresponds with a vehicle. Alternatively, if a user inputs information about the vehicle they are in or were in at a previous point in time and there is an SSID that was encountered during or close to the time that the user indicated they were in the vehicle, the SSID and vehicle information may be sent to a central database and associated with one another.

In another embodiment of a biometric monitoring device, location sensors may be used to determine the track of a user. This track may then be compared to a database of routes for different modes of transit. Modes of transit may include, but are not limited to walking, running, biking, driving, taking a bus, taking a train, taking a tram, taking the subway, and/or motorcycling. If the user's track corresponds well with a route of a specific mode of transit, it may be assumed that the user used that mode of transit for the period of time that it took them to traverse the route. Note that the speed with which the route or sections of the route were completed may improve the guess of the mode of transit. For example, a bus and a car may both be able to take the same route, but the additional stopping of the bus at bus stops may allow the device to determine that the user was taking a bus rather than a car. Similarly, the discrimination between biking and driving a route may be aided by the typical difference of speed between the two. This difference in speed may also depend on the time of day. For example, some routes may be slower by car during rush hour.

In another embodiment, a biometric monitoring device may be able to detect that the user is in or near a vehicle based on measurements of the magnetic field of vehicle. In some embodiments, the magnetic field signature of a location typically associated with the vehicle (e.g., train station, subway station, bus stop, car garage) may also be used to infer that the user is currently in, will be, or has been in a vehicle. The magnetic field signature may be time invariant or time varying.

If it is determined that the user was indeed in a vehicle for a period of time, other metrics about the user may be modified to reflect such a status. In the case that the biometric monitoring device and/or portable electronic device can measure activity metrics such as steps taken, distance walked or run, altitude climbed, and/or calories burned, these metrics may be modified based on information about vehicular travel. If any steps taken or altitude climbed were incorrectly logged during the time that the user is in a vehicle, they may be removed from the log of metrics about the user. Metrics derived from the incorrectly logged steps taken or altitude climbed such as distance traveled and calories burned may also be removed from the log of metrics about the user. In the case that it can be determined in real-time or near real-time whether or not the user is in a vehicle, the sensors detecting metrics which should not be measured while in a vehicle (e.g. steps taken, stairs climbed) may be turned off or algorithms which are used to measure these metrics may be turned off to prevent incorrectly logged metrics (as well to save power). Note that metrics regarding vehicle use such as type of vehicle taken, when it was taken, which route was taken, and how long the trip took may be recorded and used later to present the user with this data and/or to correct other activity and physiological metrics about the user.

Location Sensing Using Bluetooth

Methods similar to those described above may also be used by a biometric monitoring device to determine when the user comes into proximity of static locations. In one embodiment, Bluetooth ID's from computers (e.g., tablet computers) at restaurants or stores may be used to determine the user's location. In another embodiment, semi-fixed Bluetooth ID's from portable communication devices (e.g., smartphones) may be used to determine a user's location. In the case of semi-fixed Bluetooth ID sources, multiple Bluetooth ID's may be need to reach an acceptable level of confidence of the location of the user. For example, a database of Bluetooth ID's of the coworkers of a user may be created. If the user is within range of several of these Bluetooth ID's during typical working hours, it may be assumed that the user is at work. The detection of other Bluetooth ID's may also be used to record when two users meet up. For example, it may be determined that a user went for a run with another user by analyzing pedometer data and Bluetooth ID's. Similar such concepts are discussed in further detail in U.S. Provisional Patent Application No. 61/948,468, filed Mar. 5, 2014, and previously incorporated by reference with regard to such concepts.

Uncertainty Metric for GPS Based on Location

When fusing sensor signals with GPS signal to estimate informative biometrics, such as steps, live pace, speed, or trajectory of trips, quality of the GPS signal is often very informative. However, GPS signal quality is known to be time-varying, and one of the factors that affects the signal quality is environmental surroundings.

Location information may be used to estimate GPS signal quality. A server may store a map of area types, where the area types are pre-determined by number and kind of objects that deteriorate GPS signals. The types may, for example, be: large building area, small building area, open area, side-by-water area, and forested area. These area types are then queried when GPS sensor gets turned on with its very first few location estimates, which are expected to be rough and inaccurate. With the rough GPS estimates of the location, possible types of areas may be returned, and these area types may then be taken into account in the calculation of the GPS signal quality and reliability.

For example, if a user is in or near an urban canyon (an area surround by tall buildings) such as downtown San Francisco, a low certainty may be associated with any GNSS location measurements. This certainty may be used later by algorithms that attempt to determine the user's track, speed, and/or elevation based on, at least in part, GPS data.

In one embodiment, a database of location and GPS signal quality may be created automatically using data from one or more GNSS sensors. This may be automatically performed by comparing the GNSS tracks with a map of streets and seeing when the GNSS sensors show characteristics of a user travelling along a street (e.g., having a speed of 10 mph or higher), but their track is not located on a road. The database of GPS certainty based on approximate location may also be inferred from maps showing where there are tall buildings, canyons, or dense forests.

Location Sensing Using Vehicular GNSS and/or Dead Reckoning

Many vehicles have integrated GNSS navigation systems. Users of vehicles that don't have integrated GNSS navigations systems often buy a GNSS navigation system for their car that is typically mounted non-permanently in the driver's field of view. In one embodiment, a portable biometric monitoring device may be able to communicate with the vehicle's GNSS system. In the case where the portable biometric monitoring device is also used to track location, it may receive location information from the vehicle GNSS. This may enable the biometric monitoring device to turn off its own GNSS sensor (in the case that it has one), therefore reducing its power consumption.

In addition to GNSS location detection, a vehicle may be able to transmit data about its steering wheel orientation and/or its orientation with respect to the earth's magnetic field in addition to its speed as measured using the tire size and tire rotational velocity. This information may be used to perform dead-reckoning to determine a track and/or location in the case that the vehicle does not have a GNSS system or the vehicle's GNSS system cannot get a reliable location measurement. Dead-reckoning location information may supplement GNSS sensor data from the biometric monitoring device. For example, the biometric monitoring device may reduce the frequency with which it samples GNSS data and fill in the gap between GNSS location data with locations determined through dead reckoning.

Step Counter Data Fusion with Satellite-Based Location Determination

In some implementations of a biometric monitoring device, data from various different sensors may be fused together to provide new insights as to activities of the wearer of the biometric monitoring device. For example, data from an altimeter in the biometric monitoring device may be combined with step count data obtained by performing peak detection analysis on accelerometer data from an accelerometer of the biometric monitoring device to determine when the wearer of the biometric monitoring device is, for example, climbing stairs or walking uphill (as opposed to riding an elevator or an escalator or walking across flat ground).

In another example of sensor data fusion, data from a step counter such as that discussed above may be combined with distance measurements derived from GPS data to provide a refined estimate of total distance traveled within a given window. For example, GPS-based distance or speed data may be combined with step-counter-based distance or speed (using steps taken multiplied by stride length, for example) using a Kalman filter in order to obtain a refined distance estimate that may be more accurate than either the GPS-based distance or speed measurement or the step-counter-based distance or speed measurement alone. In another implementation, a GPS-based distance measurement may be filtered using a smoothing constant that is a function of the step rate as measured by, for example, an accelerometer. Such implementations are discussed further in U.S. Provisional Patent Application No. 61/973,614, filed Apr. 1, 2014, which was previously incorporated herein by reference in the "Cross-Reference to Related Applications" section and which is again hereby incorporated by reference with respect to content directed at distance or speed estimation refinement using data from satellite-based location systems and step count sensors.

Biometric and Environmental/Exercise Performance Correlation

Some embodiments of portable monitoring devices described herein may detect a variety of data including biometric data, environmental data, and activity data. All of this data may be analyzed or presented to a user to facilitate analysis of or correlation between two or more types of data. In one embodiment, a user's heart rate may be correlated to car speed, biking speed, running speed, swimming speed or walking speed. For example, the user may be presented with a graph that plots biking speed on the X axis and heart rate on the Y axis. In another example, a user's heart rate may be correlated to music that they were listening to. The biometric monitoring device may receive data regarding what music the user was listening to through a wireless connection (e.g., Bluetooth) to a car radio. In another embodiment, the biometric monitoring device may also function as a music player itself, and therefore can record which song was played when.

Weight Lifting Aid

Without the aid of a personal trainer or partner, it may be difficult to do a weight-lifting routine properly. A portable biometric monitoring device may aid a user in completing a weight lifting routine by communicating to the user how long they should hold up each weight, how quickly they should lift it, how quickly they should lower it, and how many repetitions of each lift to perform. The biometric monitoring device may measure the user's muscle contractions using one or moreEMG sensors or strain sensors. The user's muscle contractions may also be inferred by measuring vibrations of one or more body parts (for example using an accelerometer), sweat (e.g., using a GSR sensor), rotation of one or multiple body parts (e.g., using a gyroscope), and/or a temperature sensor on one or more body parts. Alternatively, a sensor may be placed on the weight lifting apparatus itself to determine when the using is lifting, with how much speed they are lifting or lowering, how long they are lifting for, and how many repetitions of lifts they have performed.

In one embodiment, if the biometric monitoring device or weight lifting apparatus detects that the user is approaching their failure limit (when the user can no longer support the weight), the weight lifting apparatus may automatically lift the weight or prevent the weight from being lowered. In another embodiment, a robot in communication with the biometric monitoring device or weight lifting apparatus may automatically lift the weight or prevent the weight from being lowered. This may allow the user to push themselves to their limit without needing a partner/spotter (to lift the weight in case of failure) and without risking injury from dropping the weight.

Glucose Level Monitoring Aid

In some embodiments, a portable biometric monitoring device may be configured to aid users who need to monitor their glucose levels (e.g., diabetics). In one embodiment, the portable biometric monitoring device may indirectly infer a user's glucose level or a metric related to the user's glucose level. Sensors other than those typically used in monitoring glucose monitoring (using continuous or discrete finger-prick types of sensors) may be used in addition to, as an alternative to, or as an aid to the typical glucose monitoring methods. For example, an biometric monitoring device may alert the user that they should check their blood glucose level based on data measured from sensors on the biometric monitoring device. If the user has performed a certain type of activity for a certain amount of time, their blood glucose level is likely to have decreased, and therefore, the biometric monitoring device may display an alert, create an auditory alert, or vibrate to alert the user that their blood glucose may be low and that they should check it using a typical glucose measurement device (e.g., a finger-prick type glucose monitor). The biometric monitoring device may allow the user to input the glucose level that is measured from the glucose meter. Alternatively, the glucose measurement may be automatically transmitted to the biometric monitoring device and/or a third device in direct or indirect communication with the biometric monitoring device (e.g., a smart phone or server). This glucose measurement may be used to inform the algorithm used by the biometric monitoring device to determine when the next glucose level alert should be delivered to the user. The user may also be able to enter what food they ate, are eating, or are planning to eat into the biometric monitoring device or a device in direct or indirect communication with the biometric monitoring device. This information may also be used to determine when the user should be alerted to check their blood glucose level. Other metrics and sensor data described herein (e.g., heart rate data) may also be used alone or in combination to determine when the user should be alerted to check their blood glucose.

In addition to being alerted when glucose levels should be checked, a biometric monitoring device may also display an estimate of the current glucose level. In another embodiment, data from the biometric monitoring device may be used by a secondary device (e.g., a smart phone or server) to estimate the user's glucose level and/or present this data to the user (e.g., by displaying it on a smartphone, on a webpage, and/or by communicating the data through audio).

A biometric monitoring device may also be used to correlate exercise, diet, and other factors to blood glucose level. This may aid users in seeing the positive or negative effects of these factors on their blood glucose levels. The blood glucose levels with which the activity is correlated to may be measured by the user using a different device (e.g., a finger-prick monitor or continuous blood glucose monitor), by the biometric monitoring device itself, and/or by inferring the blood glucose level or a metric related to the glucose level using other sensors. In some embodiments of biometric monitoring devices, a user may wear a continuous glucose monitoring device and a biometric monitoring device. These two devices may automatically upload data regarding activities and glucose levels to a third computing device (e.g., a server). The server may then analyze the data and/or present the data to the user so that they become more aware of the relationship between their activities and glucose levels. The server may also receive input on the user's diet (e.g., the user may enter what foods they eat) and correlate the diet with glucose levels. By helping the user understand how diet, exercise, and other factors (e.g., stress) affects their blood glucose levels, biometric monitoring devices may aid users who have diabetes.

UV Exposure Detection

In one embodiment, the biometric monitoring device may have the ability to monitor an individual's exposure to UV radiation. UVA and UVB may be measured with one or multiple sensors. For example, a photodiode having a bandpass filter which passes only UVA may detect UVA exposure and a photodiode having a bandpass filter which passes only UVB may detect UVB exposure. The user's skin pigmentation may also be measured using a camera or reflectometer (light emitter and light detector which determines the efficiency with which light is reflected off the skin). Using UVA, UVB, and skin pigmentation data, the biometric monitoring device may provide a user with information regarding the amount of UV exposure they have been subjected to. The biometric monitoring device may also provide estimates or alarms regarding over exposure to UV, potential for sunburn, and potential for increasing their risk of skin cancer.

Screen Power Saving Using User Presence Sensors

The portable biometric monitoring device may have one or more a displays to present information to the user. In one embodiment sensors on the biometric monitoring device may determine the user is using the biometric monitoring device and/or wearing the biometric monitoring device to determine the state of the display. For example, a biometric monitoring device having a PPG sensor may use the PPG sensor as a proximity sensor to determine when the user is wearing the biometric monitoring device. If the user is wearing the biometric monitoring device, the state of the screen (e.g. a color LCD screen) may be changed to "on" or "standby" from its typical state of being off.

Power Conservation with Respect to Satellite-Based Location Determination Systems In some implementations, certain systems included in a biometric monitoring device may consume relatively large amounts of power compared to other systems in the biometric monitoring device. Due to the small space constraints of many biometric monitoring devices, this may seriously affect overall battery charge life for the biometric monitoring device. For example, in some biometric monitoring devices, a satellite-based location determination system may be included. Each time the satellite-based location determination system is used to obtain a position fix using data from the GPS satellite constellation, it uses power drawn from the biometric monitoring device battery. The biometric monitoring device may be configured to alter the frequency with which the satellite-based location determination system obtains a location fix based on data from one or more sensors of the biometric monitoring device. This adaptive location fix frequency functionality may help conserve power while still allowing the satellite-based location determination system to provide location fixes at useful intervals (when appropriate).

For example, if a biometric monitoring device has an ambient light sensor, data from the ambient light sensor may be used to determine whether the lighting conditions indicate that the biometric monitoring device is likely indoors as opposed to outdoors. If indoors, the biometric monitoring device may cause the location fix frequency to be set to a level that is lower than the location fix frequency that may be used when the lighting conditions appear to indicate that the biometric monitoring device is outdoors. This has the effect of decreasing the number of location fixes that are attempted when the biometric monitoring device is indoors and thus less likely to obtain a good location fix using a satellite-based location determination system.

In another example, if motion sensors of the biometric monitoring device indicate that the wearer of the biometric monitoring device is substantially stationary, e.g., sleeping or generally not moving more than a few feet every minute, the location fix frequency of the satellite-based location determination system may be set to a lower level than if the motion sensors indicate that the wearer of the biometric monitoring device is in motion, e.g., walking or running from one location to another, e.g., moving more than a few feet.

In yet another example, the biometric monitoring device may be configured to determine if the biometric monitoring device is actually being worn by a person—if not, the biometric monitoring device may set the location fix frequency to a lower level than if the biometric monitoring device is actually being worn. Such determinations regarding whether or not the biometric monitoring device is being worn may be made, for example, when motion data collected from motion sensors of the biometric monitoring device indicate that the biometric monitoring device is substantially immobile, e.g., not even demonstrating small movements experienced by biometric monitoring devices when the wearer is sleeping or sedentary, or when data, for example, from a heart rate sensor indicates that no heart rate is detected. For optical heart rate sensors, if there is little or no change in the amount of light detected by the light detection sensor when the light source is turned on and off, this may be indicative of the fact that the heart rate sensor is not pressed against a person's skin and that, by inference, the biometric monitoring device is not being worn. Such adaptive satellite-based location determination system fix frequency concepts are discussed in more detail in U.S. Provisional Patent Application No. 61/955,045, filed Mar. 18, 2014, which was previously incorporated herein by reference in the "Cross-Reference to Related Applications" section and which is again hereby incorporated by reference with respect to content directed at power conservation in the context of satellite-based location determination systems.

It is to be understood that biometric monitoring devices, in addition to including the features discussed below in more detail, may also include one or more features or functionalities discussed above or discussed in the various applications incorporated by reference in the above discussion. Such implementations are to be understood as being within the scope of this disclosure.

While the above discussion has focused on a variety of different systems and functionality that may be included in a biometric monitoring device, the discussion that follows below focuses on some particular embodiments (some of which may also be discussed above) in further detail.

Altimeter Use in Biometric Monitoring Devices

Discussed below are several different techniques or systems in which an altimeter or altitude-measuring device may be used. Such implementations may be practiced in the context of a biometric monitoring device, although some implementations may be practiced in other devices.

In some implementations, a barometric altimeter in a biometric monitoring device (or other electronic device) may be recalibrated based on data obtained from another sensor, e.g., from a GPS or other location-determination system or from a camera, for example. In other or additional implementations, an altimeter in a biometric monitoring device may be used, in conjunction with other sensors of the biometric monitoring device, to assist in identifying particular gestures or movements that may be indicative of particular activities. In yet other or additional implementations, an altimeter in a biometric monitoring device (or other device) may be used in conjunction with an "airplane mode" that the biometric monitoring device may be placed in in order to conserve power and/or provide reduced EM emissions. These implementations are discussed in further detail below.

Automatic Altimeter Recalibration

In some implementations, a biometric monitoring device may include a barometric altimeter in addition to other biometric sensors, e.g., accelerometers, heart rate sensors, etc., and/or environmental sensors, e.g., ambient light sensors, ambient air quality sensors, etc. A barometric altimeter is, in essence, a pressure sensor that measures ambient atmospheric pressure. As the pressure sensor's altitude changes, the pressure detected by the pressure sensor will increase as the pressure sensor decreases in altitude, and will decrease as the pressure sensor increases in altitude. Pressure sensors provided by some manufacturers are designed such that they output a signal indicative of pressure, and a device using such a sensor must then convert the signal into an elevation amount (the relationship between pressure and altitude is not linear, so some form of processing beyond mere linear scaling must be performed). Some other pressure sensors are designed with pre-output circuits or processors that convert the pressure sensor signal into a signal indicative of altitude.

Figure 17:
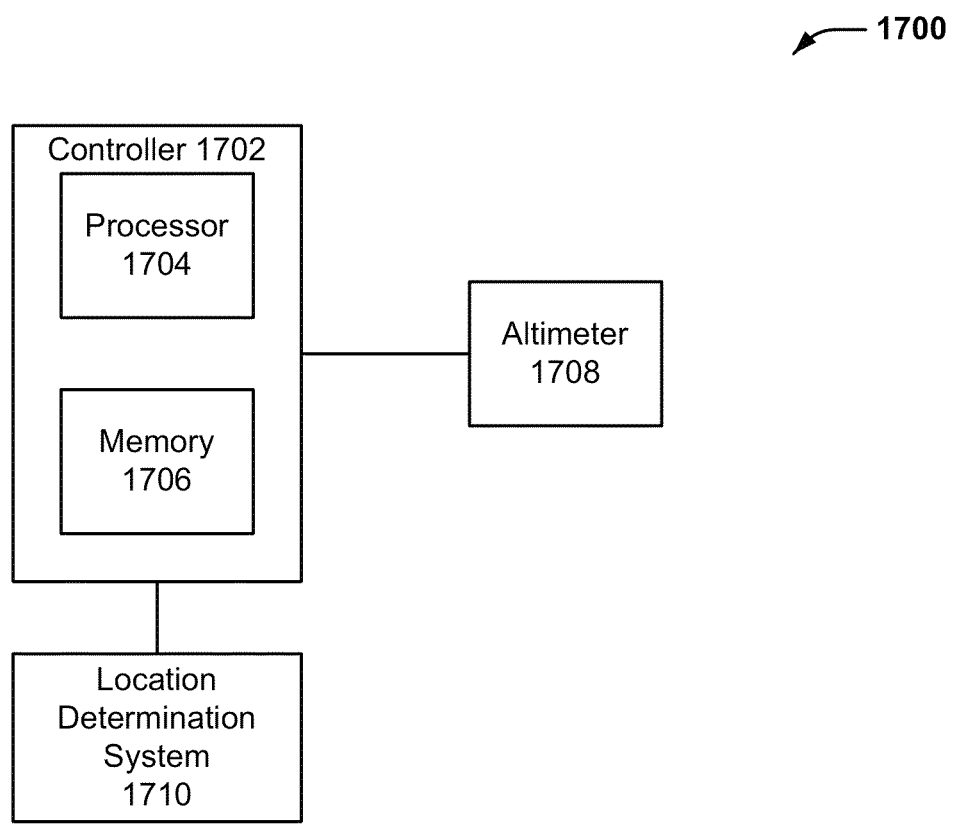
FIG. 17 depicts a simplified block diagram of a biometric monitoring device having an altimeter and a location-determination system.

FIG. 17 depicts a simplified block diagram of an example biometric monitoring device having an altimeter and a location-determination system. As can be seen, the biometric monitoring device of FIG. 17 includes one or more processors 1704 and a memory 1706 that are communicatively connected with one another to form a controller 1702. The controller 1702 is communicatively connected with an altimeter or pressure sensor 1708 and with a location-determination system 1710. Other arrangements of such components may also be used—for example, as discussed further below, the location-determination system 1710 may be located in another device external to the biometric monitoring device and its functionality may be accessed by the biometric monitoring device using, for example, a wireless communications interface.

Pressure-sensor-based altimeters may be quite sensitive, which may be useful for detecting low-magnitude elevation changes, e.g., ~+/−20 cm. However, pressure sensors may also be very susceptible to changes in pressure that are not caused by changes in elevation. For example, if a low-pressure front moves into an area, the ambient pressure may decrease without any elevation increase on the part of the pressure sensor. There are other sources of pressure change as well, including wind. Pressure sensors may also be susceptible to drift over time, which may affect their accuracy.

Some biometric monitoring devices may include pressure sensors used as altimeters, e.g., the Fitbit Ultra, Fitbit One, and Fitbit Force all include(d) a barometric altimeter/pressure sensor. Barometric altimeters may also be used in other devices, e.g., some GPS devices include altimeters as well since altimeters generally provide a more accurate elevation measurement than can be attained with a satellite-based location-determination system.

In some implementations, a device, e.g., a biometric monitoring device or other device, may be equipped with a pressure sensor used as an altimeter and a location-determination system. Such a device may take periodic measurements of XY location using the location-determination system and then use the XY location data in conjunction with a historical topographic data set to determine a topographic altitude that is based on the data in the historical topographic data set. If the altitude measured by the pressure sensor at a given location is sufficiently different from the topographic altitude that corresponds with that location, then the device may recalibrate the pressure sensor (or recalibrate how it handles data from the pressure sensor).

Figure 18:
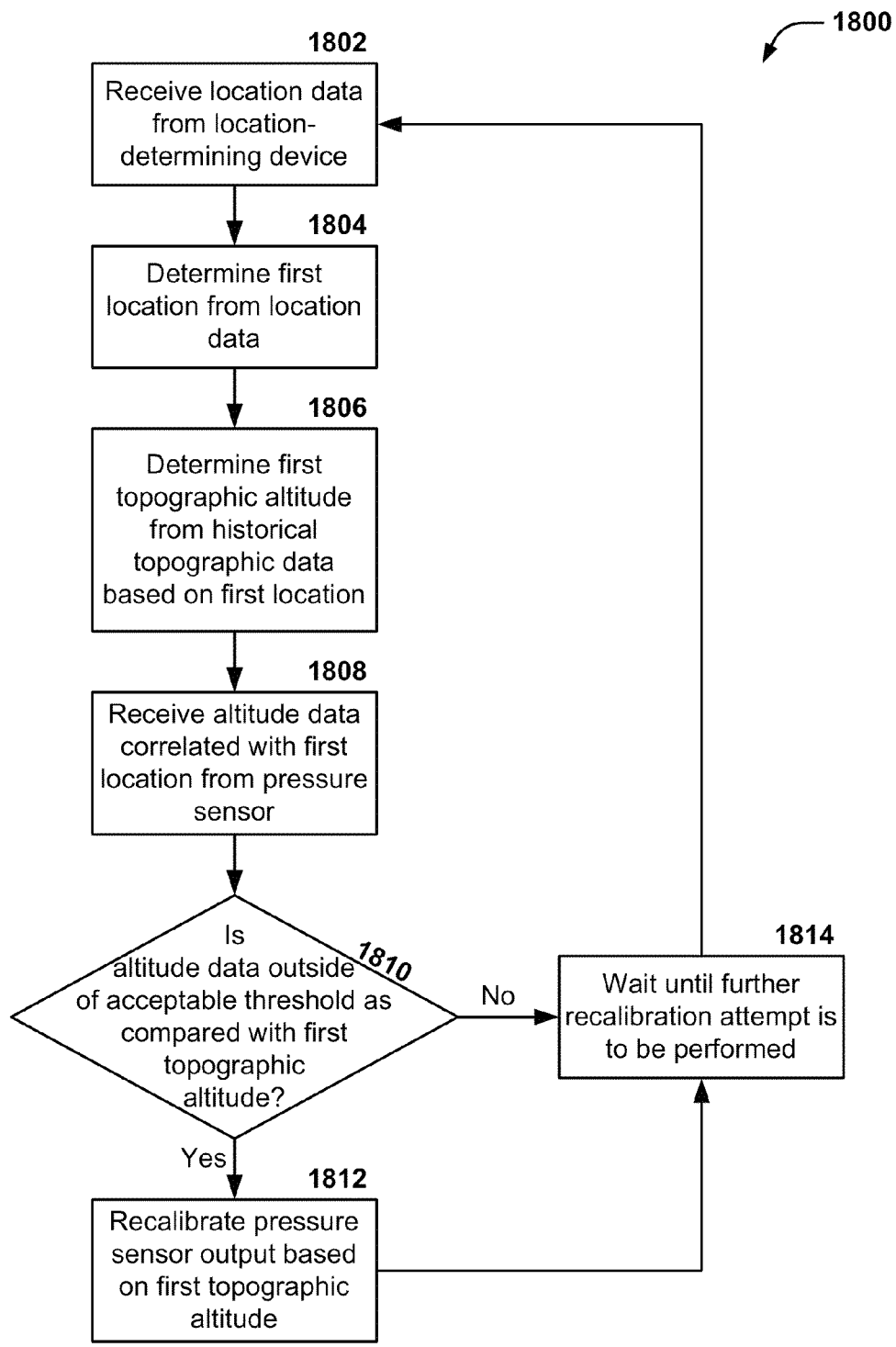
FIG. 18 depicts a flow diagram for a technique for recalibrating a pressure sensor based on topographic data.

This is discussed in more detail with reference to FIG. 18. FIG. 18 depicts a flow diagram for a technique for recalibrating a pressure sensor based on topographic data.

In FIG. 18, the technique 1800 may begin in block 1802, where a device, e.g., a biometric tracking device, may receive location data from some form of location-determination system. As used herein with respect to altimeter recalibration, location-determination systems may include satellite-based location determination systems, e.g., GPS or GLONASS; cell-tower-based triangulation systems, WiFi-based location look-up, (radio frequency identification (RFID) tag lookup systems, near-field-communications (NFC) tag lookup systems, and any other systems that may be used to provide an XY position. Generally speaking, location-determination systems typically rely on data received from devices remote from the location-determination system, e.g., satellites, RFID tags, servers, WiFi hotspots, etc. Such remote devices are typically fixed in place (cell tower and WiFi hotspots, for example) or are able to provide very accurate information regarding their location (GPS satellites, for example). Such data may then be used by the location-determination system to determine where the location-determination system is with respect to these known locations. In some implementations, however, the location-determination system may utilize a camera to obtain images, either automatically or culled from images taken by a user of the device in which the location-determination system resides, that may be analyzed to determine location. For example, such a system may analyze an image and determine that the skyline includes a particular silhouette that corresponds with image data in a database associated. That image data may be associated with a particular location in the database, and the system may determine that, based on the similarities between the image skyline and the image data, the image was taken at the particular location (and may thus use the particular location as the location data). Such image-based techniques are not limited to skyline silhouette recognition—signage (e.g., street signs, business signs, landmark signs, etc.), buildings, landmarks, etc. may all serve as potentially searchable image-based features that may correspond with a particular location and may be used by a camera-based location determination system to obtain location data.

The location data may be provided by a location-determination system that is located in the same device or a different device. For example, a smart-watch type biometric monitoring device may include both a pressure sensor and a GPS receiver, and may thus obtain the location data from the GPS receiver. However, in some other implementations, the biometric monitoring device may not include an on-board location-determination system, but may instead include communications functionality for communicating with a paired smartphone, for example. In such implementations, the smartphone may have a GPS receiver and the biometric monitoring device may obtain location data by requesting such data from the smartphone; the smartphone may thus act as a location-determination device with respect to the biometric monitoring device. This disclosure is intended to cover both devices having pressure sensors and location-determination functionality on-board and devices having pressure sensors on board but relying on accessing a location-determination system located off-board, e.g., wirelessly.

In block 1804, a first location may be determined from the location data. In some implementations, the first location may be a single coordinate obtained from the location data. In other implementations, however, the first location may be an average of multiple coordinates drawn from the location data, e.g., the last 20 location fixes. In yet other implementations, the first location may be a plurality of locations.

Figure 21A:
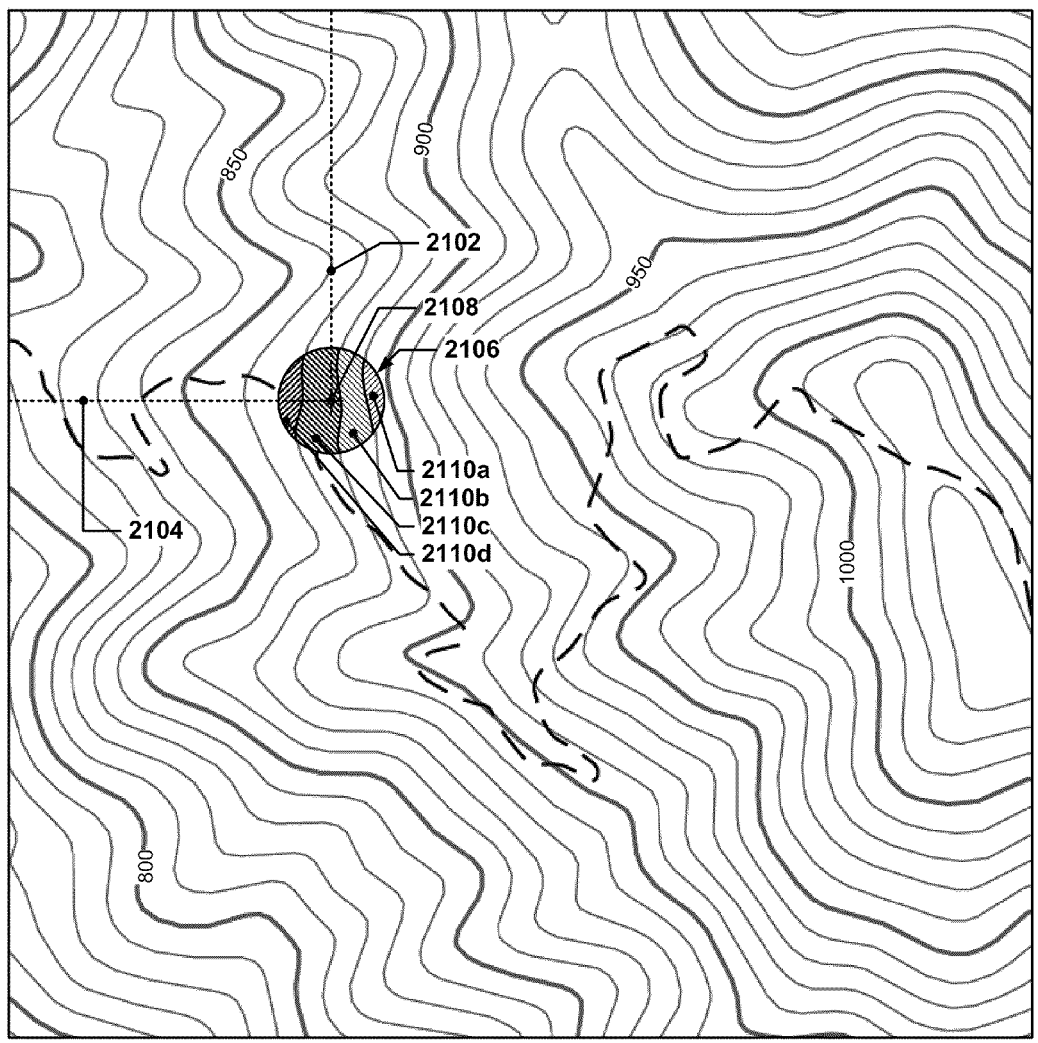
FIG. 21A demonstrates aspects of one technique for determining a topographic altitude from historical topographic data.
Figure 21B:
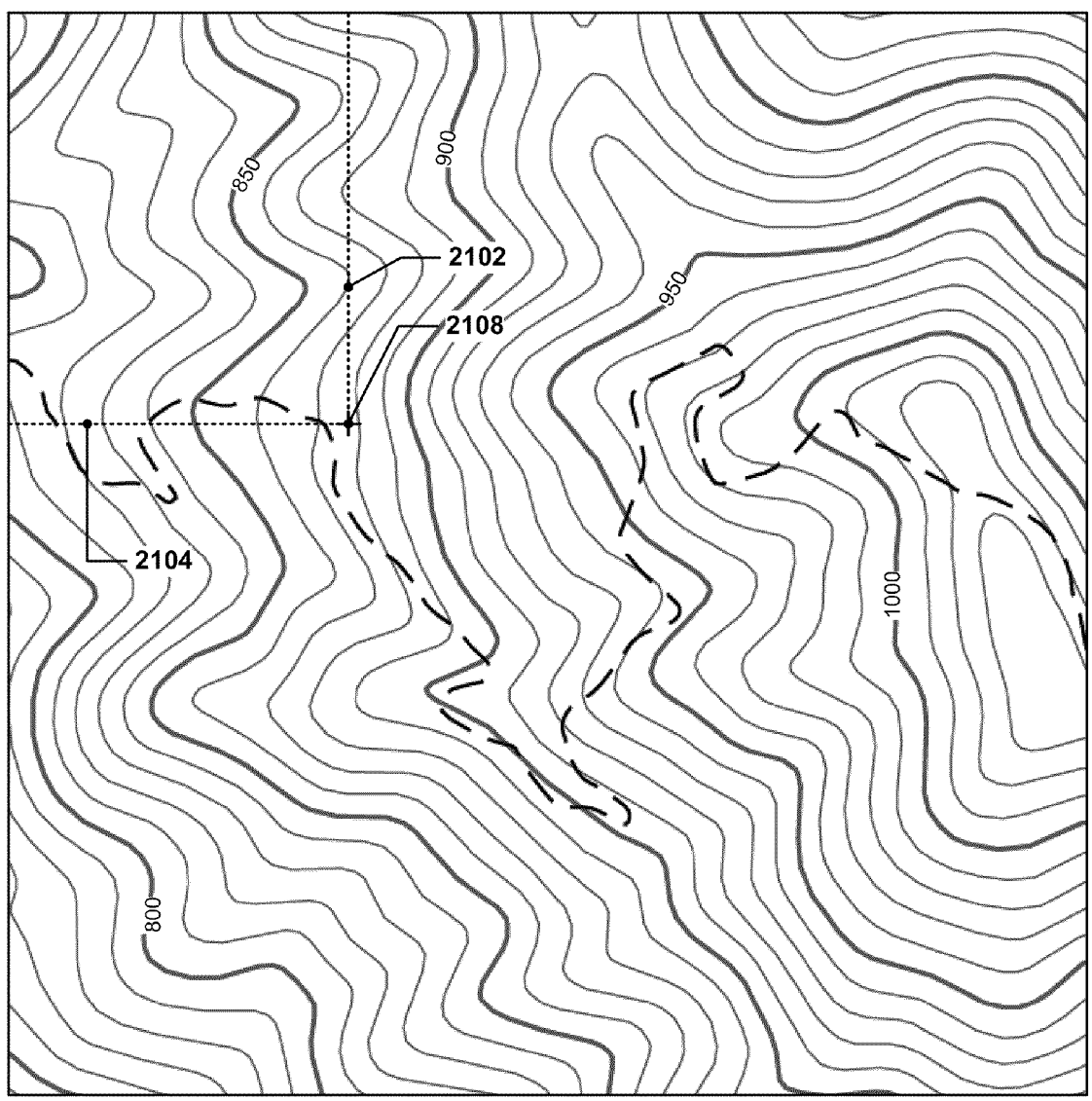
FIG. 21B demonstrates aspects of another technique for determining a topographic altitude from historical topographic data.
Figure 21C:
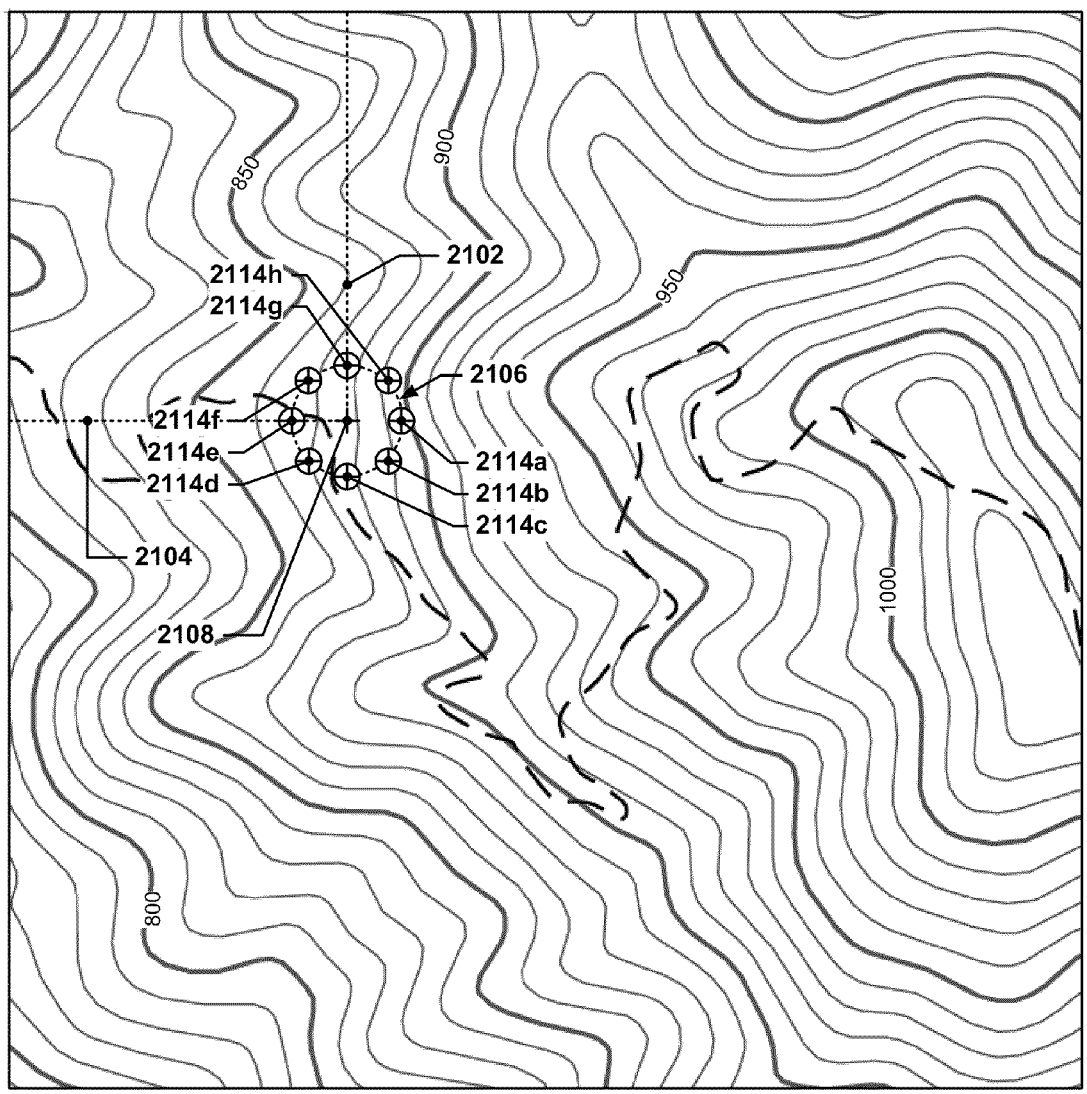
FIG. 21C demonstrates aspects of yet another technique for determining a topographic altitude from historical topographic data.

In block 1806, the device may look up the first location in a historical topographic dataset, e.g., a topographic contour database or map set, etc. Using the historical topographic dataset, the device may determine a first topographic altitude that corresponds with the first location. In some implementations, the historical topographic dataset may provide such data directly. In other implementations, it may be necessary to perform some degree of analysis to extract such topographic altitudes. FIGS. 21A through 21C discuss examples of such analysis in more depth.

In block 1808, first altitude data that is associated with the first location may be received from the pressure sensor. It is to be understood that, with respect to all of the altimeter-related disclosure presented herein, "altitude data" may be used to mean post-processed altitude data, e.g., "X ft" or "X meters"; pressure data that can be viewed as representing an altitude, e.g., "0.98 atmospheres" or "14.6 psi"; or voltage or current signals that represent either altitude or pressure. One of ordinary skill in the art would understand how to convert between these different data formats and while the discussion herein and the appended claims may reference "altitude data" or "data representative of altitude," it is to be understood that such data may be freely converted between different formats within the scope of this disclosure. For example, the first topographic altitude may be obtained in terms of feet, and the first altitude data may be obtained in terms of a voltage signal. The voltage signal may then be converted to a format allowing comparison against the first topographic altitude (or vice-versa).

In block 1810, the first altitude data may be compared against the first topographic altitude. If there is a difference between the two that exceeds a particular threshold, e.g., 5 ft, the pressure sensor may be recalibrated in block 1812 based on the first topographic altitude. Different pressure sensors may have different recalibration techniques. In some implementations, the pressure sensor may have a recalibration function that may be accessed by the device and used to recalibrate the pressure sensor. In other implementations, the pressure sensor may not be able to be recalibrated internally, and the device may need to recalibrate the output from the sensor using post-processing. Once recalibration is performed, the technique may involve progressing to block 1814, where the technique may pause before returning again to block 1802. If calibration is not needed, as determined in block 1810, the technique may proceed to block 1814 directly. It is to be understood that in some implementations, block 1814 may involve no waiting at all, i.e., wait time=0 seconds, and the recalibration technique may, in effect, always be checking the present measured altitude against topographic data. However, given that errors in pressure sensor readings are unlikely to occur quickly, e.g., due to drift or weather, it may be advantageous from a power conservation and processing overhead perspective to perform recalibration checks at spaced-apart intervals, e.g., every 5 minutes, 10 minutes, 15 minutes, 20 minutes, 30 minutes, 60 minutes, etc.

In some implementations, the intervals may be set from between 1 second and 24 hours.

Of course, the technique of FIG. 18 and the other techniques discussed below, while presented as being cyclic in nature, may also be practiced as a single-pass technique without automatic cyclic behavior.

Figure 19:
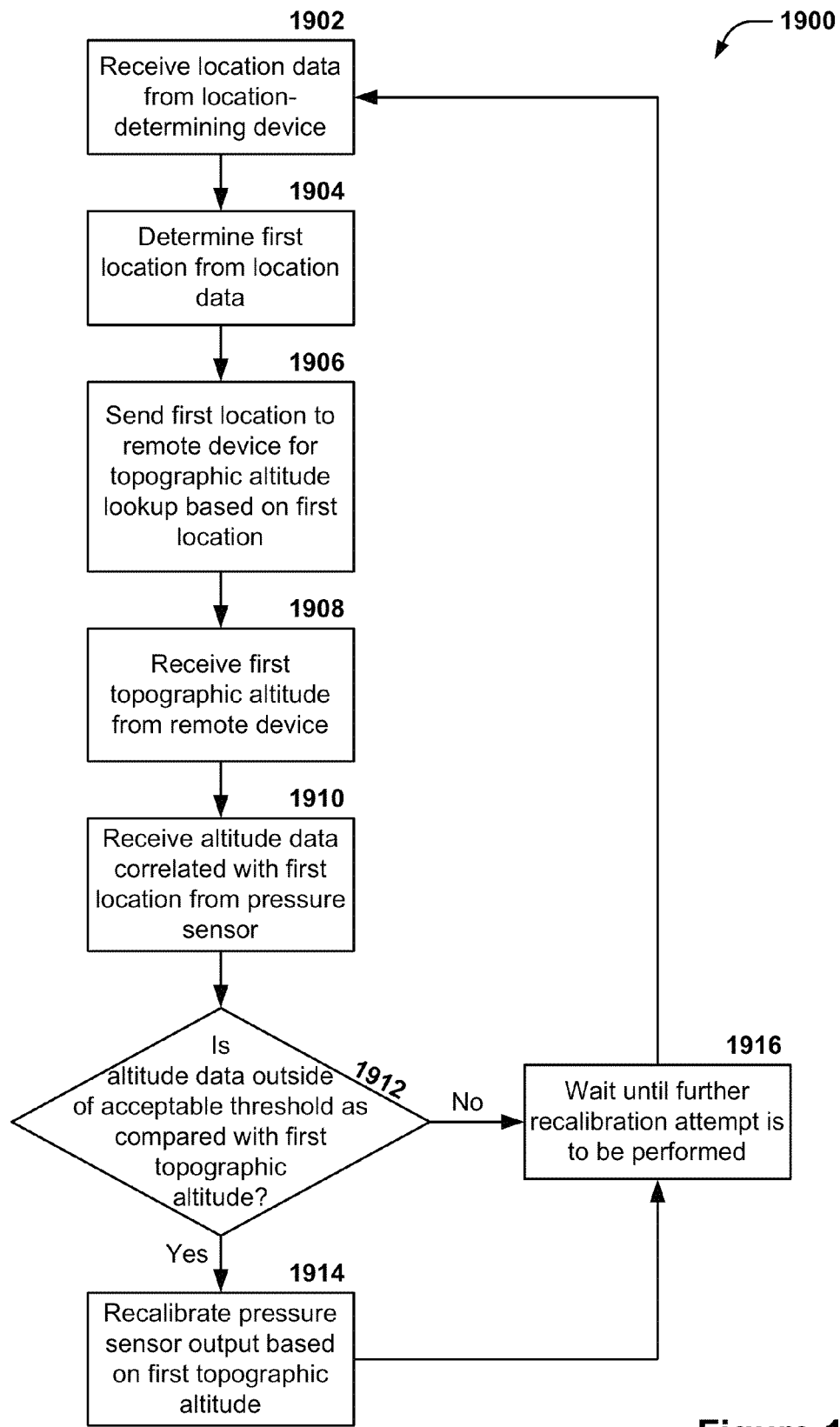
FIG. 19 depicts a flow diagram for a technique for recalibrating a pressure sensor based on topographic data obtained from a remote device.

FIG. 19 depicts a flow diagram for a technique for recalibrating a pressure sensor based on topographic data obtained from a remote device.

In FIG. 19, the technique 1900 may begin in block 1902, where a device, e.g., a biometric tracking device, may receive location data from some form of location-determination system, much as in block 1802. In block 1904, a first location may be determined from the location data, again, much as in block 1804.

In block 1906, the device may look up the first location in a historical topographic dataset, e.g., a topographic contour database or map set, etc., from a remote device in order to obtain a first topographic altitude, much as in block 1806. For example, various online databases of historical topographic data may be consulted, e.g., a United States Geological Survey database, a third-party private supplier of topographical data, or other topographical data sources, e.g., altimeter data from other users of similar biometric monitoring devices (or other devices) may be location-mapped and used to produce a historical topographic dataset that may then be subsequently used by a biometric monitoring device as a source of historical topographic data. Such a dataset may be structured so as to weight altitude data from newer biometric monitoring devices to a greater extent than altitude data from older biometric monitoring devices (or to exclude altitude data from biometric monitoring devices over a certain age). Since some pressure sensors/barometric altimeters may experience drift as they age, such weighting (or exclusion) may reduce the contributions of older biometric monitoring devices (and their altimeters) to the data pool. Such techniques may be modified to treat more favorably data from biometric monitoring devices that, while older, have been recalibrated on a regular basis and that may thus be comparable in performance to newer biometric monitoring devices as compared with older biometric monitoring devices that have not been frequently recalibrated. In block 1908, the first topographic altitude may be received by the biometric monitoring device from the remote device.

The device may utilize some form of wired or wireless communications interface, e.g., WiFi, Bluetooth, etc., as part or all of the mechanism by which communications with the remote device are established.

Generally speaking, the historical topographical data may be stored locally, e.g., in the same device that contains the pressure sensor and/or the location-determination sensor, or remotely, e.g., in a paired device such as a smartphone or in a server accessible over the Internet. Local storage may have the benefits of not requiring a communications connection to a remote device and allowing faster access to data as a result, but at the cost of increased power consumption and increased non-volatile memory storage requirements (to store the historical topographic data, which may require relatively massive amount of storage space as compared with the data normally stored by biometric monitoring devices). In some implementations, a hybrid approach may be taken where the device may download a subset of historical topographic data from a remote device and store the subset locally, e.g., local caching of topographical data that has a high likelihood of being referenced due to its association with the surrounding area. Such conventions may be applied to any device in which pressure sensor recalibration based on topographic data is performed.

In block 1910, first altitude data that is associated with the first location may be received from the pressure sensor. In block 1912, the first altitude data may be compared against the first topographic altitude. If there is a difference between the two that exceeds a particular threshold, e.g., 5 ft, the pressure sensor may be recalibrated in block 1914 based on the first topographic altitude, much as in block 1812. Once recalibration is performed, the technique may involve progressing to block 1916, where the technique may pause before returning again to block 1902. If calibration is not needed, as determined in block 1912, the technique may proceed to block 1916 directly. It is to be understood that in some implementations, block 1916 may involve no waiting at all, i.e., wait time=0 seconds, and the recalibration technique may, in effect, always be checking the present measured altitude against topographic data. However, given that errors in pressure sensor readings are unlikely to occur quickly, e.g., due to drift or weather, it may be advantageous from a power conservation and processing overhead perspective to perform recalibration checks at spaced-apart intervals, e.g., every 5 minutes, 10 minutes, 15 minutes, 20 minutes, 30 minutes, 60 minutes, etc.

Figure 20:
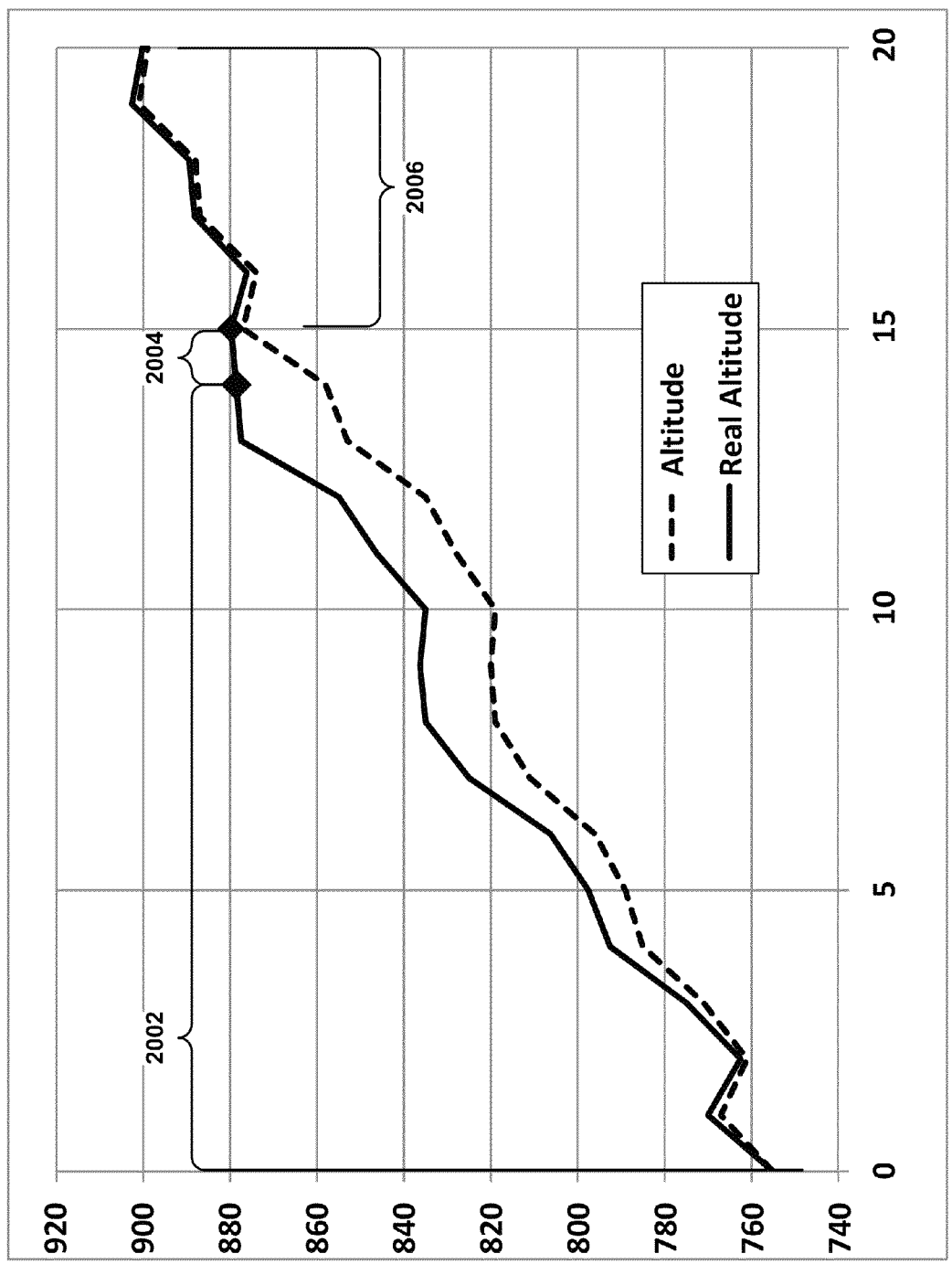
FIG. 20 shows a plot of hypothetical pressure or altitude v. time.

FIG. 20 shows a plot of hypothetical pressure or altitude v. time. As can be seen, two plots of data representing altitude are shown—one represents "actual altitude," i.e., the real altitude of the barometric altimeter, and the other represents "measured altitude," i.e., the altitude as measured by the barometric altimeter. The x-axis represents units of time. As can be seen, as time progresses, the two altitude plots drift apart due to a slight drift in the pressure sensor providing the measured altitude data. This drift grows more and more pronounced during the drift period 2002. During 2004, the pressure sensor is recalibrated based on a technique such as those described above and below. In 2006, it can be seen that the re-calibrated measured altitude closely maps to the actual altitude.

As mentioned, several techniques may be used to determine a topographic altitude from a topographic data set based on an XY location. Several such examples are presented below, although these are not intended to be limiting and various other techniques for obtaining a topographic altitude may be used in place of, or in addition to or in combination with, the listed examples.

FIG. 21A demonstrates aspects of one technique for determining a topographic altitude from historical topographic data. FIG. 21A shows a topographical map with an XY location 2108 (marked by latitudinal position 2104 and longitudinal position 2102). As is the case with many location measurements, there may be error represented by an envelope 2106 (in this case circular, although in some implementations, of other shapes). The envelope 2106 may be sectioned into segments 2110a, 2110b, 2110c, and 2110d by contour lines of the topographic data set. To arrive at a topographic altitude, the altitudes represented by each segment may be multiplied by the corresponding segment area and then added together and divided by the total area of the envelope. This may provide an average estimate of the topographic altitude within the error envelope 2106.

FIG. 21B demonstrates aspects of another technique for determining a topographic altitude from historical topographic data. FIG. 21B also shows a topographical map with an XY location 2108 (marked by latitudinal position 2104 and longitudinal position 2102). In this example, the topographic altitude may be obtained by using the closest topographic contour elevation, or by averaging the altitude of the two topographic contours that bracket the XY location, or by interpolating between the altitudes of the two topographic contours that bracket the XY location (interpolation, for example, along the shortest line that intersects both contours and the XY location).

FIG. 21C demonstrates aspects of yet another technique for determining a topographic altitude from historical topographic data. FIG. 21C also shows a topographical map with an XY location 2108 (marked by latitudinal position 2104 and longitudinal position 2102). FIG. 21C also shows an error envelope 2106, as well as a plurality of peripheral sampling points 2114a, 2114b, 2114c, 2114d, 2114e, 2114f, 2114g, and 2114h. In this technique, a topographic altitude may be obtained by averaging the topographic altitudes at each of the sampling points (and, in some further implementations, at the XY location 2108).

Of course, other techniques for obtaining a topographic altitude from a topographic data set may also be used and fall within the scope of this disclosure.

Figure 22:
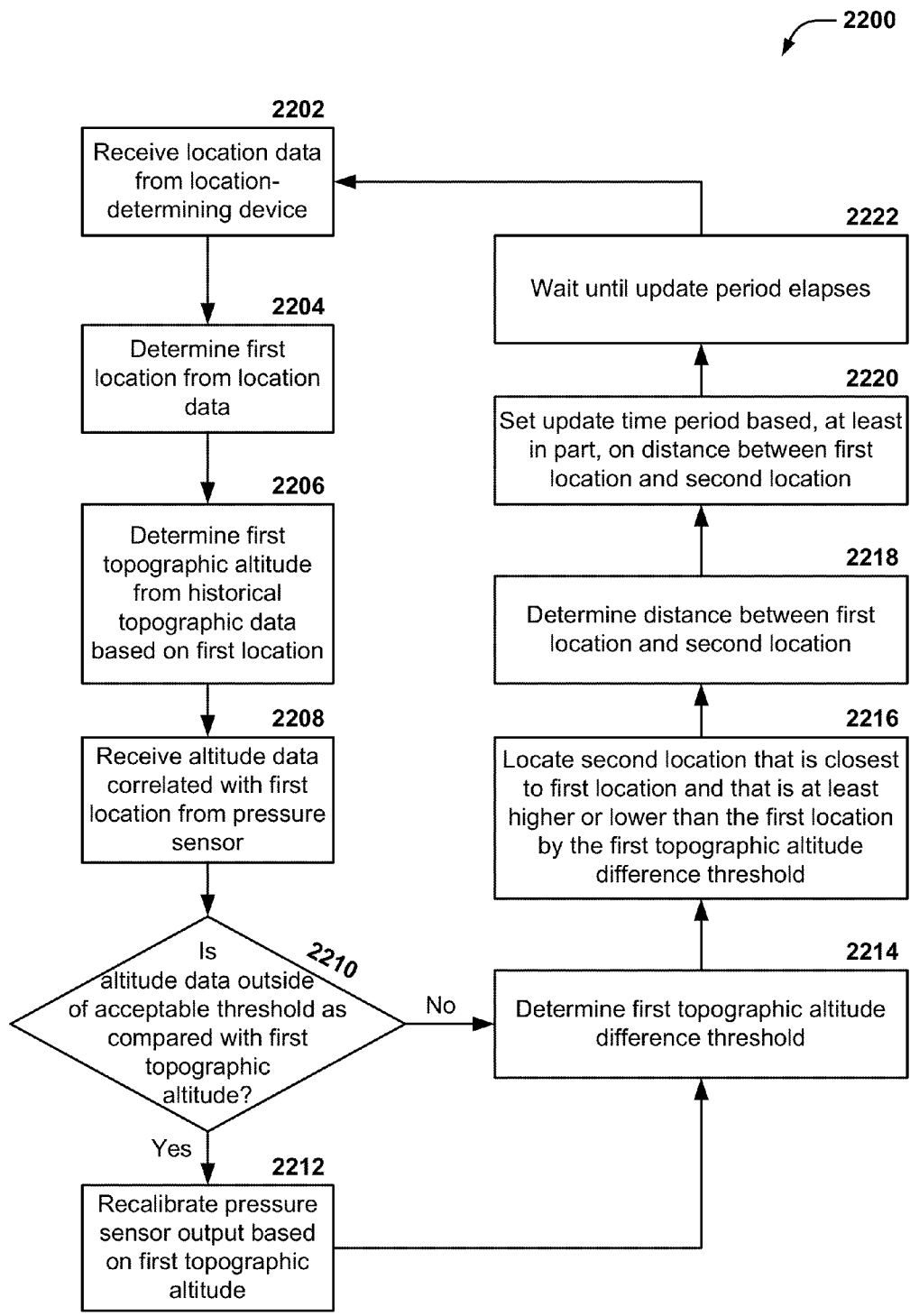
FIG. 22 depicts a flow diagram for a technique for recalibrating a pressure sensor based on changes in XY location.

In some implementations, the frequency of pressure sensor or barometric altimeter recalibrations may be adjusted based on changes in XY location. FIG. 22 depicts a flow diagram for one technique for recalibrating a pressure sensor based on changes in XY location.

In FIG. 22, the technique 2200 may begin in block 2202, where a device, e.g., a biometric tracking device, may receive location data from some form of location-determination system, much as in block 1802. In block 2204, a first location may be determined from the location data, again, much as in block 1804. In block 2206, the device may look up the first location in a historical topographic dataset, e.g., a topographic contour database or map set, much as in block 1806 or 1906. In block 2208, the biometric monitoring device may receive altitude data correlated with the first location from a pressure sensor. In block 2210, a determination may be made as to whether or not to recalibrate the pressure sensor based on the difference between the altitude data and the first topographic altitude. If the difference is above a first threshold, the pressure sensor may be recalibrated in block 2212 before proceeding to block 2214. If not, the technique may proceed directly to block 2214. In block 2214, a first topographic altitude difference threshold may be determined. In block 2216, the historical topographical data may be analyzed to determine a second location that is both closest to the first location and higher or lower than the first topographic altitude difference threshold as compared to the first location. In block 2218, the distance between the first location and the second location may be determined. In block 2220, an update time period may be set based, at least in part, on the distance between the first location and the second location. For example, the update time period may be fixed and set based on the distance or based on the distance divided by the current speed, e.g., if the distance is 5 miles and the current speed is 10 mph, the update time period may be set to 0.5 hours. Such implementations may assume that pressure sensor recalibration may not be necessary until after the wearer of the device has changed elevation beyond the first topographic altitude difference threshold, and that such a potential occurrence is unlikely to occur until the person has at least traveled sufficiently far to reach the nearest apparent location where such an occurrence is possible.

In some implementations, the update time period may be based on the distance but also be dynamic. For example, if the distance is 5 miles, the update time period may be set such that it expires when the biometric monitoring device indicates that 5 miles have been traversed, e.g., in aggregate. Once the update time period expires in block 2222, the technique may return to block 2202.

In another implementation, the first topographic altitude difference threshold may also be used to establish a "fence." When the wearer of the device has not traveled far enough to potentially reach the edge of the fence, it may be assumed that their actual altitude is not more than the first topographic altitude difference threshold—and if the pressure sensor indicates an altitude that is higher than the first topographic altitude difference threshold, it may be recalibrated to the first topographic altitude difference threshold. This may be of particular use in large, flat areas where there is very little potential for altitude change over large distances. In more advanced implementations of such a concept, the fence may actually be defined by a contour line of the historical topographic dataset, and the user's real-world XY position may be compared against the fence at regular intervals to determine if they have crossed the fence boundary—if they have not, but the pressure sensor indicates an altitude that is higher than should be possible given the altitude within the fence, then the pressure sensor may be recalibrated. For example, if a person is walking along a beach that is bounded by cliffs and the ocean, the cliffs may define a portion of a "fence." From the historical topographical data, the beach may be determined to be at an altitude of 0 ft to 10 ft, and the cliffs may be at altitudes greater than 10 ft. If the user stays on the beach, i.e., within the fence, their altitude should, in theory, be between 0 ft and 10 ft—if the pressure sensor indicates a higher altitude, recalibration of the pressure sensor based on an altitude of 10 ft may be performed. Additionally or alternatively, a recalibration check may be performed when the user of the device crosses from the beach to the "cliffs" area.

Figure 23:
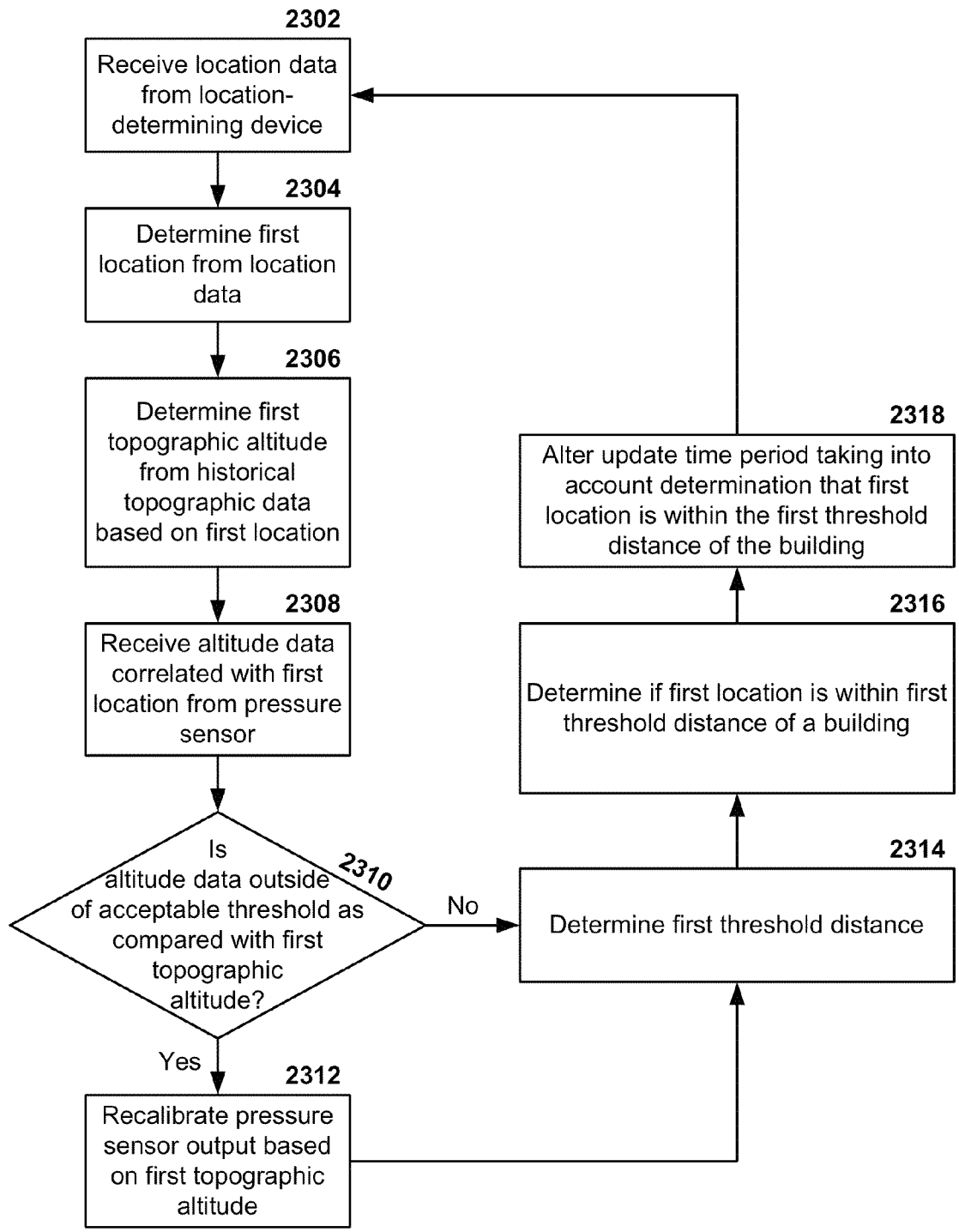
FIG. 23 depicts a flow diagram for a technique for recalibrating a pressure sensor that is dependent on the proximity of the pressure sensor to a building.

FIG. 23 depicts a flow diagram for a technique for recalibrating a pressure sensor that is dependent on the proximity of the pressure sensor to a building. The above-described techniques provide for recalibration of a barometric altimeter or pressure sensor based on differences between a topographic altitude and a measured altitude. In some situations, topographic data and measured data may not correspond for a given location although both altitudes may be largely correct. For example, if an altimeter or pressure sensor is located at an XY location that also happens to be a location where a building is located (or nearby such a building), there is a chance that the person carrying the pressure sensor is actually within the building and, if the building is multiple stories, that the person may be at an actual altitude that is tens or hundreds of feet above the ground, i.e., tens or hundreds of feet above the likely topographic altitude. Recalibrating the pressure sensor based on the topographic altitude at such locations may, in fact, incorrectly calibrate the pressure sensor. As such, some techniques for recalibrating pressure sensors may take into account the proximity of nearby buildings (or other structures that may allow a person to be at an altitude that is different from ground-level).

In FIG. 23, the technique 2300 may begin in block 2302, where a device, e.g., a biometric tracking device, may receive location data from some form of location-determination system, much as in block 1802. In block 2304, a first location may be determined from the location data, again, much as in block 1804. In block 2306, the device may look up the first location in a historical topographic dataset, e.g., a topographic contour database or map set, much as in block 1806 or 1906. In block 2308, the biometric monitoring device may receive altitude data correlated with the first location from a pressure sensor. In block 2310, a determination may be made as to whether or not to recalibrate the pressure sensor based on the difference between the altitude data and the first topographic altitude. If the difference is above a first threshold, the pressure sensor may be recalibrated in block 2312 before proceeding to block 2314. If not, the technique may proceed directly to block 2314. In block 2314, a first threshold distance may be determined. In block 2316, it may be determined if the first location is within the first threshold distance of a building (or other similar structure). Such determinations may be possible using USGS data (which frequently includes information showing the boundaries of buildings in their datasets) or other providers, e.g., Google Maps includes building boundary information (and, indeed, 3D models of buildings in many metropolitan areas). In block 2318, the update time period may be altered to take into account the proximity to the building(s). In some cases, the first threshold distance may be set to a value that is based on the error estimate of the location determination. For example, if the location determination is accurate to within 30 ft, the first threshold distance may be set to 31 ft. Thus, if the location determination indicates that a building is 30 ft away, recalibration may not be performed because the person wearing the device may actually be within the building (due to the uncertainty in the location determination). However, if the location determination indicates that a building is 32 ft away, a recalibration check may be performed since it is unlikely that the person wearing the device is inside of a building, even taking into account the uncertainty in the location determination.

For example, the update time period may be tolled or suspended while the pressure sensor is within the first threshold distance of the building (or any building) and may be restarted or terminated when the pressure sensor is at a distance greater than the first threshold distance from a building or other structure. In other implementations, the update time period may simply be lengthened, e.g., so as to check if altimeter re-calibration is necessary every half hour or hour, for example, so as to avoid the need to continually re-check where the current XY location is with respect to buildings reflected in the historical topographic data.

Figure 24:
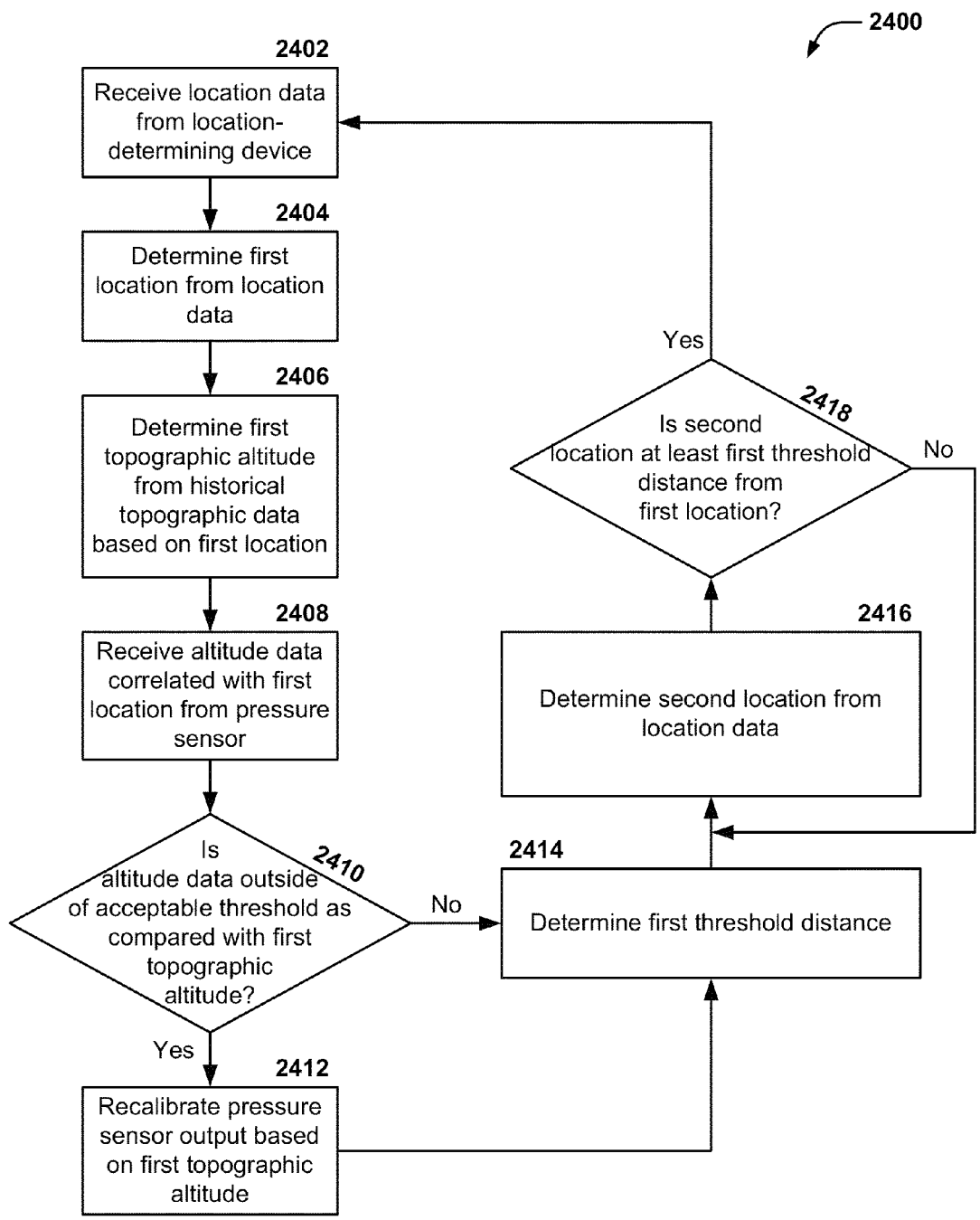
FIG. 24 depicts a flow diagram for another technique for recalibrating a pressure sensor based on changes in XY location.

FIG. 24 depicts a flow diagram for another technique for recalibrating a pressure sensor based on changes in XY location. In FIG. 24, the technique 2400 may begin in block 2402, where a device, e.g., a biometric tracking device, may receive location data from some form of location-determination system, much as in block 1802. In block 2404, a first location may be determined from the location data, again, much as in block 1804. In block 2406, the device may look up the first location in a historical topographic dataset, e.g., a topographic contour database or map set, much as in block 1806 or 1906. In block 2408, the biometric monitoring device may receive altitude data correlated with the first location from a pressure sensor. In block 2410, a determination may be made as to whether or not to recalibrate the pressure sensor based on the difference between the altitude data and the first topographic altitude. If the difference is above a first threshold, the pressure sensor may be recalibrated in block 2412 before proceeding to block 2414. If not, the technique may proceed directly to block 2414. In block 2414, a first threshold distance may be determined. In block 2416, a second location may be determined. If the second location is at least the first threshold distance away from the first location, then the technique may return to block 2402. If not, then the technique may return to block 2416 for the collection of another second location. Using such a technique, the pressure sensor recalibration check may be tolled until after the PRESSURE sensor has moved a pre-set distance, e.g., the first threshold distance, from a previous point at which the necessity of re-calibration was evaluated. The first threshold distance may, in some implementations, be an overland distance, i.e., substantially planar (aside from perhaps accounting for the curvature of the earth's surface). In other implementations, the first threshold distance may be an absolute distance, e.g., taking into account elevation changes as well. The first threshold distance may also be referred to, in this case, a translation distance threshold. Such a threshold may, for example, be between 50 ft and 200 ft, 500 ft and 1000 ft, or other values in other ranges.

Figure 25:
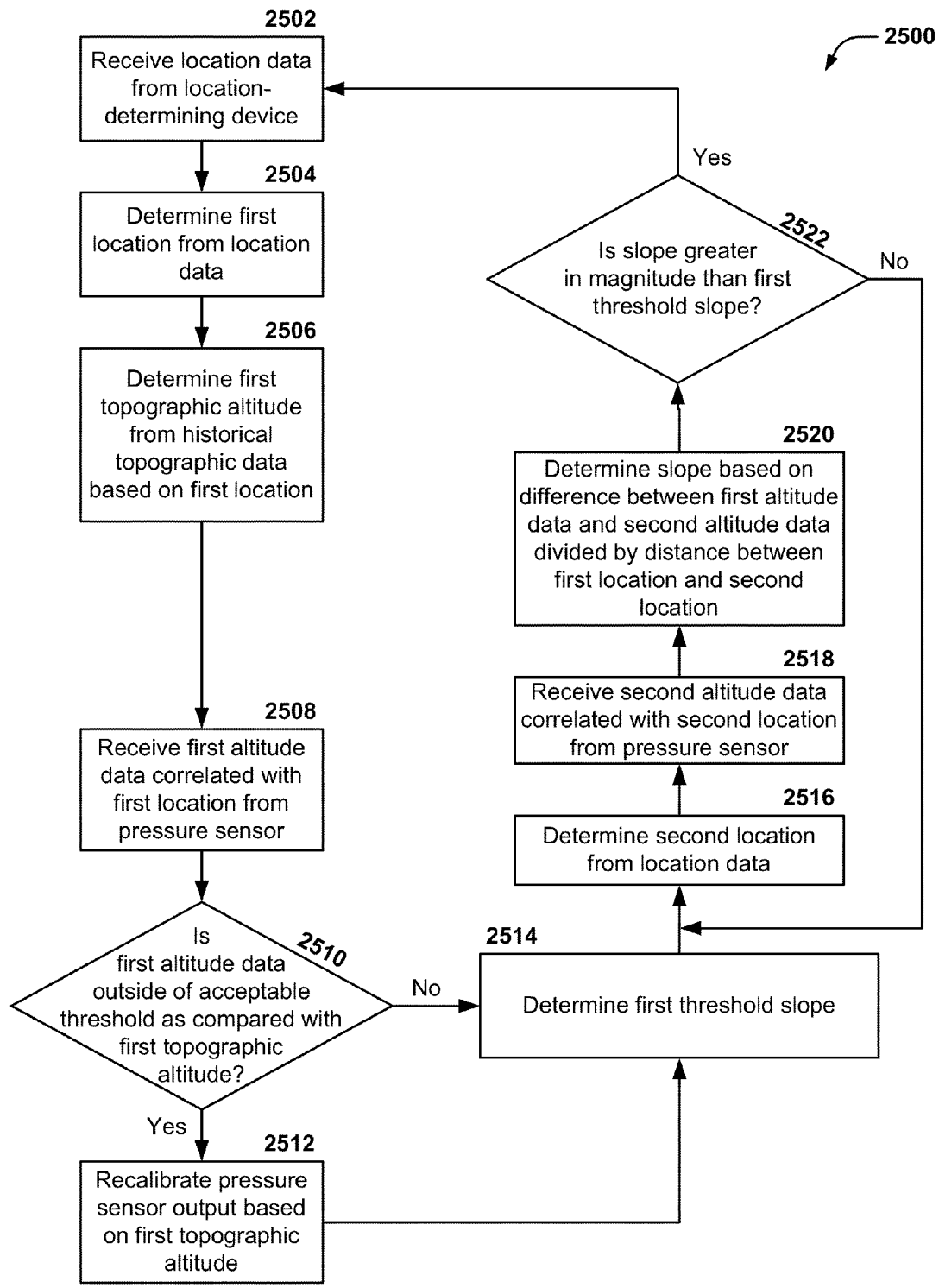
FIG. 25 depicts a flow diagram for a technique for recalibrating a pressure sensor based on slope.

FIG. 25 depicts a flow diagram for a technique for recalibrating a pressure sensor based on slope. In FIG. 25, the technique 2500 may begin in block 2502, where a device, e.g., a biometric tracking device, may receive location data from some form of location-determination system, much as in block 1802. In block 2504, a first location may be determined from the location data, again, much as in block 1804. In block 2506, the device may look up the first location in a historical topographic dataset, e.g., a topographic contour database or map set, much as in block 1806 or 1906. In block 2508, the biometric monitoring device may receive first altitude data correlated with the first location from a pressure sensor. In block 2510, a determination may be made as to whether or not to recalibrate the pressure sensor based on the difference between the first altitude data and the first topographic altitude. If the difference is above a first threshold, the pressure sensor may be recalibrated in block 2512 before proceeding to block 2514. If not, the technique may proceed directly to block 2514. In block 2514, a first threshold slope may be determined.

In block 2516, a second location may be determined from the location-determination system, and in block 2518, second altitude data correlated with the second location may be received from the pressure sensor. In block 2520, a slope may be calculated based on the altitude difference represented by the first altitude data and the second altitude data and the distance between the first location and the second location. In block 2522, the slope may be compared against the first threshold slope and if the slope exceeds the first threshold slope, the technique may return to block 2502. If the slope does not exceed the first threshold slope, the technique may return to block 2516 and further second locations and second altitude data may be gathered.

In some implementations, as discussed in some detail above, the location-determination may utilize imagery from a camera. For example, a device having a pressure sensor and access to image data from a camera may obtain a first image associated with pressure sensor altitudes or readings taken at a first location. The image may then be analyzed to determine a first image-based altitude, which may then be used in much the same manner as the topographic altitudes are in the techniques discussed above to determine if the pressure sensor needs to be recalibrated, i.e., if the difference between the first image-based altitude and the altitude measured by the pressure sensor is beyond a first threshold amount, the pressure sensor may be deemed to be out of calibration and may be re-calibrated using the first image-based altitude.

The first image-based altitude may, in some implementations, be determined by analyzing the image to determine, for example, a skyline silhouette that corresponds with a particular viewpoint associated with a particular XY location and altitude. Such data may be retrieved from a database of reference images, each reference image associated with at least an altitude. The image may be compared against reference images from the database and if a suitable match is located, the altitude data for the matching reference image may be used as the first image-based altitude.

Figure 26:
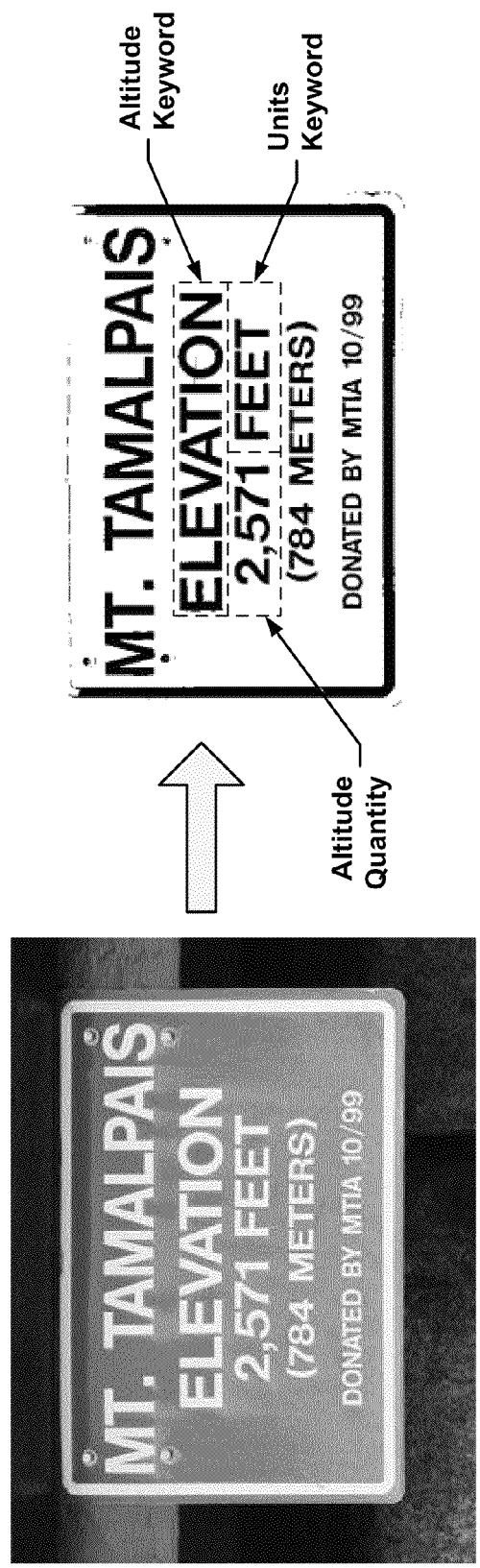
FIG. 26 depicts a photograph taken of an elevation information sign and a corresponding identification of keywords and altitude data from the sign.

In an alternative or further implementation, an image associated with an altitude measurement of a pressure sensor may be analyzed using optical character recognition (OCR) to determine if there is text-based information in the image. If there is text-based information in the image, the text-based information may be analyzed, e.g., parsed, to determine if the text-based information includes elevation data. For example, many common hiking destinations, scenic overlooks, and other points of interest include signs (see FIG. 26A for an example) that list, among other data, the elevation at that point. Such elevations are typically quite accurate as they are sourced from survey data. FIG. 26A depicts a photograph of a sign at Mt. Tamalpais, Calif., that includes the altitude keywords "elevation" and "feet" with a numeric value between them. A device using image-based pressure sensor recalibration may analyze text-based data to locate such altitude keywords (similar phrases such as "elev," "alt," "altitude," "height," and "ht," by way of non-limiting example, may also serve as indicators that numeric data that follows or that is on the following line represents altitude data). Terms such as "m," "ft," "feet," "meters," or "meters," by way of non-limiting example, may serve as unit keywords indicating the units of the numeric altitude quantity. Numeric altitude quantities are typically located between the altitude keyword and the unit keyword in such a sign, and are thus easily extracted. Once extracted from the text-based data from the image data, the altitude may be used, in effect, as the first topographic altitude used in the techniques above or the first image-based altitude in the techniques discussed above.

In a related implementation, even if a sign or other source of text-based information in an image does not have altitude data explicitly listed, the text-based information may be compared against a database of text-based entries to determine if the text-based information corresponds with a database entry that has an associated altitude. If a match is determined, the associated altitude may then be used as the first image-based altitude or the first topographic altitude in the techniques discussed above.

It is to be understood that while the above techniques discuss calibration of altimeters using location information and, for example, topographic information, similar techniques may be applied in reverse to refine location information based on altitude data from an altimeter. For example, if a GPS location determination has a large error estimate and the user is in terrain that has a large amount of topographical variation, the altimeter altitude data may be mapped to terrain in a topographic data set that is within the error estimate for the location determination. The terrain that falls within that error estimate may have a varying altitude, and the altitude data may be used to eliminate or filter out possible XY locations in the error estimate that do not, according to the topographic data, have a matching altitude (or, more likely, an altitude within a first threshold value of the altitude). For example, if a person is on terrain with a uniform slope and the error estimate results in a large, circular area on that slope within which the person's XY location is located, using the altimeter data may allow the person's XY location to be narrowed down to a narrow band within the circular area, thus improving the location determination.

While the above techniques for altimeter recalibration have been outlined with respect to a barometric altimeter, similar techniques for altimeter recalibration may be used with other types of altimeters that may be developed, and this disclosure includes such implementations within its scope.

Altimeter-Aided Gesture Recognition

In some implementations, a biometric monitoring device may include an altimeter, e.g., a barometric altimeter or pressure sensor (or other type of altimeter of similar or better performance) in addition to other biometric sensors, e.g., accelerometers, heart rate sensors, etc., and/or environmental sensors, e.g., ambient light sensors, ambient air quality sensors, etc. As discussed previously, barometric altimeters may be quite accurate, especially for measuring changes in elevation over short periods in time, e.g., several seconds (as opposed to absolute elevation).

Generally speaking, for a biometric monitoring device that is worn on a person's arm, forearm, wrist, hand, or finger (or, in some implementations, on a person's leg, lower leg, foot, or toe), altitude data (which may, as discussed above, include data that indicates an actual altitude, data that indicates pressure that may be representative of altitude, and data from a sensor that may be used to determine altitude, e.g., the voltage output of a pressure sensor) from the biometric monitoring device may be combined with temporally-corresponding motion data from one or more biometric sensors from the biometric monitoring device, e.g., accelerometers, magnetometers, gyroscopic sensors, piezoelectric sensors, electromagnetic trackers, camera-based trackers, etc., to identify various types of gestures. Such gestures may, for example, be gestures or movements that are characteristic of a particular activities or sports. For example, swinging a baseball bat may be viewed as one kind of gesture, whereas lifting a bumbbell in a bicep curl may be viewed as another kind of gesture.

Figure 27:
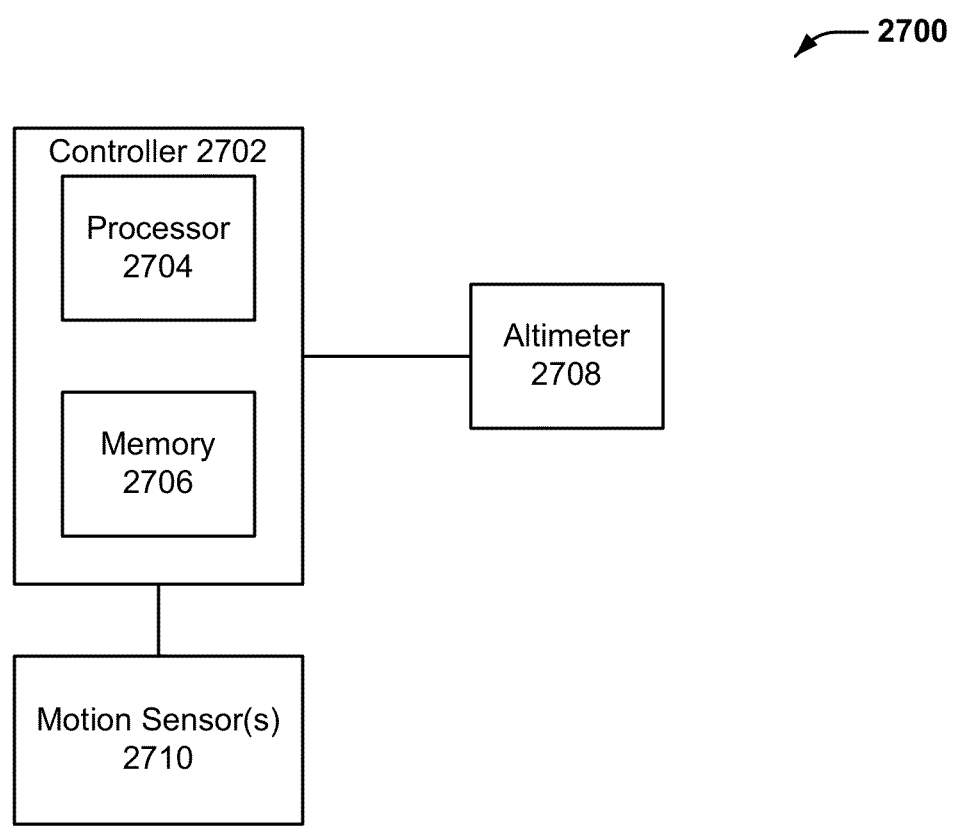
FIG. 27 depicts a simplified block diagram of a biometric monitoring device having an altimeter and one or more motion sensors.

FIG. 27 depicts a simplified block diagram of an example biometric monitoring device having an altimeter and a location-determination system. As can be seen, the biometric monitoring device of FIG. 27 includes one or more processors 2704 and a memory 2706 that are communicatively connected with one another to form a controller 2702. The controller 2702 is communicatively connected with an altimeter or pressure sensor 2708 and with one or more motion sensors 2710, e.g., sensors such as accelerometers, gyroscopic sensors, and/or magnetometers.

Figure 28:
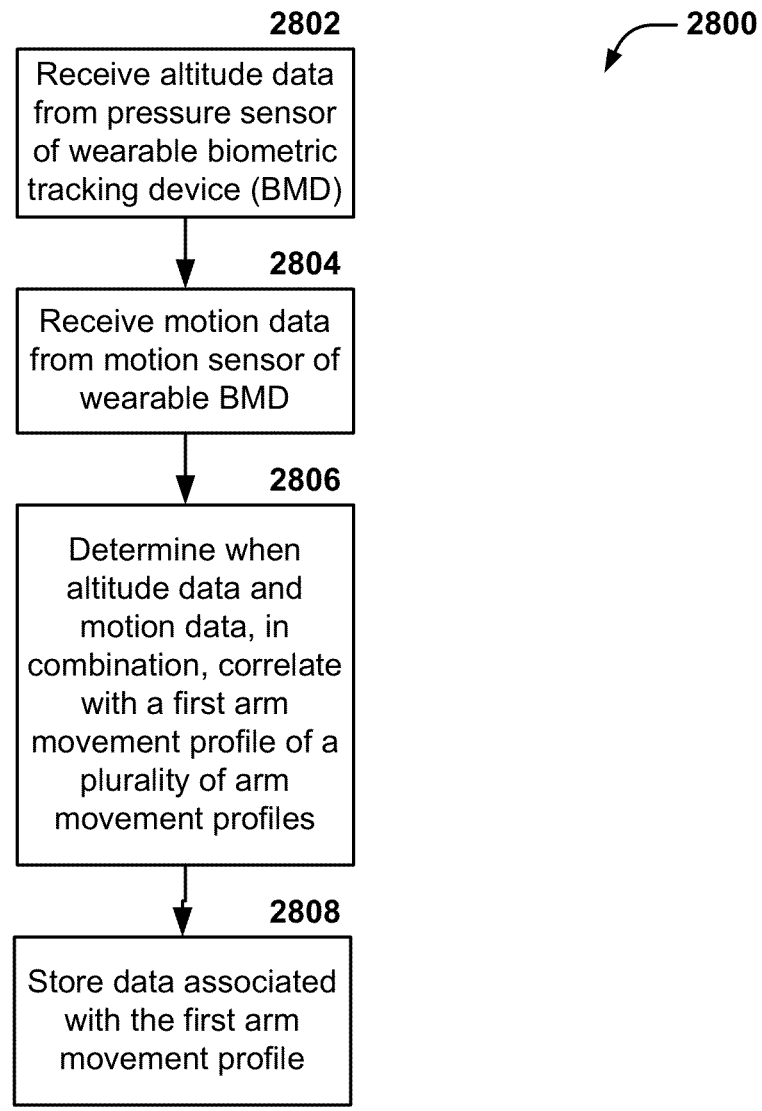
FIG. 28 depicts a flow diagram for a technique for using altitude data and motion data from a biometric monitoring device to identify a gesture made by a person wearing the biometric monitoring device.

FIG. 28 depicts a flow diagram for a technique for using altitude data and motion data from a biometric monitoring device to identify a gesture made by a person wearing the biometric monitoring device. The technique 2800 may begin in block 2802, where altitude data may be received by an altitude sensor of some sort, e.g., a barometric altimeter or other sensor capable of detecting altitude or providing output from which altitude may be determined. As discussed earlier herein with respect to altimeter recalibration, the term "altitude" is used herein to refer to both altitude and data from which altitude may be derived, including, for example, pressure data from a pressure sensor, voltage levels from a pressure sensor, and so forth. In some implementations, for example, data from a pressure sensor may never be converted into working units of linear distance measurement, e.g., feet or meters, in order to identify particular gestures—however, the pressure changes reflected in such data nonetheless may be used as indicators of altitude change, and it is to be understood that regardless of whether a device uses motion data in combination with altitude data that is processed in terms of feet or meters (distance) or altitude data that is processed in terms of pressure or some other unit, the scope of this disclosure is intended to cover such uses, and the term "altitude data" or "altitude," at least with respect to the altimeter-aided gesture recognition discussed herein, is intended to include such implementations.

In block 2804, motion data may be captured from one or more motion sensors of the biometric monitoring device. In the examples discussed herein, such motion data takes the form of accelerometer data, although other forms of motion data may be used as well, such as gyroscopic data or magnetometer data, for example. It is to be understood that with respect to the altimeter-aided gesture recognition techniques and systems discussed herein, the term "motion data" may also include data that indicates instantaneous position or orientation (without necessarily describing motion). However, given that such orientation or position sensors may provide output that changes based on changes in such orientations or positions, such data may be at least somewhat indicative of motions experienced by a biometric monitoring device. The motion data that is captured from the biometric monitoring device may reflect motions or orientations of the biometric monitoring device with respect to some external frame of reference, and may be used to infer the position or movement of a limb on which the biometric monitoring device is worn. For example, for a wrist-watch type biometric monitoring device, the biometric monitoring device may be worn on a person's forearm near the wrist joint. Thus, motion data from the biometric monitoring device may reflect the motions of the forearm on which the biometric monitoring device is worn.

In block 2806, a determination may be made as to whether the motion data and the altitude data, in combination, correlate with a first arm movement profile selected from a plurality of arm movement profiles. Such arm movement profiles may take a variety of forms, including, for example, time-windowed motion and altitude data characteristics, representative motion and altitude data patterns, etc. In some cases, a biometric monitoring device may be placed into a particular mode, e.g., a resistance-training mode, and the active mode may cause the plurality of arm movement profiles to be filtered such that only arm movement profiles that are related to the active mode are available for selection.

In block 2808, data associated with the first arm movement profile may be stored. Such data, for example, may include data such as performance or user form data (indicating how "well" a gesture was performed as compared with some standard gesture), how many repetitions of a gesture were made, how long such gestures lasted, the frequency of the gestures, etc. Thus, for example, for resistance-training exercise, a biometric monitoring device may identify various gestures associated with different types of resistance-training exercises (and avoid identification of gestures associated with non-resistance-training exercises).

Examples of arm movement profiles that may be used to identify particular gestures may include, but are not limited to, arm movement profiles approximating arm motions representative of one or more activities such as resting, running, walking, elliptical exercises, resistance-training exercises, pull-ups, push-ups, sit-ups, jumping rope, or aerobic dancing.

It is to be understood that while discussion herein with regard to altimeter-aided gesture recognition focuses on the use of a biometric monitoring device that is worn on a person's forearm, and on the recognition of arm gestures based on arm movement profiles, similar concepts and techniques may be used for biometric monitoring devices worn in other locations, e.g., on a person's leg, upper arm, finger, etc. If appropriate, the concept of arm movement profiles may be adapted to leg movement profiles (for leg-worn biometric monitoring devices), hand movement profiles, finger movement profiles, and the like. Moreover, while the discussion herein focuses on the wearing of a single biometric monitoring device, such techniques may also be practiced using multiple biometric monitoring devices. For example, a person may wear a biometric monitoring device on their forearm and a second biometric monitoring device on the same arm's upper arm; these two biometric monitoring devices may be in communication with one another to facilitate data sharing. Each such biometric monitoring device may provide altitude data and motion data, which may be used to provide additional insight as to the movement characteristics of the person's arm and the gestures that that person's arm may make.

Figure 29:
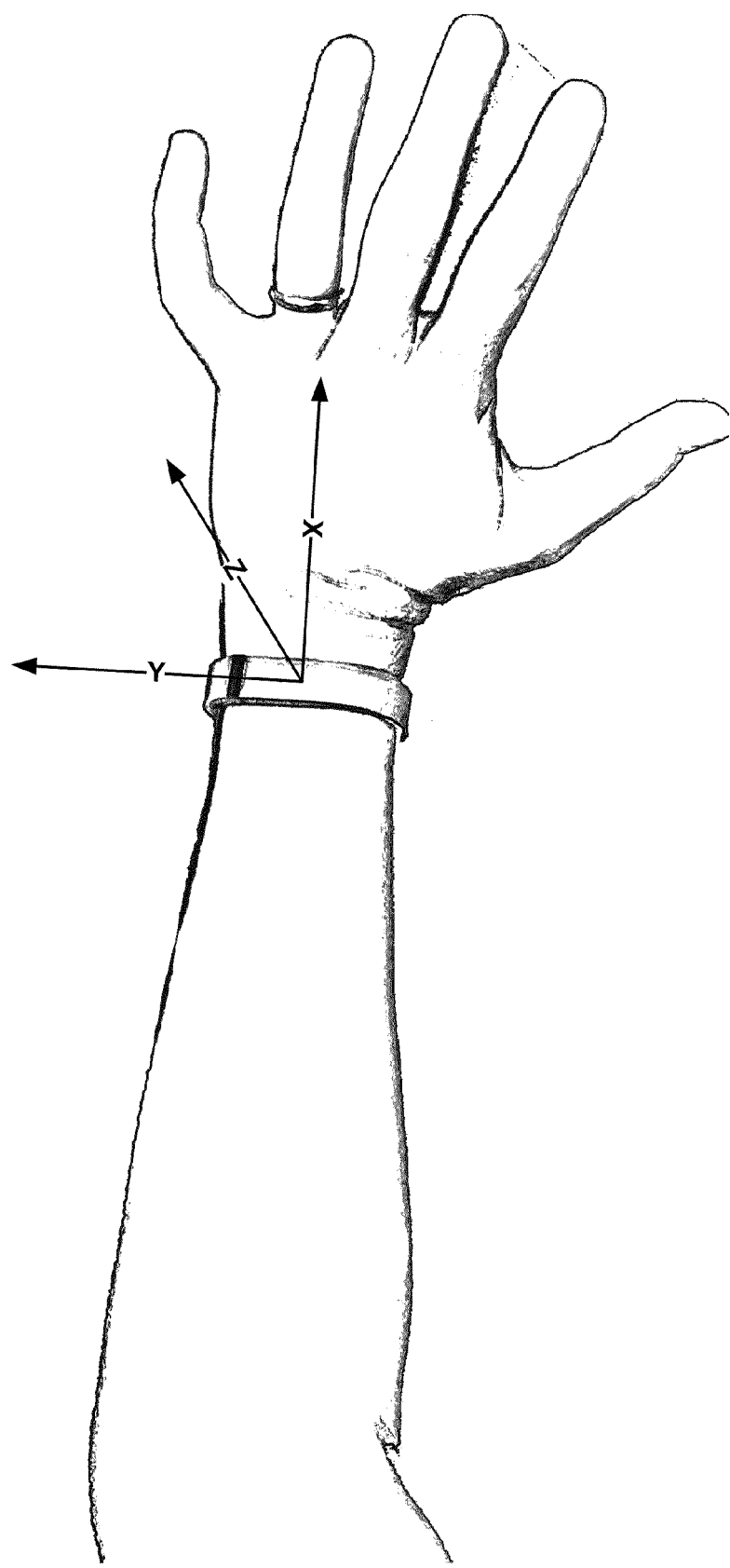
FIG. 29 depicts a biometric monitoring device worn on a person's forearm and a coordinate system for the biometric monitoring device acceleration sensor(s); this coordinate system is referenced with respect to FIGS. 30 through ZU.
Figure 30:
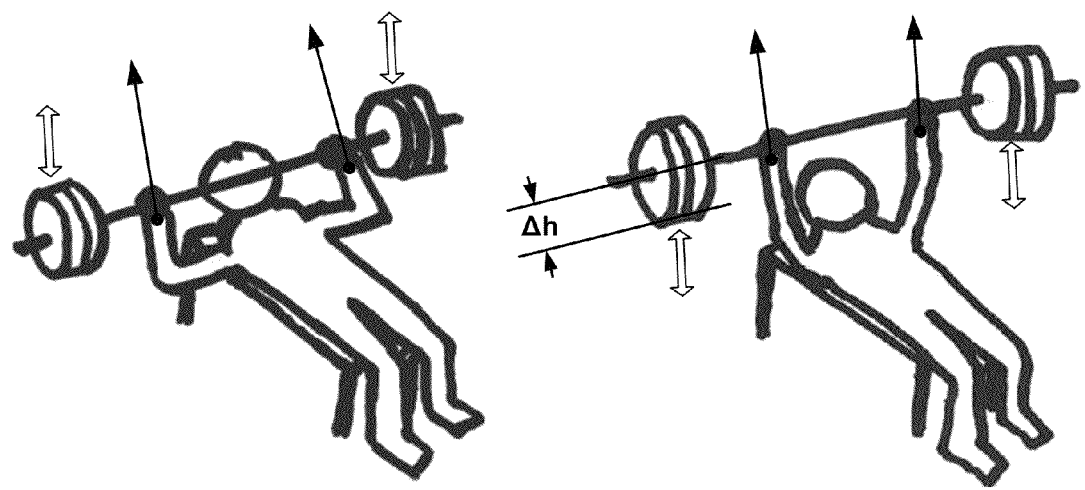
FIG. 30 depicts an example of gestures that are associated with a bench-press-type resistance-training exercise, as well as hypothetical motion and altitude data that may be used to identify such gestures.
Figure 30:
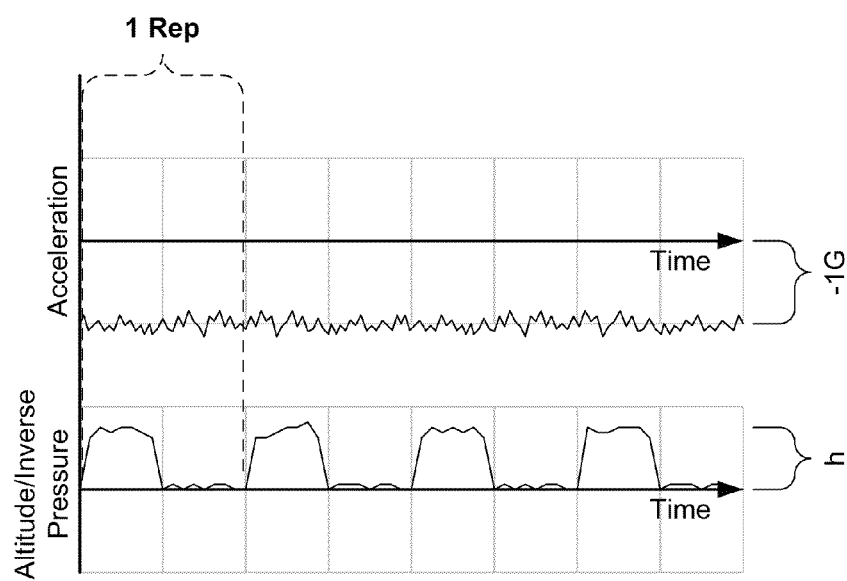

FIG. 29 depicts a biometric monitoring device worn on a person's forearm and a coordinate system for the biometric monitoring device acceleration sensor(s); this coordinate system is referenced with respect to FIGS. 30 through ZU. For clarity, FIG. 29 depicts a person's arm wearing a wrist-band style biometric monitoring device. For discussion purposes, it is assumed that a motion sensor such as a tri-axial accelerometer is included within the biometric monitoring device with an X-axis aligned with the person's forearm and extending in a positive direction towards the person's wrist on that arm, a Y-axis that is transverse to the forearm and generally parallel to the face of the biometric monitoring device (in this case, parallel to the person's hand/palm and extending away from the person's pinky finger), and a Z-axis that is transverse to the forearm and perpendicular to the Y-axis. Other coordinate systems may be used, of course, as the selection of a coordinate system is relatively arbitrary—the present coordinate system is for discussion purposes only.

FIG. 30 depicts an example of gestures that are associated with a bench-press-type resistance-training exercise, as well as hypothetical motion and altitude data that may be used to identify such gestures. A bench-press-type resistance-training exercise is an exercise in which a person lies on their back, usually on a knee-height bench, and lowers a barbell (or other weight) to chest level and then raises the barbell straight up until their arms are straight (the left diagram in FIG. 30 represents the barbell lowered to near-chest level, and the right diagram shows the person with arms straight and the barbell raised). The black arrows indicate the approximate orientation of the X-axis during a bench press; the white arrows indicate movement of the barbell. In a typical bench press, the barbell moves upwards by a distance Δh that is governed by the length of the person's upper arm and a portion of the person's forearm, e.g., a distance between the length of the person's forearm (as measured from the elbow to the wrist) and the length of the person's arm (as measured from the person's shoulder to the person's wrist). Such a distance may vary depending on the physical attributes of the person in question, of course, although typically such a Δh may be between 1 and 2 feet.

It is to be understood that for any of the techniques for gesture recognition discussed herein, the particular dimensional values that may be used to categorize a gesture may be based, for example, on default values derived from demographic information or may be custom-tailored to a person's physique. For example, a person with shorter arms may customize parameters that describe the length of their forearm and the length of their upper arm, and such custom values may be used to determine appropriate values for Δh.

The data plots shown at the bottom of FIG. 30 represent hypothetical data obtained from an accelerometer and an altimeter in the biometric monitoring device, which, in this case and the other similar examples discussed below, is worn on the person's forearm. The acceleration data shown correlates with acceleration measured by an accelerometer aligned with the X-axis. As such, the acceleration data may exhibit a largely-constant negative 1G acceleration due to the pull of Earth's gravitational field. The acceleration data may also exhibit slight changes (not shown) as the person lifts and lowers the weight, but these are likely to be smaller in magnitude than the acceleration attributable to the Earth's gravitational field. In this case, since the orientation of the person's forearms changes very little during a bench press, the X-axis acceleration may remain relatively constant. In contrast, the hypothetical altimeter data exhibits a very pronounced cyclic behavior where the person's wrist moves up and down in altitude by the distance Δh. Each such cycle of movement may correspond to one repetition or "rep" of the exercise.

Similar characteristics may be observed for squat-type exercises as well, as in a squat, a person may hold a barbell or weight across their shoulders with their upper arms oriented downwards and their forearms oriented upwards and then flex their legs to move the barbell up-and-down. In order to differentiate between squats and bench press exercises based on altitude data and motion data, it may be necessary to use additional sensors. For example, if a person wears an additional biometric tracking device on the upper arm (with a similarly-oriented coordinate system, e.g., with the X-axis aligned with the upper arm), the x-axis data of the upper-arm-located biometric monitoring system may exhibit different behavior during bench press exercises than during squat exercises. For example, in a squat, the person's arms may remain relatively fixed relative to their upper torsos, and thus the accelerations measured by the upper-arm-located biometric monitoring device may not experience any drastic changes during squat exercises. In contrast, in a bench press exercise, the upper arms transition from a horizontal or slightly-downwards-oriented position to a vertical, upwards-facing direction. Such transitions may be evident in the motion data and may be used to assist in discriminating between the two exercises. Another potential avenue for discriminating between the two exercises is by using Δh; a squat may involve a greater change in altitude than may be observable in a bench press.

An arm movement profile that looks for such behaviors may be modeled after data such as that shown in FIG. 30, although other arm movement profiles may also or alternatively be used. For example, various combinations of orientations indicated by accelerometer data (or other motion data) and altitude data may be used to determine which arm movement profile is the best fit for a given set of motion data and corresponding altitude data. For example, if the altitude data indicates that the wearable biometric monitoring device experienced an altitude increase that is approximately between one upper arm length and one upper arm length+one forearm length, e.g., between about 0.5 and 2 ft for a typical person, followed by a similar decrease in altitude during a second time period following (or, in some implementations, preceding) the first time period, and that the person's forearm remained in a substantially vertical, upwards orientation, i.e., with the hand held higher than the elbow, during the first and second time periods, then such behavior may be interpreted as being indicative of a bench press arm movement profile.

If multiple, substantially consecutive instances of motion and altitude that correlate with an arm movement profile are detected, such as the four instances evident in the data for FIG. 30, each such instance may be interpreted as a rep for the exercise associated with the selected arm movement profile. Thus, 4 reps of bench pressing are represented in FIG. 30.

In some implementations, an arm movement profile may be identified in real-time. In other implementations, however, the biometric monitoring device may examine the motion data and altitude data with some delay so that periodic behavior may be more evident. For example, in the context of resistance training exercises, it is common for people doing such training to perform multiple reps of the same exercise—there may be a high degree of commonality in the motion data and the altitude data for each such rep of an exercise, which may facilitate using any of various forms of pattern analysis to extract the data for one rep, which may then be evaluated to determine if the data for one rep correlates with the data for a selected arm movement profile. In some implementations, a biometric monitoring device may be configured such that arm movement profile analysis only occurs after a set of periodic data traces ends, which may indicate the end of a set of one type of exercise. Such post-set processing may provide a more accurate estimation of overall performance, but may be unsuitable if real-time feedback needs to be provided to a user. For example, if the biometric monitoring device is configured to chime every fifth rep for a resistance-training exercise, the biometric monitoring device will need to monitor the number of occurrences of the gestures associated with that exercise in real time in order for the rep count to be accurate and up-to-date.

Figure 31:
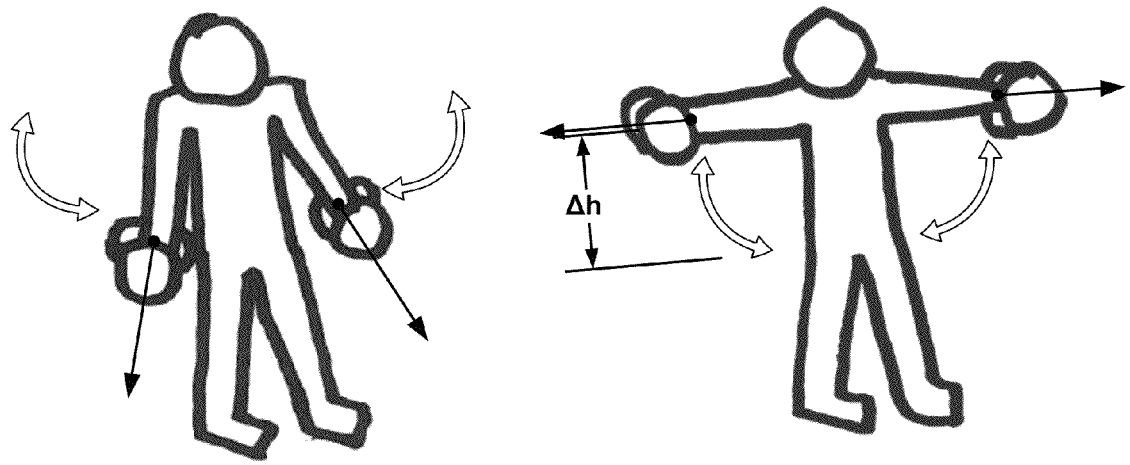
FIG. 31 depicts an example of gestures that are associated with a side-lift-type resistance-training exercise, as well as hypothetical motion and altitude data that may be used to identify such gestures.
Figure 31:
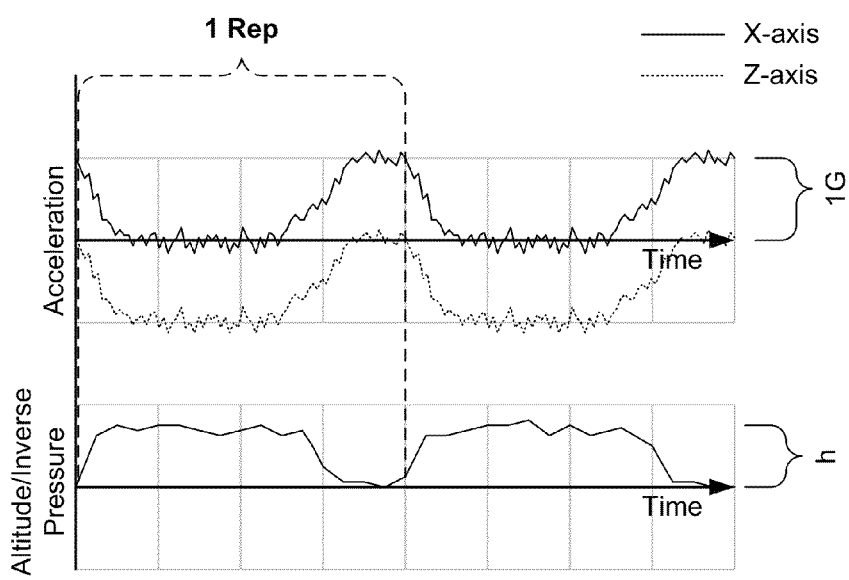

FIG. 31 depicts an example of gestures that are associated with a side-lift-type resistance-training exercise (also referred to herein as a lateral-raise-type exercise), as well as hypothetical motion and altitude data that may be used to identify such gestures.

A side-lift-type resistance-training exercise is an exercise in which a person holds a dumbbell in each hand (or holds onto a piece of equipment that approximates such weights), stands with their arms at their sides, and then rotates each arm about the shoulder such that the arms are essentially in-line with one another and horizontal. The arms are then allowed to return to the person's sides.

The left diagram in FIG. 31 represents a side-lift-type exercise when the person's arms are at their sides, and the right diagram shows the same person with the arms extended. The black arrows indicate the approximate orientation of the X-axis during the side-lift-type exercise; the white arrows indicate movement of the dumbbells. In a typical side lift, the dumbbells move upwards by a distance $\Delta h$ that is generally governed by the length of the person's upper arm and forearm together. Such a distance may vary depending on the physical attributes of the person in question, of course, although typically such a $\Delta h$ may be between 1 and 2 feet.

The data plots shown at the bottom of FIG. 31 represent hypothetical data obtained from an accelerometer and an altimeter in the biometric monitoring device. Two acceleration profiles are shown—one for the X-axis and one for the Z-axis. As can be seen, at the start of a rep, the X-axis acceleration may be at approximately 1G since the forearms are pointing downwards and the Earth's gravitational field exerts an acceleration of 1G substantially along the forearm axis. At the same time, the Z-axis acceleration is approximately 0G since the Z-axis is substantially horizontal and thus unaffected by the acceleration due to Earth's gravitational field. However, as the person raises their arm, the acceleration along the X-axis falls off in tandem with a corresponding decrease in acceleration to −1G in the Z-axis (it is negative simply because of the orientation of the coordinate system). Near the end of the rep, the X-axis acceleration and the Z-axis acceleration return to approximately their original values. At the same time, the altitude data may show an increase in height of $\Delta h$, which may, as noted above, be approximately between 1 and 2 feet.

Similar characteristics may be observed for front-raise-type exercises as well, and similar techniques used to identify such exercises.

An arm movement profile that looks for such behaviors may be modeled after data such as that shown in FIG. 31, although other arm movement profiles may also or alternatively be used. For example, if the altitude data indicates that the wearable biometric monitoring device experienced an altitude increase during a first time period that is approximately one upper arm length+one forearm length in height, e.g., between about 1 and 2 ft, or 1.5 ft and 2 ft, for a typical person, followed by a similar decrease in altitude during a second time period following (or, in some implementations, preceding) the first time period, and the motion data indicates that the person's forearm transitioned during the first time period from a substantially vertical, downwards orientation, i.e., with the hand held lower than the elbow, to a substantially horizontal position, and that the person's forearm transitioned during the second time period from the substantially horizontal position to the substantially vertical position, then such behavior may be interpreted as being indicative of a lateral raise, side lift, or front raise movement profile.

Figure 32:
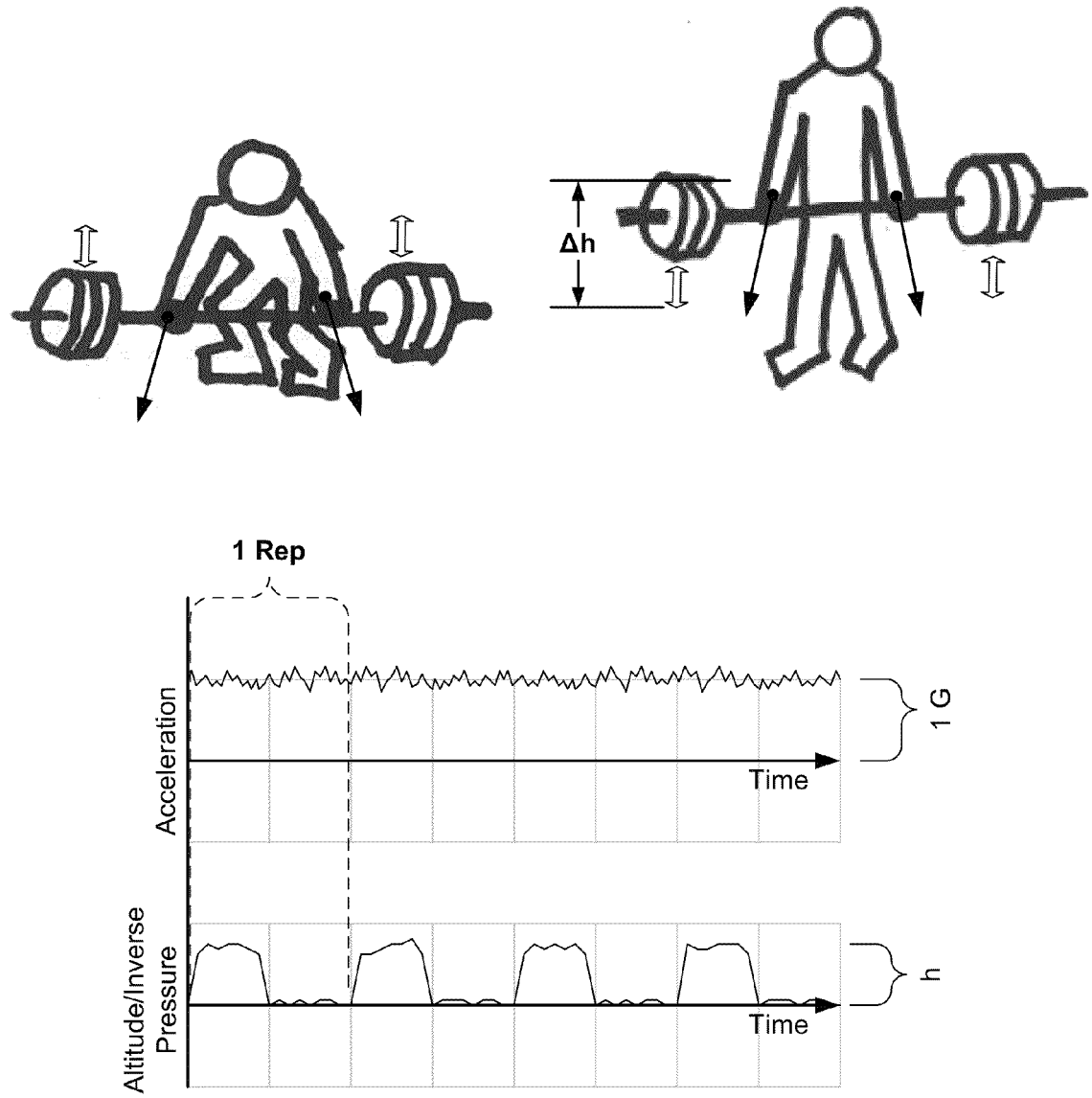
FIG. 32 depicts an example of gestures that are associated with a deadlift-type resistance-training exercise, as well as hypothetical motion and altitude data that may be used to identify such gestures.

FIG. 32 depicts an example of gestures that are associated with a deadlift-type resistance-training exercise, as well as hypothetical motion and altitude data that may be used to identify such gestures.

A deadlift-type resistance-training exercise is typically an exercise in which a person lifts a barbell off the floor and up to hip-height and then sets the barbell down again. The lifting is primarily accomplished through back and leg movements; the arms stay extended in a downwards-facing direction.

The left diagram in FIG. 32 represents a deadlift-type exercise just prior to the person lifting the barbell; the right diagram represents the deadlift-type exercise just after the person has lifted the barbell. The black arrows indicate the approximate orientation of the X-axis during the deadlift-type exercise; the white arrows indicate movement of the barbell. In a typical deadlift, the barbell moves upwards by a distance $\Delta h$ that is generally governed by the distance, as measured when a person is standing with their hands at their sides, between a person's fist and a point approximately 2" to 8" of the ground (depending on the diameter of the barbells discs used, which may govern the distance through which the deadlift exercise may lift). Such a distance may vary depending on the physical attributes of the person in question, of course, although typically such a $\Delta h$ may be between 1.5 and 2 feet.

The data plots shown at the bottom of FIG. 32 represent hypothetical data obtained from an accelerometer and an altimeter in the biometric monitoring device. As can be seen, during a rep of a deadlift, the X-axis acceleration may be at approximately 1G since the forearms are pointing downwards during the entire lift and the Earth's gravitational field exerts an acceleration of 1G substantially along the forearm axis. At the same time, the altitude data may show an increase in height of $\Delta h$, which may, as noted above, be approximately between 1.5 and 2 feet.

An arm movement profile that looks for such behaviors may be modeled after data such as that shown in FIG. 32, although other arm movement profiles may also or alternatively be used. For example, if the altitude data indicates that the wearable biometric monitoring device experienced an altitude increase during a first time period of approximately $\Delta h$, e.g., between about 1.5 and 2 ft for a typical person, followed by a similar decrease in altitude during a second time period following the first time period, and the motion data indicates that the person's forearm remained in a substantially vertical, downwards orientation during the first time period and the second time period, then such behavior may be interpreted as being indicative of a deadlift arm movement profile.

Figure 33:
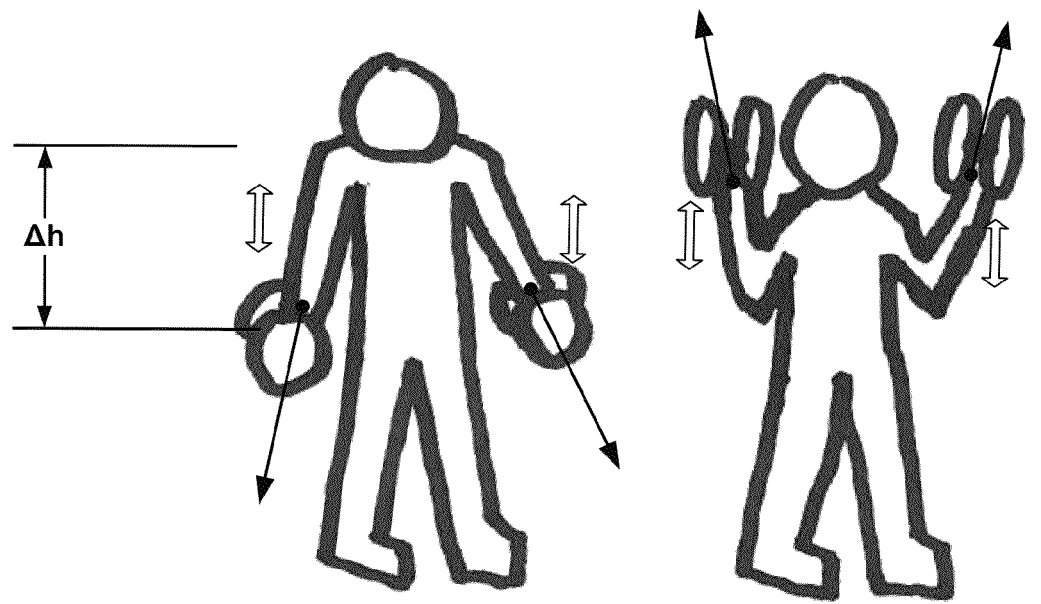
FIG. 33 depicts an example of gestures that are associated with a bicep-curl-type resistance-training exercise, as well as hypothetical motion and altitude data that may be used to identify such gestures.
Figure 33:
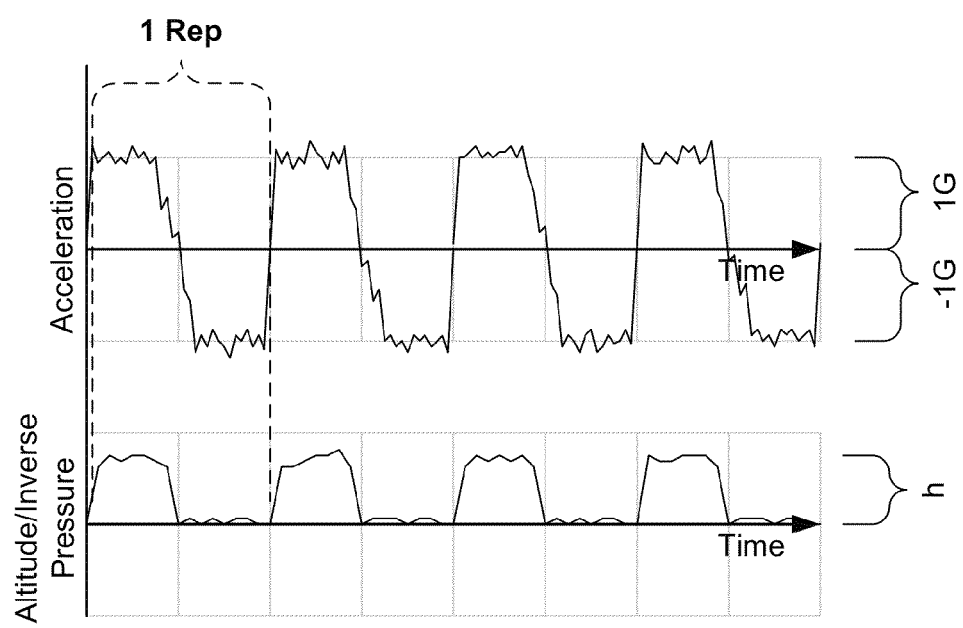

FIG. 33 depicts an example of gestures that are associated with a bicep-curl-type resistance-training exercise, as well as hypothetical motion and altitude data that may be used to identify such gestures.

A bicep-curl-type resistance-training exercise is typically an exercise in which a person lifts a dumbbell from a position in which their arm is typically extended downwards into a position where their forearm is drawn up against their upper arm, and returns the dumbbell to the starting position.

The left diagram in FIG. 33 represents a bicep-curl-type exercise just prior to the person lifting the dumbbell (in this case, each hand is lifting a dumbbell, although bicep-curls may be done in alternating fashion or one arm at a time—since each arm may move independently, a biometric monitoring device on each forearm may be needed to accurately track the number of reps performed with each arm); the right diagram represents the bicep-curl-type exercise just after the person has lifted the dumbbells. The black arrows indicate the approximate orientation of the X-axis during the bicep-curl-type exercise; the white arrows indicate movement of the dumbells. In a typical bicep-curl, the dumbbells move upwards by a distance Δh that is generally governed by the distance that is approximately twice the length of a person's forearm. Such a distance may vary depending on the physical attributes of the person in question, of course, although typically such a Δh may be between 1 ft and 2 ft.

The data plots shown at the bottom of FIG. 33 represent hypothetical data obtained from an accelerometer and an altimeter in the biometric monitoring device. As can be seen, during a rep of a bicep-curl, the X-axis acceleration may be at approximately 1G during a first time period and −1G during a second time period; this is due to the fact that the forearm is essentially reversing direction during the bicep-curl. At the same time, the altitude data may show an increase in height of Δh during the first time period and a decrease in height of Δh during the second time period. Δh may, as noted above, be approximately between 1 and 2 feet.

An arm movement profile that looks for such behaviors may be modeled after data such as that shown in FIG. 33, although other arm movement profiles may also or alternatively be used. For example, if the motion data indicates that the forearm on which the biometric monitoring device is worn transitioned from a downward-pointing orientation to an upward-pointing orientation during a first time period, followed by a transition back to a downward-pointing orientation during a second time period following the first time period, and if the altitude data indicates that the wearable biometric monitoring device experienced an altitude increase of Δh, e.g., typically between about 1 and 2 feet, during the first time period, then this may be interpreted as being indicative of a bicep-curl exercise arm movement profile.

Figure 34:
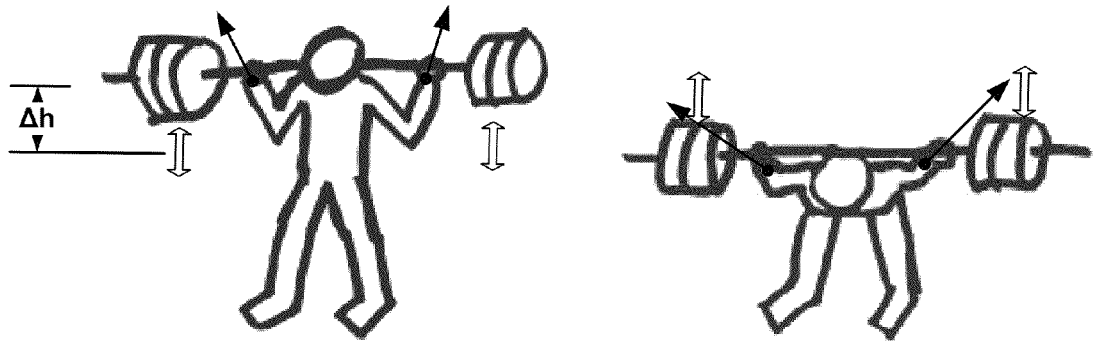
FIG. 34 depicts an example of gestures that are associated with a good-morning-sir-type resistance-training exercise, as well as hypothetical motion and altitude data that may be used to identify such gestures.
Figure 34:
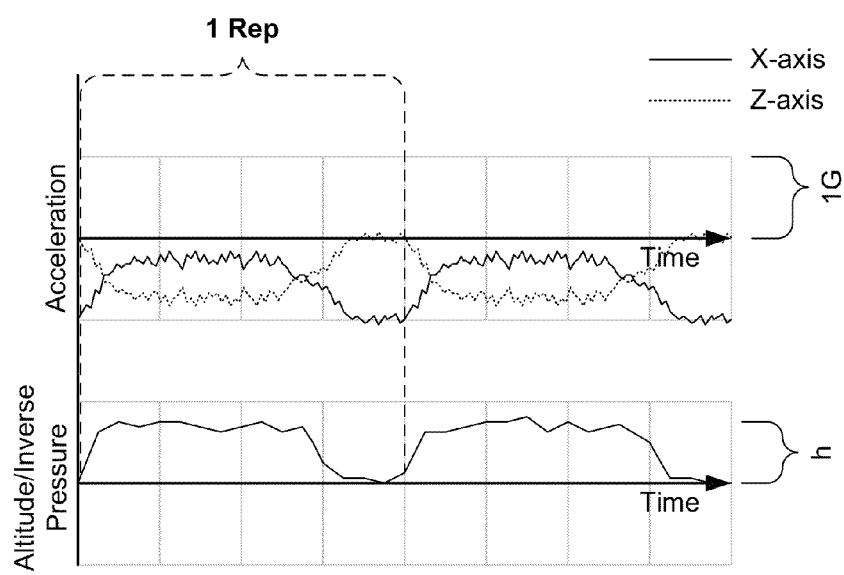

FIG. 34 depicts an example of gestures that are associated with a good-morning-sir-type resistance-training exercise, as well as hypothetical motion and altitude data that may be used to identify such gestures.

A good-morning-sir-type resistance-training exercise is an exercise, for example, in which a person stands with a barbell resting on their shoulders with the bar crossing behind their neck and held in both hands. Starting from a standing position, the person then pivots their torso forward, with some optional bending of the knees, until their torso is substantially horizontal, as if to bow to someone. The person then returns to the upright position.

The left diagram in FIG. 33 represents a good-morning-sir-type exercise just prior to the person pivoting their torso to the horizontal position; the right diagram represents the good-morning-sir-type exercise just after the person has transitioned to the horizontal-torso position. The black arrows indicate the approximate orientation of the X-axis during the good-morning-sir-type exercise; the white arrows indicate movement of the barbell. In a typical good-morning-sir, a biometric monitoring device worn on the forearm may move upwards and downwards by a distance Δh that is generally governed by the distance that is approximately equal to the torso length of the person performing the good-morning-sir. Such a distance may vary depending on the physical attributes of the person in question, of course, although typically such a Δh may be between 1.5 ft and 2 ft.

The data plots shown at the bottom of FIG. 33 represent hypothetical data obtained from an accelerometer and an altimeter in the biometric monitoring device. As can be seen, during a rep of a good-morning-sir, the X-axis acceleration may be at approximately 1G at the start of a good-morning-sir rep due to the upward-facing orientation of the forearm at this stage, and the Z-axis acceleration may be at or near zero due to such an orientation. As the person bows forward, the X-axis acceleration may approach zero and the Z-axis acceleration may decrease to approximately −1G. When the person straightens up, the accelerations may return to their original states. At the same time, the altitude sensor may indicate altitude changes of Δh, which may typically range from between 1.5 ft to 2 ft.

An arm movement profile that looks for such behaviors may be modeled after data such as that shown in FIG. 33, although other arm movement profiles may also or alternatively be used. For example, if the motion data indicates that the forearm on which the biometric monitoring device is worn transitioned from an upward-pointing orientation to substantially horizontal orientation during a first time period, followed by a transition back to the upward-pointing orientation during a second time period following the first time period, and if the altitude data indicates that the wearable biometric monitoring device experienced an altitude decrease of Δh, e.g., typically between about 1 and 2 feet, during the first time period and a corresponding altitude increase during the second time period, then this may be interpreted as being indicative of a good-morning-sir exercise arm movement profile.

While the above examples have all focused on resistance-training exercise gesture recognition, altimeters may be used in conjunction with motion sensors to sense a wide variety of gestures used in a variety of sports.

In one such implementation, the biometric monitoring device may be configured to identify the use of an elliptical exercise machine. In an elliptical exercise machine, a person may walk, run, or climb stairs in place. The person's feet usually rest on platforms that follow an elliptical path; because the person's feet are continually supported by the platforms, there is little impact on the person's feet and their joints from the walking/running/stair-climbing activity simulated by the elliptical exercise machine. Many elliptical exercise machines also feature handlebars that users may grasp while using the machine; the handles typically move in shallow, horizontally-oriented arcs in synchronicity with the steps taken.

Figure 35:
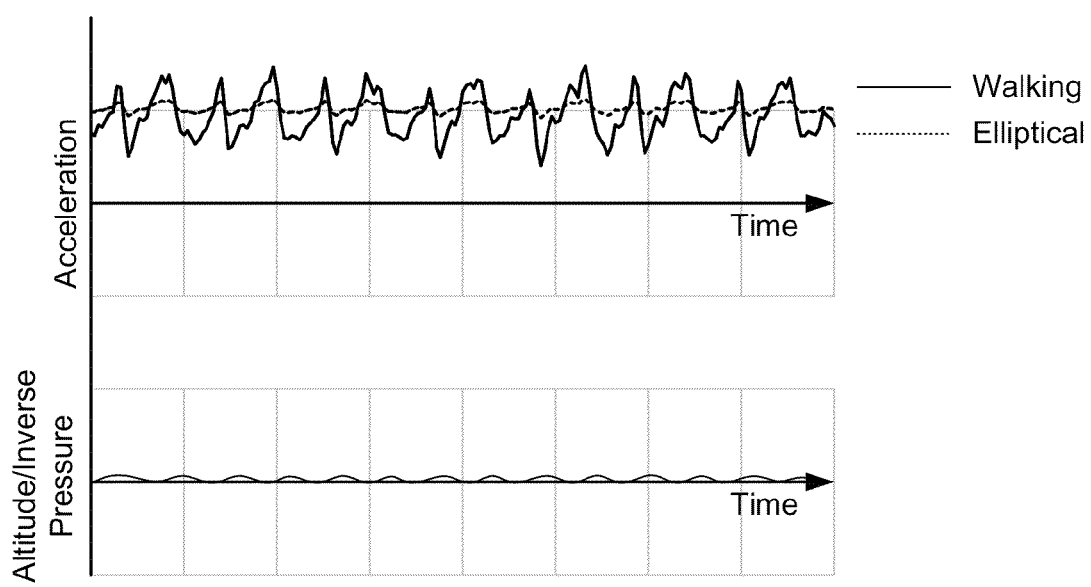
FIG. 35 depicts an example of hypothetical motion and altitude data that may be used to differentiate between gestures associated with walking and gestures associated with using an elliptical trainer.

FIG. 35 depicts an example of hypothetical motion and altitude data that may be used to differentiate between gestures associated with walking and gestures associated with using an elliptical trainer. For example, a biometric monitoring device may detect the use of an elliptical exercise machine in much the same manner that it detects walking behavior, e.g., using a peak-counting algorithm. Accelerometer data representing actual walking behavior may have a regular series of sharp peaks, e.g., such as is shown in FIG. 35. By contrast, accelerometer data representing walking on an elliptical machine may exhibit similar periodicity, but may exhibit drastically-decreased magnitudes due to the low impact experienced when using elliptical exercise machines, as demonstrated in the acceleration plot for walking on an elliptical machine shown in FIG. 35. However, there are also other activities that may produce such regular cyclic behavior with decrease magnitudes, e.g., bicycling. In such situations, the motion data may be combined with altitude data to potentially discriminate between elliptical exercise machine usage and other low-impact, cyclic activities such as biking. For example, because a person using an elliptical exercise machine may have their handles on the handle bars of the elliptical exercise machine, their hands (and thus the biometric monitoring device worn on their forearm) may experience shallow, cyclic altitude changes in synchronicity with the steps taken—such altitude changes would not occur on a bicycle since the handlebars on a bicycle stay at a constant altitude when pedaling. Thus, an elliptical exercise machine arm movement profile may be based on factors such as the characteristics discussed above.

For example, altitude data obtained by a biometric monitoring device may exhibit cyclic behavior during a first time period with small altitude changes during each cycle that are commensurate with altitude changes experienced by handles of an elliptical machine during normal use. During the first time period, motion data obtained by the biometric monitoring device may exhibit cyclic behavior that is substantially of the same frequency as the cyclic behavior in the altitude data. The motion data may include acceleration data that indicates acceleration magnitudes during the first time period that are less than acceleration magnitudes used by the biometric monitoring device in other circumstances to determine, for example, if a step counter should be incremented due to acceleration data that indicates that a person wearing the wearable biometric tracking device is engaged in normal walking or running activity in which the person's feet leave the ground. Altitude data and motion data with such characteristics may correlate with an elliptical exercise machine arm movement profile.

In some implementations, a biometric monitoring device with an altimeter and motion sensor(s) may be configured to compare the data provided by such sensors, or data derived, at least in part, on data from such sensors, against a particular reference motion profile and to determine a degree of deviation between the reference motion profile and such data. In the context of such discussion, an arm motion profile, e.g., a first arm motion profile, may refer to a data profile that is indicative of movements that a person wearing the biometric monitoring device performed, e.g., to movements of a person's forearm. The first arm motion profile may include motion-sensor-based data, as well as altimeter-sensor-based data; it may also include orientation or positional data at fixed points in time, in some implementations. By contrast, a reference motion profile may refer to information that is indicative of data that would be produced by such sensors, or derived therefrom, when such sensors are used to record data during a "normally" or "ideally" executed gesture for a particular activity.

For example, in the context of resistance-training exercises, a particular resistance-training exercise may involve making certain motions at certain speeds, and in remaining in certain positions for certain periods of time. For example, it may be considered bad form (or poor practice) in a bicep-curl to move the dumbbell quickly at the start of a bicep-curl since that may have the effect of imbuing the dumbbell with inertia that may reduce the workout on the muscles during the lift. An arm motion profile derived from data obtained during such a poor-form bicep-curl may reflect such undesirable behaviors. In contrast, a reference motion profile for a bicep-curl gesture may include information reflective of a slower lift speed at the start of the bicep-curl since such slower speeds produce a more strenuous workout and are considered more ideal.

In some implementations, reference motion profiles may be defined so as to encompass "ideal" gestures, whereas in other implementations, reference motion profiles may be more relaxed and may encompass "normal" or "acceptable" gestures.

The biometric monitoring device may be configured to determine a degree of deviation between the reference motion profile and the arm motion profile; such deviation information may be used to provide an estimate of the person's form in performing the gesture in question. The degree of deviation may be evaluated using any of a variety of techniques. For example, in some implementations, a reference motion profile may include defined boundaries for various parameters over time, and if corresponding parameters in the arm motion profile fall within those boundaries, the arm motion profile may be determined to be indicative of "good form" or be given a low or zero degree of deviation from the reference profile. In some other or additional implementations, the reference motion profile may be a collection of datasets, each dataset indicating "ideal" values for various sensor outputs (or data derived therefrom) for a particular gesture over time, and the deviation analysis may include comparing how well corresponding sensor outputs (or data derived therefrom) from the arm motion profile match with the ideal data sets. For example, a reference motion profile may include tri-axial acceleration, tri-axial velocity, tri-axial jerk, and tri-axial positional data that are representative of an ideal gesture for a particular activity, and corresponding data from an arm motion profile may then be compared against the reference motion profile data to determine how much deviation there is between the two profiles.

In some cases, the first arm movement profile may also serve as the corresponding reference motion profile for a particular gesture, although in other implementations, the two profiles may be different. For example, a more relaxed set of criteria may be used in the first arm movement profile to identify a particular motion or gesture, and a more stringent set of criteria may be used in the corresponding reference motion profile to determine how well that motion or gesture was performed.

Implementations of biometric monitoring devices in which the biometric monitoring device is configured to evaluate form of a gesture may be configured to utilize first reference motion profiles associated with one or more gestures such as: swinging a baseball bat; swinging a softball bat; swinging a tennis racket; swinging a badminton racket; swinging a squash racket; swinging a racketball racket; swinging a golfing wood; swinging a golfing iron; swinging a golfing wedge; swinging a golfing putter; swinging a golfing chipper; swinging a golfing hybrid; performing a resistance-training exercise; performing a martial arts motion; performing a gymnastics motion; performing a yoga exercise; taking a shot in a cue sport such as billiards; taking a shot in a cue sport such as snooker; taking a shot in a cue sport such as pool; taking a swimming stroke; bowling a bowling ball; firing a rifle; firing a pistol; thrusting a blade; swinging a blade; and parrying with a blade.

In biometric monitoring devices where there is gesture form evaluation, such as is discussed above, the biometric monitoring device may determine if the degree of deviation between the arm motion profile and the reference motion profile for a gesture exceeds a particular threshold of deviation. If the threshold of deviation is exceeded, the biometric monitoring device may be configured to provide some form of feedback or indication to the user. For example, the biometric monitoring device may include a feedback mechanism such as a display, one or more lights, an audio device, and/or a vibramotor. The feedback or indication may, for example, be (depending on the feedback mechanism(s) available) a numerical score, a vibration, a sound, a graphic, an icon, an animation, a message indicating potential user fatigue, a message cautioning the user to slow down, and/or a message cautioning the user to take a rest. Some implementations of biometric monitoring devices may also store evaluations of form based on the degree of deviation for future reference, e.g., for download to a website for later review. This may allow a person's progress in terms of form to be evaluated over a prolonged time interval so as to be able to observe any improvements (or deteriorations) in form.

As discussed above, a biometric monitoring device may be configured to track reps of some activities, e.g., of resistance-training exercises. For example, a biometric monitoring device may analyze motion and altitude data and determine that there are 5 reps (also referred to herein, with respect to altimeter-aided gesture recognition, as "instances") of a particular gesture. In some such implementations, the biometric monitoring device may use the number of apparent reps to assist in determining whether or not the repeated gestures represent a particular activity. For example, if a person is riding a merry-go-round, they may sit on a horse that moves up and down and grasp a pole with their hands such that their forearms are aligned with the pole. When the merry-go-round is in motion, a wrist-worn biometric monitoring device may produce data that is somewhat similar to that produced during a bench-press exercise set, e.g., repeated altitude changes of 1-2 ft coupled with a substantially vertical orientation of the person's forearm. However, the person might experience several hundred reps of up-and-down motion on the merry-go-round, whereas such a number of reps for resistance-training would be highly atypical. Thus, the rep-count may also be used as a factor for identifying a gesture or series of gestures.

In some implementations, a biometric tracking device may be configured to track between 1 to 5 instances or reps, ii) 5 to 8 instances or reps, iii) 8 to 10 instances or reps, iv) 10 to 12 instances or reps, v) 12 to 15 instances or reps, or vi) 15 to 20 instances or reps of a particular gesture. In some implementations, a biometric monitoring device may adapt the number of reps that are considered "typical" of a user's resistance-training depending on the type of resistance training that the user is engaged in, e.g., training emphasizing strength, training emphasizing strength and muscle bulk substantially equally, training emphasizing muscle bulk with some emphasis on strength, training emphasizing muscle bulk with some emphasis on endurance, training emphasizing endurance with some emphasis on muscle, and training emphasizing mostly endurance. Thus, the number of reps that may be "typical" of a bench-press exercise may change depending on the type of resistance-training that is being pursued by a person, which may, in situations where the biometric monitoring device uses rep count to assist in identifying gestures, alter how the biometric monitoring device identifies gestures when rep-count is factored in.

In some implementations, a biometric monitoring device may include a display that changes what is displayed based on certain movements or gestures. For example, if a person wearing such a biometric monitoring device on their forearm moves the forearm into a watch-viewing position, such a movement may be evaluated as corresponding to an arm movement profile for watch-viewing. Such an implementation is described in more detail in U.S. patent application Ser. No. 14/029,763, filed Sep. 17, 2013, which is hereby incorporated by reference in its entirety for such purposes. If the biometric monitoring device includes an altimeter, then the biometric monitoring device may combine altitude data from the altimeter with the motion data to provide a more accurate determination as to when a person has moved their forearm into a watch-viewing position. For example, the motion data may indicate that the person has moved their forearm from a downward-oriented position to a horizontally-oriented position, coupled with an altitude change of approximately the length of the forearm, e.g., approximately 1 ft. In some implementations, biometric monitoring device may further determine that the altitude remains constant for a non-zero time period immediately subsequent to the time period in which the motion occurs before changing what is displayed. The biometric monitoring device may change what is displayed in response to detecting a watch-viewing motion by, for example, turning on the display and displaying the time or other data.

In some implementations of an altimeter-equipped biometric monitoring device, the altimeter may serve as a mechanism for determining when the biometric monitoring device is being worn (or not worn). For example, a biometric monitoring device with an altimeter may monitor the altimeter data to determine if the altitude indicates that the biometric monitoring device has not experienced an altitude-rate-of-change exceeding a first altitude rate-of-change threshold during a first time period. If the first altitude rate-of-change threshold is not exceeded within the first time period, then the biometric monitoring device may determine that it is not presently being worn and may, for example, transition to a low-power, standby, or off state. In some such implementations, the biometric monitoring device may also include a shock or acceleration sensor and may only perform such altitude rate-of-change threshold monitoring after a shock event, e.g., a shock event such as may occur when the biometric monitoring device is placed on a hard surface, is detected from such a shock or acceleration sensor.

In some further such implementations, the biometric monitoring device may, after transitioning to a low-power state, monitor the altitude data to determine if the altitude rate-of-change changes beyond a second altitude rate-of-change threshold (which may, for example, be any non-zero altitude rate-of-change—any change in altitude may be a sufficient indicator that the biometric monitoring device has been picked up and should turn on). If such an altitude change is detected, the biometric monitoring device may transition to a higher-power state from the low-power state and/or turn on a display of the biometric monitoring device to display a message.

While the above discussion has focused on the wearing of a single biometric monitoring device, such techniques may also be practiced using multiple biometric monitoring devices. For example, a person may wear a biometric monitoring device on their forearm and a second biometric monitoring device on the same arm's upper arm.

Altimeter-Aided Airplane Mode

In some implementations, a biometric monitoring device having an altimeter (or other electronic device having an altimeter) may analyze the altimeter data to determine when to transition itself to an "airplane mode." This concept was discussed briefly earlier in this disclosure and is explored in more depth here.

Generally speaking, most altimeters are pressure-driven devices, and are thus likely to provide inaccurate altitude data in aircraft that are pressurized above certain altitudes. However, the techniques below may also be practiced using non-pressure-based altimeters, e.g., such as altitude measurements obtained via GPS measurements (such measurements are notoriously inaccurate, although they may be more than adequate for the purposes of airplane mode determination given the large magnitudes of elevations involved). If a non-pressure-based altimeter is used, the portions of the techniques discussed below that account for the pressurization of aircraft may be omitted since they are unnecessary.

It is also to be understood that, as used herein with respect to airplane mode implementations of biometric monitoring devices, the term "altitude sensor data" refers to data that is typically used to determine altitude (although, as discussed above, the altitudes that are calculated from such data may be inaccurate in some cases where the altitude measurement is pressure-based and the plane is pressurized above a certain altitude). Such data may be provided from the altimeter in units that are directly proportional to altitude or in units that require conversion or other post-processing to provide an altitude, e.g., pressure or voltage that may be indicative of pressure. The techniques outlined below may be performed using altitude sensor data in any of these formats, with some modification.

Figure 36:
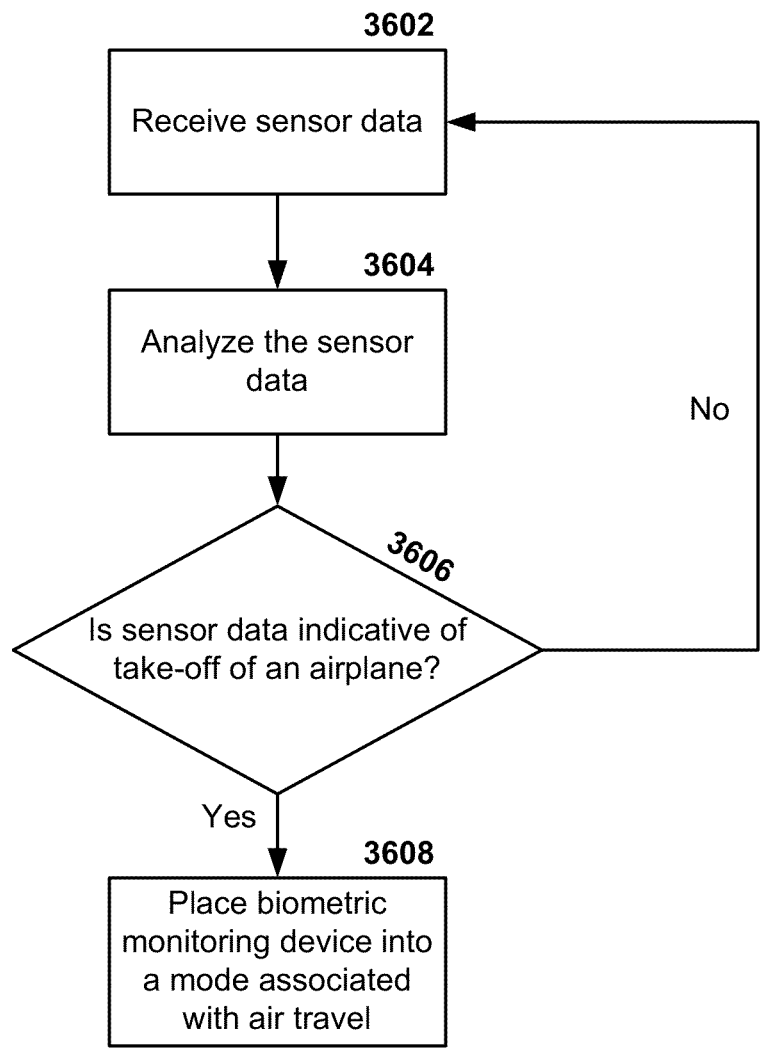
FIG. 36 shows a flow diagram detailing an example algorithm used by a biometric tracking device to determine whether to place the biometric tracking device into a mode associated with airplane travel.

FIG. 36 shows a flow diagram detailing an example algorithm that may be used by a biometric tracking device to determine whether to place the biometric tracking device into a mode associated with airplane travel. In certain implementations, the biometric tracking device may detect a change in pressure and/or motion characteristic of an airplane taking off or landing by receiving altitude sensor data from an altitude sensor. The biometric tracking device may have a controller that includes memory containing computer-executable instructions to control a processor to analyze the data from the altitude sensor or other sensor(s) to determine if the sensor data is indicative of an airplane taking off or landing.

The memory may contain various algorithms to determine if the altitude sensor data or other sensor data is indicative of an airplane taking off or landing. FIG. 36 is an example of such an algorithm. In block 3602, the controller may receive sensor data. The sensor data may, for example, be altitude sensor data from an altitude sensor or may be sensor data from other sensors. The sensor data may be solely the altitude sensor data or may be a combination of the altitude sensor data and other sensor data. The altitude sensor may, for example, be an altimeter that measures the ambient atmospheric pressure surrounding the biometric tracking device and outputs the altitude sensor data as a voltage to the controller. Other sensor data may, for example, be acceleration data from an acceleration sensor, communications data from a communications interface, or audio data from an audio sensor. The controller may then analyze the sensor data in block 3604.

In block 3606, the controller may determine if the sensor data is indicative of takeoff of an airplane. The controller may make this determination through a variety of ways. Some implementations of the biometric tracking device may make this determination using just the altitude sensor data, while other implementations may make this determination using the altitude sensor data paired with other sensor data. Yet other implementations may make this determination through a combination of such different approaches. For example, in some implementations, the biometric monitoring device may make use of multiple algorithms, with one algorithm using just the altitude sensor data and another algorithm using the altitude sensor data paired with acceleration data. In such an implementation, the controller may determine that the sensor data is indicative of takeoff if any one of the multiple algorithms determines that the data is indicative of takeoff. Other implementations may require a subset of or all of the multiple algorithms to be indicative of takeoff to before determining that the data from the various sensors is indicative of takeoff. The algorithms described herein that a controller may use to determine whether sensor data indicates an airplane takeoff may also be used by the controller to determine whether sensor data indicates that the airplane is landing. Algorithms used to determine whether sensor data indicates that the airplane is landing may have threshold values changed, either from a positive to a negative value or vice versa, or to a different value altogether.

The controller may analyze the altitude sensor data and determine that the altitude sensor data is indicative of takeoff through a variety of different algorithms. For example, if the altitude sensor data indicates a rate of altitude change that exceeds a rate of altitude change threshold, the controller may determine that the altitude sensor data is indicative of an airplane takeoff. The rate of altitude change threshold may be any rate of altitude change that is indicative of an airplane takeoff or landing, such as, for example, a rate of altitude change above 500 feet per minute. Other rates of altitude change may also be used. For example, commercial airplanes have a rate of altitude change of around 2,000 feet per minute at takeoff, so a rate of altitude change at or above this amount may be a reliable indicator of airplane takeoff. An implementation of the biometric tracking device that would primarily be used to detect take off for commercial airplanes may have the threshold rate of altitude change be 2,000 feet per minute or a little less than 2,000 feet per minute.

In certain implementations, a biometric monitoring device may determine that an airplane has taken off if the rate of altitude change exceeds an altitude rate of change threshold throughout an entire altitude change time period. For example, some implementations of the biometric tracking device may contain an algorithm requiring that the rate of altitude change exceed the rate of altitude change threshold for an altitude change time period of approximately 90 seconds before the processor determines that the altitude sensor data is indicative of an airplane takeoff. If the altitude sensor data indicates that the rate of altitude change falls below the rate of altitude change threshold at any time during the altitude change time period, the processor may determine that the altitude sensor data is not indicative of an airplane taking off. Other implementations may have an altitude change time period of more than 90 seconds and/or may have different rate of altitude change thresholds. For example, a certain implementation may have an altitude rate of change threshold of 1,000 feet per minute and an altitude change time period of at least 120 seconds.

An alternative algorithm to determine if the altitude sensor data is indicative of an airplane taking off is to determine the total change of altitude over a unit time. If the total change of altitude over a unit time exceeds a threshold altitude change over a threshold time period, then the controller may determine that the altitude sensor data is indicative of an airplane taking off. For example, a certain implementation may have a threshold altitude change value of 1,500 feet and a threshold time period of 180 seconds. If altitude sensor data, paired with time data, indicates an altitude change of 1,500 feet over a period of 180 seconds, then the controller may determine that the altitude sensor is indicative of an airplane taking off (or landing). Such an alternative algorithm may be useful to determine that an airplane is taking off or landing in a situation where the airplane pauses at a certain altitude during the middle of the takeoff or landing period. Other implementations may have different threshold altitude change values and threshold time periods.

The controller may also utilize other sensor data in addition to altitude sensor data. For example, the controller may receive acceleration data and analyze the acceleration data to determine whether the acceleration data indicates vibration consistent with vibration from an airplane engine or engines. In some implementations, the biometric monitoring device may use a motion sensor, such as a single-axis or multi-axis accelerometer, e.g., a triaxial acceleration sensor that detects acceleration along three orthogonal linear axes, a magnetometer to detect an orientation of the biometric tracking device, a gyroscope to detect rotational motion of the biometric monitoring device, or any combination of the above. In other implementations, the controller may analyze acceleration data to determine whether the acceleration data indicates horizontal and/or vertical acceleration consistent with acceleration of an airplane takeoff. Takeoff may be indicated by sustained horizontal or vertical acceleration such as sustained acceleration of more than 10 ft/sec$^2$ over a period of 20 seconds or more, or from sustained acceleration such that total velocity from the sustained acceleration at the end of a time period would be more than a threshold velocity. Any reasonable threshold velocity consistent with airplane takeoff speeds may be used, such as a speed of 150 mph.

In addition to acceleration data, the controller may analyze other sensor data such as audio data to determine whether the audio data indicates background noise consistent with the engine noise of an airplane, or communications data to determine whether the communications data indicates communications consistent with communications from an airplane communications device such as airplane WiFi signals.

If the controller does not determine that the altitude sensor data is indicative of takeoff of an airplane, the controller may return to block 3602. Otherwise, if the controller determines that the altitude sensor data is indicative of takeoff of an airplane in block 3606, the biometric tracking device may be placed into a mode associated with air travel in block 3608. The mode associated with air travel may vary depending on implementation. For example, in a certain implementation, the mode associated with air travel may be an "airplane mode" where wireless communications circuitry of the biometric tracking device is placed in a standby or off state. The communication circuitry may be communication circuitry utilizing WiFi, Bluetooth, ANT, near field communications, ZigBee, IEEE 802.11, IEEE 802.15, Infrared Data Association (IrDA) protocols, and other communication protocols. In another implementation, the mode associated with air travel may be a mode in which the biometric tracking device is placed in a low-power or sleep state. A further implementation of the biometric tracking device may include a stair-climbing mode that tracks a number of flights of stairs climbed by a wearer and such a biometric monitoring device may, when placed in the mode associated with air travel, turn off the stair-climbing mode.

Alternatively, the biometric tracking device may also be placed into a mode associated with air travel through external inputs. For example the biometric tracking device may be placed into the mode associated with air travel upon receiving an input signal via a wireless communications interface such as through receiving a signal from a personal computing or communications device such as a smartphone. In certain implementations, the smartphone may contain an app or functionality that would send the signal to the biometric tracking device automatically when the smartphone is placed into an airplane mode. Thus, when the smartphone is placed into the airplane mode, the biometric tracking device may also be placed into a mode associated with air travel such as an airplane mode. Similarly, when the smartphone airplane mode is deactivated, the smartphone may send a signal to the biometric monitoring device to cause the biometric monitoring device to exit airplane mode (such implementations may require that the biometric monitoring device periodically activate (or keep powered on) a receiver to scan for such a signal). Other implementations may place the biometric tracking device into a mode associated with air travel upon receiving input from the user of the biometric tracking device.

Figure 37:
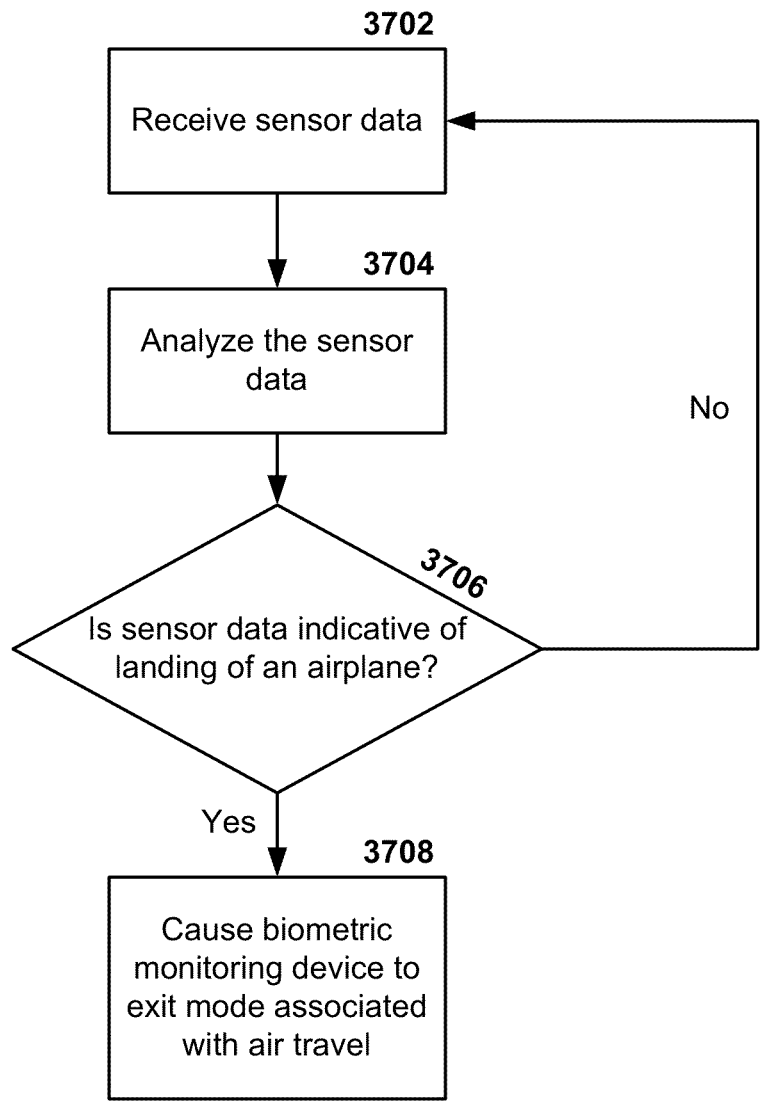
FIG. 37 shows a flow diagram detailing an example algorithm used by a biometric tracking device to determine whether to exit the mode associated with airplane travel.

FIG. 37 shows a flow diagram detailing an example algorithm used by a biometric tracking device to determine whether to exit the mode associated with airplane travel. Blocks 3702 and 3704 are similar to blocks 3602 and 3604 in FIG. 36. However, in block 3702 of FIG. 37, the biometric tracking device may receive sensor data while in a mode associated with airplane travel instead of in a normal operating mode. The sensor data in FIG. 37 is similar to the sensor data described in FIG. 36 and may be altitude sensor data or a combination of altitude sensor data and data from other sensors, as previously described. In block 3704, the controller analyzes the sensor data.

In block 3706, the controller determines whether the sensor data is indicative of an airplane during landing. The controller may determine that the sensor data is indicative of an airplane during landing using any of the ways described for block 3606 above, possibly with certain values changed or reversed in magnitude to reflect the fact that the plane is descending instead of ascending. For example, the total altitude increase threshold of 1,500 feet described in block 3606 may be a threshold of altitude gain of 1,500 feet in block 3606, while in block 3706 the threshold may be an altitude loss of 1,500 feet. Other implementations may have threshold values that are different between the algorithms for calculating whether an airplane is taking and whether an airplane is landing. For example, a certain implementation may have a total altitude change threshold of a gain of 1,500 feet in altitude to determine that an airplane is takeoff, but a total altitude change threshold of a loss of 2,000 feet in altitude to determine that an airplane is landing. Using another example from block 3606, the altitude change time period for determining whether an airplane is taking off may be a time period of 60 seconds or more, but to determine whether an airplane is landing, the altitude change time period may be a time period of 180 seconds or less. The differences between the altitude change time period to determine takeoff and landing may be due to how an airplane is typically operated. Airplanes may take off and gain altitude at a higher initial rate than the rate that airplanes lose altitude when landing. Hence, the altitude change time period to determine takeoff may be less than the altitude change time period to determine landing.

In addition, before determining that the sensor data is indicative of landing of an airplane in block 3706, the controller may further determine a period where the altitude of the biometric tracking device changes little, as detected by the altitude sensor, before determining that the altitude sensor data is indicative of an airplane landing and causing the biometric tracking device to exit the mode associated with air travel. Alternatively, detecting a sustained period of little altitude change after a period of altitude decrease may allow the controller to determine that the airplane has actually landed. Commercial airplanes often spend a period of several minutes taxiing and sitting on a flat runway after landing. This period of little altitude change may correspond to the period of taxiing and may allow the biometric tracking device to determine that the airplane has actually landed and is taxiing or stationary on the ground before exiting the mode associated with air travel.

Various implementations of the biometric tracking device may have their controllers determine that the airplane has landed and is taxiing through a variety of different ways. For example, the controller may determine that the airplane has landed when it determines, from the altitude sensor data, and possibly other sensor data, that the rate of altitude change over a time period does not exceed a threshold amount (after detecting a prolonged decrease in altitude). An implementation of the biometric tracking device may make the determination that the airplane has landed and is taxiing when the controller determines that the altitude sensor data indicates a rate of altitude change of less than 50 feet per minute for a period of 120 to 600 seconds, possibly 300 seconds, after the controller determined that the altitude sensor data indicated an altitude decrease or rate of altitude decrease exceeding a threshold altitude decrease amount, e.g., what had previously been described in this disclosure for block 3706. Other implementations may make the determination that the airplane has landed and is taxiing when the controller determines that the altitude sensor data indicates that the total altitude change does not exceed a threshold amount, such as 100 feet or less, over a threshold time period, such as 600 seconds or less (after a prolonged altitude decrease occurs). Additional implementations may have different threshold amounts.

If, in block 3706, the controller determines that the sensor data is indicative of landing of an airplane, the controller may then cause the biometric monitoring device to exit the mode associated with air travel in block 3708. The controller may exit the mode associated with air travel by turning on the communication circuitry of the biometric tracking device, by placing the biometric tracking device into a normal power state, by turning on a stair climbing mode, or by causing other changes in the operation of the biometric monitoring device. The controller in block 3708 may exit the mode associated with air travel by reversing any action taken or command issued by the controller in block 3608.

Figure 38:
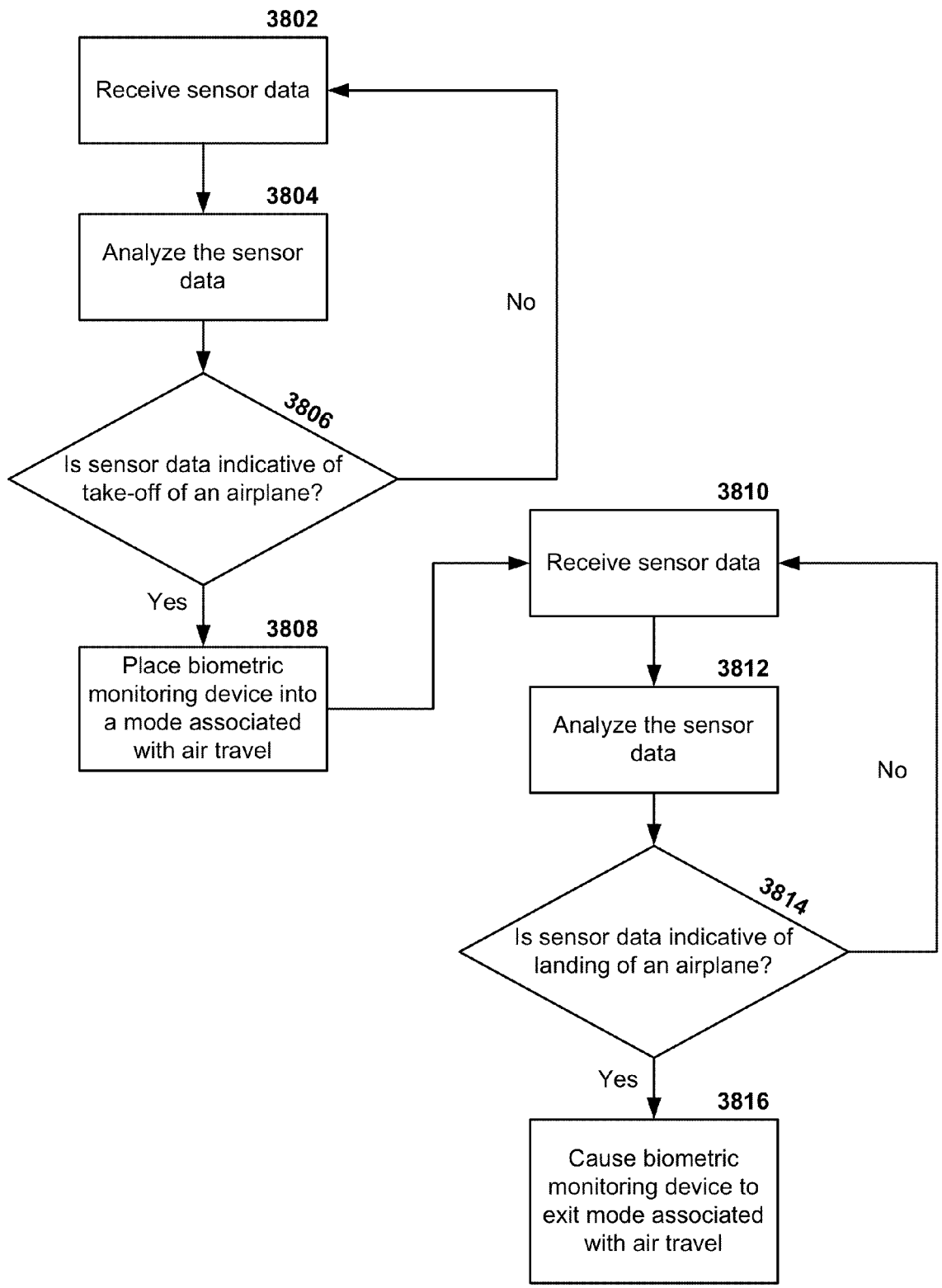
FIG. 38 shows a flow diagram detailing an example algorithm used by a biometric tracking device to determine whether to first place the biometric tracking device into a mode associated with airplane travel and then to determine whether to exit the mode associated with airplane travel.

FIG. 38 shows a flow diagram detailing an example algorithm used by a biometric tracking device to determine whether to first place the biometric tracking device into a mode associated with airplane travel and then to determine whether to exit the mode associated with airplane travel. The flow diagram of FIG. 38 is a combination of the flow diagrams of FIGS. 36 and 37 and details the entire process of the biometric tracking system entering and then exiting the mode associated with air travel. Blocks 3802-08 correspond to blocks 3602-08 of FIG. 36 while blocks 3810-16 correspond to blocks 3702-08 of FIG. 37. The previously description for the blocks in FIGS. 36 and 37 also apply to the corresponding blocks in FIG. 38.

Figure 39A:
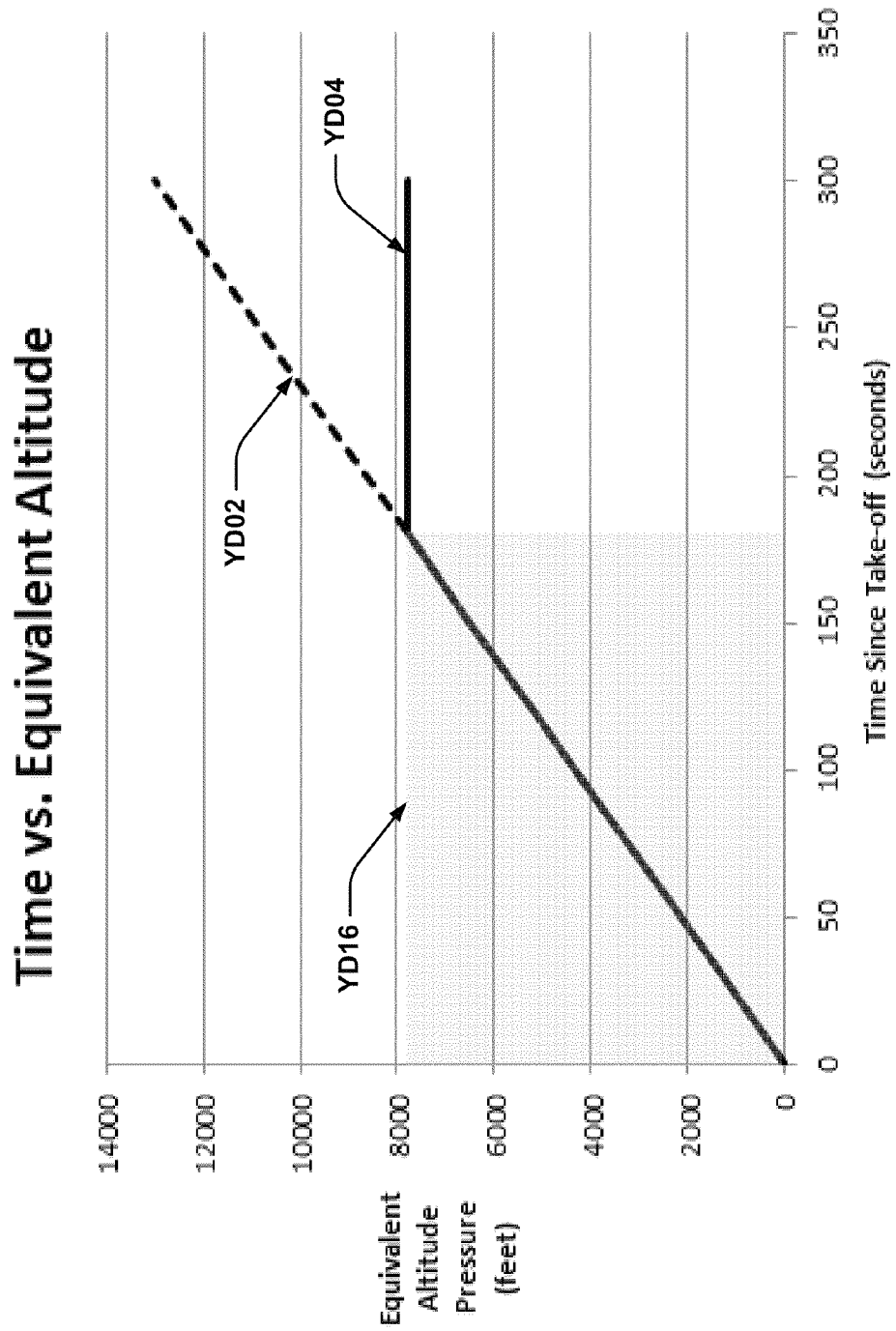
FIG. 39A is an example graph showing an equivalent air pressure inside a pressurized cabin of an example airplane taking off compared to unpressurized air pressure at the same altitude.

FIG. 39A is an example graph showing an equivalent air pressure inside a pressurized cabin of an example airplane taking off compared to ambient air pressure at the same altitude. FIG. 39A is a representative graph. In FIG. 39A, the x-axis represents time in seconds while the y-axis represents the equivalent altitude pressure in feet. Equivalent altitude pressure is the barometric pressure that is typically experienced at a reference altitude. For example, the barometric pressure of 29.92 inHg would correspond to an equivalent altitude pressure of 0 feet in FIG. 39A since 29.92 inHg is the average barometric pressure at sea level. As another example, the equivalent altitude pressure of 8,000 feet in FIG. 39A would correspond to the average barometric pressure at 8,000 feet. Please note that a higher equivalent altitude pressure in FIG. 39A corresponds to a lower barometric pressure as barometric pressure decreases when altitude increases. Certain implementations of the biometric tracking device may utilize the barometric pressure data in algorithms without converting the barometric pressure data into an equivalent altitude.

Broken line 3902 represents the air pressure outside of an airplane that includes a biometric tracking device. In FIG. 39A, the airplane is taking off, thus as time increases, the broken line 3902 shows the equivalent altitude pressure increasing in altitude to correspond to the higher altitude that the airplane is reaching.

Solid line 3904 represents the air pressure experienced by a biometric tracking device inside the airplane. The airplane in FIG. 39A is an airplane with a pressurized cabin similar to that of most civilian airliner planes. The cabin in the airplane is pressurized to the equivalent of 7,800 feet during flight. Thus, in FIG. 39A, as altitude initially increases, the equivalent altitude pressure experienced by the biometric tracking device inside the airplane, represented by solid line 3904, increases similar to that of broken line 3902. However, after the airplane passes 7,800 feet in altitude at 180 seconds, the cabin is pressurized to stay at the same barometric pressure. Thus, after 180 seconds, the cabin of the airplane is pressurized to the equivalent of 7,800 feet and the equivalent altitude pressured experienced by the biometric tracking device stays at a constant 7,800 feet even though the actual altitude of the airplane is still increasing.

Region 3916, represented by a cross-hatched box in FIG. 39A, represents the period when the equivalent altitude pressure experienced by the biometric tracking device matches the equivalent altitude pressure outside the airplane as the airplane takes off, which is the period of FIG. 39A from 0 seconds to 180 seconds. Since the equivalent altitude pressure experienced by the biometric tracking device stays constant after 180 seconds in FIG. 39A, the biometric tracking device in FIG. 39A would perform best at detecting the takeoff of an airplane if it only had to rely on altitude sensor data below the equivalent altitude of 7,800 feet. Thus, attempting to detect too high of an equivalent altitude with the altitude sensor may complicate using the altitude sensor to detect an airplane takeoff. Accordingly, certain implementations of the biometric tracking device may limit the equivalent altitude pressure used by the controller to determine whether an airplane is taking off or landing to altitudes less than the equivalent altitudes that common airliner planes are pressurized to.

Figure 39B:
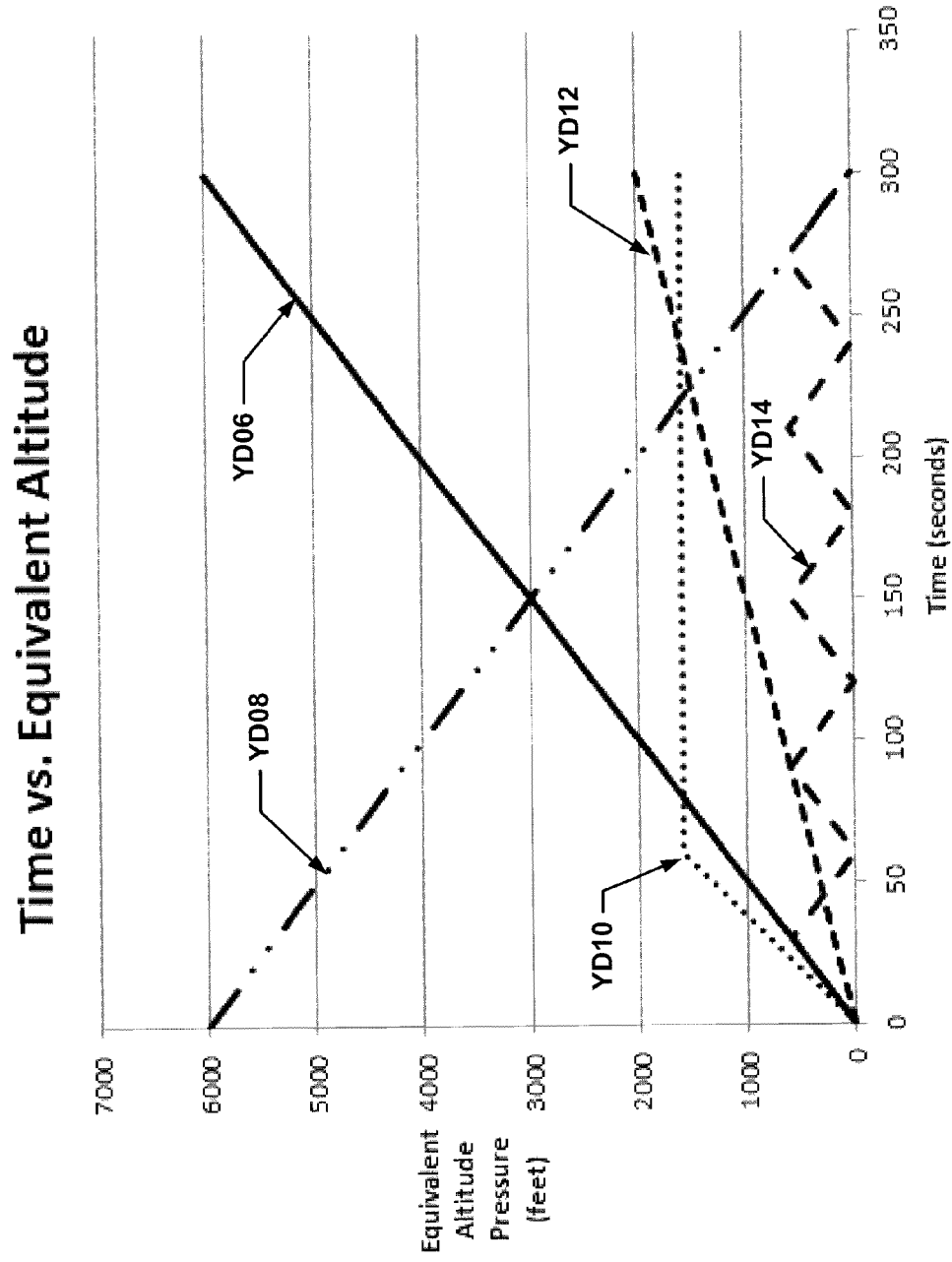
FIG. 39B is an example graph illustrating altitude sensor data from various example scenarios.

FIG. 39B is an example graph illustrating altitude sensor data from various example scenarios. FIG. 39B is a representative graph. In FIG. 39B, the x-axis represents time in seconds while the y-axis represents the equivalent altitude pressure in feet. Equivalent altitude pressure in FIG. 39B is the similar to the equivalent altitude pressure described in FIG. 39A.

In FIG. 39B, line 3906 represents a biometric tracking device in an airplane taking off. Line 3908 represents a biometric tracking device in an airplane landing. Line 3910 represents a biometric tracking device in an elevator of a skyscraper. Line 3912 represents a biometric tracking device in a car driving up a steep mountain. Line 3914 represents a biometric tracking device on an extreme amusement park ride.

Line 3906 is similar to line 3904 in FIG. 39A. However, FIG. 39B only shows the airplane of line 3906 before it reaches 6,000 feet and thus the interior of the airplane in line 3906 has not yet been pressurized. Line 3906 shows a linear rise in equivalent altitude pressure as the airplane takes-off.

Line 3908 represents the equivalent altitude pressure experienced by a biometric tracking device in an airplane landing. The equivalent altitude pressure of line 3908 decreases from 6,000 feet at 0 seconds to 0 feet at 300 seconds. Thus, at zero 300 seconds, the airplane of line 3908 may have landed at sea-level. The absolute value of the rate of altitude decrease in line 3908 is the same as the absolute value of the rate of altitude increase in line 3906.

Line 3910 represents the equivalent altitude pressure experienced by a biometric tracking device in an elevator of a skyscraper. The equivalent altitude pressure of line 3910 initially increases at a faster rate than line 3906. This is due to a high speed elevator of a skyscraper often gaining altitude at a faster rate than the rate that airplanes gain altitude during takeoff. However, since buildings are limited in height, at 50 seconds, the elevator reaches the top of the building and line 3910 no longer gains equivalent altitude after 50 seconds. Thus, while a controller with an algorithm that analyzes portions of sensor data less than 50 seconds of duration may determine that the altitude sensor data of line 3910 from 0 seconds to 50 seconds is equivalent to that of an airplane takeoff, a controller with an algorithm that analyzes portions of sensor data greater than 50 seconds of duration may be able to determine that altitude sensor data of line 3910 is not indicative of an airplane takeoff.

Line 3912 represents the equivalent altitude pressure experienced by a biometric tracking device in a car driving up a steep mountain. While the altitude sensor data of line 3912 determines a gain of 2,000 feet in altitude, the rate of the altitude gain may be too slow for the controller of a biometric tracking device to determine that the altitude sensor data indicates an airplane takeoff. Alternatively, if the controller of the biometric tracking device only analyzes a limited duration of altitude sensor data, the controller may determine that the total magnitude of altitude gain of line 3912 during the limited duration may not exceed the threshold magnitude of altitude gain to indicate that the altitude sensor data is indicative of an airplane takeoff.

Line 3914 represents the equivalent altitude pressure experienced by a biometric tracking device on an extreme amusement park ride. The amusement park ride illustrated by line 3914 may be an amusement park ride with constant up and down motions, such as that of an extreme rollercoaster ride. While the rate of altitude gain and loss of line 3914 is equivalent to that of an airplane takeoff or landing, the total magnitude of the altitude gain is much less than an airplane takeoff or landing. Thus, a controller that includes an algorithm that utilizes altitude gain over a set duration or total altitude gain in its determination of whether the altitude sensor data is indicative of an airplane takeoff or landing may be able to determine that altitude change of line 3912 does not represent that of an airplane takeoff or landing due to the constant changes in positive and negative values of altitude change or due to the total magnitude of altitude change not exceeding a threshold amount.

Figure 40:
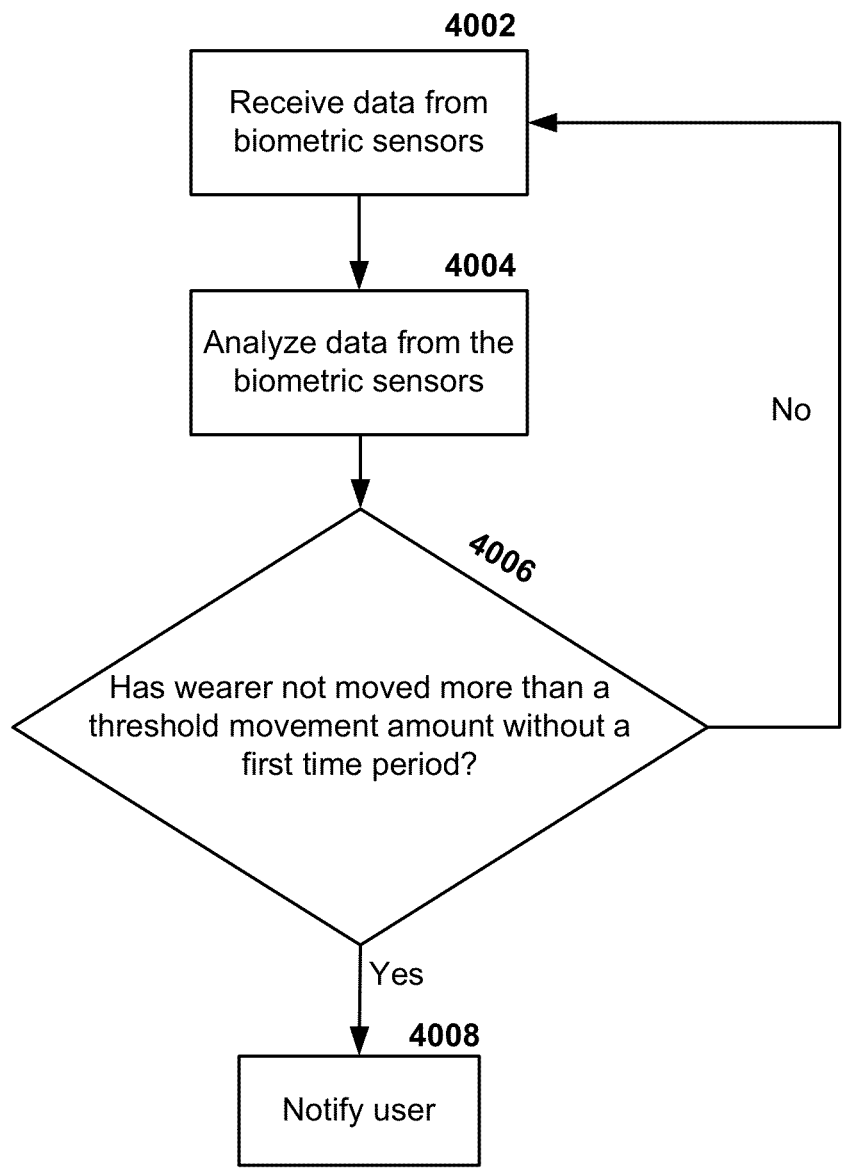
FIG. 40 shows a flow diagram detailing an example algorithm used by a biometric tracking device to determine whether to notify a user that the user has been inactive for a period greater than the inactivity time period.

FIG. 40 shows a flow diagram detailing an example algorithm used by a biometric tracking device to determine whether to notify a user that the user has been inactive for a period greater than the inactivity time period. The example algorithm illustrated by FIG. 40 may be an algorithm to monitor the movements of a user and notify the user when the controller of the biometric tracking device determines that the user has not moved more than a threshold amount within a set time period.

The example algorithm illustrated by FIG. 40 may be linked to the mode associated with airplane travel described in FIGS. 36 to 38. Accordingly, the biometric tracking device may utilize the algorithm when the biometric tracking device is placed into a mode associated with air travel. Such an algorithm may be useful when the biometric tracking device is placed in a mode associated with air travel because a user of the biometric tracking device on an airplane may be mostly stationary and in a sitting position, allowing blood to pool around his or her lower extremities. Having an algorithm that would remind the user to periodically move would help circulate the blood of the user around his or her body, preventing potential harm from blood clotting and other potentially serious afflictions that may strike people who sit still too long.

In block 4002, the controller of the biometric tracking system may receive data from biometric sensors. The biometric sensors may be sensors embedded in the biometric tracking device or biometric sensors located on other devices with biometric sensor data communicated to the biometric tracking device via, for example, a WiFi or Bluetooth connection. The biometric sensors may be any sensor that may detect movement of the user either directly or indirect, such as a heart rate sensor, a pedometer, an acceleration sensor, a light sensor, a gyroscope, or any other sensor described elsewhere in this disclosure.

In block 4004, the controller analyzes the data from the biometric sensors according to algorithms stored by the memory of the controller.

In block 4006, the controller determines whether the wearer has not moved more than a threshold movement amount within a first time period. The controller may make this determine through a variety of ways. For example, the biometric tracking device may include a biometric sensor that detects the heart rate of the user and, if the heart rate of the user has remained at a resting pulse rate for the duration of a first time period, the controller may determine that the user has not moved the threshold movement amount within the first time period. Alternatively, the biometric tracking device may utilize the pedometer to detect steps that a user has taken and, if the number of steps detected does not exceed a threshold amount for a first time period, the controller may determine that the user has not moved the threshold movement amount within the first time period. Other implementations of the biometric tracking device may utilize the acceleration sensor or the gyroscope to detect movement of the user to determine that the user has not moved the threshold movement amount within the first time period. The first time period may be any reasonable time period for tracking the movement of the user on an airplane flight, such as a time period of 15 hours or less. The controller may also include different threshold amounts for detecting the movement of the user such as, for the implementation using the pedometer, having the threshold step count be 100, 300, 500, or 1,000 steps.

If the controller in block 4006 determines that the user has moved more than the threshold movement amount within the first time period, then the controller reverts back to block 4002. If the controller in block 4006 determines that the user has not moved more than the threshold movement amount within the first time period, the controller continues to block 4008.

In block 4008, the biometric tracking device notifies the user via a user interface that the user has not moved more than the threshold movement amount. The user interface may be a variety of different types of interfaces including, for example, a graphical display, a vibramotor embedded within the biometric tracking device to generate haptic feedback, or a sound generating component such as a speaker or piezoelectric device. The user interface may notify the user via a variety of different ways including a message on the graphical display, haptic feedback such as a vibration or a series of vibrations, a beep, multiple beeps, or a melodic tune.

In certain implementations, the memory of the biometric tracking device may include code to determine that the user is asleep, likely asleep, or possibly asleep and thus delay notifying the user. The controller of the biometric tracking device may determine that the user is asleep, likely asleep, or possibly asleep through a variety of different ways. For example, the biometric tracking device may include a light sensor and the controller may analyze the light sensor data to determine that the light sensor data is indicative of light levels normally associated with a sleeping environment in an airplane and thus determine that the user is asleep, likely asleep, or possibly asleep. Alternatively, the controller may determine that the user is asleep, likely asleep, or possibly asleep when the biometric tracking device may be manually placed into a sleep tracking mode by the user. Additionally, the controller may determine that the user is asleep, likely asleep, or possibly asleep when analysis of the biometric data shows that the biometric data indicates or possibly indicates that the user is asleep.

If the controller determines that the user is asleep or likely asleep, the controller may delay providing notification that the user has not moved more than the threshold movement amount to the user to a later time period, such as a time period when the controller determines that the wearer is not asleep or likely not to be asleep.

The concepts and examples discussed above with respect to altimeter recalibration, altimeter-assisted gesture recognition, and altimeter-assisted airplane mode may be implemented in a device, e.g., a biometric monitoring device, using, for example, computer-executable instructions that are stored in a computer-readable memory. The instructions may be executed by a processor or processors that are communicatively connected with the memory and that is/are also communicatively connected with pressure sensor or barometric altimeter. Such instructions may be provided using any of a variety of programming languages, including, but not limited to, C++, Java, iOS, Android, etc. In some implementations, some or all of the instructions may be hard-coded into an application-specific integrated circuit (ASIC). The term "control logic" may be used herein, with respect to the altimeter recalibration, altimeter-assisted gesture recognition, and altimeter-assisted airplane mode techniques and systems discussed herein, to refer to any combination of hardwired circuits and processor/memory/software-based components that may be used to practice such techniques or implement such systems.

It is to be understood that the concepts and examples discussed above with respect to altimeter recalibration, altimeter-assisted gesture recognition, and altimeter-assisted airplane mode may be implemented in a device or system, e.g., a biometric monitoring or tracking device or other electronic device; as computer-, processor-, or circuit-assisted methods; or as computer-executable instructions transmitted to a device or stored on non-transitory, machine-readable media.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

Importantly, the present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

What is claimed is:

1. A wearable biometric tracking device, the wearable biometric tracking device comprising:
   one or more biometric sensors;
   an altitude sensor, the altitude sensor configured to detect altitude of the wearable biometric tracking device and to output altitude sensor data; and
   control logic, wherein the one or more biometric sensors, the altitude sensor, and the control logic are communicatively coupled and the control logic is configured to:
   a) receive the altitude sensor data,
   b) analyze the altitude sensor data to determine if the altitude sensor data is indicative of flight in an airplane, and
   c) place, responsive at least in part to a determination in (b) that the altitude sensor data is indicative of flight in an airplane, the wearable biometric tracking device into a mode associated with air travel.

2. The wearable biometric tracking device of claim 1, wherein the altitude sensor data is indicative of flight in an airplane when the altitude sensor data indicates a rate of altitude change that exceeds a rate of altitude change threshold.

3. The wearable biometric tracking device of claim 2, wherein the rate of altitude change threshold is above 30 feet per minute.

4. The wearable biometric tracking device of claim 1, wherein:
   the altitude sensor data is indicative of flight in an airplane when the altitude sensor data indicates a total altitude increase over an altitude increase time period for the wearable biometric tracking device, and
   the total altitude increase over the altitude increase time period exceeds a total altitude increase threshold.

5. The wearable biometric tracking device of claim 4, wherein the total altitude increase threshold is at least 130 feet in altitude and the altitude increase time period is 180 seconds or less.

6. The wearable biometric tracking device of claim 1, wherein the altitude sensor data is indicative of flight in an airplane when:
   the altitude sensor data indicates a rate of altitude change that exceeds an altitude rate of change threshold throughout an altitude change time period, and
   the rate of altitude change threshold is at least 30 feet per minute.

7. The wearable biometric tracking device of claim 6, wherein the altitude change time period is a time period of at least 13 seconds.

8. The wearable biometric tracking device of claim 1, wherein the mode associated with air travel is a mode in which the wearable biometric tracking device is placed in a low power state.

9. The wearable biometric tracking device of claim 1, further comprising wireless communication circuitry, the communication circuitry communicatively coupled to the control logic and configured to wirelessly communicate with associated devices, wherein the mode associated with air travel is a mode in which the communication circuitry is placed in a standby or off state.

10. The wearable biometric tracking device of claim 1, wherein the control logic is further configured to:

d) further analyze the altitude sensor data to determine if the altitude sensor data is indicative of landing of the airplane, and
e) cause, responsive at least in part to a determination in (d) that the altitude sensor data is indicative of landing of the airplane, the wearable biometric tracking device to exit the mode associated with air travel.

11. The wearable biometric tracking device of claim 10, wherein the altitude sensor data is indicative of the landing of the airplane when:
f) the altitude sensor data indicates a total altitude decrease for the wearable biometric tracking device that exceeds a total altitude decrease threshold over an altitude decrease time period; and
g) the altitude sensor data indicates a rate of altitude change of less than 3 feet per minute for a period of 300 seconds after (f).

12. The wearable biometric tracking device of claim 11, wherein the altitude decrease time period is 180 seconds or less.

13. The wearable biometric tracking device of claim 11, wherein the control logic is further configured to:
h) receive biometric data from the one or more biometric sensors;
i) analyze the biometric data to determine if the biometric data indicates that a wearer of the wearable biometric tracking device has taken at least a predetermined number of steps; and
j) determine that the altitude sensor data is indicative of the landing of the airplane when the control logic further detects (i) after (f).

14. The wearable biometric tracking device of claim 11, wherein the total altitude decrease threshold is an altitude decrease of at least 130 feet.

15. The wearable biometric tracking device of claim 1, wherein the control logic is further configured to monitor biometric data from the one or more biometric sensors and to determine when the biometric data indicates that a wearer of the biometric monitoring device has not moved more than a threshold movement amount relative to an aircraft reference frame within a first time period after (b).

16. The wearable biometric tracking device of claim 15, further comprising a user interface, wherein the control logic is further configured to cause a notification to be provided to the wearer via the user interface responsive, at least in part, to the determination that the wearer of the biometric monitoring device has not moved more than the threshold movement amount relative to the aircraft reference frame within the first time period.

17. The wearable biometric tracking device of claim 16, further comprising a light sensor configured to measure an amount of ambient light around the biometric tracking device and to output detected light data, wherein the control logic is further configured to:
analyze the detected light data to determine if the detected light data is indicative of light levels normally associated with a sleeping environment in an airplane, and
cause the notification to be provided to the wearer via the user interface responsive to the determination that the wearer of the biometric monitoring device has not moved more than the threshold movement amount relative to the aircraft reference frame within the first time period and responsive to a determination that the detected light data is not indicative of the light levels normally associated with the sleeping environment in an airplane.

18. The wearable biometric tracking device of claim 16, wherein the control logic is further configured to:
place the wearable biometric tracking device into a sleep-tracking mode responsive to a stimulus selected from the group consisting of: (i) a deliberate request provided by the wearer of the wearable biometric tracking device and (ii) analysis of the biometric data indicating that the wearer of the wearable biometric tracking device is likely asleep;
cause the notification to be provided to the wearer via the user interface when the wearable biometric tracking device is not in the sleep-tracking mode and responsive to the determination that the wearer of the biometric monitoring device has not moved more than the threshold movement amount relative to the aircraft reference frame within the first time period.

19. The wearable biometric tracking device of claim 16, wherein the user interface includes a digital display and the notification is a message displayed on the digital display.

20. The wearable biometric tracking device of claim 16, wherein the user interface includes an audio device and the notification is an audio notification.

21. The wearable biometric tracking device of claim 16, wherein the user interface includes a haptic feedback mechanism and the notification is a tactile notification.

22. The wearable biometric tracking device of claim 1, further comprising an audio sensor configured to output audio data, wherein the control logic is further configured to:
receive the audio data; and
analyze the audio data to determine whether the audio data indicates background noise consistent with engine noise of an aircraft, wherein the control logic is further configured to place the wearable biometric monitoring device into the mode associated with air travel responsive, at least in part, to the determination in (b) that the altitude sensor data is indicative of flight of the airplane and to the determination that the audio data indicates background noise consistent with the engine noise of the aircraft.

23. The wearable biometric tracking device of claim 1, further comprising an acceleration sensor configured to detect acceleration and output acceleration data, wherein the control logic is further configured to:
receive the acceleration data; and
analyze the acceleration data to determine whether the acceleration data indicates vibration consistent with vibration from an aircraft engine, wherein the control logic is further configured to place the wearable biometric monitoring device into the mode associated with air travel responsive, at least in part, to the determination in (b) that the altitude data is indicative of flight of the airplane and to the determination that the acceleration data indicates vibration consistent with the vibration of the aircraft engine.

24. The wearable biometric tracking device of claim 1, further comprising a communications interface configured to receive communications data, wherein the control logic is further configured to:
receive the communications data; and
analyze the communications data to determine whether the communications data indicates communications consistent with communications from an airplane communications device, wherein the control logic is further configured to place the wearable biometric monitoring device into the mode associated with air travel responsive, at least in part, to the determination in (b) that the altitude sensor data is indicative of flight of the airplane and also to the determination that the communications data indicates communications consistent with the communications from the airplane communications device.

25. The wearable biometric tracking device of claim 1, wherein the control logic is further configured to:
provide a stair-climbing mode that tracks a number of flights of stairs climbed by a wearer of the wearable biometric tracking device, and
turn off the stair-climbing mode responsive to (c).

26. The wearable biometric tracking device of claim 1, further comprising a wireless communications interface, wherein the control logic is further configured to:
receive a first input signal via the wireless communications interface, and
cause, responsive to the receipt of the first input signal, the wearable biometric tracking device to enter into the mode associated with air travel.

27. The wearable biometric tracking device of claim 26, wherein the control logic is further configured to cause the wearable biometric tracking device to exit the mode associated with air travel upon receipt of a second input signal, wherein the second input signal is indicative of activity selected from the group consisting of: an associated external device powering on, tapping the wearable biometric tracking device, selection of a menu option through a user interface of the wearable biometric tracking device, and pressing of a button of the wearable biometric monitoring device.

28. A system comprising:
a wearable biometric tracking device comprising:
one or more biometric sensors,
a biometric tracking device communications interface, and
biometric tracking device control logic, wherein the one or more biometric sensors, the biometric tracking device communications interface, and the biometric tracking device control logic are communicatively coupled and the biometric tracking device control logic is configured to:
a) receive a signal associated with an airplane mode;
b) responsive to (a), place the wearable biometric tracking device into a mode associated with air travel; and
a mobile communications device separate from the wearable biometric tracking device, the mobile communications device comprising:
a mobile communications device communications interface, and
mobile communications device control logic, wherein the mobile communications device communications interface and the mobile communications device control logic are communicatively coupled and the mobile communications device control logic is configured to:
transmit the signal associated with the airplane mode via the mobile communications device communications interface.

* * * * *

UNITED STATES PATENT AND TRADEMARK OFFICE
CERTIFICATE OF CORRECTION

PATENT NO. : 8,965,730 B2
APPLICATION NO. : 14/297397
DATED : February 24, 2015
INVENTOR(S) : Shelten Gee Jao Yuen It is certified that error appears in the above-identified patent and that said Letters Patent is hereby corrected as shown below:

In the claims

Line 2 of claim 3 (col. 106, line 30), which reads "wherein the rate of altitude change threshold is above 30 feet", should be changed to "wherein the rate of altitude change threshold is above --500-- feet".

Line 2 of claim 5 (col. 106, line 41), which reads "wherein the total altitude increase threshold is at least 130 feet", should be changed to "wherein the total altitude increase threshold is at least --1500-- feet".

Line 7 of claim 6 (col. 106, line 50), which reads "the rate of altitude change threshold is at least 30 feet per", should be changed to "the rate of altitude change threshold is at least --500-- feet per".

Line 3 of claim 7 (col. 106, line 54), which reads "least 13 seconds", should be changed to "least --60-- seconds".

Line 9 of claim 11 (col. 107, line 17), which reads "of less than 3 feet per minute for a period of 300 seconds", should be changed to "of less than --50-- feet per minute for a period of 300 seconds".

Line 3 of claim 14 (col. 107, line 35), which reads "decrease of at least 130 feet", should be changed to "decrease of at least --1500-- feet".

Signed and Sealed this
Sixteenth Day of August, 2016

Michelle K. Lee
*Director of the United States Patent and Trademark Office*